(12) United States Patent
Gibson et al.

(10) Patent No.: US 7,544,812 B2
(45) Date of Patent: Jun. 9, 2009

(54) PEROXISOME PROLIFERATOR ACTIVATED RECEPTOR AGONISTS

(75) Inventors: Tracey Ann Gibson, Indianapolis, IN (US); Richard Duane Johnston, Greenfield, IN (US); Nathan Bryan Mantlo, Brownsburg, IN (US); Richard Craig Thompson, Frankfort, IN (US); Leonard Larry Winneroski, Greenwood, IN (US); Yanping Xu, Fishers, IN (US); Xiaodong Wang, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 391 days.

(21) Appl. No.: 10/496,770

(22) PCT Filed: Nov. 26, 2002

(86) PCT No.: PCT/US02/36128

§ 371 (c)(1), (2), (4) Date: May 25, 2004

(87) PCT Pub. No.: WO03/048130

PCT Pub. Date: Jun. 12, 2003

(65) Prior Publication Data

US 2005/0020652 A1 Jan. 27, 2005

Related U.S. Application Data

(60) Provisional application No. 60/334,453, filed on Nov. 30, 2001.

(51) Int. Cl.
*A61K 31/4166* (2006.01)
*C07D 233/32* (2006.01)

(52) U.S. Cl. .................. 548/319.1; 548/323.5; 514/398

(58) Field of Classification Search ............... 548/319.1, 548/323.5
See application file for complete search history.

(56) References Cited

U.S. PATENT DOCUMENTS 3,452,041 A 6/1969 Bell et al.
4,241,073 A * 12/1980 Jamieson et al. ............ 514/389

FOREIGN PATENT DOCUMENTS

| DE | 27 24 948 A | 12/1977 |
|---|---|---|
| EP | 0 005 647 A | 11/1979 |
| WO | WO 97 31907 A | 9/1997 |
| WO | WO 98 39303 A | 9/1998 |
| WO | WO 01 16120 A | 3/2001 |

OTHER PUBLICATIONS

Swain, CA 43:1769b-h, 1949.*
Burton et al., CA 43:6978d-g, 1949.*

Souillac, et al., Characterization of Delivery Systems, Differential Scanning Calorimetry in Encyclopedia of Controlled Drug Delivery, 1999, John Wiley & Sons, pp. 212-227.*

Vippagunta et al., Advanced Drug Delivery Reviews, 48 (2001), pp. 3-26.*

Colagiuri et al., American Journal of Public Health, Sep. 2006, vol. 96, No. 9, pp. 1562-1569.*

Bruno et al., Expert Opinion Emerging Drugs, (2005), 10(4), pp. 747-771.*

Park, Diabetes Research and Clinical Practice 66S (2004), S33-S35.*

Curtis et al., The Journal of the American Board of Family Practice, vol. 18, pp. 37-43, (2005).*

J. Knabe, et al.: "Razemate und Enantiomere Basich Substituierter 5-Phenylhtdabtoine, Synthese und Antiarrhythmische Wirkung": Pharmazeutische, vol. 52, (1997), pp. 912-919.

Stanley C. Bell, et al.: "Rearrangement Reactions of Phenyl Chloroformate Derivatives of 2-hydroxyaminoacetanilides to Hydantoins, Ureas and Hydantoic Acid Derivatives": Journal of Heterocyclic Chemistry, vol. 13, No. 1, (1976), pp. 51-55.

Joseph Weinstock, et al.: "Synthesis of a 10,10a-dihydro-1H-imidazo-(3, 4-b)(1, 2)benzothianzine 5,5-dioxide": Journal of Organic Chemistry, vol. 33, No. 8, (1968), pp. 3342-3343.

(Continued)

*Primary Examiner*—Laura L. Stockton
(74) *Attorney, Agent, or Firm*—MaCharri Vorndran-Jones

(57) ABSTRACT

The present invention is directed to compounds represented by the following structural Formula (I), (a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and —$CH_2$—C(O)—R17-R18, wherein R17 is O or NH and R18 is optionally substituted benzyl; (b) R2 is selected from the group consisting of $C_1$-$C_6$ alkyl, $C_1$-$C_6$ alkenyl, aryl-$C_{0-4}$-alkyl, heteroaryl-$C_{0-4}$-alkyl, $C_1$-$C_4$ alkyl sulfonamide, $C_1$-$C_4$ alkyl amide, OR10 and $C_3$-$C_6$ cycloalkyl; (c) W is O or S; (d) X is an optionally substituted $C_1$-$C_5$ alkylene linker wherein one carbon atom of the linker may optionally be replaced with O, NH, S, and optionally two carbons together may form a double bond; (e) Y is selected from the group consisting of C, O, S, NH and a single bond; and (f) E is selected from the group consisting of C(R3)(R4)A, A, and a substituted or unsubstituted group selected from the group consisting of (CH_2)n COOR19.

(I)

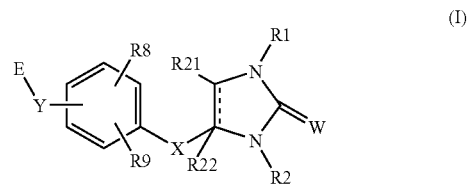

23 Claims, No Drawings

OTHER PUBLICATIONS

Walfredd S. Sarr, et al.: "*Tyrosine Hydrolase Inhibitors. Synthesis and Activity of Substituted Aromatic Amino Acids*": Journal of Medicinal Chemistry, vol. 10, No. 6, (1967), pp. 1008-1014.

Steiman, David M., et al.: "*Synthesis of Side Chain-protected Amino Acid Phenyithiohydantoins and Their Use in Quantitative Solid-phase Edman Degradation*": Chemical Abstracts, vol. 102, No. 17, Apr. 29, 1985, Columbus, OH, U.S.: Abstract No. 145646z.

Kent, Stephen B. H., et al.: "*A Study of the Edman Degradation in the Assessment of the Purity of Synthetic Peptides*": Chemical Abstracts, vol. 99, No. 3, Jul. 18, 1983, Columbus, OH: Abstract No. 22893q.

Robert C. Glen, et al.: "*Computer-aided Design and Synthesis of 5-sbustituted Tryptamines and Their Pharmacology at the 5-HTID Receptor: Discovery of Compounds with Potential Anti-migraine Properties*": Journal of Medicinal Chemistry, vol. 38, No. 18, (1995), pp. 3566-3580.

Donald L. Ross, et al.: "*N-(gamma-L-Glutamyl)aminobenzioic Acids*": Journal of Medicinal Chemistry, vol. 6, (1963), pp. 208-210.

*Silver Halide Color Photographic Material*: Chemical Abstracts, vol. 102, No. 12, Mar. 25, 1985, Columbus, OH, U.S.: Abstract No. 103450a.

Jandu, Karamjit Singh, et al.: "*Discovery of 4-(3-trans-3-dimethylaminocyclobutyl)-1H-indiol-5-ylmethyl)-(4S)-oxazolidin-2-one(4991W93), a 5HT1H///1D Receptor Partial Agonist and a Potent Inhibitor of Electrically Induced Plasma Extravasation*": Chemical Abstracts, vol. 134, 2001, Columbus, OH, US: Abstract No. 246873n.

\* cited by examiner

PEROXISOME PROLIFERATOR ACTIVATED RECEPTOR AGONISTS

This Application claims the benefit of U.S. Provisional Application Ser. No. 60/334,453 filed Nov. 30, 2001, and PCT Application Serial No. PCT/US02/36128, filed Nov. 26, 2002.

Information disclosed and/or claimed in this patent application has been generated pursuant to a joint research agreement among Eli Lilly and Company and Ligand Pharmaceuticals, Inc.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include, for example, PPARα, PPARγ and PPARδ.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists which have been shown to increase the sensitivity of insulin sensitive cells. Increasing insulin sensitivity rather than the amount of insulin in the blood reduces the likelihood of hypoglycemic coma. However, TZDs and ISEs typically have little effect in preventing the cardiovascular part of Syndrome X in that their administration usually does not result in the lowering of triglycerides and LDL-cholesterol while raising HDL-cholesterol. Furthermore, clinically significant side effects are commonly associated with treatment with TZDs. Therefore, a need exists for new pharmaceutical agents which affect treat or prevent cardiovascular disease, particularly that associated with Syndrome X, while preventing or minimizing weight gain, and more preferably while improving insulin sensitivity. The present invention provides novel compounds exhibiting desired pharmacological activity.

SUMMARY OF THE INVENTION

The present invention is directed to compounds represented by the following structural formula:

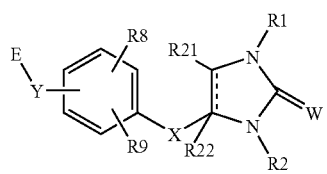

I and pharmaceutically acceptable salts, solvates and hydrates thereof, wherein:

(a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and —$CH_2$—C(O)—R17-R18, wherein R17 is O or NH and R18 is optionally substituted benzyl;

(b) R2 is H or a substituted or unsubstituted group selected from the group consisting of C1-C6 alkyl, C1-C6 alkenyl, aryl-C0-4-alkyl, heteroaryl-C0-4-alkyl, C1-C4 alkyl sulfonamide, C1-C4 alkyl amide, OR10 and C3-C6 cycloalkyl;

(c) W is O or S;

(d) X is an optionally substituted $C_1$-$C_5$ alkylene linker wherein one carbon atom of the linker may optionally be replaced with O, NH, S, and optionally two carbons together may form a double bond;

(e) Y is selected from the group consisting of C, O, S, NH and a single bond; and (f) E is selected from the group consisting of C(R3)(R4)A, A, and a substituted or unsubstituted group selected from the group consisting of $(CH_2)_n$COOR19; and wherein (i) n is 0, 1, 2 or 3;

(ii) A is an functional group selected from the group consisting of carboxyl, $C_1$-$C_3$alkylnitrile, carboxamide, substituted or unsubstituted sulfonamide, substituted or unsubstituted acylsulfonamide substituted or unsubstituted tetrazole, and substituted or unsubstituted isoxazole;

(iii) R3 is selected from the group consisting of H, $C_1$-$C_5$ alkyl, aryl$C_0$-$C_2$alkoxy, and $C_1$-$C_5$ alkoxy, and (iv) R4 is selected from the group consisting of H, halo, and a substituted or unsubstituted group selected from $C_1$-$C_5$ alkyl, $C_1$-$C_5$ alkoxy, $C_3$-$C_6$ cycloalkyl, aryl $C_0$-$C_4$ alkyl, aryl$C_0$-$C_2$alkoxy and phenyl; or R3 and R4 are combined to form a $C_3$-$C_8$ cycloalkyl;

(v) R19 is selected from the group consisting of hydrogen, optionally substituted arylmethyl and optionally substituted C1-C4alkyl;

(g) R8 is selected from the group consisting of hydrogen, $C_1$-$C_4$ alkyl, $C_1$-$C_4$ alkylenyl, and halo;

(h) R9 is selected from the group consisting of hydrogen, $C_1$-$C_4$ alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ alkenyl, and OR10;

(i) R10 is independently selected from the group consisting of hydrogen and $C_1$-$C_4$ alkyl;

(j) R21 is selected from the group consisting of hydrogen, =O, and a substituted or unsubstituted group selected from the group consisting of $C_1$-$C_6$ alkyl, aryl, $C_1$-$C_4$ alkylaryl, and heteroaryl;

(k) R22 is selected from the group consisting of hydrogen, and a substituted or unsubstituted group selected from the group consisting of $C_1$-$C_6$ alkyl, aryl, $C_1$-$C_4$ alkylaryl, and heteroaryl; and (l) ---- represents an optional double bond.

A compound of Formula I'

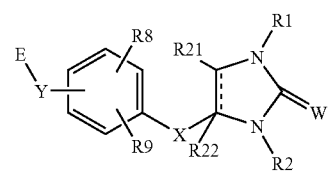

I' and pharmaceutically acceptable salts, solvates and hydrates thereof, wherein:

(a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, C3-C6 cycloalkylaryl-$C_{0-2}$-alkyl, and —$CH_2$—C(O)—R17-R18, wherein R17 is O or NH and R18 is optionally substituted benzyl;

(b) R2 is H or a substituted or unsubstituted group selected from the group consisting of $C_1$-$C_6$ alkyl, $C_1$-$C_6$ alkenyl, aryl-$C_{0-4}$-alkyl, heteroaryl-$C_{0-4}$-alkyl, $C_1$-$C_4$ alkyl sulfonamide, $C_1$-$C_4$ alkyl amide, OR10 and $C_3$-$C_6$ cycloalkyl;

(c) W is O or S;

(d) X is an optionally substituted $C_1$-$C_5$ alkylene linker wherein one carbon atom of the linker may be replaced with O, NH or S;

(e) Y is C, O, S, NH or a single bond; and (f) E is selected from the group consisting of C(R3)(R4)A, A, substituted or unsubstituted selected from the group consisting of $(CH_2)_n$ COOR19; and wherein (i) n is 0, 1, 2 or 3, (ii) A is an functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;

(iii) R3 is H, saturated or unsaturated $C_1$-$C_5$ alkyl, aryl$C_0$-$C_2$alkoxy, $C_1$-$C_5$ alkoxy, and (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl, aryl$C_0$-$C_2$alkoxy and phenyl, or R3 and R4 are combined to form a $C_3$-$C_8$ cycloalkyl;

(v) R19 is selected from the group consisting of hydrogen, optionally substituted arylmethyl and optionally substituted C1-C4 alkyl;

(g) R8 is selected from the group consisting of hydrogen, $C_1$-$C_4$ alkyl, $C_1$-$C_4$ alkylenyl, and halo;

(h) R9 is selected from the group consisting of hydrogen, $C_1$-$C_4$ alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ alkenyl, and OR10;

(i) R10 is independently selected from the group consisting of hydrogen and $C_1$-$C_4$ alkyl;

(j) R21 is selected from the group consisting of hydrogen, =O, and a substituted or unsubstituted group selected from the group consisting of $C_1$-$C_6$ alkyl, aryl, $C_1$-$C_4$ alkylaryl, and heteroaryl;

(k) R22 is selected from the group consisting of hydrogen, and a substituted or unsubstituted group selected from the group consisting of $C_1$-$C_6$ alkyl, aryl, $C_1$-$C_4$ alkylaryl, and heteroaryl; and (l) ---- represents an optional double bond.

An additional embodiment is a compound and pharmaceutically acceptable salts, solvates and hydrates of Structural Formula II:

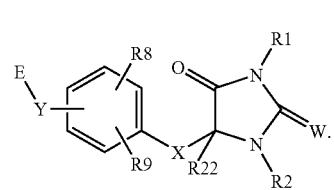

An additional embodiment is a compound and pharmaceutically acceptable salts, solvates and hydrates of Structural Formula III:

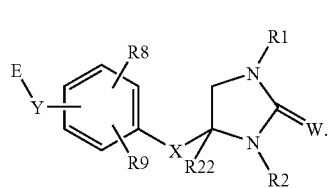

Another embodiment of this invention is a compound of Formula IV represented by the following structure:

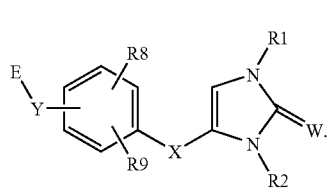

and salts, solvates and hydrates thereof.

One preferred embodiment of this invention is a compound selected from the group consisting of 2-Methyl-3-(4-{2-[3-methyl-2-oxo-1-(4-trifluoromethyl-benzyl)-imidazolidin-4-yl]-ethoxy}-phenyl)-2-phenoxy-propionic acid and 2-methyl-3-(4-{3-[3-methyl-2-oxo-1-(4-trifluoromethyl-benzyl)-imidazolidin-4-yl]-propyl}-phenyl)-2-phenoxy-propionic acid.

In another feature of this invention, a compound claimed herein is radiolabeled.

In one embodiment, the present invention also relates to pharmaceutical compositions which comprising at least one compound of the present invention, or a pharmaceutically acceptable salt, solvate, hydrate or prodrug thereof, and a pharmaceutically acceptable carrier.

In another embodiment, the present invention relates to a method of modulating one or more PPAR receptor(s) by contacting the receptor with at least one compound represented by Structural Formula I, and pharmaceutically acceptable salts, solvates and hydrates thereof.

In another embodiment, the present invention relates to a method of selectively modulating a PPAR receptor by contacting the receptor with at least one compound represented by Structural Formula I, and pharmaceutically acceptable salts, solvates and hydrates thereof. Another embodiment of this invention is preferentially modulating one PPAR receptor and additionally modulating a second, different, PPAR receptor to provide desired dual agonism.

In a further embodiment, the present invention relates to a method of making a compound represented by Structural Formula I.

The compounds of the present invention and pharmaceutically acceptable salts, solvates and hydrates thereof are believed to be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. In addition, the compounds exhibit fewer side effects than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, alkyl groups include straight chained or branched hydrocarbons, which are completely saturated. Said branched hydrocarbon may be primary, secondary, tertiary, or quaternary, as appropriate.

As used herein, alkylene linker is a $C_1$-$C_5$ straight or branched chain hydrocarbon group. However, the term "alkylene linker wherein one carbon of the linker may optionally be replaced with O, NH, S, and optionally two carbons together may form a double bond" refers to an alkylene linking having an O, NH or S in the link. Alkylene linkers having two carbons together forming a double bond means for example, —CH═CHCH$_2$—, —CH$_2$CHCH—, —CH$_2$CH$_2$CHCH—, and the like. For example, but not limited to, —CH$_2$CH$_2$O—, —CH$_2$CH$_2$NH—, CH$_2$CH$_2$S—, —CH$_2$OCH$_2$—, —OCH$_2$CH$_2$—, and the like.

Cycloalkyl groups, as used herein, include cyclic hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl).

Heterocyclic group, as used herein, is a ring system having at least one heteroatom such as nitrogen, sulfur or oxygen. Heterocyclic groups include benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl and thienyl.

Heteroaryl, as used herein is an aromatic ring system, fused polycyclic aromatic ring systems and aromatic ring systems fused to non-aromatic ring systems wherein at least one carbon atom is replaced with a heteroatom such as nitrogen, sulfur or oxygen. It may be preferred that heteroaryl contains from 1-3 heteroatoms. It may be preferred that heteroaryl contains 1-2 nitrogen atoms. One heteroaryl group that may be desired is

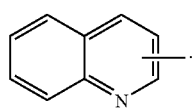

Another heteroaryl group that may be desired is:

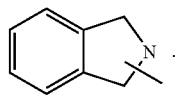

The term "arylalky", "arylmethyl", "arylC$_0$-C$_2$alkoxy" and "aryloxy" each represent a substituent in which the aryl group is linked to the parent molecule via the alkyl, methyl, and oxy, respectively. Additionally, when the phrase "arylC$_0$-C$_2$alkoxy" is C$_0$ alkoxy, this means that the aryl is linked to the parent molecule via an oxy group.

Examples of R1, R5, E, R19 and R9 suitable substituents when said R1, E, R5, R19 or R9 are at least one or more independently selected from the group consisting of $C_1$-$C_8$alkyl, $C_1$-$C_4$ alkyl, aryl, arylmethyl, $(CH_2)_n$COOR19, $C_1$-$C_6$alkenyl, thio-$C_1$-$C_4$alkyl, thioaryl, $C_1$-$C_4$alkoxyaryl, $C_1$-$C_4$alkoxy $C_1$-$C_4$alkyl, aminoaryl, amino$C_1$-$C_4$alkyl, aryl-Co$_{0-4}$alkyl, heteroarylC$_{0-4}$alkyl, heterocyclic, —CH$_2$—C(O)—R17-R18, $(C_3$-$C_6)$cycloalkylaryl-C$_{0-2}$-alkyl and cycloalkyl, then suitable substituted groups include, for example, $C_1$-$C_5$ alkyl, $C_1$-$C_5$ alkoxy, $C_0$-$C_5$ haloalkyl, $C_1$-$C_5$ trihaloalkyl, $C_1$-$C_5$ trihaloalkoxy, $C_1$-$C_5$ haloalkoxy, nitro, cyano, CHO, ═O, hydroxyl, C1-C4 alkanoic acid, phenyl, aryloxy, SO$_2$R7, SR7, benzyloxy, alkylcarboxamido or COOH. R7 is an alkyl or a haloalkyl. When R1, R5, E, R19 or R9 is substituted, it is preferred that there are from 1-3 substitutions on said R1, R5, E, R19 or R9 group. An especially preferred trihaloalkyl group is trifluoro C1-C5 alkyl.

Examples of suitable substituents for an "optionally substituted C$_2$-C$_5$ alkylene linker," include one or more independently selected from the group consisting of $C_1$-$C_6$alkyl, oxo, substituted or unsubstituted arylC$_0$-C$_3$alkyl, $C_1$-C$_3$alkoxy, hydroxy, $C_3$-$C_6$cycloalkyl and halo. When the alkylene linker is substituted, it is preferred that there are from one to three independent substitutions.

Examples of suitable substituents for a substituted $C_1$-$C_3$ alkylene, include one or more independently selected from $C_1$-$C_6$alkyl, oxo, aryl C$_0$-C$_3$alkyl, $C_1$-$C_3$alkoxy, hydroxy, and halo. When the alkylene is substituted it is preferred that there are from 1-3 independent substitutions.

Suitable substituents for substituted R2 groups wherein R2 is $C_1$-$C_6$alkyl, $C_1$-$C_6$alkenyl, arylC$_0$-C$_4$alkyl, arylC$_0$-C$_4$alkyl, $C_1$-$C_4$ alkyl sulfonamide, $C_1$-$C_4$ alkyl amide, OR10, or $C_3$-$C_6$cycloalkyl, include for example, one or more independently selected from the group consisting of OH, alkoxy, haloalkyl, amino, COOH, heteroaryl-O—, heteroaryl-C(O)—, alkyl-O—, alkyl-C(O)—, C3-C6 cycloalkyl, aryl-O—, aryl-C(O)—, heteroaryl, aryl, heterocycloalkyl, heterocycloalkyl-O—, and heterocycloalkyl-C(O)—. When R2 is substituted it is preferred that there are from 1-3 independent substitutions on the R2 group.

Examples of suitable substituents for A groups, wherein the A is a sulfonamide, include one or more independently selected from C1-C4 alkyl, C1-C4 haloalkyl, substituted or unsubstituted heteroaryl, or substituted or unsubstituted aryl. When the A group is substituted, it is preferred that there are from 1-3 independent substitutions on the A group.

Examples of suitable substituents for A groups, wherein A is acylsulfonamide and tetrazole include, for example, one or more independently selected from C1-C4 alkyl, C1-C4 haloalkyl, substituted or unsubstituted heteroaryl, or substituted or unsubstituted aryl.

Suitable substituents for R4 wherein R4 is $C_1$-$C_5$ alkyl, $C_1$-$C_5$alkoxy, $C_1$-$C_6$cycloalkyl, arylC$_0$-C$_4$alkyl, arylC$_0$-

$C_2$alkoxy or phenyl, include, for example halo, phenyl, $C_1$-$C_4$ alkoxy, hydroxy, and aryl$C_0$-$C_2$alkoxy. When R4 is substituted, it is preferred that there are from 1-4 independently selected substitutions on the R4 group.

Preferably, for the compounds of the present invention, represented by Structural Formula I, and with their respective pharmaceutical compositions, W is an oxygen.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may also exist in the form of solvates, for example hydrates, and the present invention includes each solvate and mixtures thereof.

"Pharmaceutically-acceptable salt" refers to salts of the compounds of the Structural Formula I which are substantially non-toxic to mammals. Typical pharmaceutically acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium and magnesium; and ammonium or substituted ammonium salts. Examples of substituted ammonium salts include, for instance, those with lower alkylamines such as trimethylamine, triethylamine; hydroxyalkylamines such as 2-hydroxyethylamine, bis-(2-hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydroabietylamine, glucamine, N-methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

These salts may be prepared by methods known to those skilled in the art.

Certain compounds of Structural Formula I and their salts may also exist in the form of solvates, for example hydrates, and the present invention includes each solvate and mixtures thereof.

In addition, it is generally not desirable to formulate pharmaceuticals containing substantial amounts of organic solvent (e.g., ethyl acetate) due to potential solvent toxicity to the recipient thereof and changes in potency of the pharmaceutical as a function of the solvent. In addition, from a manufacturing perspective, it is also generally less desirable to prepare non-crystalline materials whenever said preparation involves a collection of the final product via filtration. Such filtrations are often more difficult to perform when the material collected is non-crystalline. Moreover, it is also generally less desirable, from a manufacturing perspective, to formulate pharmaceuticals containing substantial amounts of water (hydrates) because the level of hydration will typically be some function of the relative humidity at which the pharmaceutical is produced and stored. In other words, potency variability is typically more problematic with a hydrate relative to its anhydrous form. The present invention provides a desired crystalline form.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of Formula I in a medium such as methanol with an acid or base esterification catalyst (e.g., NaOH, $H_2SO_4$). Ethyl ester prodrugs are prepared in similar fashion using ethanol in place of methanol.

Morpholinylethyl ester prodrugs may be prepared by reaction of the sodium salt of a compound of Structural Formula I (in a medium such as dimethylformamide) 4-(2-chloroethyl)morphine hydrochloride (available from Aldrich Chemical Co., Milwaukee, Wis. USA, Item No. C4,220-3).

The term, "active ingredient" means the compounds generically described by Structural Formula I as well as the salts, solvates, and prodrugs of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well-known and readily available ingredients.

"Preventing" refers to reducing the likelihood that the recipient will incur or develop any of the pathological conditions described herein.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, hydrate or prodrug thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the PPAR mediated condition. Such an amount is intended to include an amount which is sufficient to modulate a PPAR receptor or to prevent or mediate a disease or condition. Conditions prevented or treated by PPAR receptors include, but are not limited to, diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention can be useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are considered risk factors for the development of heart disease, stroke, and circulatory system disorders and diseases.

The compounds and compositions of the present invention can also be useful for treating and/or preventing obesity.

Further, these compounds and compositions can be useful for the treatment and/or prophylaxis of non-insulin dependent diabetes mellitus (NIDDM) with reduced or no body weight gains by the patients. Furthermore, the compounds and compositions of the present invention can be useful to treat or prevent acute or transient disorders in insulin sensitivity, such as sometimes occur following surgery, trauma, myocardial infarction, and the like. The physician of ordinary skill can identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbAlc, of a patient by about 0.7% or more.

Advantageously, compositions containing the compound of Structural Formula I and/or the salts thereof may be provided in dosage unit form. Preferably each dosage unit contain from about 1 to about 500 mg of active ingredient. Although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compounds of the present invention can be useful for treating PPAR mediated conditions and for use as research tools. Certain compounds and conditions within the scope of this invention are preferred. The following conditions, invention embodiments, and compound characteristics listed in tabular form may be independently combined to produce a variety of preferred compounds and treatment conditions. The following list of embodiments of this invention is not intended to limit the scope of this invention in any way.

Some preferred characteristics of compounds of Formula I are:
  (a) R3 is methyl;
  (b) R3 is aryl$C_0$-$C_2$alkoxy;
  (c) R4 is aryl$C_0$-$C_2$alkoxy;

(d) R4 is arylalkyl;
(e) R3 and R4 are each $C_1$-$C_6$ alkyl;
(f) A is carboxyl;
(g) W is O;
(h) W is S;
(i) X is —$CH_2CH_2CH_2$—;
(j) X is —$CH_2CH_2O$—;
(k) R9 is methyl;
(l) R9 is benzyl;
(m) R9 is heteroarylalkyl;
(n) R8 is hydrogen;
(O) R10 is methyl
(p) Y is $CH_2$;
(q) Y is O;
(r) R21 is =O;
(s) R21 is H;
(t) R22 is H;
(u) R1 is arylalkyl;
(v) R1 is substituted arylalkyl;
(w) R2 is methyl;
(x) R2 is H;
(y) E is C(R3) (R4)A;
(z) A is tetrazole;
(aa) A is acylsulfonamide;
(bb) R21 is arylalkyl;
(cc) R1 arylalkyl is substituted by $CF_3$;
(dd) Aryl is a phenyl group;
(ee) Heteroaryl group contains a N;
(ff) "----" represents a double bond, as shown by Formula I herein;
(gg) A compound of Formula I that selectively modulates an alpha receptor;
(hh) A compound of Formula I that is a PPAR coagaonist that modulates an alpha receptor and a gamma receptor; and
(ii) A compound of Formula I for use in the treatment of cardiovascular disease.
(jj) A compound of Formula I for use in the treatment of Type II diabetes and/or Syndrome X.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier, to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container.

When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

In yet another embodiment of the compounds of the present invention, the compound is radiolabelled, such as with carbon-14, or tritiated. Said radiolabelled or tritiated compounds are useful as reference standards for in vitro assays to identify new PPARα and or PPARδ agonists.

Synthesis

Compounds of the present invention have been formed as specifically described in the examples. Further, many compounds were prepared as more generally as shown in the following schematic. Alternative synthesis methods may also be effective and known to the skilled artisan.

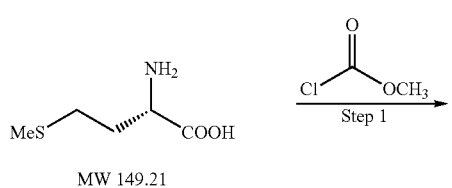

MW 149.21

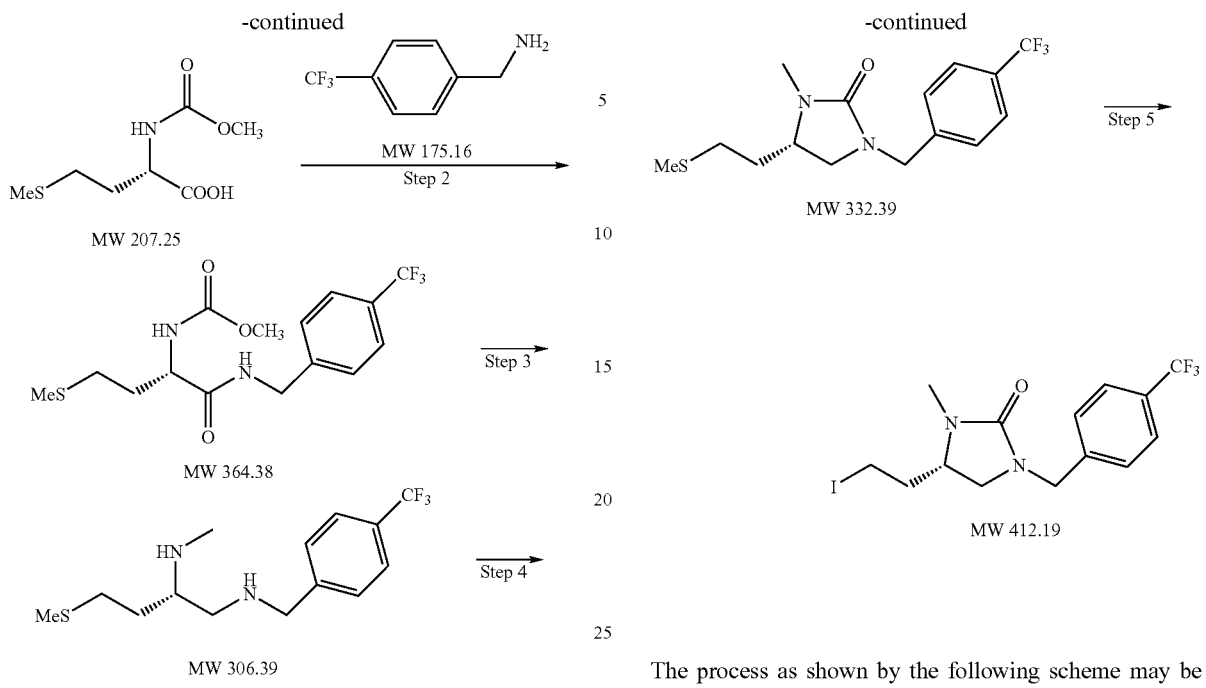
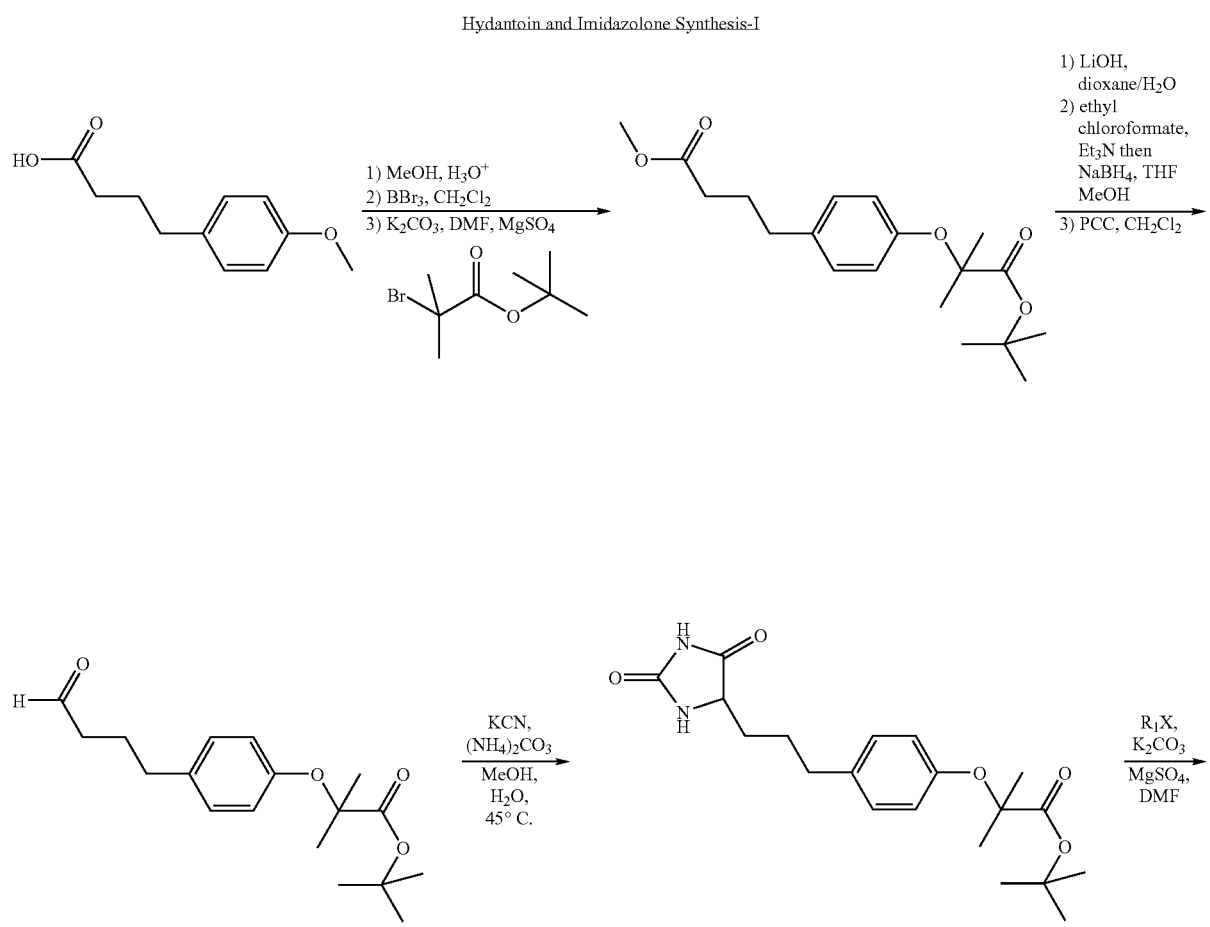
The process as shown by the following scheme may be used to make certain compounds of this invention:

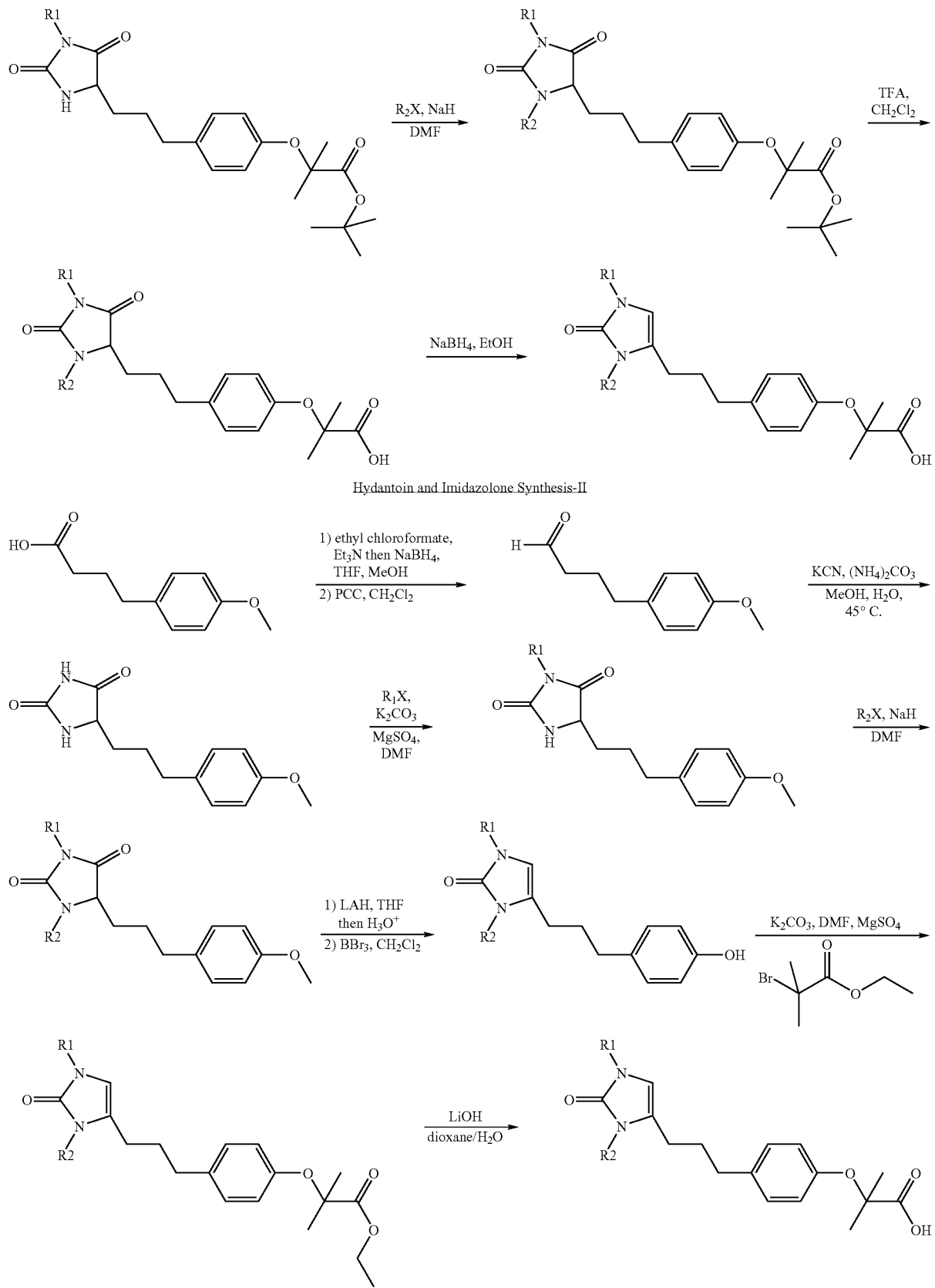
Hydantoin and Imidazolone Synthesis-II

-continued
Hydantoin and Imidazolone Synthesis-III
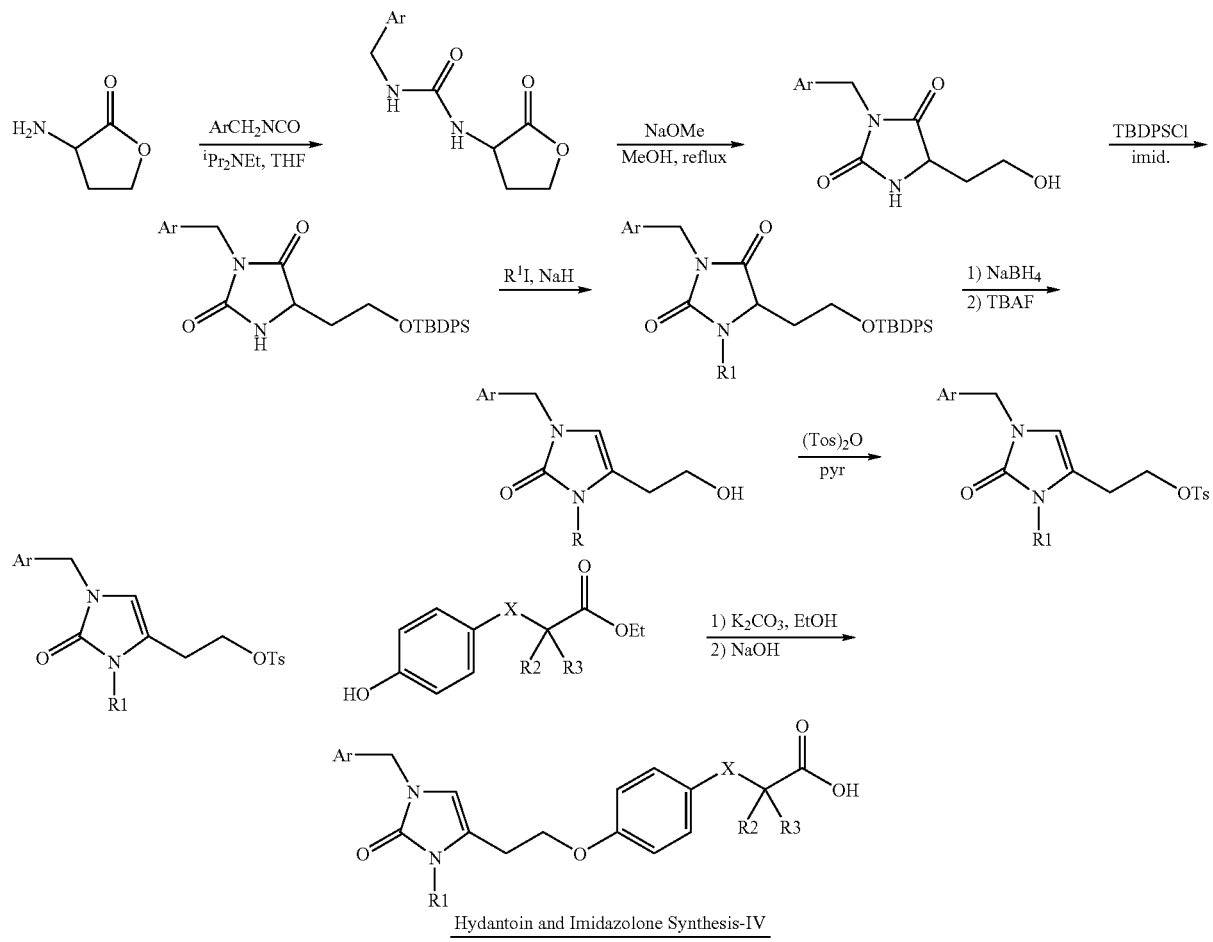
Hydantoin and Imidazolone Synthesis-IV
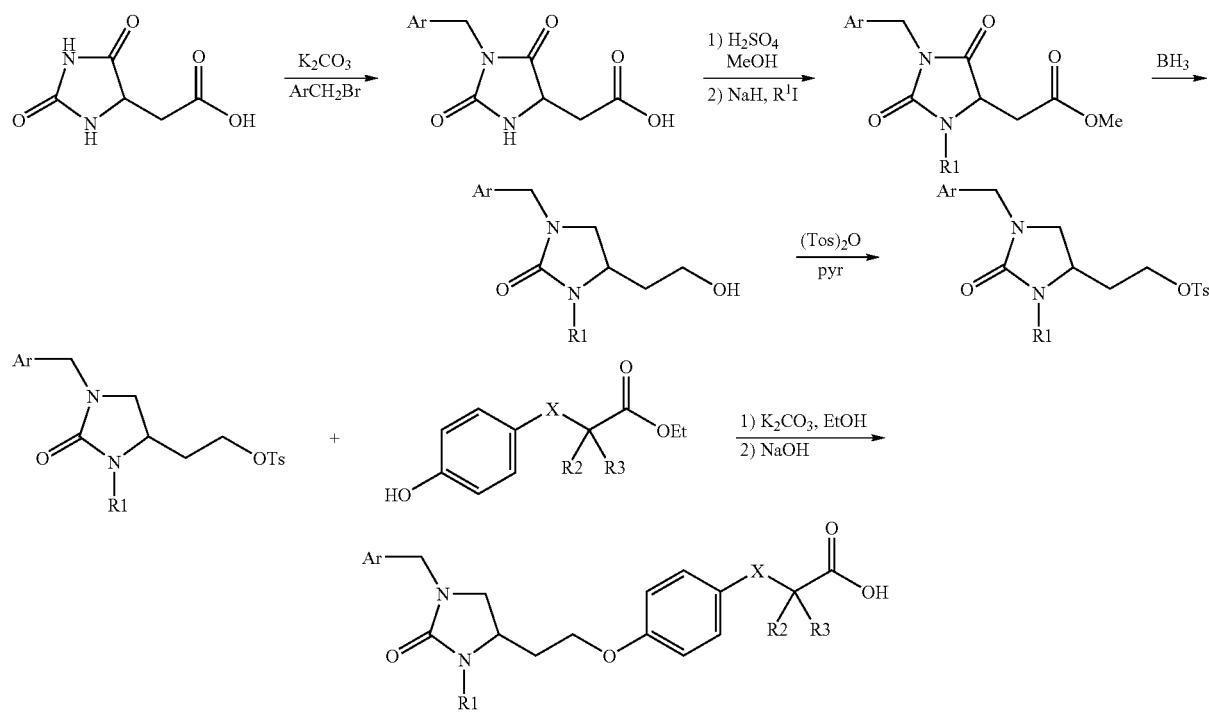

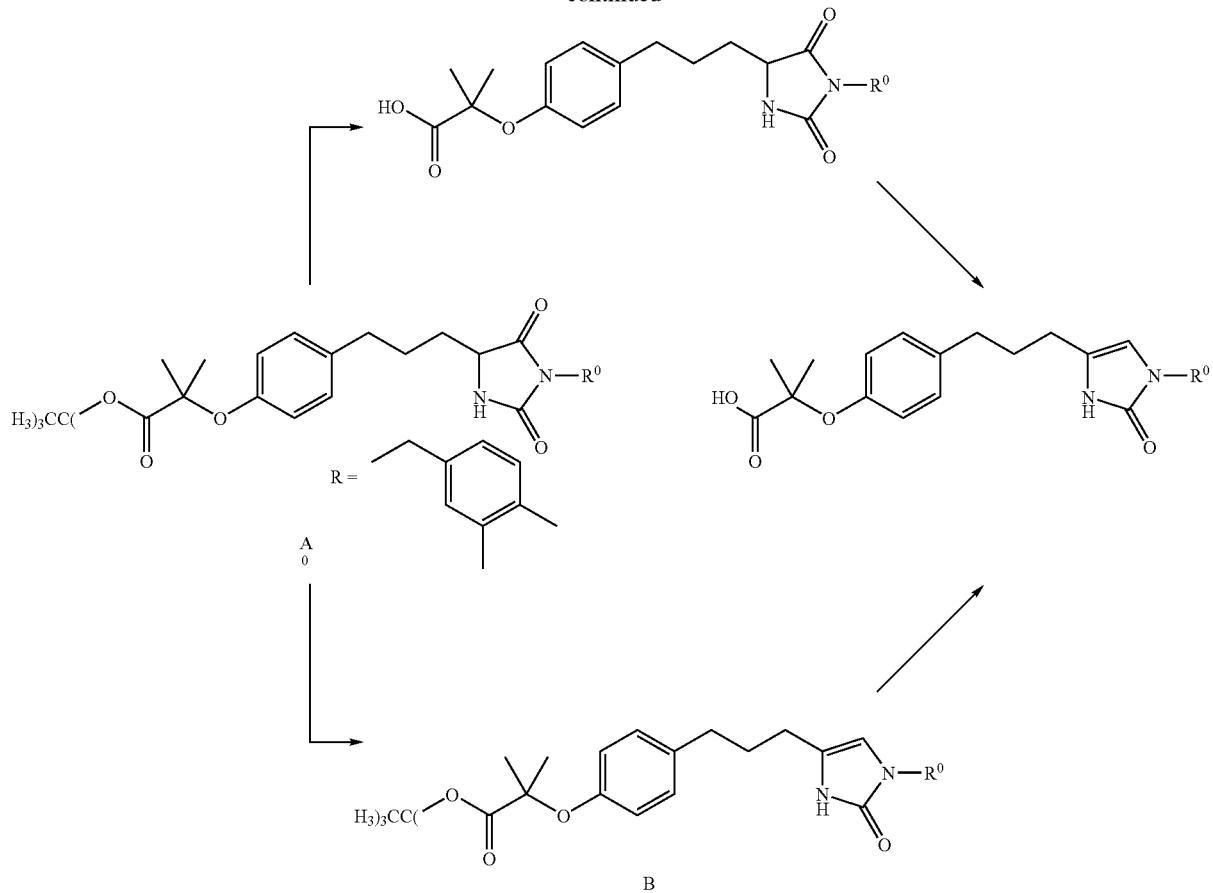

The reaction of intermediate A with an excess of trifluoroacetic acid at ambient temperature in methylene chloride overnight produces the fibrate acid (see Scheme immediately above). The fibrate acid was washed until only traces of trifluoroacetic acid were present in the crude product, and then the fibrate acid is used to prepare compounds claimed here.

Scheme 1

General Example A: 2-Ethoxy-2-methyl-3-(4-{2-[3-[methyl-2-

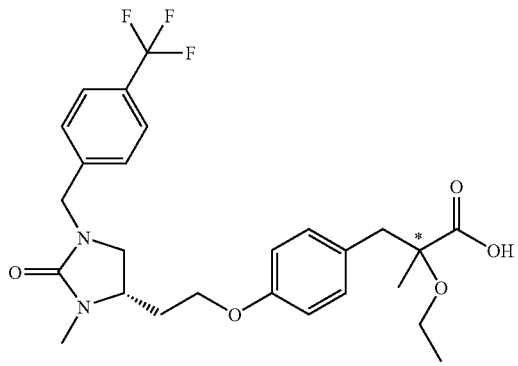

oxo-1-(4-trifluoromethyl-benzyl)-imidazolidin-4-yl]-ethoxy}-phenyl)propionic ethyl ester To the solution of the α-hydroxy ester (0.04 g, (0.08 mmol) in DMF, is added silver oxide (0.28 g, 1.2 mmol) and ethyl iodide (0.07 mL, 1.0 mmol). The mixture is stirred at room temperature for 16 h, and then stirred at 50° C. for another 16 h. Filtered, the filtrate is washed with water and extracted with EtOAc. The organic layer is evaporated, dried (MgSO$_4$), concentrated and chromatographed (silica gel; hexane/EtOAc, 1:1 to 0:1). An oil is isolated as the ethyl ester (25 mg, 59%). MS (ESI) m/z 537 (M+H)$^+$. The ester is then hydrolyzed with 5.0N NaOH in methanol at 60° C. for 4 h. Acidified with conc.HCl, extracted with EtOAc, the organic layer is dried (MgSO$_4$) and concentrated to afford the title acid. MS (ESI) m/z 509 (M+H)$^+$. Other members of this family could be prepared using the same method and the appropriate alkyl iodide.

Scheme 2

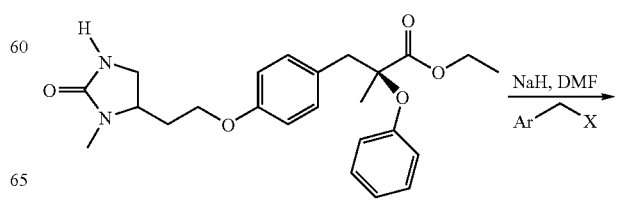

-continued

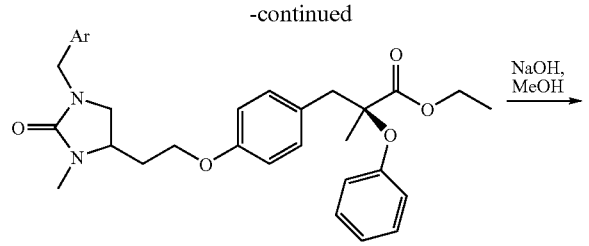

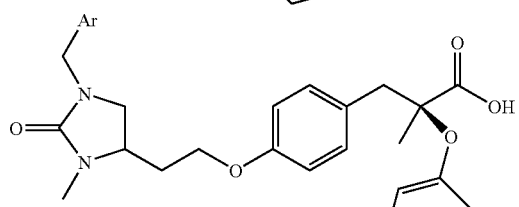

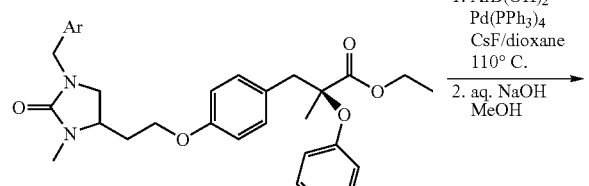

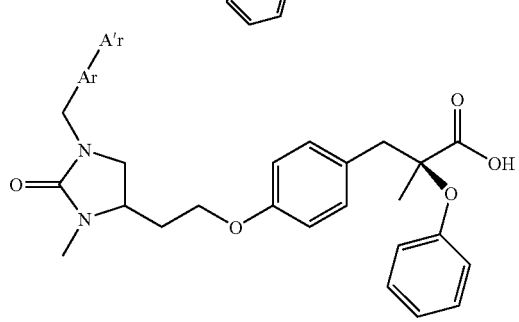

A'r = substituted phenyl, 3-pyridynl, 2-substituted-thiephenyl.

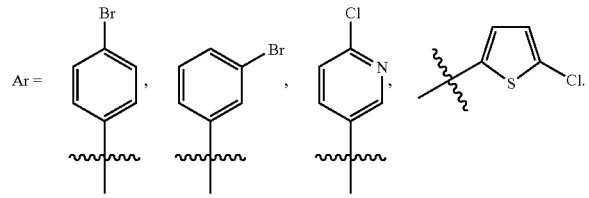

General example B:

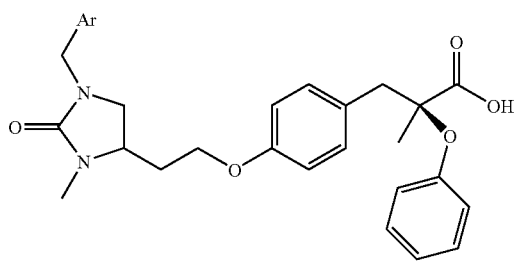

To a mixture of 54 mg (0.13 mmol) of 2-Methyl-3-{4-[2-(3-methyl-2-oxo-imidazolidin-4-yl)-ethoxy]-phenyl}-2-phenoxy-propionic acid ethyl ester in 2 mL of dry DMF at 0° C. under an atmosphere of nitrogen, 10 mg of NaH (0.253 mmol) is added. The resulting solution is allowed to stand at r.t. for 20 min. Then 0.26 mmol of the appropriate aryl halide is added and resulting mixture is allowed to stand at r.t. for 3 h. The reaction mixture is diluted with ethyl acetate and 1N HCl. The organic layer is then washed with 1N HCl (2×10 mL), brine (2×10 mL), dried over $Na_2SO_4$, filtered and concentrated under vacuum. The resulting esters were purified by flash chromatography, and could be used as starting materials in subsequent coupling reactions, or hydrolized to final compounds: To hydrolize, the ester is dissolved in 2 mL of MeOH and 0.3 mL of 5N NaOH, and the mixture is heated to 50° C. for 2 h. The organic solvent is then removed under vacuum and the residue is dissolved in $CH_2Cl_2$ and 1N HCl. Aqueous layer is washed with $CH_2Cl_2$ (2×10 mL). Combined organic layer is dried over $Na_2SO_4$, filtered and concentrated under vacuum. The crude material is purified by MS/LC or flash chromatography to give the final products.

General example C: Suzuki couplings

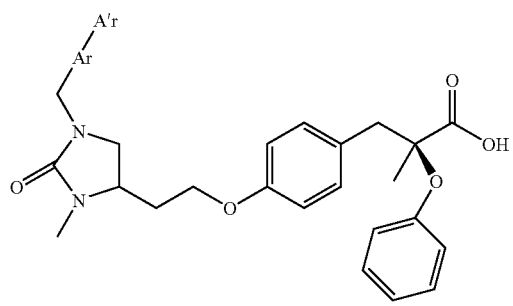

To the aryl bromide (or chloride) (0.07 mmol) in 1,4 dioxane (2 mL) in a $N_2$ purged sealed tube, is added aryl boronic acid (0.12 mmol), Cesium fluoride (0.18 mmol) and tetrakis (triphenylphosphine) Pd (0) (0.007 mmol). The reaction mixture is stirred at 110° C. for 2 h. Cooled, diluted with EtOAc and quenched with water. The organic layer is dried ($MgSO_4$), filtered and concentrated. The residue is then hydrolyzed with 5.0 N NaOH in methanol at 60° C. for 2 h. Acidified, extracted with EtOAc, the crude acid is chromatographed (silica gel; EtOAc/MeOH, 10:0 to 10:1).

General Example D

Buchwald Couplings

General Procedure:

The phenyl bromide (0.04 g, 0.067 mmol), phenol (12 mg, 0.13 mmol), $Cs_2CO_3$ (33 mg, 0.1 mmol), $(CuOTf)_2 \cdot PhH$ (2 mg), ethyl acetate (0.0033 mmol, 5.0 mol %) and toluene were added to a sealed tube which is purged with nitrogen. The mixture is heated to 100° C. until the phenyl bromide is consumed as determined by LC-MS. Cooled, diluted with ethyl acetate and washed with $H_2O$. The organic layer is dried ($MgSO_4$), concentrated to afford the crude product. The crude ester is then hydrolyzed with 5.0N NaOH in MeOH at 60° C. for 2 h. Acidified, extracted with ethyl acetate, the organic layer is dried ($MgSO_4$), concentrated and chromatographed (silica gel; EtOAc/MeOH, 10:0 to 10:1) to afford the pure acid.

Scheme 4

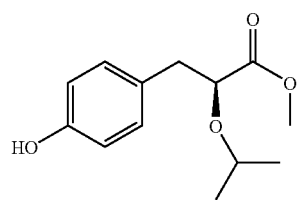

+

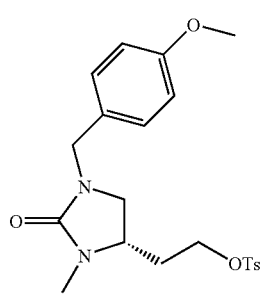

Cs₂CO₃, DMF
60° C., 86%
→

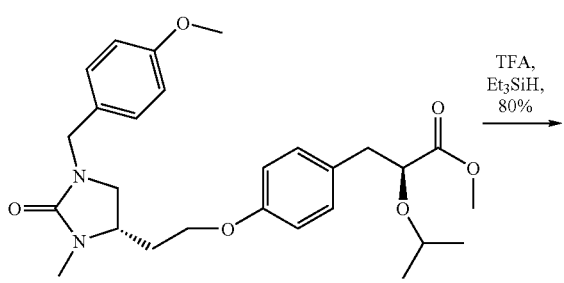

TFA, Et₃SiH, 80%
→

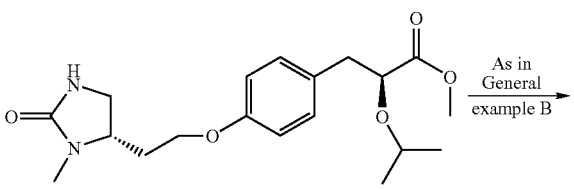

As in General example B
→

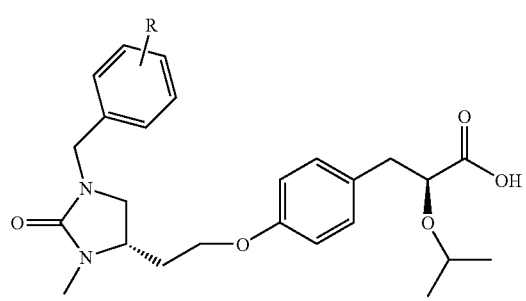

2-Isopropoxy-3-(4-{2-[1-(4-methoxy-benzyl)-3-methyl-2-oxo-imidazolidin-4-yl]-ethoxy}-phenyl)-propionic acid methyl ester

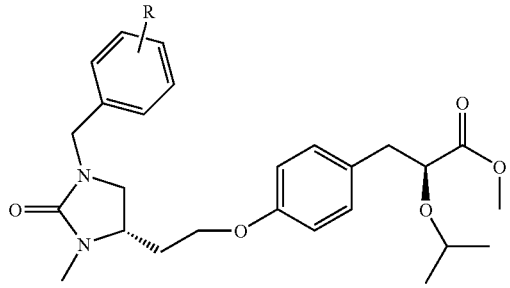

3-(4-Hydroxy-phenyl)-2-isopropoxy-propionic acid methyl ester (1.7 g, 7.3 mmol), Toluene-4-sulfonic acid 2-[1-(4-methoxy-benzyl)-3-methyl-2-oxo-imidazolidin-4-yl]-ethyl ester (3.4 g, 8.0 mmol), and Cs₂CO₃ (3.6 g, 11 mmol) were combined in 10 mL of DMF and heated at 55° C. for 18 h. After cooling, the mixture is diluted with 100 mL of water and extracted with 3×20 mL of ethyl acetate. The organics were dried, concentrated, and the residue is purified by flash chromatography using 7/3 ethyl actate/hexanes to give 3.0 g (86%) of the title compound as an oil. NMR

General Example E

3-{4-[2-(1-Substitutedbenzyl-3-methyl-2-oxo-imidazolidin-4-yl)-ethoxy]-phenyl}-2-isopropoxy-propionic acid methyl ester

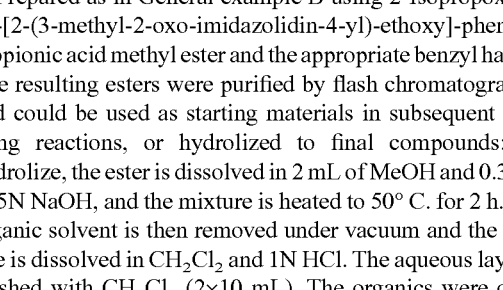

Prepared as in General example B using 2-Isopropoxy-3-{4-[2-(3-methyl-2-oxo-imidazolidin-4-yl)-ethoxy]-phenyl}-propionic acid methyl ester and the appropriate benzyl halide. The resulting esters were purified by flash chromatography, and could be used as starting materials in subsequent coupling reactions, or hydrolized to final compounds: To hydrolize, the ester is dissolved in 2 mL of MeOH and 0.3 mL of 5N NaOH, and the mixture is heated to 50° C. for 2 h. The organic solvent is then removed under vacuum and the residue is dissolved in CH₂Cl₂ and 1N HCl. The aqueous layer is washed with CH₂Cl₂ (2×10 mL). The organics were combined, dried over Na₂SO₄, filtered and concentrated under vacuum. The crude material is purified by MS/LC or flash chromatography to give the final products.

General Example F

3-{4-[2-(1-Substituted-biphenyl-4-ylmethyl-3-methyl-2-oxo-imidazolidin-4-yl)-ethoxy]-phenyl}-2-isopropoxy-propionic acid

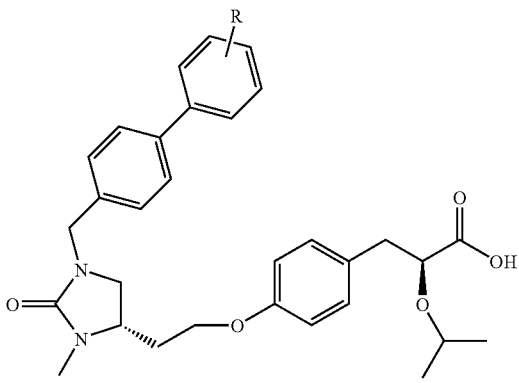

Prepared as in General example C by coupling 3-(4-{2-[1-(4-bromo-benzyl)-3-methyl-2-oxo-imidazolidin-4-yl]-ethoxy}-phenyl)-2-isopropoxy-propionic acid methyl ester and the appropriate boronic acid, followed by hydrolysis to the carboxylic acid.

The Examples provided herein are illustrative of the invention claimed herein and are not intended to limit the scope of the claimed invention in any way.

EXEMPLIFICATION

Instrumental Analysis

Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses were performed by Eli Lilly and Company Microanalytical Laboratory. High-resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Preparations

Preparation 1

Preparation of toluene-4-sulfonic acid 2-[1-(4-methoxy-benzyl)-3-methyl-2-oxo-imidazolidin-4-yl]-ethyl ester

Step A (2,5-Dioxo-imidazolidin-4-yl)-acetic acid methyl ester

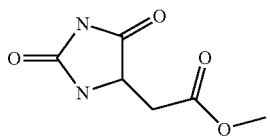

5-Hydantoin acetic acid (20.57 g, 0.130 mol) in MeOH (210 mL) was treated with conc. H$_2$SO$_4$ (7 mL) and heated to reflux under N$_2$ for 2.5 h. The resultant clear solution was cooled and the solvent removed in vacuo to give an oil which was diluted with water (65 mL) and extracted 4 times with EtOAc. The organic layer was dried (MgSO$_4$) and the solvent removed in vacuo to afford 19.81 g (88%) of (2,5-dioxo-imidazolidin-4-yl)-acetic acid methyl ester. MS (ES$^+$) Calc'd for C$_6$H$_9$N$_2$O$_4$ (M+1) 173. Found m/z 173 (100%). $^1$H NMR.

Step B

[1-(4-Methoxy-benzyl)-2,5-dioxo-imidazolidin-4-yl]-acetic acid methyl ester

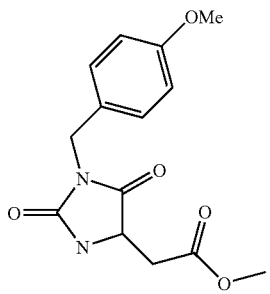

A solution of (2,5-dioxo-imidazolidin-4-yl)-acetic acid methyl ester (26.6 g, 0.155 mol) in DMF (500 mL) was treated with 4-methoxybenzyl chloride (26.6 g, 0.170 mol), MgSO$_4$ (18.6 g, 0.154 mol) and then 325 mesh K$_2$CO$_3$ (42.71 g, 0.309 mol) at 0° C. The resultant mixture was warmed to room temperature under N$_2$ and then heated at 45° C. for 4 h. The reaction mixture was filtered, and then aqueous 1N HCl (200 mL) was added to the filtrate. The filtrate was extracted with EtOAc and the organic layer dried (MgSO$_4$). The solvent was removed in vacuo to give 11.43 g crude product which was purified by flash chromatography using a gradient of 3:1 to 1:1 hexanes:acetone to give 9.81 g (22%) [1-(4-methoxy-benzyl)-2,5-dioxo-imidazolidin-4-yl]-acetic acid methyl ester. MS (ES$^+$) Calc'd for C$_{14}$H$_{17}$N$_2$O$_5$ (M+1) 293. Found m/z 293 (100%). $^1$H NMR.

Step C

[1-(4-methoxy-benzyl)-3-methyl-2,5-dioxo-imidazolidin-4-yl]-acetic acid methyl ester

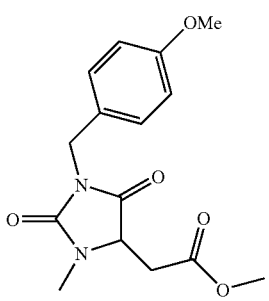

A 0° C. solution of compound [1-(4-methoxy-benzyl)-2,5-dioxo-imidazolidin-4-yl]-acetic acid methyl ester (9.84 g, 33.7 mmol) in DMF (30 mL) was treated with sodium hydride (60% dispersion, 1.37 g, 34.3 mmol) and warmed to room temperature and stirred under $N_2$ for 20 minutes. The resultant mixture was cooled to 0° C. and then treated with methyl iodide (6.16 g, 43.4 mmol) and then warmed to room temperature and stirred for 16 h. The reaction was quenched with aqueous 1 N HCl (60 mL) and then worked up extractively with EtOAc and water. The organic layer was dried ($MgSO_4$) and the solvent removed in vacuo to give crude product that was purified by flash chromatography using 3:1 hexanes:actetone to afford 7.46 g (85%) [1-(4-methoxy-benzyl)-3-methyl-2,5-dioxo-imidazolidin-4-yl]-acetic acid methyl ester. MS ($ES^+$) Calc'd for $C_{15}H_{19}N_2O_5$ (M+1) 307. Found m/z 307 (100%). $^1$H NMR.

Step D 4-(2-Hydroxy-ethyl)-1-(4-methoxy-benzyl)-3-methyl-imidazolidin-2-one

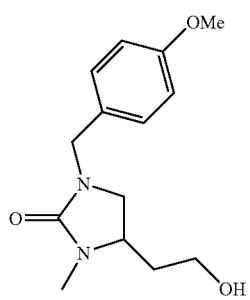

A solution of [1-(4-methoxy-benzyl)-3-methyl-2,5-dioxo-imidazolidin-4-yl]-acetic acid methyl ester (7.45 g, 24.3 mmol) in methanol (100 mL) was treated with aqueous 5 N NaOH (49 mL) and heated to reflux 1 h. The reaction mixture was cooled, the solvent removed in vacuo. The resultant residue was acidified with aqueous 1 N HCl (300 mL) and extracted with EtOAc and water. The organic layer was dried ($MgSO_4$) and the solvent removed in vacuo to afford 7.73 g (100%) acid that was utilized without purification. A solution of crude acid (7.73 g, assume 24.3 mmol) in THF (100 mL) was treated dropwise with 1 M solution of borane-THF complex in THF (146 mL, 0.145 mol) and then stirred at room temperature under $N_2$ for 16 h. The reaction was quenched with methanol (100 mL) and stirred at room temperature for 1 h. The solvent was removed in vacuo to give crude product that was purified by flash chromatography using 2:1 hexanes:acetone to afford 4.76 g (74%) 4-(2-hydroxy-ethyl)-1-(4-methoxy-benzyl)-3-methyl-imidazolidin-2-one. MS ($ES^+$) Calc'd for $C_{14}H_{21}N_2O_3$ (M+1) 265. Found m/z 265 (100%). $^1$H NMR.

Step E

Toluene-4-sulfonic acid 2-[1-(4-methoxy-benzyl)-3-methyl-2-oxo-imidazolidin-4-yl]-ethyl ester

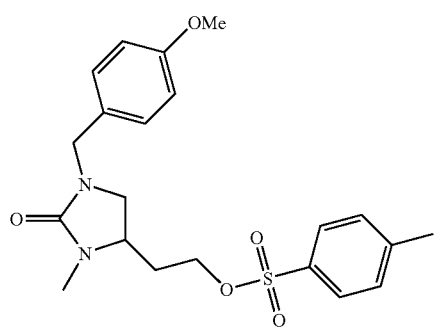

A solution of 4-(2-hydroxy-ethyl)-1-(4-methoxy-benzyl)-3-methyl-imidazolidin-2-one (4.75 g, 18.0 mmol), pyridine (4.98 g, 62.9 mmol) and 4-dimethyl amino pyridine (0.66 g, 5.40 mmol) in $CH_2Cl_2$ (200 mL) was treated with p-toluenesulfonic anhydride (9.38 g, 28.7 mmol) and the reaction stirred at room temperature for under $N_2$ for 1.5 h. The reaction mixture was washed with aqueous 1 N HCl (140 mL), the organic layer was dried ($MgSO_4$), and the solvent removed in vacuo to afford crude product that was purified by flash chromatography using 3:1 hexanes:acetone to afford 6.93 g (92%) toluene-4-sulfonic acid 2-[1-(4-methoxy-benzyl)-3-methyl-2-oxo-imidazolidin-4-yl]-ethyl ester. MS ($ES^+$) Calc'd for $C_{21}H_{27}N_2O_5S$ (M+1) 419. Found m/z 419 (100%). $^1$H NMR.

EXEMPLIFIED COMPOUNDS

Example 1

2-(4-{2-[1-(4-tert-Butyl-benzyl)-3-methyl-2-oxo-imidazolidin-4-yl]-ethoxy}-2-methyl-phenoxy)-2-methyl-propionic acid

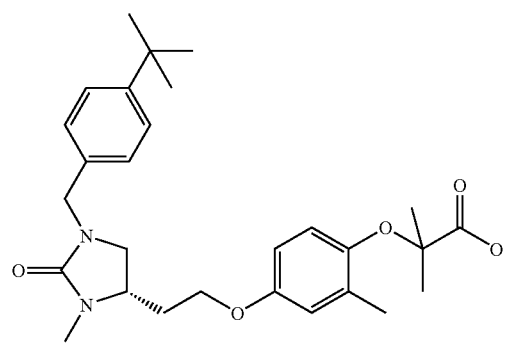

Step A 2-(4-{2-[1-(4-Methoxy-benzyl)-3-methyl-2-oxo-imidazolidin-4-yl]-ethoxy}-2-methyl-phenoxy)-2-methyl-propionic acid ethyl ester

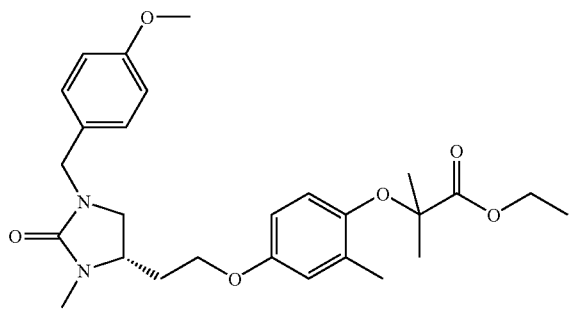

To a mixture of toluene-4-sulfonic acid 2-[1-(4-methoxy-benzyl)-3-methyl-2-oxo-imidazolidin-4-yl]-ethyl ester (0.100 g, 0.239 mmole) and 2-(4-hydroxy-2-methyl-phenoxy)-2-methyl-propionic acid ethyl ester (0.063 g, 0.262 mmole) in anhydrous DMF (2.0 mL), is added cesium carbonate (0.093 g, 0.287 mmole). After heating at 65° C. for about 16 hours, the reaction mixture is partitioned between ethyl acetate (5 ml) and 1.0 N HCl aq. (5 ml), the aqueous layer is extracted with more ethyl acetate (2×5 ml). The combined organic layer is washed with brine (3×5 ml). The organic layer is dried over $Na_2SO_4$, filtered, and concentrated in vacuo. Chromatography using silica gel (0-40% acetone/hexane) produces a colorless oil (0.107 g, 91%). Mass [EI+] 485 (M+H)$^+$.

Step B

2-Methyl-2-{2-methyl-4-[2-(3-methyl-2-oxo-imidazolidin-4-yl)-ethoxy]-phenoxy}-propionic acid ethyl ester

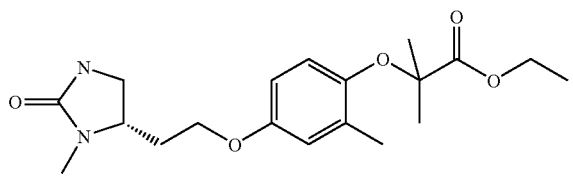

2-(4-{2-[1-(4-Methoxy-benzyl)-3-methyl-2-oxo-imidazolidin-4-yl]-ethoxy}-2-methyl-phenoxy)-2-methyl-propionic acid ethyl ester (0.105 g, 0.217 mmole) is treated with tryethylsilane (0.064 g, 0.743 mmole) in TFA (8.0 mL) at room temperature for about 6 hours. After evaporating the solvents, the residue is purified using silica gel (0-50% acetone/hexane). Colorless oil (0.041 g, 51%). Mass [EI+] 365 (M+H)$^+$, 729 (2M+H)$^+$.

Step C 2-(4-{2-[1-(4-tert-Butyl-benzyl)-3-methyl-2-oxo-imidazolidin-4-yl]-ethoxy}-2-methyl-phenoxy)-2-methyl-propionic acid To a solution of 2-methyl-2-{2-methyl-4-[2-(3-methyl-2-oxo-imidazolidin-4-yl)-ethoxy]-phenoxy}-propionic acid ethyl ester (0.040 g, 0.110 mmole) in DMF (2.0 mL), is added sodium hydride (60% in mineral oil, 0.0066 g, 0.165 mmole) in one portion. The mixture is stirred for 15 minutes at room temperature, then was added 4-tert-butyl-benzyl bromide (0.030 mL, 0.165 mmole). After stirring at room temperature for 4 hours, the reaction mixture is partitioned between ethyl acetate (5 ml) and saturated $NH_4Cl$ aq. (5 ml), the aqueous layer is extracted with more ethyl acetate (2×5 ml). The combined organic layer is washed with brine (3×5 ml), dried over $Na_2SO_4$, filtered, and concentrated in vacuo. The crude product was purified by silica gel (0-40% Acetone/Hexane). The ethyl ester obtained above is treated with a mixture of MeOH (2 mL)/5.0N NaOH (1 mL) at room temperature overnight, and then concentrated. The resulting residue is diluted with water (2 mL), cooled down to 0° C., acidified to pH=2 by adding concentrated HCl dropwise. The aqueous suspension is loaded on a Chem elut 1005 tube, eluted with DCM (50 mL). Evaporation of methylene chloride gives the titled compound as an colorless oil (0.022 g, 42%). Mass [EI+] 483 (M+H)$^+$, [EI−] 481 (M−H)$^-$.

Example 2

2-(4-{2-[1-(4-tert-Butyl-benzyl)-3-methyl-2-oxo-imidazolidin-4-yl]-ethoxy}-3-propyl-phenoxy)-2-methyl-propionic acid

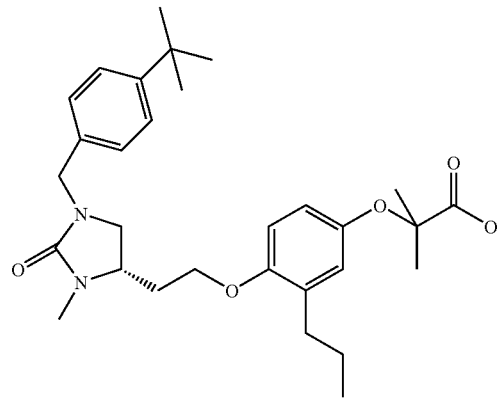

Step A 2-(4-{2-[1-(4-Methoxy-benzyl)-3-methyl-2-oxo-imidazolidin-4-yl]-ethoxy}-3-propyl-phenoxy)-2-methyl-propionic acid ethyl ester The titled compound is prepared, according to the procedure of Example 1, Step A, using toluene-4-sulfonic acid 2-[1-(4-methoxy-benzyl)-3-methyl-2-oxo-imidazolidin-4-yl]-ethyl ester (0.200 g, 0.478 mmole) and 2-(4-hydroxy-3-propyl-phenoxy)-2-methyl-propionic acid ethyl ester (0.140 g, 0.526 mmole) to produce a colorless oil (0.122 g, 50%). Mass [EI+] 513 (M+H)$^+$.

Step B

2-Methyl-2-{4-[2-(3-methyl-2-oxo-imidazolidin-4-yl)-ethoxy]-3-propyl-phenoxy}-propionic acid ethyl ester The titled compound is prepared, according to the procedure of Example 1, Step B, using 2-(4-{2-[1-(4-methoxy-benzyl)-3-methyl-2-oxo-imidazolidin-4-yl]-ethoxy}-3-propyl-phenoxy)-2-methyl-propionic acid ethyl ester (0.120 g, 0.234 mmole) to produce a colorless oil (0.054 g, 57%). Mass [EI+] 393 (M+H)+, 785 (2M+H)+.

Step C

2-(4-{2-[1-(4-tert-Butyl-benzyl)-3-methyl-2-oxo-imidazolidin-4-yl]-ethoxy}-3-propyl-phenoxy)-2-methyl-propionic acid The titled compound is prepared, according to the procedure of Example 1, Step B, using 2-methyl-2-{4-[2-(3-methyl-2-oxo-imidazolidin-4-yl)-ethoxy]-3-propyl-phenoxy}-propionic acid ethyl ester (0.054 g, 0.138 mmole) to produce a colorless oil (0.051 g, 72%). Mass [EI+] 511 (M+H)+, [EI−] 509 (M−H)−.

Example 3

2-(4-{3-[1-(4-tert-Butyl-benzyl)-3-methyl-2-oxo-imidazolidin-4-yl]-propyl}-2-methyl-phenoxy)-2-methyl-propionic acid

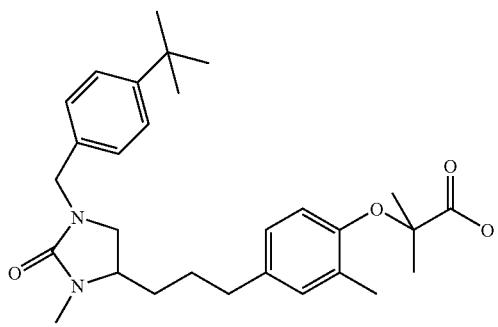

Step A

1-(4-tert-Butyl-benzyl)-4-[3-(3-iodo-4-methoxy-phenyl)-propyl]-3-methyl-imidazolidin-2-one

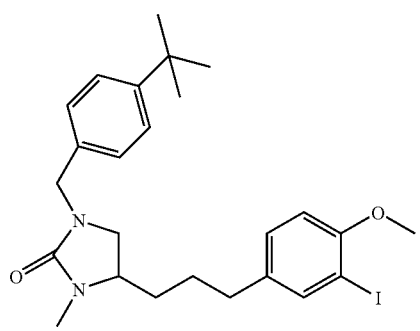

To a solution of 1-(4-tert-Butyl-benzyl)-4-[3-(4-methoxy-phenyl)-propyl]-3-methyl-imidazolidin-2-one (0.630 g, 1.60 mmole) in ethanol (15 mL), is added iodine (0.810 g, 3.20 mmole) followed by silver sulfate (0.998 g, 3.20 mmole). The reaction mixture is stirred at room temperature overnight. The precipitate is removed through filtration, and the solution is concentrated in vacuo. The residue is purified by column chromatography (silica gel, gradient elution 0-20% acetone in hexane) to provide a white foamy solid (0.584 g, 70%). Mass [EI+] 521 (M+H)+.

Step B

1-(4-tert-Butyl-benzyl)-4-[3-(4-methoxy-3-methyl-phenyl)-propyl]-3-methyl-imidazolidin-2-one

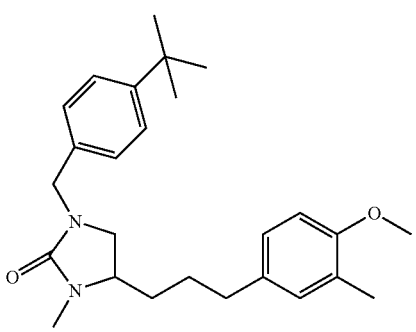

1-(4-tert-Butyl-benzyl)-4-[3-(3-iodo-4-methoxy-phenyl)-propyl]-3-methyl-imidazolidin-2-one (0.300 g, 0.580 mmole), methyl boronic acid (0.069 g, 1.16 mmole) and cesium carbonate (0.264 g, 1.74 mmole) are mixed in dioxane (6.0 mL). After bubbling with nitrogen for 15 minutes, 1,1'-bis(diphenylphosphino)ferrocence palladium (II) chloride (0.060 g, 0.015 mmole) is added. The reaction is heated at 80° C. for 4 hours. The solvent is removed on rota-vapor, and the crude product is purified by column chromatography (silica gel, gradient elution 0-20% acetone in hexane) to provide a yellow oil (0.153 g, 65%). Mass [EI+] 409 (M+H)+, 817(M+H)+.

Step C

1-(4-tert-Butyl-benzyl)-4-[3-(4-hydroxy-3-methyl-phenyl)-propyl]-3-3-methyl-imidazolidin-2-one

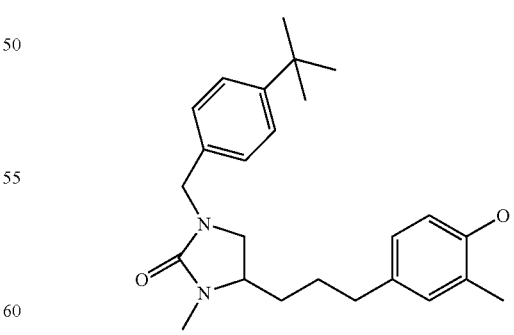

To a solution of 1-(4-tert-Butyl-benzyl)-4-[3-(4-methoxy-3-methyl-phenyl)-propyl]-3-methyl-imidazolidin-2-one (0.250 g, 0.612 mmole) in DCM (2.0 mL) at −78° C., is added dropwise the solution of BBr3 (0.230 mL, 2.44 mmole) in methylene chloride (2.0 mL). The reaction is kept for 30 minutes at about −78° C., then warmed up to 0° C. and stirred for an hour. It is then quenched by 1:1 MeOH/DCM (20 mL), stirred for another hour at 0° C. The reaction mixture is partitioned between DCM (25 mL) and water (25 mL), the organic layer is separated, washed by brine (3×25 mL), dried over $Na_2SO_4$, filtered and concentrated in vacuo. The crude product is purified by column chromatography (silica gel, gradient elution 0-20% acetone in hexane) to provide a yellow oil (0.126 g, 53%). Mass [EI+] 395 (M+H)$^+$, 789(M+H)$^+$, [EI−] 393 (M−H)$^-$.

Step D 2-(4-{3-[1-(4-tert-Butyl-benzyl)-3-methyl-2-oxo-imidazolidin-4-yl]-propyl}-2-methyl-phenoxy)-2-methyl-propionic acid ethyl ester

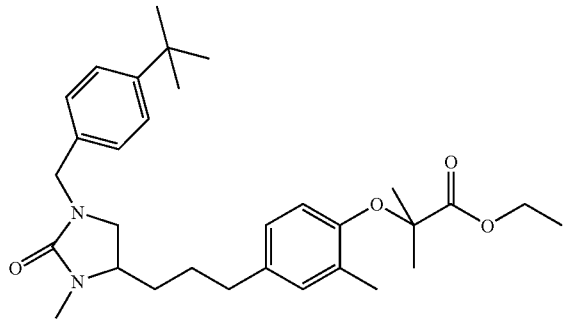

1-(4-tert-Butyl-benzyl)-4-[3-(4-hydroxy-3-methyl-phenyl)-propyl]-3-methyl-imidazolidin-2-one (0.060 g, 0.152 mmol) is dissolved in DMF (1.5 mL), to it is added ethyl 2-bromoisobutyrate (0.141 g, 0.760 mmol) followed by potassium carbonate (0.105 g, 0.760 mmol). After heating at 50° C. overnight, the reaction mixture is diluted with ethyl acetate (2 mL), washed with water (2 mL), the separated organic layer is passed through a chem elut tube, and the tube is washed with more DCM (50 mL). Evaporation of solvent followed by chromatography on silica gel, (gradient elution 0-40% ethyl acetate in hexane) to provide an oil (0.068 g, 88%). Mass [EI+] 510 (M+H)$^+$.

Step E 2-(4-{3-[1-(4-tert-Butyl-benzyl)-3-methyl-2-oxo-imidazolidin-4-yl]-propyl}-2-methyl-phenoxy)-2-methyl-propionic acid 2-(4-{3-[1-(4-tert-Butyl-benzyl)-3-methyl-2-oxo-imidazolidin-4-yl]-propyl}-2-methyl-phenoxy)-2-methyl-propionic acid ethyl ester (0.065 g, 0.128 mmole) is treated with 3:1 MeOH/5.0N NaOH (4 mL) at room temperature overnight, and then concentrated. The resulting residue is diluted with water (2 mL), cooled down to 0° C., acidified to pH=2 by adding concentrated HCl dropwise. The aqueous suspension is loaded on a Chem elut tube and eluted with DCM (50 mL). Evaporation of methylene chloride gives the titled compound as an oil (0.060 g, 98%). Mass [EI+] 481 (M+H)$^+$, [EI−] 479 (M−H)$^-$.

Example 4

2-(2-Butyl-4-{3-[3-methyl-2-oxo-1-(4-trifluoromethyl-benzyl)-imidazolidin-4-yl]-propyl}-phenoxy)-2-methyl-propionic acid

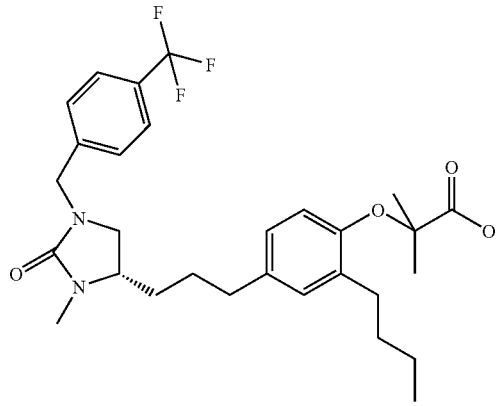

Step A

2-Methyl-2-(4-{3-[3-methyl-2-oxo-1-(4-trifluoromethyl-benzyl)-imidazolidin-4-yl]-propyl}-phenoxy)-propionic acid ethyl ester

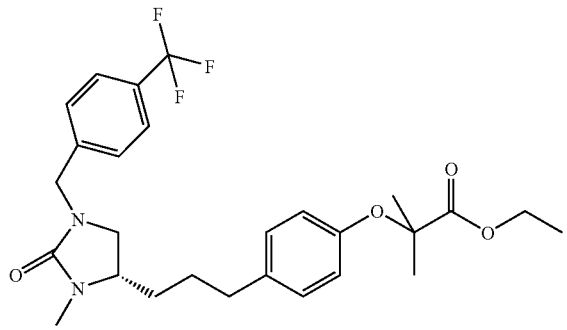

The titled compound is prepared, according to the procedure of Example 3, Step D, using 4-[3-(4-Hydroxy-phenyl)-propyl]-3-methyl-1-(4-trifluoromethyl-benzyl)-imidazolidin-2-one (0.445 g, 1.13 mmole) to produce an oil (0.464 g, 85%). Mass [EI+] 507 (M+H)$^+$.

Step B 2-(2-Iodo-4-{3-[3-methyl-2-oxo-1-(4-trifluoromethyl-benzyl)-imidazolidin-4-yl]-propyl}-phenoxy)-2-methyl-propionic acid ethyl ester

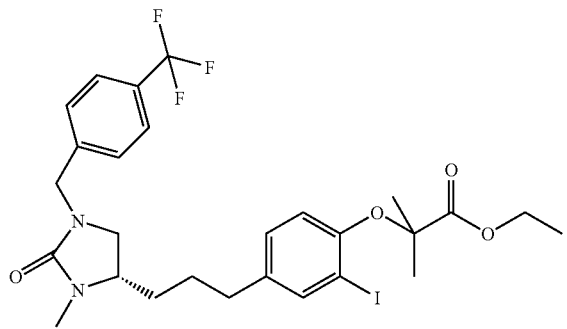

The titled compound is prepared, according to the procedure of Example 3, Step A, using 2-Methyl-2-(4-{3-[3-methyl-2-oxo-1-(4-trifluoromethyl-benzyl)-imidazolidin-4-yl]-propyl}-phenoxy)-propionic acid ethyl ester (0.460 g, 0.960 mmole) to produce an oil (0.273 g, 48%). Mass [EI+] 633 (M+H)+.

Step C 2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester

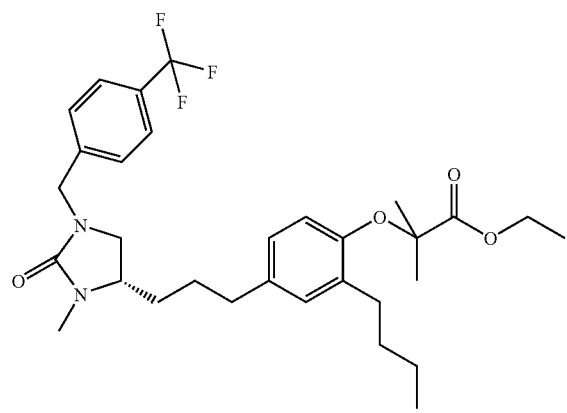

The titled compound is prepared, according to the procedure of Example 3, Step B, using 2-(2-Iodo-4-{3-[3-methyl-2-oxo-1-(4-trifluoromethyl-benzyl)-imidazolidin-4-yl]-propyl}-phenoxy)-2-methyl-propionic acid ethyl ester (0.270 g, 0.430 mmole) and n-butyl boronic acid (0.218 g, 0.215 mmole) to produce an oil (0.115 g, 48%). Mass [EI+] 563 (M+H)+.

Step D 2-(2-Butyl-4-{3-[3-methyl-2-oxo-1-(4-trifluoromethyl-benzyl)-imidazolidin-4-yl]-propyl}-phenoxy)-2-methyl-propionic acid The titled compound is prepared, according to the procedure of Example 3, Step E, using 2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester (0.11 g, 0.196 mmole) to produce an oil (0.029 g, 28%). Mass [EI+] 535 (M+H)+, [EI−] 533 (M−H)−.

The following Examples are prepared substantially as described herein above to yield the title compounds:

Example 5

2-Methyl-3-(4-{2-[3-methyl-2-oxo-1-(3-phenoxy-benzyl)-imidazolidin-4-yl]-ethoxy}-phenyl)-2-phenoxy-propionic acid

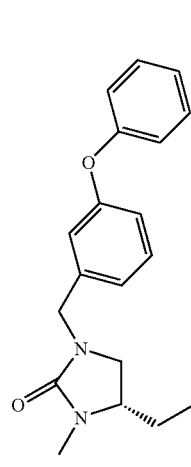

Yield(0.135 g, 86%). Mass [EI+] 581 (M+H)+, [EI−] 579 (M−H)−

Example 6

2-Methyl-3-(4-{2-[3-methyl-2-oxo-1-(3-phenoxy-benzyl)-imidazolidin-4-yl]-ethoxy}-phenyl)-2-phenoxy-propionic acid

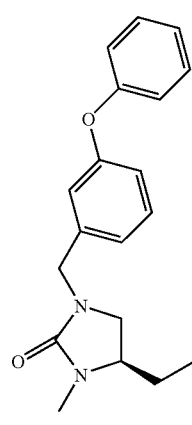

Yield (0.192 g, 52%). Mass [EI+] 581 (M+H)+, [EI−] 579 (M−H)−

Example 7

2-Methyl-3(4-{2-[3-methyl-2-oxo-1-(3-trifluoromethoxy-benzyl)-imidazolidin-4-yl]-ethoxy}-phenyl)-2-phenoxy-propionic acid Yield (0.127 g, 35%). Mass [EI+] 573 (M+H)+, [EI−] 571 (M−H)−

Example 8

2-Methyl-3(4-{2-[3-methyl-2-oxo-1-(3-trifluoromethoxy-benzyl)-imidazolidin-4-yl]-ethoxy}-phenyl)-2-phenoxy-propionic acid

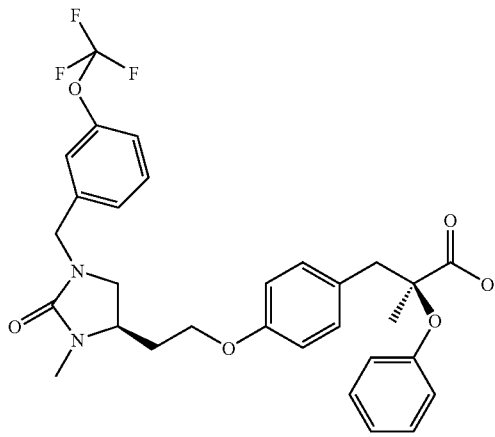

Yield (0.238 g, 63%). Mass [EI+] 573 (M+H)⁺, [EI−] 571 (M−H)⁻

Example 9

2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid

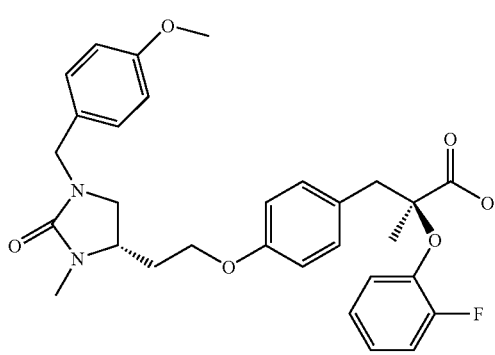

Step A 2-(2-Fluoro-phenoxy)-3-(4-hydroxy-phenyl)-2-methyl-propionic acid methyl ester

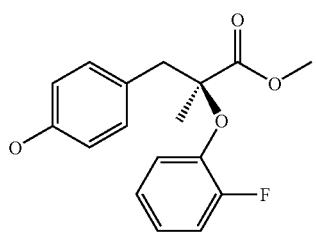

To a solution of LDA (1.5 M in cyclohexane, 33 mL, 49.5 mmole) in THF (40 mL), at −78° C., is added dropwise a solution of 2-(2-fluoro-phenoxy)-propionic acid ethyl ester (7.70 g, 36.3 mmole) in THF (100 mL). After stirring for 30 minutes at −78° C., a solution of toluene-4-sulfonic acid 4-iodomethyl-phenyl ester (12.8 g, 33.0 mmole) is injected to the reaction mixture. The reaction is stirred at −78° C. for one hour, then warmed up to room temperature and stirred overnight. The reaction is treated with 5.0N NaOH (50 mL) in presence of methanol (200 mL). After evaporating methanol, the aqueous solution is acidified with concentrated HCl to pH=1 and is extracted with ethyl acetate (2×300 mL). The combined organic layers are dried, filtered and concentrated in vacuo. The residue is dissolved in MeOH (200 mL) and treated with concentrated sulfuric acid (2 mL) at 80° C. overnight. The reaction mixture is partitioned between ethyl acetate (500 mL) and water (500 mL), the organic layer is washed by brine (3×500 mL), dried, filtered and concentrated in vacuo. The compound is purified by chromatography (silica gel, gradient elution 0-20% ethyl acetate in hexane) to provide an oil (6.02 g, 60%), which is then resolved by chiral HPLC to generate the enantiomer as an oil (2.30 g). Mass [EI+] 322 (M+NH₄)⁺, [EI−] 303 (M−H)⁻.

Step B 2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid methyl ester

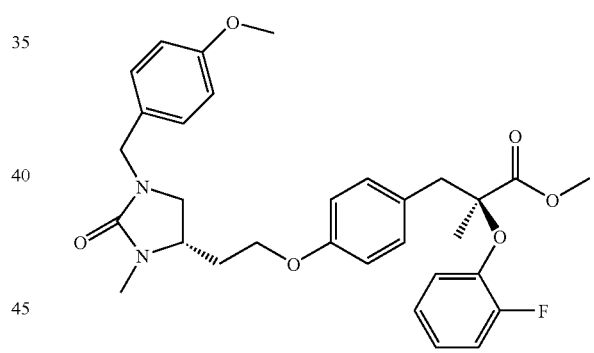

The titled compound is prepared, according to the procedure of Example 1, Step A, using toluene-4-sulfonic acid 2-[1-(4-methoxy-benzyl)-3-methyl-2-oxo-imidazolidin-4-yl]-ethyl ester (0.888 g, 2.12 mmole) and 2-(2-Fluoro-phenoxy)-3-(4-hydroxy-phenyl)-2-methyl-propionic acid methylester (0.645 g, 2.12 mmole) to produce an oil (0.95 g, 81%). Mass [EI+] 551 (M+H)⁺.

Step C 2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid The titled compound is prepared, according to the procedure of Example 3, Step E, using 2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid methyl ester (0.224 g, 0.406 mmole) to produce a white foamy solid (0.199 g, 91%). Mass [EI+] 537 (M+H)⁺, [EI–] 535 (M–H)⁻.

Example 10

3-{4-[2-(1-Biphenyl-4-ylmethyl-3-methyl-2-oxo-imidazolidin-4-yl)-ethoxy]-phenyl}-2-(2-fluoro-phenoxy)-2-methyl-propionic acid

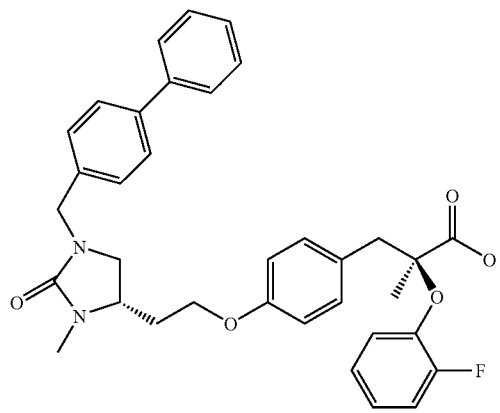

The titled compound is prepared using substantially the processes described herein above to produce a white foamy solid (0.0858 g, 40%). Mass [EI+] 583 (M+H)⁺, [EI–] 581 (M–H)⁻.

Example 11

3-(4-{2-[1-(4-tert-Butyl-benzyl)-3-methyl-2-oxo-imidazolidin-4-yl]-ethoxy}-phenyl)-2-(2-fluoro-phenoxy)-2-methyl-propionic acid

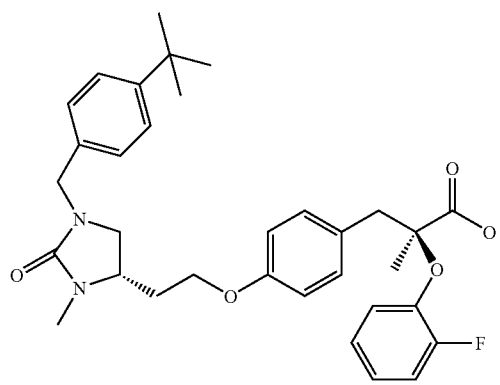

The titled compound is prepared, according to the procedures substantially as described hereinabove to produce a white foamy solid (0.101 g, 77%). Mass [EI+] 563 (M+H)⁺, [EI–] 561 (M–H)⁻.

Example 12

2-(2-Fluoro-phenoxy)-2-methyl-3-{4-[2-(3-methyl-1-naphthalen-2-ylmethyl-2-oxo-imidazolidin-4-yl)-ethoxy]-phenyl}-propionic acid

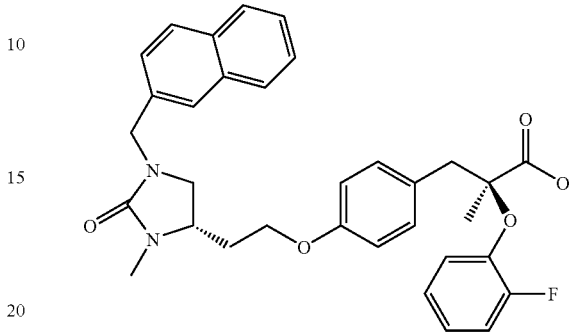

The titled compound is prepared, substantially as described herein above to yield (0.0753 g, 58%). Mass [EI+] 543 (M+H)⁺, [EI–] 541 (M–H)⁻.

Example 13

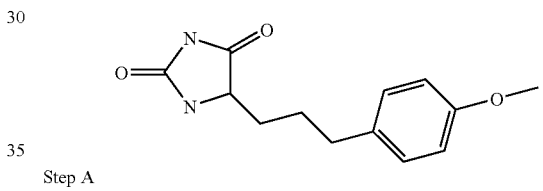

Step A

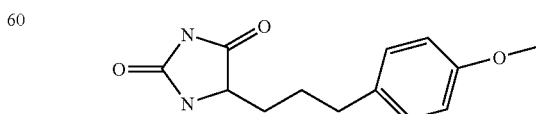

A methylene chloride solution (300 ml) of 4-(4-methoxyphenyl)butanol (10.0 g, 0.055 mol) is cooled to 0° C. and stirred. Pyridinium chlorochromate (17.8 g, 0.082 mol) is added slowly to the solution which is stirred, placed under a drying tube and warmed to room temperature overnight. The reaction mixture is filtered and the filtrate washed with aqueous brine then dried over sodium sulfate. Evaporation of the solvent gives the crude product as an oil. Purification by flash chromatography (hexanes:ethyl acetate) gives the desired aldehyde (6.8 g).

$C_{11}H_{14}O_2$ (MW=178.23); ¹H NMR

Step B

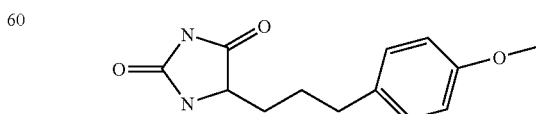

Potassium cyanide (10.3 g, 0.158 mol) and ammonium carbonate (38.1 g, 0.396 mol) are combined in methanol (100 ml) and water (100 ml). The product from Example 13, Step A (6.7 g, 0.038 mol) is added and the reaction is stirred while heating to 45° C. overnight. The reaction is cooled and the precipitate filtered and washed with water. The obtained solid is dissolved in THF and dried with sodium sulfate. Evaporation of the solvent results in a solid which is washed with ethyl acetate:hexanes (50:50) then air-dried to yield the desired hydantoin (16.6 g).

$C_{13}H_{16}N_2O_3$ (MW=248.3); $^1H$ NMR

Example 14

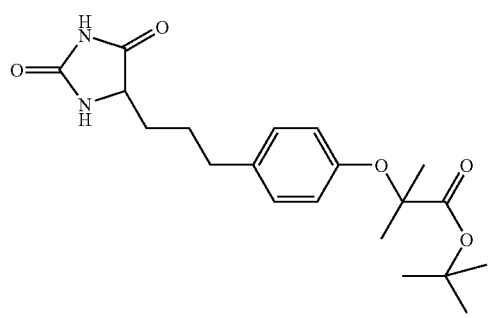

Step A
Preparation of:

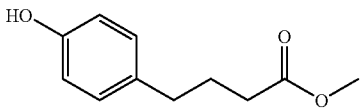

To a cooled (0° C.) solution of boron tribromide (50 g, 200 mmol) in $CH_2Cl_2$ (50 ml) is added a solution of methyl 4-(4-methoxyphenyl)butyrate (15.5 g, 74.4 mmol) in $CH_2Cl_2$ (100 ml) dropwise over one hour. After stirring for an additional hour at 0° C., the reaction mixture is treated with 1:1 $CH_3OH$:$CH_2Cl_2$ (120 ml) with cooling and stirred overnight at ambient temperature. Concentration of the mixture gives an oil which is partitioned between ethyl acetate (150 ml) and water (150 ml). The aqueous layer is extracted with ethyl acetate (2×50 ml), and the combined organic extracts washed with water (50 ml), brine (50 ml), dried, then concentrated to give the desired phenol as an oil.

$C_{11}H_{14}O_3$ (MW=194.23); MS: m/z ($M^+$+1)=195

Step B

Preparation of

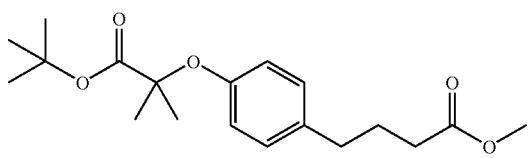

The phenol from Step A (18.6 g, 96 mmol) is dissolved in DMF (300 ml) and treated with t-butyl 2-bromoisobutyrate (50 ml, 288 mmol), powdered $K_2CO_3$ (53.0 g, 384 mmol) and $MgSO_4$ (1.6 g, 96 mmol), and the resulting mixture heated at 75° C. overnight. After cooling to ambient temperature, the reaction mixture is decanted into 1N aqueous HCl (300 ml) and extracted with diethyl ether (3×150 ml). The remaining solids from the decantation are washed several times with diethyl ether. The diethyl ether extracts and washes are combined and washed with 1N aqueous HCl (150 ml), dried ($Na_2SO_4$), and concentrated to a dark oil. Purification by flash chromatography (gradient elution, hexanes to 95:5 hexanes:ethyl acetate) gives the desired ether as an oil.

$C_{19}H_{28}O_5$ (MW=336.43); MS: m/z ($M^+$+1)=337

Step C

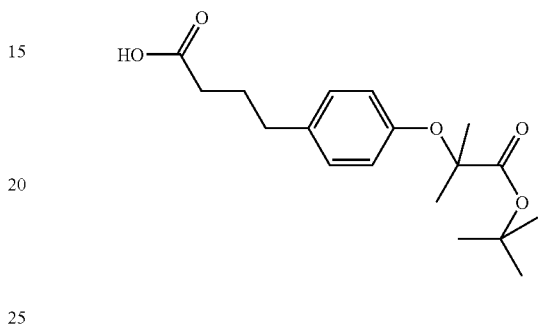

The diester from Step B (10.7 g, 0.032 mol) is dissolved in dioxane (100 mL) then treated with an aqueous solution (50 mL) of LiOH (1.5 g, 0.063 mol). The resulting mixture is stirred at room temperature for 2 hr at which time TLC indicates complete reaction. The solvent is concentrated to approximately 10 mL which is then diluted with $H_2O$ (200 mL) and washed with ether (1×100 mL). The aqueous extract is acidified with 5 N HCl (25 mL) and extracted with ethyl acetate (2×150 mL). The combined organic extracts are dried over $Na_2SO_4$ and concentrated to give the desired carboxylic acid (10.6 g, >99%).

$C_{18}H_{26}O_5$ (MW=322.40); mass spectroscopy: ($M+NH_4^+$)= 340.3, (M−H)=321.3

Step D

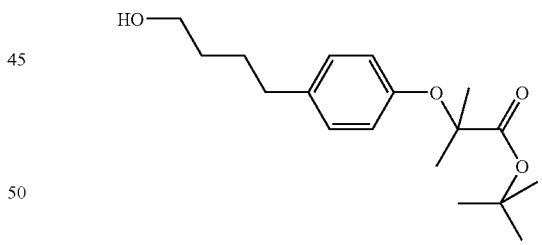

A THF solution (100 mL) of the carboxylic acid from Step C (10 g, 0.031 mol) is cooled to 0° C. and treated with triethylamine (5.6 mL, 0.040 mol) followed by ethyl chloroformate (3.8 mL, 0.040 mol). A thick white precipitate forms almost immediately. The reaction mixture is warmed to room temperature, and after stirring overnight, the mixture is filtered. The filtrate is cooled to 0° C. and treated with sodium borohydride (3.5 g, 0.092 mol). A solution of methanol (20 mL) in THF (40 mL) is added dropwise over a 30-40 minute period then the resulting mixture is warmed to room temperature and stirred for 1 hour. Again the solution is cooled to 0° C. and carefully quenched by the addition of 1 N HCl (100 mL). The mixture is diluted with water (400 mL0 and extracted with $CH_2Cl_2$ (2×300 mL). The combined organic extracts are dried over Na$_2$SO$_4$, filtered and concentrated. The crude oil is purified by flash chromatography (5:1 hexanes:ethyl acetate) to give the desired alcohol as a colorless oil (8.69 g, 88%).

Step E

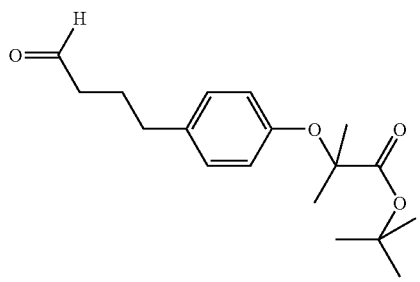

The alcohol from Step D (8.7 g, 0.028 mol) is dissolved in CH$_2$Cl$_2$ and cooled to 0° C. Pyridinium chlorochromate (9.0 g, 0.042 mol) was added to the solution in portions after which the mixture is warmed to room temperature. After stirring overnight the reaction mixture is filtered using celite. The filtrate is concentrated and the resulting crude oil is purified by chromatography (10:1 hexanes:ethyl acetate) to give the desired aldehyde as a colorless oil (4.45 g, 52%).

Step F

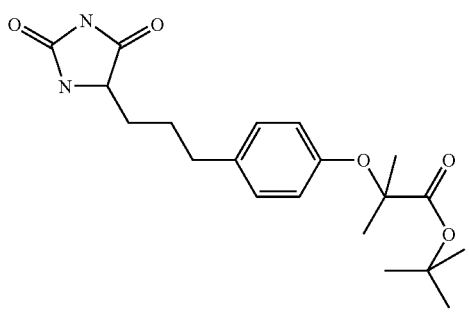

Potassium cyanide (1.1 g, 7.2 mmol) and ammonium carbonate (1.7 g, 18.0 mmol) are combined in methanol (15 ml) and water (15 mL). The aldehyde from Step E (1.1 g, 3.6 mmol) is added and the reaction is stirred while heating to 50° C. After 3 hr, additional ammonium carbonate is added (1.7 g, 18.0 mmol) and the resulting mixture is stirred overnight at 50° C. The reaction is cooled to room temperature, diluted with water, then extracted with ethyl acetate (2×). The combined organic extracts are washed with brine, dried over Na$_2$SO$_4$, and concentrated. Purification by chromatography (gradient: 10:1 to 3:1 to 3:2 hexanes:ethyl acetate) gives the desired hydantoin (0.9 g, 66%)

C$_{20}$H$_{28}$N$_2$O$_5$ (MW=376.46); mass spectroscopy: (MH$^+$–t-butyl)=321.2, (MH$^-$)=375.4

Example 15

Step A

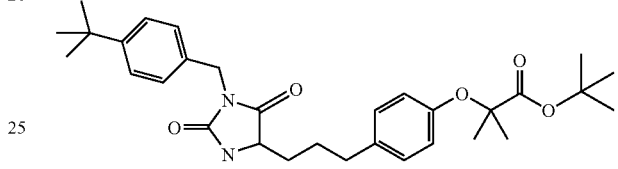

The hydantoin from Example 14 (1.0 g, 2.66 mmol) and 4-(tert-butyl)benzyl bromide (0.63 ml, 2.93 mmol) are stirred together in DMF (20 ml). Potassium carbonate (powdered, 1.5 g, 10.64 mmol) and magnesium sulfate (0.5 g, 4.00 mmol) are added and the mixture stirred at ambient temperature overnight. The reaction mixture is carefully added to 1 N hydrochloric acid (50 ml) and the resulting solution is extracted twice with ethyl acetate. The organic layers are combined, washed with aqueous brine then dried over sodium sulfate. Evaporation of the solvent and subsequent purification by flash chromatography (hexanes:ethyl acetate) gives the desired product (1.05 g).

C$_{31}$H$_{42}$N$_2$O$_5$ (MW=522.7)

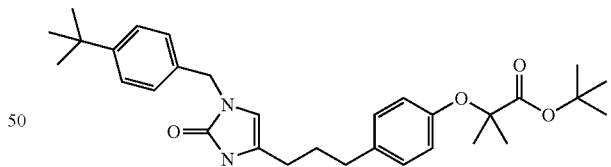

Step B

The hydantoin from Example 15, Step A (0.15 g, 0.29 mmol) is stirred in ethanol, sodium borohydride (0.11 g, 2.90 mmol) added slowly and the mixture was stirred at ambient temperature, under a drying tube, overnight. The reaction mixture was concentrated and the residue dissolved in ethyl acetate, washed with water and aqueous brine then dried. Evaporation of the solvent and subsequent purification by flash chromatography (ethyl hexanes:ethyl acetate) gives the desired product (0.071 g).

C$_{31}$H$_{42}$N$_2$O$_4$ (MW=506.7)

Step C

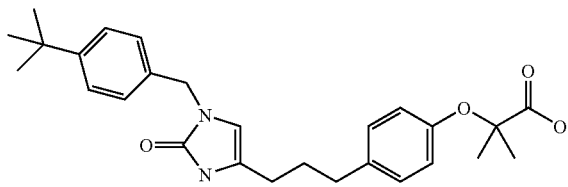

The product from Example 15, Step B (0.071 g, 0.14 mmol) is stirred in methylene chloride (4 ml) with triflouroacetic acid (0.1 ml, 1.3 mmol), under a drying tube, overnight. The solvent is evaporated and subsequent purification by flash chromatography (ethyl acetate:hexanes) gives the desired product (0.035 g).

$C_{27}H_{34}N_2O_4$ (MW=450.6); MS (M+, 451.3)

Example 16

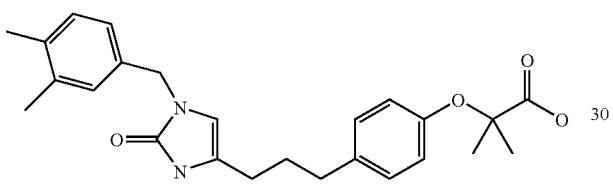

$C_{25}H_{30}N_2O_4$ (MW=422.5); MS (M+, 423.3)

Step A

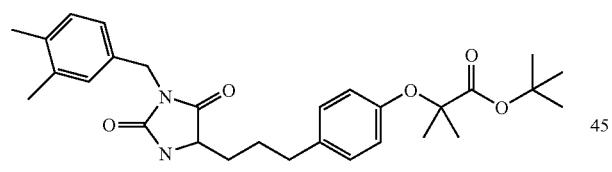

Following the procedure of Example 15, Step A, the product was obtained using the hydantoin from Example 14 (1.0 g, 2.66 mmol) and 3,4-dimethylbenzyl chloride (Transworld, 0.42 ml, 2.93 mol). This reaction was heated to 50° C. to affect reaction completion, yielding the product (0.550 g).

$C_{29}H_{38}N_2O_5$ (MW=494.6)

Step B

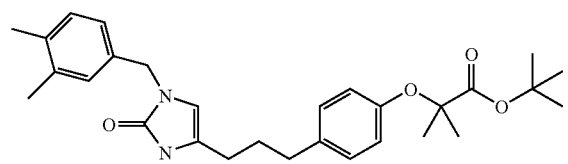

Following the procedure of Example 15, Step B, the alkylated hydantoin from Example 16, Step A (0.15 g, 0.3 mmol) and sodium borohydride (0.11 g, 3.00 mmol) were used to yield the desired imidazolone (0.032 g).

$C_{29}H_{38}N_2O_4$ (MW=478.6)

Step C

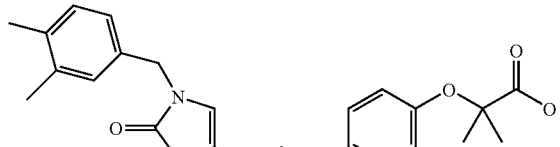

Following the procedure of Example 15, Step C, the imidazolone from Step B (0.032 g, 0.066 mmol) and triflouroacetic acid (0.1 ml) were used to yield the desired product (0.026 g).

$C_{25}H_{30}N_2O_4$ (MW=422.5); MS (M+, 423.3)

Example 17

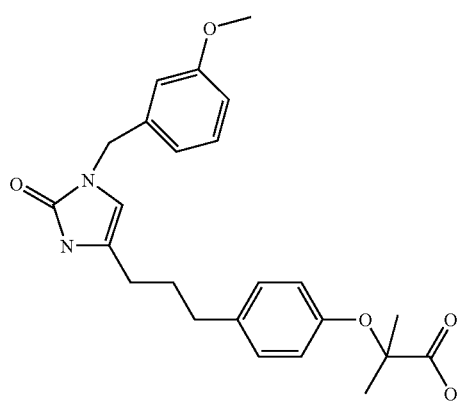

The title compound is prepared using substantially the procedures described herein above. Yield: 26% for two steps.

$C_{24}H_{28}N_2O_5$ (MW=424.50); mass spectroscopy: (MH+)= 425.3

Example 18

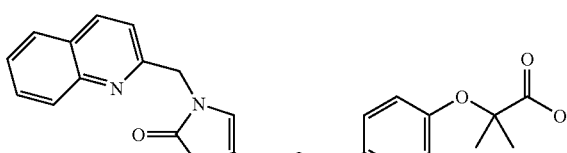

The title compound is prepared using substantially the procedures described herein above.

$C_{26}H_{27}N_3O_4$ (MW=445.5); MS (M+, 446.3)

Example 19

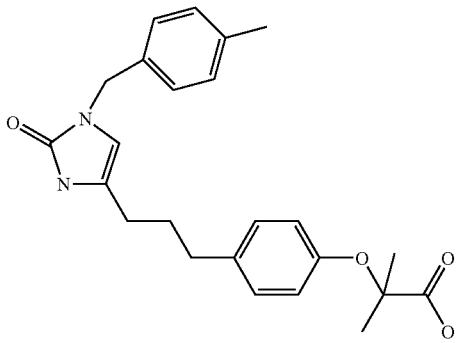

The title compound is prepared using substantially the procedures described herein above to yield the product.

$C_{24}H_{28}N_2O_4$ (MW=408.50); mass spectroscopy: (MH$^+$)= 409.2

Example 20

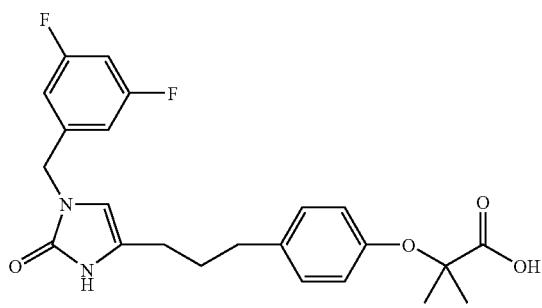

Step A

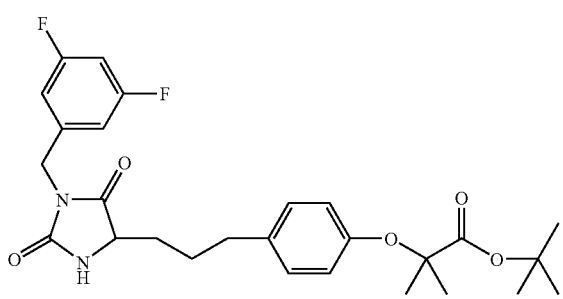

The hydantoin from Example 14 (0.500 g, 0.0013 mol) is dissolved in DMF and treated with 3, 5 difluoro bromobenzene (0.189 g, 0.0015 mol) and powdered $K_2CO_3$ (0.718 g, 0.0052 mol). The resulting mixture is stirred at room temperature overnight. The reaction mixture is poured into 1N HCl and combined with ethyl acetate. The organic layer is extracted and washed with brine then dried and concentrated. Purification of the crude material by flash chromatography (4:1 hexanes:ethyl acetate, 1:1 hexanes:ethyl acetate) yields the desired hydantoin as a clear oil (0.420 g, 64%).

$C_{27}H_{32}F_2N_2O_5$ (MW=502.23); mass spectroscopy (MH+)= 447.1

Step B

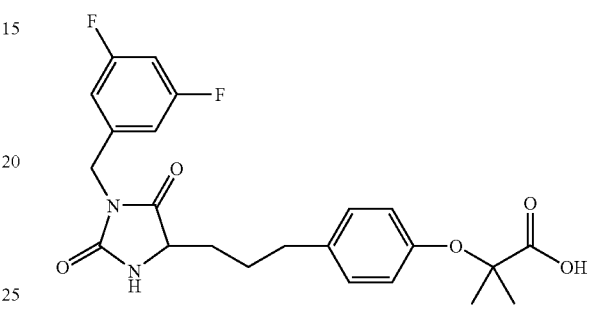

The hydantoin from Step A (0.410 g, 0.00082 mol) is dissolved in methylene chloride (5 ml) and treated with trifluoroacetic acid (0.315 ml, 0.0041 mol) and stirred overnight. The solvent is concentrated and the product is vacuum dried.

$C_{23}H_{24}F_2N_2O_5$ (MW=446.17); mass spectroscopy (MH+)= 447.2

Step C

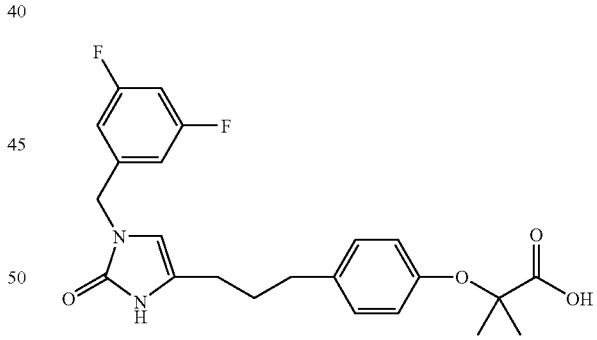

The acid from Step B (0.428 g, 0.00096 mol) is dissolved in ethanol (20 ml) and treated with sodium borohydride (0.363 g, 0.0096 mol). One hour later, additional sodium borohydride (0.363 g) is added and the reaction is stirred overnight. Fifty milliliters of 5N HCl is added to the reaction mixture followed by water (50 ml). The aqueous solution is extracted with ethyl acetate (2×, 50 ml). The organic layer is washed, dried, and concentrated. Purification by flash chromatography (100% ethyl acetate) gives the desired acid as a burgundy solid (150 g, 36%).

$C_{23}H_{24}F_2N_2O_4$ (MW=430.17); mass spectroscopy (MH+)= 431.1

Example 21

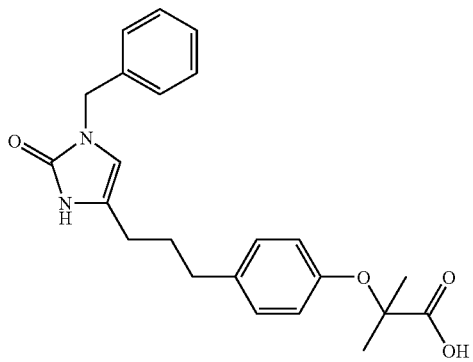

Step A

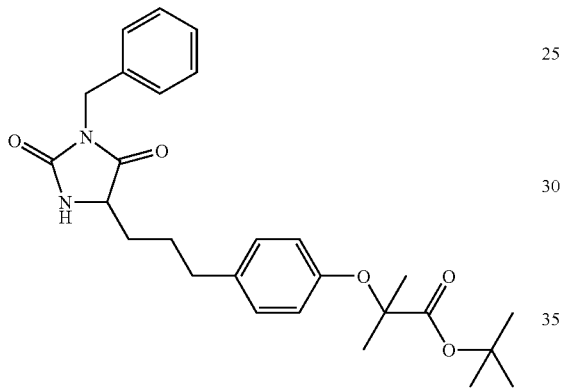

A DMF solution (20 mL) of the hydantoin from Example 14 (455.2 mg, 1.21 mmol) is treated sequentially with benzyl bromide (160 μL, 1.35 mmol), $K_2CO_3$ (0.44 g, 3.2 mmol), and $MgSO_4$ (0.48 g, 4.0 mmol). The resulting mixture is stirred at room temperature overnight. The reaction is quenched by the slow addition of 1 N HCl. The resulting mixture is extracted with ethyl acetate (2×75 mL). The combined organic extracts are washed with brine then dried over $Na_2SO_4$ and concentrated. Purification by chromatography (2:1 hexanes:ethyl acetate) gives the desired alkylated hydantoin as a white solid (512.0 mg, 91%).

$C_{27}H_{34}N_2O_5$ (MW=466.58); mass spectroscopy: ($MH^+$-t-butyl)=411.1, ($MH^-$)=465.3

Step B

A $CH_2Cl_2$ solution (15 mL) of the ester from Step A (495.5 mg, 1.06 mmol) is cooled to 0° C. and treated with TFA (2 mL, 26 mmol). The mixture is warmed to room temperature and stirred overnight. The solvent is concentrated to give the crude acid. Trace amounts of TFA are removed by concentration from toluene (3×15 mL) after which the product is used in the subsequent reaction without further purification.

$C_{23}H_{26}N_2O_5$ (MW=410.47); mass spectroscopy: ($MH^+$)=411.1, ($MH^-$)=409.2

Step C

The hydantoin from Step B is dissolved in ethanol (20 mL) and treated with $NaBH_4$ (400 mg, 10.5 mmol). Additional $NaBH_4$ is added to the reaction mixture after 3 hr (200 mg, 4.8 mmol). The resulting mixture is stirred at room temperature overnight. Additional $NaBH_4$ is added to the reaction mixture (370 mg, 9.7 mmol) and stirring is continued for about two days. The reaction is quenched by the careful addition of 5 N HCl. The mixture is stirred for 30 minutes then diluted with $H_2O$ and extracted with ethyl acetate. The combined organic extracts are washed, dried, and concentrated. Purification by chromatography (gradient: 100% $CH_2Cl_2$ to 5% methanol in $CH_2Cl_2$) gives the desired imidazolone as a glass-like solid (93.2 mg, 22% for two steps).

$C_{23}H_{26}N_2O_4$ (MW=394.47); mass spectroscopy: ($MH^+$)=395.1, ($MH^-$)=393.2

Example 22

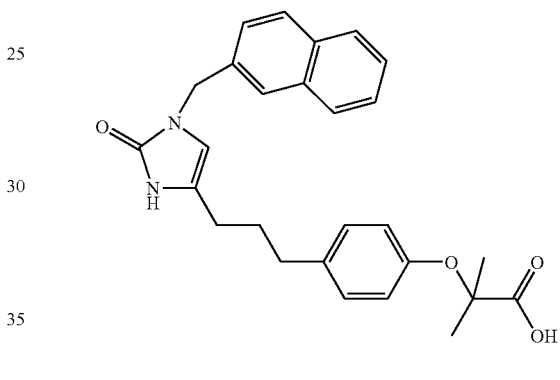

Step A

The corresponding hydantoin is prepared using substantially the procedures described herein above.

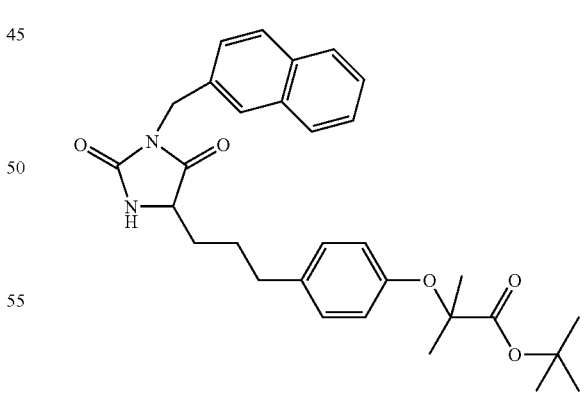

Yield: 84%. $C_{31}H_{36}N_2O_5$ (MW=516.64); mass spectroscopy: ($MH^+$-t-butyl)=461.2, ($MH^-$)=515.4

Step B

A $CH_2Cl_2$ solution (15 mL) of the ester from Step A (387.8 mg, 0.751 mmol) is cooled to 0° C. and treated with TFA (2 mL, 26 mmol). The mixture is warmed to room temperature and stirred overnight. The solvent is concentrated to give the crude acid. Trace amounts of TFA are removed by concentration from toluene (3×15 mL) after which the product is used in the subsequent reaction without further purification.

$C_{27}H_{28}N_2O_5$ (MW=460.53); mass spectroscopy: (MH$^+$)=461.2, (MH$^-$)=459.3

Step C

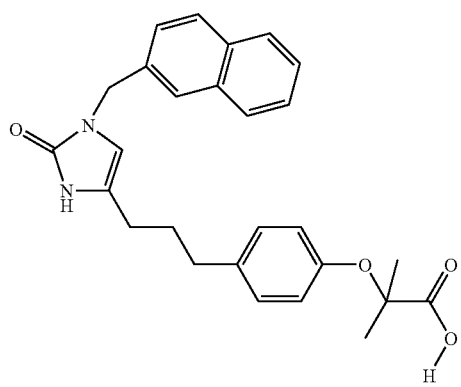

The hydantoin from Step B is dissolved in ethanol:THF (2:1, 30 mL) and treated with NaBH$_4$ (313 mg, 8.2 mmol). Additional NaBH$_4$ is added to the reaction mixture after 3 hr (180 mg, 4.7 mmol). The resulting mixture is stirred at room temperature overnight. The reaction is quenched by the careful addition of 5 N HCl. The mixture is stirred for 30 minutes then diluted with H$_2$O (75 mL) and extracted with ethyl acetate (2×75 mL). The combined organic extracts are washed, dried, and concentrated. Purification by chromatography (gradient: 100% CH$_2$Cl$_2$ to 5% methanol in CH$_2$Cl$_2$) gives the desired imidazolone as a white foam (109.0 mg, 33% for two steps).

$C_{27}H_{28}N_2O_4$ (MW=444.54); mass spectroscopy: (MH$^+$)=445.2, (MH$^-$)=443.1

The following Examples are prepared using substantially the procedures described herein before.

Example 23

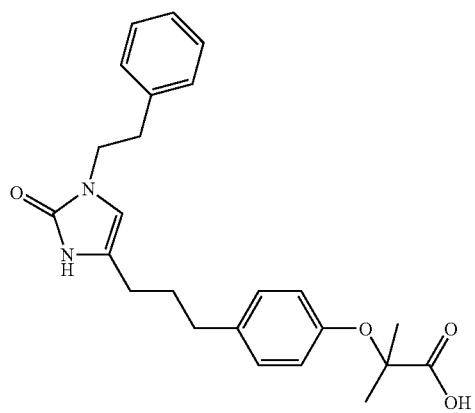

$C_{24}H_{28}N_2O_4$ (MW=408.50); mass spectroscopy: (MH$^+$)=409.2, (MH$^-$)=407.1

Example 24

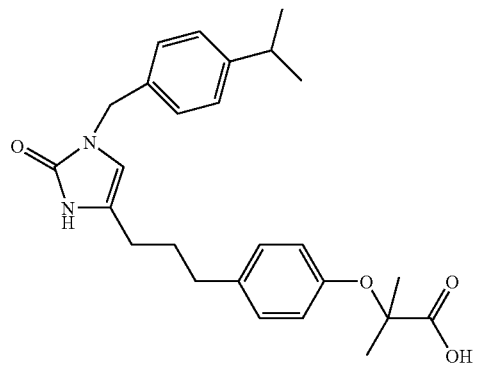

$C_{26}H_{32}N_2O_4$ (MW=436.56); mass spectroscopy: (MH$^+$) 437.2, (MH$^-$)=435.1

Example 25

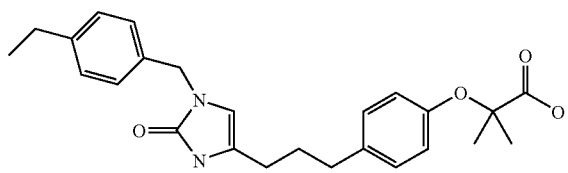

Step A

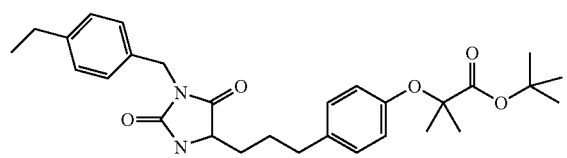

Following the procedure of Example 15, Step A, the product was obtained using the hydantoin from Example 14 (0.5 g, 1.33 mmol) and 4-ethylbenzyl chloride (Aldrich, 0.2 ml, 1.46 mol). This reaction was heated to 45° C. to affect reaction completion, yielding, after purification, the product (0.41 g).

$C_{29}H_{38}N_2O_5$ (MW=494.6); MS (M+, 495.3, M+18, 512.3)

Step B

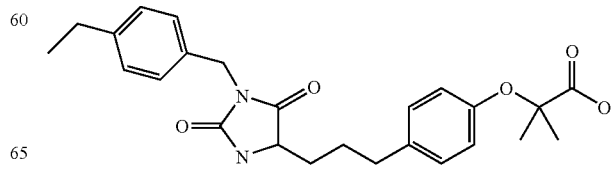

The product from Example 25, Step A (0.4 g, 0.8 mmol) was stirred in methylene chloride (10 ml) with trifluoroacetic acid (Aldrich, 2 ml), under a drying tube, overnight. The solvent was evaporated and the obtained residue was placed under vacuum to yield the desired carboxylic acid (0.36 g).

$C_{25}H_{30}N_2O_5$ (MW=438.5); MS (M−, 437.1)

Step C

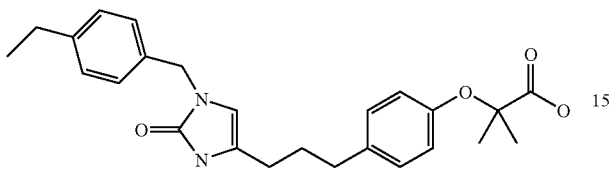

The product from Example 25, Step B (0.33 g, 0.75 mmol) was stirred in ethanol (30 ml) and sodium borohydride (0.28 g, 7.5 mmol) added slowly. After stirring overnight, 5 N hydrochloric acid (5 ml) was added slowly and allowed to stir for 1 hr. Water (50 ml) added and the mixture was extracted twice with ethyl acetate. The organic layers were combined, washed with aqueous brine and dried over sodium sulfate. Evaporation of the solvent and subsequent purification by flash chromatography (methylene chloride:methanol) gave the desired product (0.120 g).

$C_{25}H_{30}N_2O_4$ (MW=422.5); MS (M+, 423.3, M−, 421.1)

Example 26

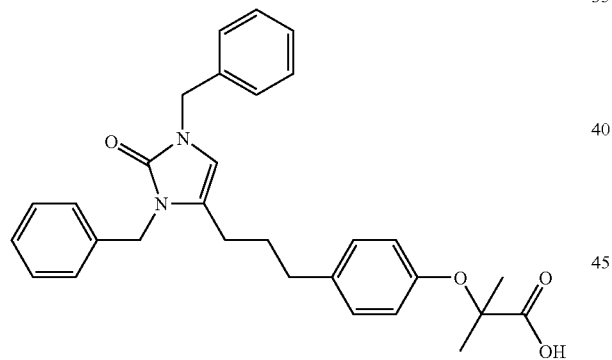

Step A

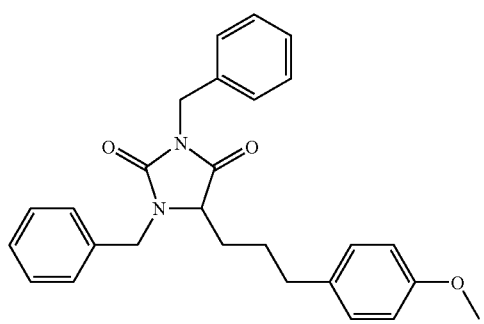

A DMF solution (75 mL) of the hydantoin from Example 13(1.5 g, 6.0 mmol) is treated sequentially with benzyl bromide (1.8 mL, 15 mmol), $K_2CO_3$ (3.7 g, 27 mmol), and $MgSO_4$ (4.2 g, 35 mmol). The resulting mixture is stirred at room temperature overnight. The reaction is quenched by the slow addition of 1 N HCl (100 mL). The resulting mixture is extracted with ethyl acetate (2×100 mL). The combined organic extracts are washed with brine then dried over $Na_2SO_4$ and concentrated. Purification by chromatography (5:1 hexanes:ethyl acetate) gives the desired alkylated hydantoin as a colorless oil (1.33 g, 52%).

$C_{27}H_{28}N_2O_3$ (MW=428.21); mass spectroscopy: (MH+)=429.2

Step B

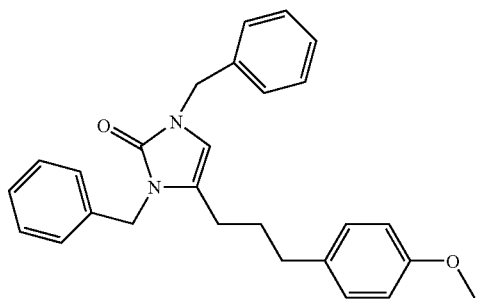

To a slurry of LAH (122 mg, 3.2 mmol) in THF (10 mL) at 0° C. under $N_2$ is added the hydantoin from Step A (1.02 g, 2.38 mmol) as a solution in THF (10 mL). After 10 minutes the reaction is quenched by the addition of 5 N HCl (4 mL) in THF (2 mL), stirred for 30 minutes, then diluted with $H_2O$ (75 mL). The resulting mixture is extracted with ethyl acetate (2×75 mL). The combined organic extracts are washed with brine, dried and concentrated. Purification by chromatography (gradient: 5:1 to 1:1 hexanes:ethyl acetate) gives the desired imidazolone as a colorless oil (0.873 g, 89%).

$C_{27}H_{28}N_2O_2$ (MW=412.54); mass spectroscopy: (MH+)=413.1

Step C

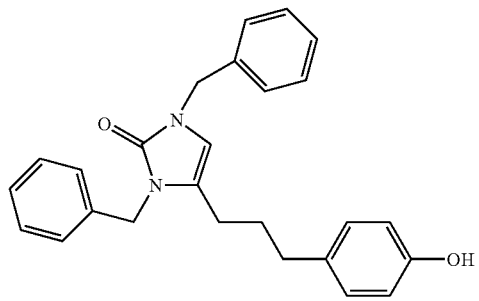

The imidazolone from Step B (0.81 g, 2.0 mmol) is dissolved in $CH_2Cl_2$ and cooled to 0° C. under an atmosphere of $N_2$. A solution of $BBr_3$ (600 μL, 6.3 mmol) in $CH_2Cl_2$ (15 mL) is added dropwise, then the reaction mixture is warmed to room temperature. After 1 hr, the solution is again cooled to 0° C. and quenched by the slow addition of a methanol (10 mL) solution in $CH_2Cl_2$ (50 mL). The resulting mixture is extracted with $H_2O$ (150 mL). The organic extract is washed with brine, dried over Na$_2$SO$_4$, and concentrated to give the desired phenol as a foam-like solid (0.78 g, 98%).

C$_{26}$H$_{26}$N$_2$O$_2$ (MW=398.51); mass spectroscopy: (MH$^+$)=399.2, (MH$^-$)=397.3

Step D

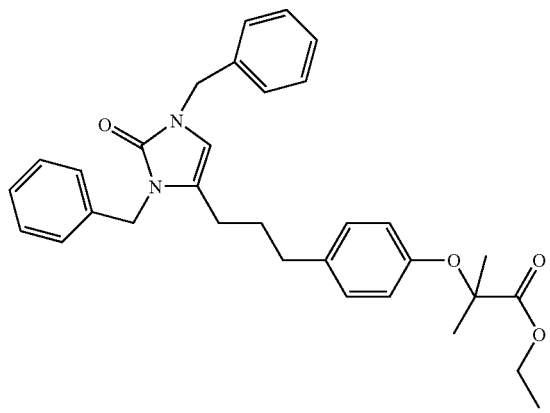

An ethanol solution (40 mL) of the phenol from Step C (0.78 g, 1.9 mmol) is treated sequentially with ethyl 2-bromoisobutyrate (1.5 mL, 10.2 mmol), K$_2$CO$_3$ (1.4 g, 10.1 nmol), and MgSO$_4$ (1.2 g, 10 mmol). The resulting mixture is heated to 50° C. for two days. The reaction is quenched by the slow addition of 1 N HCl (15 mL) then poured into 0.5 N HCl (100 mL). The resulting mixture is extracted with ethyl acetate (2×70 mL). The combined organic extracts are washed, then dried and concentrated. Purification by chromatography (gradient: 3:1 to 1:1 hexanes:ethyl acetate) gives the desired ester as a slightly yellow oil (0.79 g, 81%).

C$_{32}$H$_{36}$N$_2$O$_4$ (MW=512.65); mass spectroscopy: (MH$^+$)=513.3

Step E

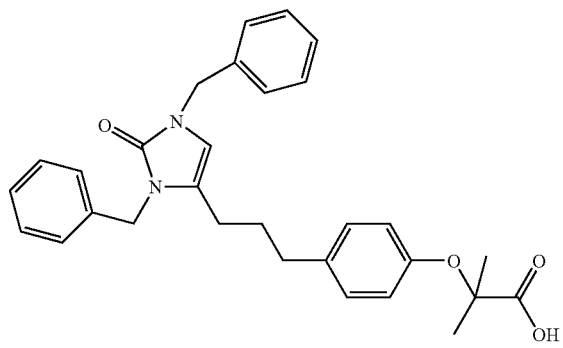

A dioxane solution (15 mL) of the ester from Step D (0.741, 1.45 mmol) is treated with an aqueous solution (5 mL) of LiOH (120.4 mg, 5.0 mmol). After stirring overnight the solvent is concentrated and the resulting oil is diluted with H$_2$O (70 mL) and extracted with Et$_2$O (70 mL). The aqueous extract is acidified with 1 N HCl and extracted with ethyl acetate (2×70 mL). The combined organic extracts are washed, dried, and concentrated to give the desired carboxylic acid as a slightly yellow foam-like solid (0.601 g, 86%)

C$_{30}$H$_{32}$N$_2$O$_4$ (MW=484.60); mass spectroscopy: (MH$^+$)=485.3, (MH$^-$)=483.3

Example 27

3-{4-[2-(1-Benzyl-3-methyl-2-oxo-imidazolidin-4-yl)-ethoxy]-phenyl}-2-(2-fluoro-phenoxy)-2-methyl-propionic acid

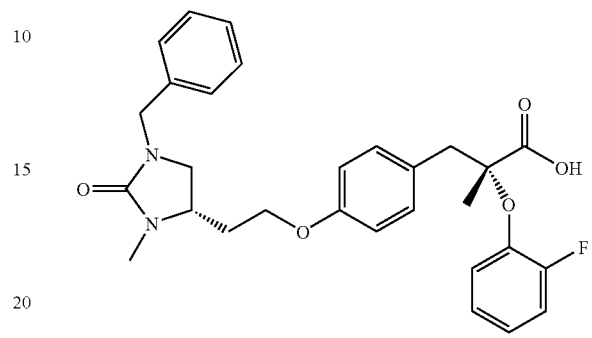

Step A

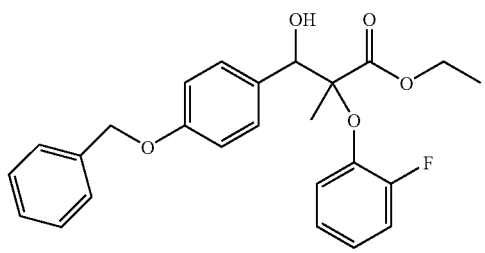

2-(2-Fluoro-phenoxy)-propionic acid ethyl ester: Cesium carbonate (65.69 g, 201.61 mmol) is added to a solution of 2-fluorophenol (9 mL, 100.84 mmol, d=1.256) in anhydrous DMF (300 mL) at room temperature under an atmosphere of nitrogen. After five minutes, ethyl 2-bromopropionate (130.1 mL, 100.84 mmol, d=1.394) is added rapidly dropwise and the resultant mixture is allowed to stir at 90° C. for 18 h. The reaction mixture is diluted with diethyl ether, then extracted twice with 1N HCl and twice with water. The organic layer is dried, concentrated, and purified by flash chromatography (25% ether in hexanes) to provide the titled compound (20.14 g, 94%). $^1$H NMR (400 MHz, CDCl$_3$): □. 7.07-6.96 (m 2H), 6.93-6.87 (m, 2H), 4.73, 4.71 (AB$_q$, 1H, J=6.7 Hz). 4.21-4.15 (m, 2H), 1.61 (d, 3H, J=6.7 Hz), 1.21 (t, 3H, J=6.7 Hz). MS [EI+] 507 (M+H)$^+$.

R$_f$=0.39 in 20% acetone in hexanes.

Step B

3-(4-Benzyloxy-phenyl)-2-(2-fluoro-phenoxy)-3-hydroxy-2-methyl-propionic acid ethyl ester:

A solution of LDA (49.6 mL, 99.15 mmol, 2M in cyclohexane) in anhydrous THF (150 mL) is cooled to −78° C. in a dry ice/acetone bath and added to a solution of 2-(2-Fluoro-phenoxy)-propionic acid ethyl ester in anhydrous THF (150 mL) also cooled to −78° C. under an atmosphere of nitrogen. After five minutes, 4-benzyloxybenzaldehyde (10.52 g, 99.15 mmol) is added in one portion. After stirring for one minute, the reaction mixture is quenched with acetic acid (9.5 mL, 165.3 mmol, d=1.049) and a saturated solution of aqueous NH$_4$Cl (100 mL). The biphasic mixture is allowed to warm to room temperature and is diluted with diethyl ether (1 L). The organic layer is washed, dried, and concentrated. The residue is purified by flash chromatography (20% acetone in hexanes) to provide a mixture of diastereomers of 3-(4-Benzyloxy-phenyl)-2-(2-fluoro-phenoxy)-3-hydroxy-2-methyl-propionic acid ethyl ester (16.21 g, 69%). $^1$H NMR (400 MHz, CDCl$_3$): δ 7.45-7.33 (m, 7H), 7.09-6.95 (m, 6H), 5.07 (s, 2H), 4.21-4.17 (m, 2H), 3.10 (d, 1H, J=5.4 Hz), 1.39 (s, 3H), 1.20 (t, 3H, J=6.1 Hz) R$_f$=0.06 in 25% acetone in hexanes.

Step C

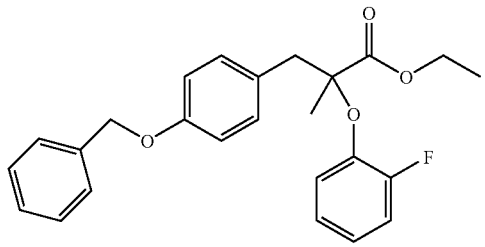

3-(4-Benzyloxy-phenyl)-2-(2-fluoro-phenoxy)-2-methyl-propionic acid ethyl ester:

Boron trifluoride etherate (21.62 mL, 171.85 mmol, d=1.128) is added dropwise rapidly to a 0° C. solution of 3-(4-Benzyloxy-phenyl)-2-(2-fluoro-phenoxy)-2-methyl-propionic acid ethyl ester (16.21 g, 38.19 mmol) and triethylsilane (27.45 mL, 171.85 nmol, d=0.728) in anhydrous CH$_2$Cl$_2$ (150 mL). The mixture is stirred for 90 minutes, gradually warming to ambient temperature. The reaction mixture is quenched with a saturated solution of aqueous sodium carbonate and extracted with CH$_2$Cl$_2$. The organic layer is dried over MgSO$_4$, concentrated in vacuo, and purified by flash chromatography (20% acetone in hexanes) to provide the titled compound (12.8 g, 82%). $^1$H NMR (400 MHz, CDCl$_3$): δ 7.46 (d, 2H, J=6.7 Hz), 7.42 (d, 2H, J=6.7 Hz), 7.39-7.33 (m, 1H), 7.26 (d, 2H, J=8.2 Hz), 7.11-7.06 (m, 1H), 7.01-6.93 (m, 5H), 4.23 (q, 2H, J=7.2 Hz), 3.31, 3.21 (AB$_q$, 2H, J=13.4 Hz), 1.45 (s, 3H), 1.26 (t, 3H, J=7.2 Hz). R$_f$=0.25 in 20% acetone in hexanes.

Step D

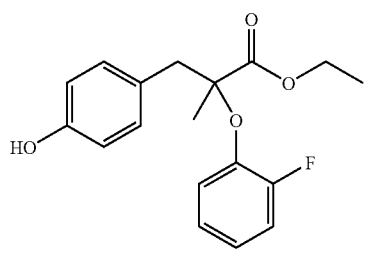

2-(2-Fluoro-phenoxy)-3-(4-hydroxy-phenyl)-2-methyl-propionic acid ethyl ester:

3-(4-Benzyloxy-phenyl)-2-(2-fluoro-phenoxy)-2-methyl-propionic acid ethyl ester (12.8 g, 31.34 mmol) is dissolved in ethanol (500 mL), treated with 10% palladium on carbon (6.0 g), and stirred under an atmosphere of hydrogen for 90 minutes. The suspension is filtered through celite and concentrated to provide 2-(2-Fluoro-phenoxy)-3-(4-hydroxy-phenyl)-2-methyl-propionic acid ethyl ester (9.65 g, 97%). The title compound is separated by chiral chromatography (Column OJ, 40% IPA in heptane, 1 mL/mmin, 240 nm UV. $^1$H NMR (400 MHz, CDCl$_3$): δ 7.13 (d, 2H, J=8.0 Hz), 7.07-7.02 (m, 1H), 6.98-6.88 (m, 3H), 6.74 (d, 2H, J=8.0 Hz), 6.05 (s, 1H), 4.20 (q, 2H, J=6.9 Hz), 3.24, 3.16 (AB$_q$, 2H, J=13.4 Hz), 1.39 (s, 3H), 1.23 (t, 3H, J=6.8 Hz).

Step E

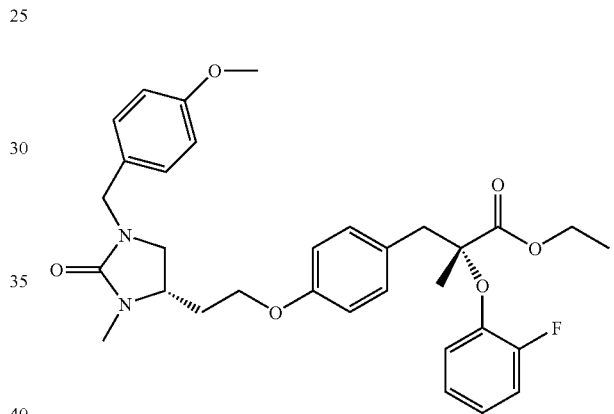

2-(2-Fluoro-phenoxy)-3(4-{2-[1-(4-methoxy-benzyl)-3-methyl-2-oxo-imidazolidin-4-yl]-ethoxy}-phenyl)-2-methyl-propionic acid ethyl ester:

Cesium carbonate (8.23 g, 25.3 nmol) is added to a solution of 2-(2-Fluoro-phenoxy)-3-(4-hydroxy-phenyl)-2-methyl-propionic acid ethyl ester (2.68 g, 8.43 mmol) and toluene-4-sulfonic acid 2-[1-(4-methoxy-benzyl)-3-methyl-2-oxo-imidazolidin-4-yl]-ethyl ester (3.88 g, 9.27 mmol) in DMF (30 mL). The resultant mixture is stirred at 65° C. under an atmosphere of nitrogen for 18 h, then diluted with ethyl acetate. The organic layer is washed with 1N HCl, water, and brine. The organic layer is dried, concentrated in vacuo, and purified by flash chromatography (17% acetone in hexanes) to provide the title compound (4.4 g, 93%). $^1$H NMR 400 MHz, CDCl$_3$): δ 7.19-7.15 (m, 4H), 7.06-7.01 (m, 1H), 6.97-6.87 (m, 3H), 6.83 (d, 2H, J=8.6 Hz), 6.74 (d, 2H, J=8.6 Hz), 4.31, 4.27 (AB$_q$ 2H, J=14.8 Hz), 4.21, 4.17 (AB$_q$, 2H, J=7.2 Hz), 3.96-3.92 (m, 2H), 3.76 (s, 3H), 3.60-3.53 (m, 1H), 3.33 (t, 1H, J=8.6 Hz), 3.25, 3.13 (AB$_q$ 2H, J=13.8 Hz), 2.994-2.83 (m, 2H), 2.82 (s, 3H), 2.24-2.16 (m, 1H), 1.89-1.80 (m, 1H), 1.37 (s, 3H), 1.22 (t, 3H, J=7.2 Hz). MS [EI+] 565 (M+H)+. $R_f$=0.56 in 50% acetone in hexanes.

Step F

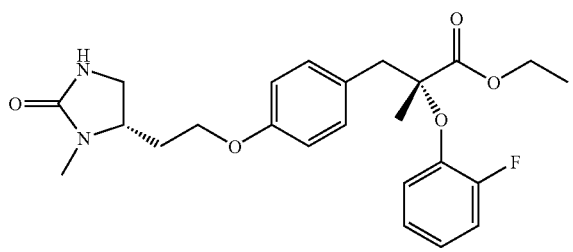

2-(2-Fluoro-phenoxy)-2-methyl-3-{4-[2-(3-methyl-2-oxo-imidazolidin-4-yl)-ethoxy]-phenyl}-propionic acid ethyl ester: Trifluoroacetic acid (70 mL) is added dropwise to a solution of triethylsilane (2.5 mL, 15.73 mmol, d=0.728) and 2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid ethyl ester (4.44 g, 7.86 mmol). The reaction mixture is stirred 2 h, then concentrated in vacuo. The residue is diluted with ethyl acetate, then washed with a saturated solution of aqueous sodium carbonate, water, and brine. The organic layer is dried and concentrated to provide the title compound (3.5 g, 100%). $^1$H NMR (400 MHz, CDCl$_3$): δ 7.20 (d, 2H, J=8.7 Hz), 7.06-7.01 (m, 1H), 6.97-6.87 (m, 3H), 6.79 (d, 2H, J=8.7 Hz), 5.04-4.98 (m, 1H), 4.20 (q, 2H, J=6.8 Hz), 4.02 (t, 2H, J=6.8 Hz), 3.76-3.69 (m, 1H), 3.55 (t, 1H, J=8.7 Hz), 3.26, 3.14 (AB$_q$, 2H, J=14.5 Hz), 3.21 (t, 1H, J=8.7 Hz), 2.78 (s, 3H), 2.27-2.20 (m, 1H), 1.99-1.90 (m, 1H), 1.38 (s, 3H), 1.23 (t, 3H, J=6.8 Hz), 0.96 (t, 2H, J=7.7 Hz). MS [EI+] 445 (M+H)+. $R_f$=0.50 in 10% methanol in methylene chloride.

Step G

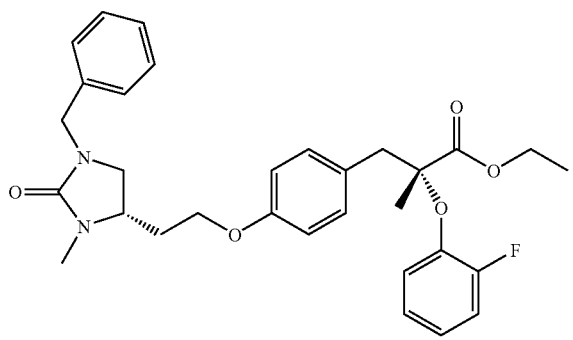

3-{4-[2-(1-Benzyl-3-methyl-2-oxo-imidazolidin-4-yl)-ethoxy]-phenyl}-2-(2-fluoro-phenoxy)-2-methyl-propionic acid ethyl ester: Benzyl bromide (0.02 mL, 0.172 mmol, d=1.438) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.051 g, 0.115 mmol) and sodium hydride (0.011 g, 0.287 mmol, 60% suspension on mineral oil), pre-stirred for 1 h at ambient temperature. The reaction mixture is stirred at ambient temperature for 18 h, diluted with ethyl acetate, and washed with 1N HCl, water, and brine. The organic layer is dried and concentrated in vacuo to provide the title compound, which is used in the next step. MS [EI+] 535 (M+H)+.

Step H

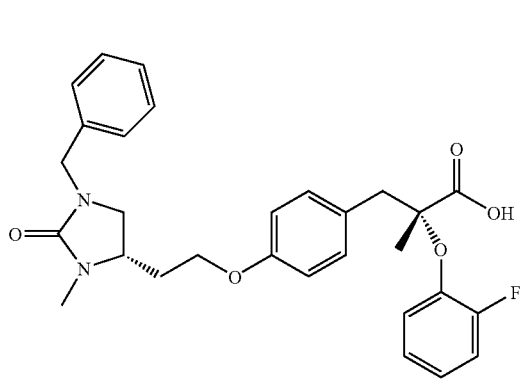

3-{4-[2-(1-Benzyl-3-methyl-2-oxo-imidazolidin-4-yl)-ethoxy]-phenyl}-2-(2-fluoro-phenoxy)-2-methyl-propionic acid: A solution of 3-{4-[2-(1-Benzyl-3-methyl-2-oxo-imidazolidin-4-yl)-ethoxy]-phenyl}-2-(2-fluoro-phenoxy)-2-methyl-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with CH$_2$Cl$_2$, dried, concentrated in vacuo, and purified by LCMS to provide the title compound. $^1$H NMR (400 MHz, CDCl$_3$): δ 7.55 (d, 1H, J=8.4 Hz), 7.34-7.21 (m, 6H), 7.10-7.01 (m, 4H), 6.74 (d, 2H, J=8.4 Hz), 4.46-3.36 (m, 2H), 3.96 (q, 2H, J=6.0 Hz), 3.74-3.65 (m, 1H), 3.45-3.39 (m, 1H), 3.28, 3.16 (AB$_q$, 2H, J=14.7 Hz), 3.05 (q, 1H, J=8.6 Hz), 2.26-2.19 (m, 1H), 1.93-1.86 (m, 1H), 1.41 (s, 3H). MS [EI+] 507 (M+H)+.

Example 28

3-(4-{2-[1-(4-Chloro-benzyl)-3-methyl-2-oxo-imidazolidin-4-yl]-ethoxy}-phenyl)-2-(2-fluoro-phenoxy)-2-methyl-propionic acid

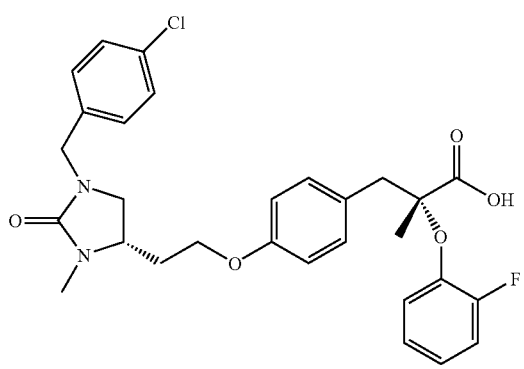

4-Chlorobenzyl bromide (0.037 g, 0.179 mmol) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.053 g, 0.119 mmol) and sodium hydride (0.012 g, 0.298 mmol, 60% suspension on mineral oil), pre-stirred for 1 h at ambient temperature. The reaction mixture is stirred at ambient temperature for 18 h, diluted with ethyl acetate, and washed. The organic layer is dried, concentrated, and purified by LCMS to provide the title compound. $^1$H NMR (400 MHz, CDCl$_3$): δ 7.31-7.21 (m, 4H), 7.16 (d, 2H, J=8.3 Hz), 7.11-7.00 (m, 4H), 6.74 (d, 2H, J=8.3 Hz), 4.33, 4.31 (AB$_q$, 2H, J=15.5 Hz), 3.96 (t, 2H, J=6.0 Hz), 3.71-3.64 (m, 1H), 3.39 (t, 1H, J=8.3 Hz), 3.29, 3.17 (AB$_q$, 2H, J=14.3 Hz), 3.01 (t, 1H, J=8.3 Hz), 2.84 (s, 3H), 2.25-2.20 (m, 1H), 1.93-1.84 (m, 1H), 1.41 (s, 3H). MS [ES+] m/z exact mass calcd for C$_{29}$H$_{31}$N$_2$O$_5$ 541.1906, found 541.1913.

Example 29

2-(2-Fluoro-phenoxy)-2-methyl-3-(4-{2-[3-methyl-2-oxo-1-(4-trifluoromethyl-benzyl)-imidazolidin-4-yl]-ethoxy}-phenyl)-propionic acid

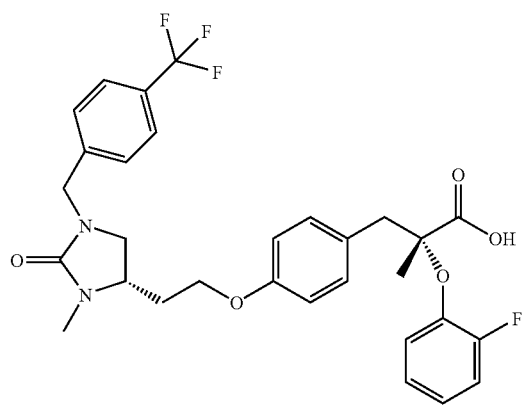

4-Trifluoromethylbenzyl bromide (0.03 mL, 0.169 mmol, d=1.546) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.050 g, 0.112 mmol) and sodium hydride (0.011 g, 0.281 mmol, 60% suspension on mineral oil), and pre-stirred for 1 h at ambient temperature. The reaction mixture is stirred at ambient temperature for 18 h, diluted with ethyl acetate, and washed with 1N HCl, water, and brine. The organic layer is dried, concentrated, and purified by LCMS. $^1$H NMR (400 MHz, CDCl$_3$): δ 7.54 (d, 1H, J=7.8 Hz), 7.35 (d, 1H, J=7.8 Hz), 7.25-7.21 (m, 3H), 7.16 (d, 1H, J=7.8 Hz), 7.08-6.95 (m, 4H), 6.73 (d, 2H, J=7.8 Hz), 4.45, 4.37 (AB$_q$, 2H, L=15.0 Hz), 3.95 (t, 2H, J=5.9 Hz), 3.68-3.60 (m, 1H), 3.38 (t, 1H, J=8.5 Hz), 3.29, 3.15 (AB$_q$, 2H, J=13.7 Hz), 3.02-2.97 (m, 1H), 2.84 (s, 3H), 2.25-2.19 (m, 1H), 1.92-1.83 (m, 1H), 1.39 (s, 3H). MS [ES+] m/z exact mass calcd for C$_{30}$H$_{31}$N$_2$O$_5$F$_4$ 575.2169, found 575.2172.

Example 30

2-(2-Fluoro-phenoxy)-2-methyl-3(4-{2-[3-methyl-2-oxo-1-(3-trifluoromethyl-benzyl)-imidazolidin-4-yl]-ethoxy}-phenyl)-propionic acid Step A

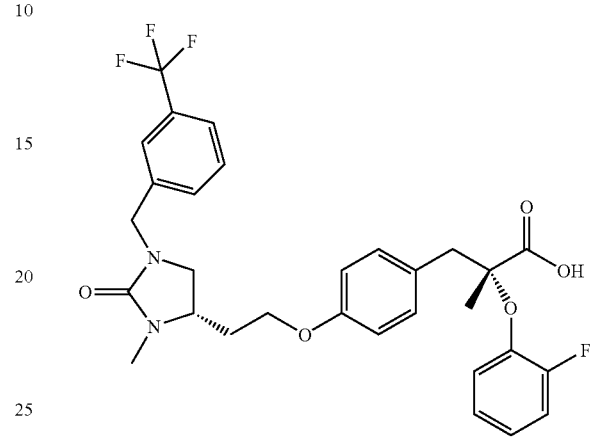

2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid ethyl ester: 3-Trifluoromethylbenzyl bromide (0.03 mL, 0.175 mmol, d=1.565) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.052 g, 0.117 mmol) and sodium hydride (0.012 g, 0.292 mmol, 60% suspension on mineral oil), and pre-stirred for 1 h at ambient temperature. The reaction mixture is stirred at ambient temperature for 18 h, diluted with ethyl acetate, and washed with 1N HCl, water, and brine. The organic layer is dried, concentrated, and carried into the next step. MS [EI+] 603 (M+H)$^+$.

Step B

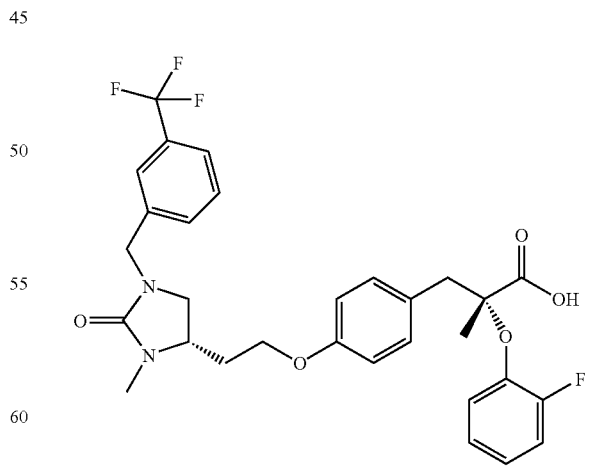

2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid: A solution of 2-(2-Fluoro-phenoxy)-2-methyl-3-(4-{2-[3-methyl-2-oxo-1-(3- trifluoromethyl-benzyl)-imidazolidin-4-yl]-ethoxy}-phenyl)-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with CH$_2$Cl$_2$, dried, concentrated in vacuo, and purified by LCMS to provide the title compound. $^1$H NMR (400 MHz, CDCl$_3$): δ 7.53-7.42 (m, 2H), 7.29-6.93 (m, 7H), 6.85-6.73 (m, 3H), 4.49-4.29 (m, 2H), 3.99-3.95 (m, 2H), 3.81-3.68 (m, 1H), 3.46-3.41 (m, 1H), 3.28, 3.16 (AB$_q$, 2H, J=13.7 Hz), 3.09-3.04 (m, 1H), 2.86 (d, 3H, J=5.6 Hz), 2.25-2.21 (m, 1H), 1.93-1.87 (m, 1H), 1.40 (s, 3H). MS [ES+] m/z exact mass calcd for C$_{30}$H$_{31}$N$_2$O$_5$F$_4$ 575.2169, found 575.2156.

Example 31

2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid Step A

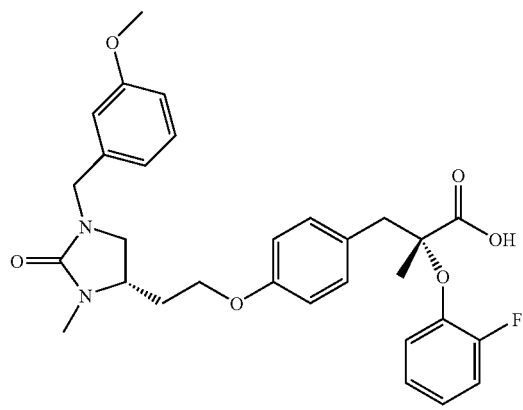

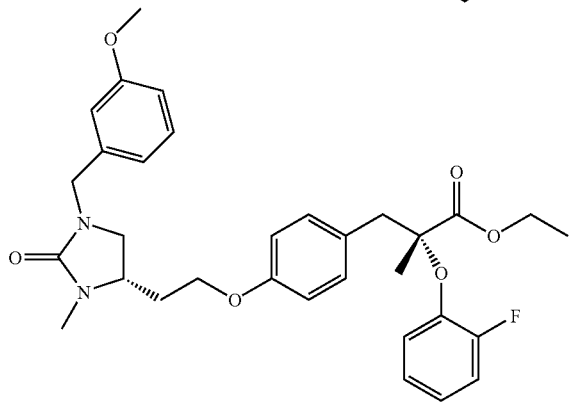

2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester: 3-Methoxybenzyl bromide (0.02 mL, 0.172 mmol, d=1.436) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.051 g, 0.115 mmol) and sodium hydride (0.011 g, 0.287 mmol, 60% suspension on mineral oil), and pre-stirred for 1 h at ambient temperature. The reaction mixture is stirred at ambient temperature for 18 h, diluted with ethyl acetate, and washed with 1N HCl, water, and brine. The organic layer is dried over MgSO$_4$, concentrated in vacuo, and carried into the next step. MS [EI+] 565 (M+H)$^+$.

Step B

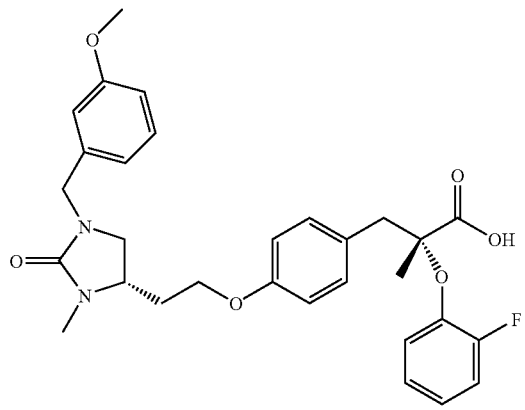

2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester: A solution of 2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester and 5N NaOH (0.2 mL) in ethanol (2 mL) is refluxed under nitrogen for 1 h, cooled to ambient temperature, and concentrated. The residue is diluted with 1N HCl, extracted with CH$_2$Cl$_2$, dried, concentrated, and purified by LCMS to provide the title compound. $^1$H NMR (400 MHz, CDCl$_3$): δ 7.33-7.20 (m, 6H), 7.10-7.01 (m, 3H), 6.81-6.73 (m, 3H), 4.36, 4.30 (AB$_q$, 2H, J=14.9 Hz), 3.95 (t, 2H, J=6.5 Hz), 3.71-3.68 (m, 1H), 3.45-3.40 (m, 1H), 3.29, 3.17 (AB$_q$, 2H, J=14.0 Hz), 3.08-3.03 (m, 1H), 2.85 (s, 3H), 2.24-2.20 (m, 1H), 1.94-1.85 (m, 1H), 1.41 (s, 3H). MS [ES+] m/z exact mass calcd for C$_{30}$H$_{34}$N$_2$O$_6$ 537.2401, found 537.2418.

Example 32

3-{4-[2-(1-Benzyl-3-methyl-2-oxo-imidazolidin-4-yl)-ethoxy]-phenyl}-2-(2-fluoro-phenoxy)-2-methyl-propionic acid Step A

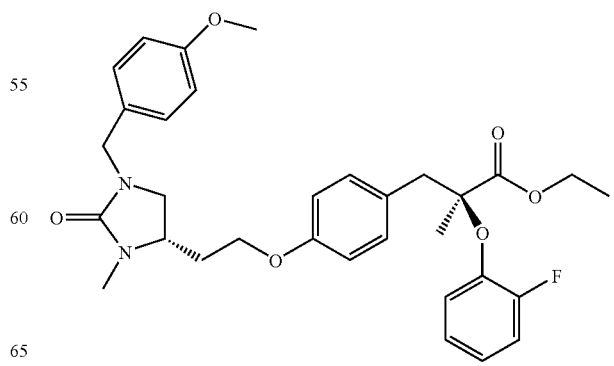

2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid ethyl ester Cesium carbonate (6.12 g, 18.76 nmol) is added to a solution of 2-(2-Fluoro-phenoxy)-3-(4-hydroxy-phenyl)-2-methyl-propionic acid ethyl ester 1.99 g, 6.26 mmol) and toluene-4-sulfonic acid 2-[1-(4-methoxy-benzyl)-3-methyl-2-oxo-imidazolidin-4-yl]-ethyl ester (2.88 g, 6.88 mmol) in DMF (20 mL). The resultant mixture is stirred at 65° C. under an atmosphere of nitrogen for 18 h, then diluted with ethyl acetate. The organic layer is washed with 1N HCl, water, and brine. The organic layer is dried over MgSO$_4$, concentrated in vacuo, and purified by flash column chromatography (17% acetone in hexanes) to provide the title compound (3.4 g, 97%). $^1$H NMR (400 MHz, CDCl$_3$): δ 7.19 (d, 2H, J=5.4 Hz), 7.17 (d, 2H, J=5.4 Hz), 7.07-7.01 (m, 1H), 6.97-6.87 (m, 3H), 6.83 (d, 2H, J=8.6 Hz), 6.74 (d, 2H, J=8.6 Hz), 4.32, 4.28 (AB$_q$, 2H, J=14.6 Hz), 4.20 (q, 2H, J=7.5 Hz), 3.94 (t, 2H, J=5.9 Hz), 3.77 (s, 3H), 3.60-3.53 (m, 1H), 3.33 (t, 1H, J=8.6 Hz), 3.26, 3.14 (AB$_q$, 2H, J=14.0 Hz), 2.92 (t, 1 h, J=8.6 Hz), 2.82 (s, 3H), 2.24-2.17 (m, 1H), 1.89-1.82 (m, 1H), 1.38 (s, 3H), 1.23 (t, 3H, J=7.5 Hz). MS [EI+] 565 (M+H)$^+$. R$_f$=0.48 in 50% acetone in hexanes.

Step B

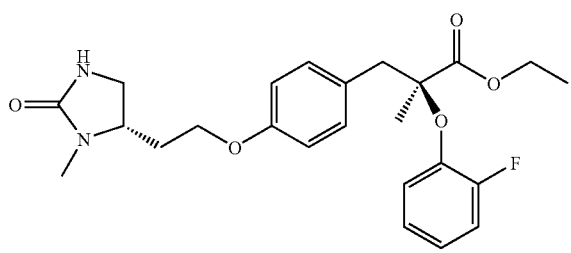

2-(2-Fluoro-phenoxy)-2-methyl-3-{4-[2-(3-methyl-2-oxo-imidazolidin-4-yl)-ethoxy]-phenyl}-propionic acid ethyl ester: Trifluoroacetic acid (55 mL) is added dropwise to a solution of triethylsilane (1.95 mL, 12.18 mmol, d=0.728) and 2-(2-Fluoro-phenoxy)-3-(4-{2-[1-(4-methoxy-benzyl)-3-methyl-2-oxo-imidazolidin-4-yl]-ethoxy}-phenyl)-2-methyl-propionic acid ethyl ester (3.44 g, 6.09 mmol). The reaction mixture is stirred under nitrogen at ambient temperature for 2 h, then concentrated. The residue is diluted with ethyl acetate, then washed. The organic layer is dried and concentrated in vacuo to provide the title compound (2.7 g, 78%). $^1$H NMR (400 MHz, CDCl$_3$): δ 7.20 (d, 2H, J=8.7 Hz), 7.06-7.01 (m, 1H), 6.97-6.87 (m, 3H), 6.79 (d, 2H, J=8.7 Hz), 5.04-4.98 (m, 1H), 4.20 (q, 2H, J=6.8 Hz), 4.02 (t, 2H, J=6.8 Hz), 3.76-3.69 (m, 1H), 3.55 (t, 1H, J=8.7 Hz), 3.26, 3.14 (AB$_q$, 2H, J=14.5 Hz), 3.21 (t, 1H, J=8.7 Hz), 2.78 (s, 3H), 2.27-2.20 (m, 1H), 1.99-1.90 (m, 1H), 1.38 (s, 3H), 1.23 (t, 3H, J=6.8 Hz), 0.96 (t, 2H, J=7.7 Hz). MS [EI+] 445 (M+H)$^+$.

R$_f$=0.38 in 10% methanol in methylene chloride.

Step C

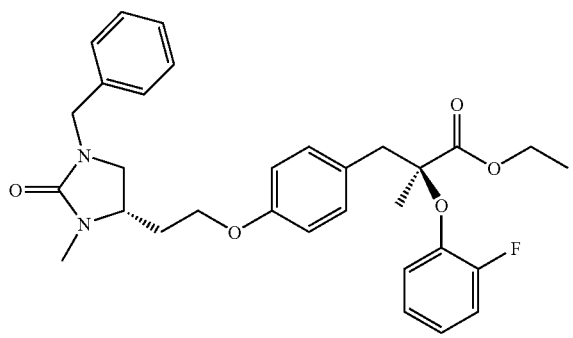

3-{4-[2-(1-Benzyl-3-methyl-2-oxo-imidazolidin-4-yl)-ethoxy]-phenyl}-2-(2-fluoro-phenoxy)-2-methyl-propionic acid ethyl ester Benzyl bromide (0.02 mL, 0.179 mmol, d=1.438) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.053 g, 0.119 mmol) and sodium hydride (0.012 g, 0.298 mmol, 60% suspension on mineral oil), pre-stirred for 1 h at ambient temperature. The reaction mixture is stirred at ambient temperature for 18 h, diluted with ethyl acetate, and washed with 1N HCl, water, and brine. The organic layer is dried over MgSO$_4$ and concentrated in vacuo to provide the title compound, which is carried into the next step. MS [EI+] 535 (M+H)$^+$.

Step H

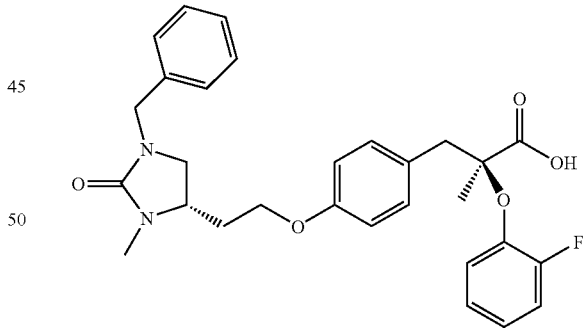

3-{4-[2-(1-Benzyl-3-methyl-2-oxo-imidazolidin-4-yl)-ethoxy]-phenyl}-2-(2-fluoro-phenoxy)-2-methyl-propionic acid: A solution of 3-{4-[2-(1-Benzyl-3-methyl-2-oxo-imidazolidin-4-yl)-ethoxy]-phenyl}-2-(2-fluoro-phenoxy)-2-methyl-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with CH$_2$Cl$_2$, dried, concentrated, and purified by LCMS to provide the title compound. $^1$H NMR (400 MHz, CDCl$_3$): δ 7.55 (d, 1H, J=8.4 Hz), 7.34-7.21 (m, 6H), 7.10-7.01 (m, 4H), 6.74 (d, 2H, J=8.4

Hz), 4.46-3.36 (m, 2H), 3.96 (q, 2H, J=6.0 Hz), 3.74-3.65 (m, 1H), 3.45-3.39 (m, 1H), 3.28, 3.16 (AB$_q$, 2H, J=14.7 Hz), 3.05 (q, 1H, J=8.6 Hz), 2.26-2.19 (m, 1H), 1.93-1.86 (m, 1H), 1.41 (s, 3H). MS [ES+] m/z exact mass calcd for $C_{29}H_{32}N_2O_5F$ 507.2295, found 507.2308.

Example 33

3-(4-{2-[1-(4-Chloro-benzyl)-3-methyl-2-oxo-imidazolidin-4-yl]-ethoxy}-phenyl)-2-(2-fluoro-phenoxy)-2-methyl-propionic acid

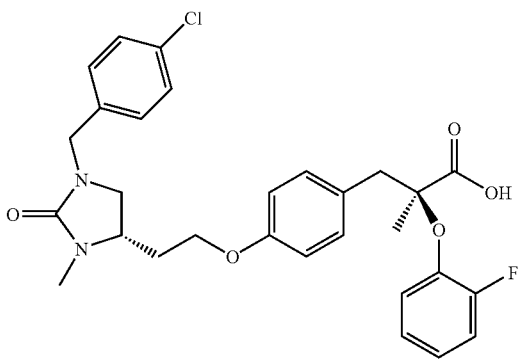

4-Chlorobenzyl bromide (0.035 g, 0.172 mmol) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.051 g, 0.115 mmol) and sodium hydride (0.011 g, 0.287 mmol, 60% suspension on mineral oil), pre-stirred for 1 h at ambient temperature. The reaction mixture is stirred at ambient temperature for 18 h, diluted with ethyl acetate, and washed. The organic layer is dried, concentrated, and purified by LCMS to provide the title compound. $^1$H NMR (400 MHz, CDCl$_3$): δ 7.31-7.22 (m, 5H), 7.15-7.01 (m, 5H), 6.74 (d, 2H, J=7.8 Hz), 4.34 (d, 2H, J=14.3 Hz), 3.96 (s, 2H), 3.73-3.71 (m, 1H), 3.46-3.40 (m, 1H), 3.28, 3.16 (AB$_q$, 2H, J=14.3 Hz), 3.08-3.06 (m, 1H), 2.85 (s, 3H), 2.23-2.20 (m, 1H), 1.91-1.89 (m, 1H), 1.41 (s, 3H). MS [ES+] m/z exact mass calcd for $C_{29}H_{31}N_2O_5FCl$ 541.1906, found 541.1909.

Example 34

2-(2-Fluoro-phenoxy)-2-methyl-3-(4-{2-[3-methyl-2-oxo-1-(4-trifluoromethyl-benzyl)-imidazolidin-4-yl]-ethoxy}-phenyl)-propionic acid

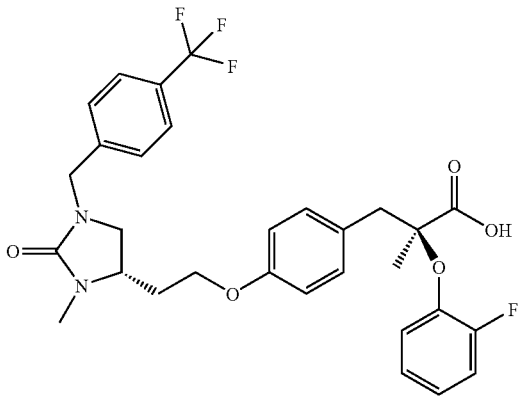

Step A

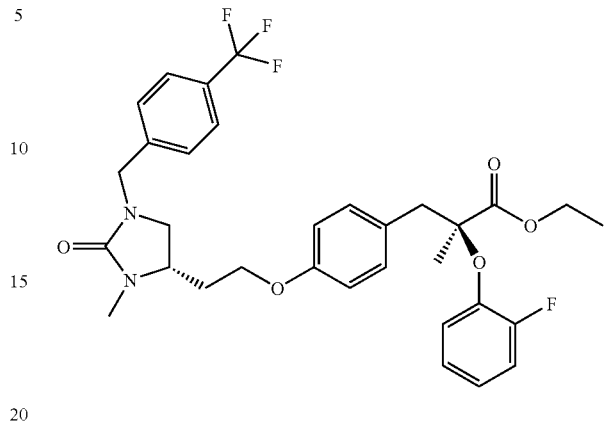

2-(2-Fluoro-phenoxy)-2-methyl-3-(4-{2-[3-methyl-2-oxo-1-(4-trifluoromethyl-benzyl)-imidazolidin-4-yl]-ethoxy}-phenyl)-propionic acid ethyl ester: 4-Trifluoromethylbenzyl bromide (0.03 mL, 0.169 mmol, d=1.546) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.050 g, 0.113 mmol) and sodium hydride (0.011 g, 0.281 mmol, 60% suspension on mineral oil), and pre-stirred for 1 h at ambient temperature. The reaction mixture is stirred at ambient temperature for 18 h, diluted with ethyl acetate, and washed with 1N HCl, water, and brine. The organic layer is dried, concentrated, and carried into the next step. MS [EI+] 603 (M+H)$^+$.

Step B

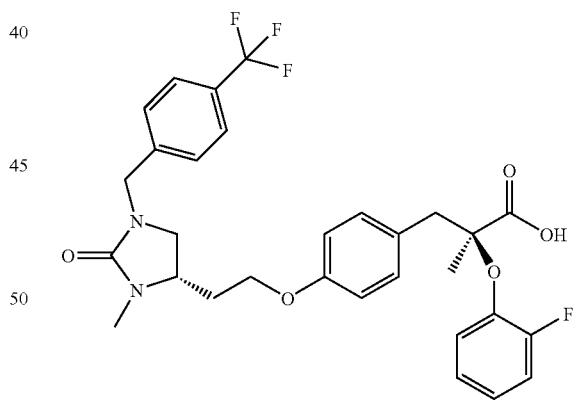

2-(2-Fluoro-phenoxy)-2-methyl-3-(4-{2-[3-methyl-2-oxo-1-(4-trifluoromethyl-benzyl)-imidazolidin-4-yl]-ethoxy}-phenyl)-propionic acid: A solution of 2-(2-Fluoro-phenoxy)-2-methyl-3-(4-{2-[3-methyl-2-oxo-1-(4-trifluoromethyl-benzyl)-imidazolidin-4-yl]-ethoxy}-phenyl)-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with CH$_2$Cl$_2$, dried, concentrated, and purified by LCMS to provide the title compound. $^1$H NMR (400 MHz, CDCl$_3$): δ 7.56-7.51 (m 1H), 7.48-7.33 (m, 2H), 7.26-7.21 (m, 3H), 7.11-6.98 (m, 4H), 6.74 (d, 2H, J=8.4 Hz), 4.49-4.34 (m, 2H), 3.98 (t, 2H, J=5.3 Hz), 3.74-3.67 (m, 1H), 3.42 (t, 1H, J=8.4 Hz), 3.35, 3.23 (AB$_q$, 2H, J=14.5 Hz), 3.08-3.03 (m, 1H), 2.86 (s, 3H), 2.27-2.20 (m, 1H), 1.95-1.88 (m, 1H), 1.42 (s, 3H). MS [ES+] m/z exact mass calc'd for $C_{30}H_{31}N_2O_5F_4$ 575.2169, found 575.2175.

Example 35

2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid

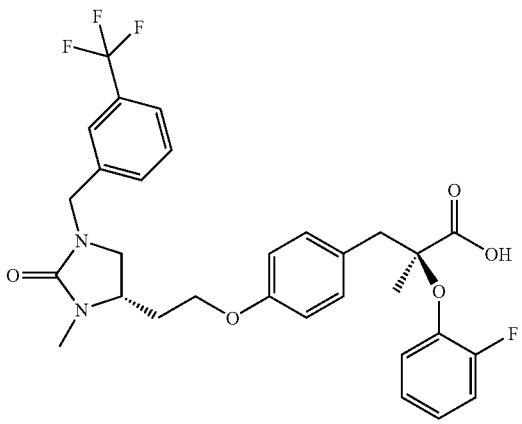

Step A 2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid ethyl ester: 3-Trifluoromethylbenzyl bromide (0.03 mL, 0.165 mmol, d=1.565) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.049 g, 0.110 mmol) and sodium hydride (0.011 g, 0.276 mmol, 60% suspension on mineral oil), pre-stirred for 1 h at ambient temperature. The reaction mixture is stirred at ambient temperature for 18 h, diluted with ethyl acetate, and washed. The organic layer is dried, concentrated, and carried into the next step. MS [EI+] 603 (M+H)$^+$.

Step B

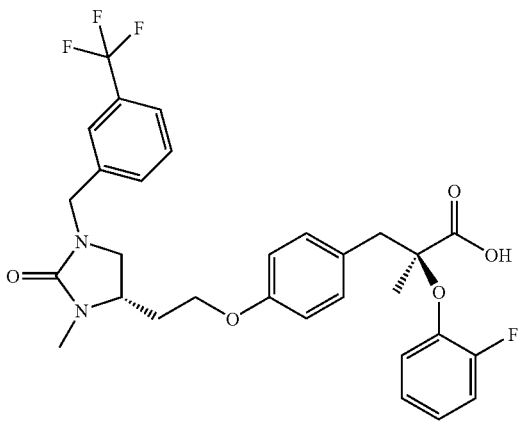

2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid ethyl ester: A solution of 2-(2-Fluoro-phenoxy)-2-methyl-3-(4-{2-[3-methyl-2-oxo-1-(3-trifluoromethyl-benzyl)-imidazolidin-4-yl]-ethoxy}-phenyl)-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with $CH_2Cl_2$, dried, concentrated, and purified by LCMS to provide the title compound. $^1$H NMR (400 MHz, CDCl$_3$): δ 7.51-7.41 (m, 2H), 7.28-7.19 (m, 3H), 7.09-6.99 (m, 4H), 6.81-6.73 (m, 3H), 4.48-4.28 (m, 2H), 3.98-3.94 (m, 2H), 3.73-3.65 (m, 1H), 3.42 (t, 1H, J=8.7 Hz), 3.29, 3.15 (AB$_q$, 2H, J=13.6 Hz), 3.06-3.01 (m, 1H), 2.85 (d, 3H, J=5.6 Hz), 2.25-2.21 (m, 1H), 1.93-1.87 (m, 1H), 1.40 (s, 3H). MS [ES+] m/z exact mass calcd for $C_{30}H_{31}N_2O_5F_4$ 575.2169, found 575.2172.

Example 36

2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester

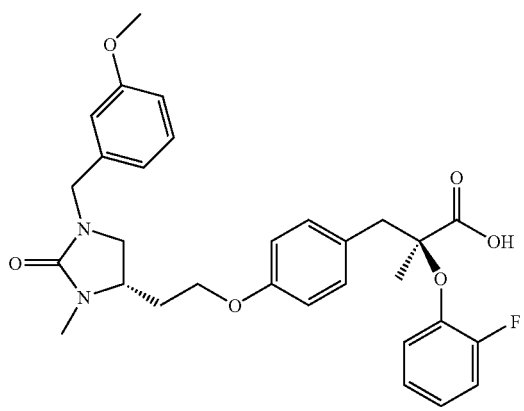

Step A 2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester: 3-Methoxybenzyl bromide (0.03 mL, 0.179 mmol, d=1.436) and tetrabutyl ammonium iodide (catalytic amount) are added to a 0° C. suspension of 2-(2-Fluoro-phenoxy)-2-methyl-3-{4-[2-(3-methyl-2-oxo-imidazolidin-4-yl)-ethoxy]-phenyl}-propionic acid ethyl ester (0.053 g, 0.119 mmol) and sodium hydride (0.012 g, 0.298 mmol, 60% suspension on mineral oil), and pre-stirred for 1 h at ambient temperature. The reaction mixture is stirred at ambient temperature for 18 h, diluted with ethyl acetate, and washed. The organic layer is dried, concentrated, and carried into the next step. MS [EI+] 565 (M+H)$^+$.

Step B

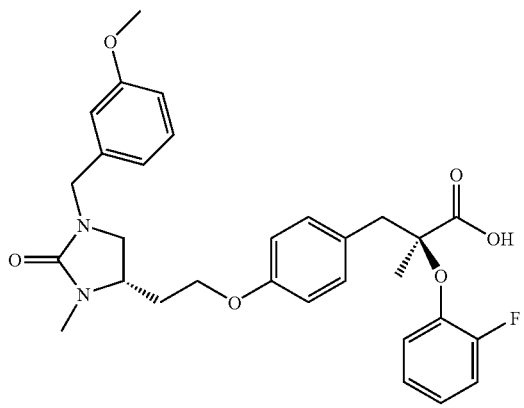

2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester: A solution of 2-(2-Fluoro-phenoxy)-3-(4-{2-[1-(3-methoxy-benzyl)-3-methyl-2-oxo-imidazolidin-4-yl]-ethoxy}-phenyl)-2-methyl-propionic acid ethyl ester and 5N NaOH (0.2 mL) in ethanol (2 mL) is refluxed under nitrogen for 1 h, cooled to ambient temperature, and concentrated in vacuo. The residue is diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$): δ 7.26-7.19 (m, 3H), 7.08-6.99 (m, 4H), 6.83-6.78 (m, 3H), 6.74 (d, 2H, J=8.4 Hz), 4.36, 4.30 ($AB_q$, 2H, J=14.9 Hz), 3.95 (t, 2H, J=6.5 Hz), 3.77 (s, 3H), 3.65-3.58 (m, 1H), 3.37 (t, 1H, J=8.8 Hz), 3.28, 3.16 ($AB_q$, 2H, J=14.4 Hz), 2.97 (t, 1H, J=8.8 Hz), 2.83 (s, 3H), 2.25-2.17 (m, 1H), 1.92-1.83 (m, 1H), 1.40 (s, 3H). MS [ES$^+$] m/z exact mass calcd for $C_{30}H_{34}N_2O_6F$ 537.2401, found 537.2413.

Example 37

3-{4-[2-(1-Benzyl-3-methyl-2-oxo-imidazolidin-4-yl)-ethoxy]-phenyl}-2-butoxy-2-methyl-propionic acid

Step A

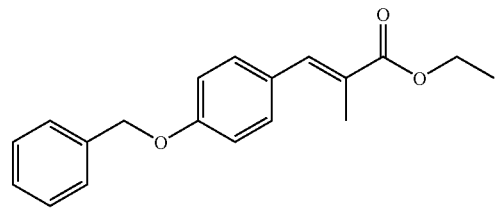

3-(4-Benzyloxy-phenyl)-2-methyl-acrylic acid ethyl ester: Triethyl-2-phosphonopropionate (22.2 mL, 103.65 mmol, d=1.111) is added to a 0° C. slurry of sodium hydride (4.15 g, 103.65 µmmol, 60% dispersion on mineral oil) in anhydrous THF (150 mL), then allowed to warm to ambient temperature over thirty minutes. The slurry is re-cooled to 0° C. and 4-benzyloxybenzaldehyde (20 g, 94.23 mmol) is added in one portion as a solid. The reaction mixture is stirred 18 h at ambient temperature, then diluted with diethyl ether. The organic layer is washed with a saturated solution of aqueous ammonium chloride, water, and brine, then dried over $MgSO_4$ and concentrated in vacuo. The residue is purified by flash chromatography to provide the title compound (24.3 g, 87%). $^1$H NMR (400 MHz, $CDCl_3$): δ 7.67 (s, 1H), 7.46-7.35 (m, 6H), 7.01 (d, 2H, J=8.1 Hz), 5.10 (s, 2H), 4.28 (q, 2H, J=7.2 Hz), 2.15 (s, 3H), 1.36 (t, 3H, J=7.2 Hz). $R_f$=0.31 in 20% acetone in hexanes.

Step B

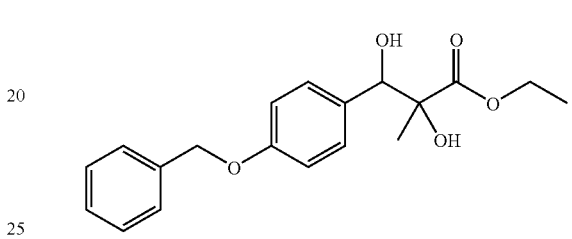

3-(4-Benzyloxy-phenyl)-2,3-dihydroxy-2-methyl-propionic acid ethyl ester: 3-(4-Benzyloxy-phenyl)-2-methyl-acrylic acid ethyl ester (13.84 g, 46.70 mmol) is added to a solution of acetone (235 mL), 4-methylmorpholine N-oxide (6.02 g, 51.37 mmol), tert-butyl alcohol (24 mL), and 4% osmium tetroxide in water (14.7 mL), then stirred 20 h. The reaction is quenched with sodium hydrosulphite (4.7 g, 26.81 mmol), diluted with ethyl acetate, washed with water. The organic layer is dried, concentrated, and purified by flash chromatography to provide the title compound (12.9 g, 83%). $^1$H NMR (400 MHz, $CDCl_3$): δ 7.44-7.32 (m, 7H), 6.82 (d, 2H, J=9.3 Hz), 5.06 (s, 2H), 4.78 (d, 1H, J=6.0 Hz), 4.32-4.27 (m, 2H), 3.52 (s, 1H), 2.66 (d, 1H, J=7.3 Hz), 1.33 (t, 3H, J=7.3 Hz), 1.17 (s, 3H). $R_f$=0.48 in 50% acetone in hexanes.

Step C

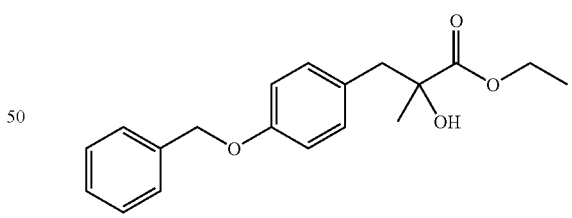

3-(4-Benzyloxy-phenyl)-2-hydroxy-2-methyl-propionic acid ethyl ester: Boron trifluoride etherate was added to a 0° C. solution of 3-(4-Benzyloxy-phenyl)-2,3-dihydroxy-2-methyl-propionic acid ethyl ester (12.9 g, 38.96 mmol) and triethylsilane (28 mL, 175.3 mmol, d=0.728) in anhydrous $CH_2Cl_2$, then the reaction is allowed to gradually warm to ambient temperature over 3 h. The reaction is quenched with a saturated aqueous solution of sodium bicarbonate and extracted with additional $CH_2Cl_2$. The organic layer is dried, concentrated, and separated by chiral chromatography to provide the title compound (11.7 g, 96%). $^1$H NMR (400 MHz, $CDCl_3$): δ 7.44-7.33 (m, 5H), 7.12 (d, 2H, J=6.85 Hz), 6.90

(d, 2H, J=6.85 Hz), 5.04 (s, 2H), 4.22-4.14 (m, 2H), 3.03 (d, 1H, J=13.69 Hz), 2.87 (d, 1H, J=13.69 Hz), 1.48 (s, 3H), 1.27 (t, 3H, J=7.34 Hz). $R_f$=0.60 in 50% acetone in hexanes.

Step D

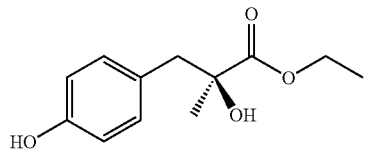

2-Hydroxy-3-(4-hydroxy-phenyl)-2-methyl-propionic acid ethyl ester: 3-(4-Benzyloxy-phenyl)-2-hydroxy-2-methyl-propionic acid ethyl ester (5.9 g, 18.77 mmol) is dissolved in ethanol (375 mL), treated with 10% palladium on carbon (2.95 g), and stirred under an atmosphere of hydrogen for 2 h. The suspension is filtered and concentrated to provide the title compound. $^1$H NMR (400 MHz, CDCl$_3$): δ 7.00 (d, 2H, J=8.3 Hz), 6.69 (d, 2H, J=8.3 Hz), 4.18-4.13 (m, 2H), 2.99, 2.83 (AB$_q$, 2H, J=13.7 Hz), 1.47 (s, 3H), 1.24 (t, 3H, J=7.34 Hz). $R_f$=0.58 in 50% acetone in hexanes.

Step E

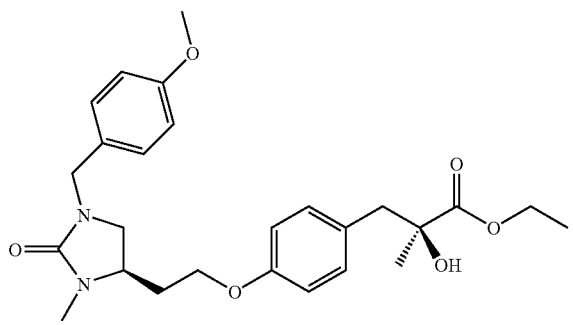

2-Hydroxy-3-(4-{2-[1-(4-methoxy-benzyl)-3-methyl-2-oxo-imidazolidin-4-yl]-ethoxy}-phenyl)-2-methyl-propionic acid ethyl ester: Cesium carbonate (21.9 g, 67.3 mmol) is added to a solution of 2-hydroxy-3-(4-{2-[1-(4-methoxy-benzyl)-3-methyl-2-oxo-imidazolidin-4-yl]-ethoxy}-phenyl)-2-methyl-propionic acid ethyl ester (5.03 g, 22.4 mmol) and toluene-4-sulfonic acid 2-[1-(4-methoxy-benzyl)-3-methyl-2-oxo-imidazolidin-4-yl]-ethyl ester (10.33 g, 24.7 mmol) in DMF (100 mL). The resultant mixture is stirred at 55° C. under an atmosphere of nitrogen for 18 h, then diluted with ethyl acetate. The organic layer is washed. The organic layer is dried, concentrated, and purified by flash chromatography to provide the title compound (735 g, 70%). $^1$H NMR (400 MHz, CDCl$_3$): δ 7.16 (d, 2H, J=8.7 Hz), 7.07 (d, 2H, J=7.9 Hz), 6.82 (d, 2H, J=7.9 Hz), 6.70 (d, 2H, J=8.7 Hz), 4.31, 4.27 (AB$_q$, 2H, J=15.1 Hz), 4.19-4.11 (m, 2H), 3.91 (t, 2H, J=7.2 Hz), 3.77 (s, 3H), 3.59-3.52 (m, 1H), 3.32 (t, 1H, J=8.7 Hz), 3.01-2.83 (m, 6H), 2.81 (s, 3H), 2.23-2.15 (m, 1H), 1.88-1.80 (m, 1H), 1.45 (s, 3H), 1.26 (t, 6H, J=6.65 Hz), 0.87 (t, 3H, J=6.5 Hz). $R_f$=0.4$^1$ in 50% acetone in hexanes.

Step F

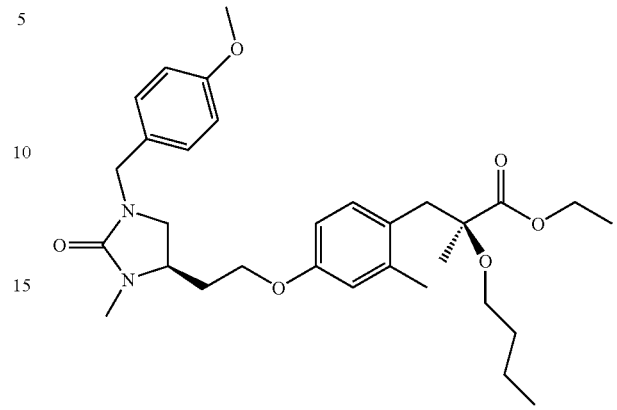

2-Butoxy-3-(4-{2-[1-(4-methoxy-benzyl)-3-methyl-2-oxo-imidazolidin-4-yl]-ethoxy}-phenyl)-2-methyl-propionic acid ethyl ester: A slurry of 2-hydroxy-3-(4-{2-[1-(4-methoxy-benzyl)-3-methyl-2-oxo-imidazolidin-4-yl]-ethoxy}-phenyl)-2-methyl-propionic acid ethyl ester (7.35 g, 15.62 mmol) and sodium hydride (2.5 g, 62.5 mmol, 60% dispersion on mineral oil) in DMF (50 mL) i stirred for 45 minutes, then cooled to 0° C. Iodobutane (36 mL, 312 mmol, d=1.617) and 18-crown-6 16.5 g, 62.5 mmol) are added, then the reaction mixture is stirred 18 h at ambient temperature and diluted with ethyl acetate. The organic layer is washed, then dried concentrated in vacuo, and diluted with ethanol (400 mL) and 5N NaOH (40 mL). The reaction mixture is refluxed for 1 h, cooled to ambient temperature, and concentrated in vacuo. The residue is washed, dried, concentrated, and re-dissolved in ethanol (300 mL). Concentrated H$_2$SO$_4$ (30 mL) is added to the reaction solution, then the mixture is refluxed 1 h, cooled to ambient temperature, concentrated, and diluted with ethyl acetate. The organic layer is washed, dried, and concentrated to provide the title compound (5.3 g, 65%). $^1$H NMR (400 MHz, CDCl$_3$): δ 7.17 (d, 2H, J=8.8 Hz), 7.09 (d, 2H, J=8.8 Hz), 6.84 (d, 2H, J=8.8 Hz), 6.70 (d, 2H, J=8.8 Hz), 4.32, 4.28 (AB$_q$, 2H, J=14.7 Hz), 4.17-4.11 (m, 2H), 3.93 (t, 2H, J=5.9 Hz), 3.78 (s, 3H), 3.61-3.53 (m, 3H), 3.40-3.31 (m, 3H), 2.97-2.89 (m, 3H), 2.97-2.89 (m, 3H), 2.81 (s, 3H), 2.25-2.15 (m, 1H), 1.89-1.81 (m, 1H), 1.59-1.49 (m, 2H), 2-Butoxy-2-methyl-3-{4-[2-(3-methyl-2-oxo-imidazolidin-4-yl)-ethoxy]-phenyl}-propionic acid ethyl ester: Trifluoroacetic acid (110 mL) is added dropwise to a solution of 2-Butoxy-3-(4-{2-[1-(4-methoxy-benzyl)-3-methyl-2-oxo-imidazolidin-4-yl]-ethoxy}-phenyl)-2-methyl-propionic acid ethyl ester (5.31 g, 10.1 mmol) and triethylsilane (3.22 mL, 20.2 mmol, d=0.728). The reaction mixture is stirred at ambient temperature for 4 h, concentrated in vacuo, and diluted with ethyl acetate. The solution is washed, then dried, concentrated, and purified by flash chromatography to provide the title compound (4.1 g, 100%). $^1$H NMR (400 MHz, CDCl$_3$): δ 7.09 (d, 2H, J=8.4 Hz), 6.74 (d, 2H, J=8.4 Hz), 5.36 (s, 1H), 4.17-4.07 (m, 2H), 4.02-3.96 (m, 2H), 3.76-3.68 (m, 2H), 3.55 (t, 1H, J=8.8 hz), 3.40-3.31 (m, 2H), 3.20 (t, 1H, J=8.0 Hz), 2.95, 2.91 (AB$_q$, 2H, J=13.6 Hz), 2.76 (s, 3H), 2.24-2.18 (m, 1H), 1.97-1.88 (m, 1H), 1.58-1.51 (m, 2H), 1.41-1.31 (m, 2H), 1.27 (s, 3H), 1.22 (t, 3H, J=7.2 Hz), 0.89 (t, 3H, J=7.2 Hz). R$_f$=0.44 in 10% CH$_3$OH in CH$_2$Cl$_2$.

Step H

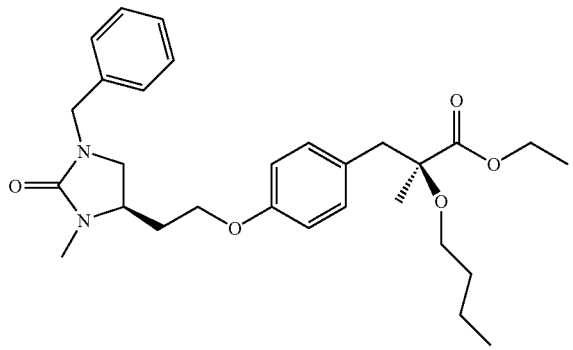

3-{4-[2-(1-Benzyl-3-methyl-2-oxo-imidazolidin-4-yl)-ethoxy]-phenyl}-2-butoxy-2-methyl-propionic acid ethyl ester: Benzyl bromide (0.0.21 mL, 0.174 mmol, d=1.438) and tetrabutyl ammonium iodide (catalytic amount) are added to a 0° C. suspension of 2-butoxy-2-methyl-3-{4-[2-(3-methyl-2-oxo-imidazolidin-4-yl)-ethoxy]-phenyl}-propionic acid ethyl ester (0.047 g, 0.116 mmol) and sodium hydride (0.012 g, 0.29 mmol, 60% suspension on mineral oil), pre-stirred for 1 h at ambient temperature. The reaction mixture is stirred at ambient temperature for 48 h, diluted with ethyl acetate, and washed with 1N HCl and water. The organic layer is dried, concentrated, and used in the next step. MS [EI+] 497 (M+H)$^+$.

Step I

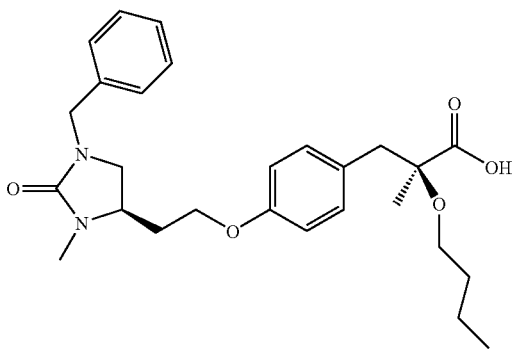

3-{4-[2-(1-Benzyl-3-methyl-2-oxo-imidazolidin-4-yl)-ethoxy]-phenyl}-2-butoxy-2-methyl-propionic acid: A solution of 3-{4-[2-(1-Benzyl-3-methyl-2-oxo-imidazolidin-4-yl)-ethoxy]-phenyl}-2-butoxy-2-methyl-propionic acid ethyl ester and 5N NaOH (0.3 mL) in ethanol (3 mL) is refluxed under nitrogen for 1 h, cooled to ambient temperature, and concentrated. The residue is diluted with 1N HCl, extracted with CH$_2$Cl$_2$, dried, concentrated, and purified by LCMS to provide the title compound. $^1$H NMR (400 MHz, CDCl$_3$): δ 7.33-7.22 (m, 5H), 7.07 (d, 2H, J=8.6 Hz), 6.71 (d, 2H, J=8.6 Hz), 4.39, 4.35 (AB$_q$, 2H, J=15.3 Hz), 3.94 (t, 2H, J=5.7 Hz), 3.69-3.62 (m, 1H), 3.58-3.52 (m, 1H), 3.50-3.44 (m, 1H), 3.40 (t, 1H, J=9.1 Hz), 3.04-3.01 (m, 1H), 3.02, 2.94 (AB$_q$, 2H, J=13.9 Hz), 2.85 (s, 3H), 2.25-2.18 (m, 1H), 1.92-1.85 (m, 1H), 1.62-1.54 (m, 1H), 1.46 (s, 3H), 1.42-1.32 (m, 2H), 0.92 (t, 3H, J=7.2 Hz). MS [EI+] 469 (M+H)$^+$, [EI−] 467 (M−H)$^+$.

Example 38

2-Butoxy-3-(4-{2-[1-(3-methoxy-benzyl)-3-methyl-2-oxo-imidazolidin-4-yl]-ethoxy}-phenyl)-2-methyl-propionic acid Step A 2-Butoxy-3-(4-{2-[1-(3-methoxy-benzyl)-3-methyl-2-oxo-imidazolidin-4-yl]-ethoxy}-phenyl)-2-methyl-propionic acid ethyl ester: 3-Methoxybenzyl bromide (0.024 mL, 0.170 mmol, d=1.436) and tetrabutyl ammonium iodide (catalytic amount) are added to a 0° C. suspension of 2-butoxy-2-methyl-3-{4-[2-(3-methyl-2-oxo-imidazolidin-4-yl)-ethoxy]-phenyl}-propionic acid ethyl ester (0.046 g, 0.114 mmol) and sodium hydride (0.011 g, 0.28 mmol, 60% suspension on mineral oil), pre-stirred for 1 h at ambient temperature. The reaction mixture is stirred at ambient temperature 48 h, diluted with ethyl acetate, and washed with 1N HCl and water. The organic layer is dried, concentrated, and used in the next step. MS [EI+] 527 (M+H)$^+$.

Step B

2-Butoxy-3-(4-{2-[1-(3-methoxy-benzyl)-3-methyl-2-oxo-imidazolidin-4-yl]-ethoxy}-phenyl)-2-methyl-propionic acid: A solution of 2-Butoxy-3-(4-{2-[1-(3-methoxy-benzyl)-3-methyl-2-oxo-imidazolidin-4-yl]-ethoxy}-phenyl)-2-methyl-propionic acid ethyl ester and 5N NaOH (0.3 mL) in ethanol (3 mL) is refluxed under nitrogen for 1 h, cooled to ambient temperature, and concentrated in vacuo. The residue is diluted with 1N HCl, extracted, dried, concentrated, and purified by LCMS to provide the title compound. $^1$H NMR (400 MHz, CDCl$_3$): δ 7.22 (t, 1H, J=8.0 Hz), 7.07 (d, 2H, J=8.5 Hz), 6.83-6.79 (m, 3H), 6.72 (d, 2H, J=8.5 Hz), 4.38, 4.30 (AB$_q$, 2H, J=15.1 Hz), 3.95 (t, 2H, J=6.0 Hz), 3.78 (s, 3H), 3.69-3.62 (m, 1H), 3.60-3.54 (m, 1H), 3.50-3.45 (m, 1H), 3.50-3.45 (m, 1H), 3.40 (t, 1H, J=9.0 Hz), 3.03-3.00 (m, 1H), 3.01, 2.95 (AB$_q$, 2H, J=14.6 Hz), 2.85 (s, 3H), 2.26-2.19 (m, 1H), 1.92-1.85 (m, 1H), 1.62-1.55 (m, 2H), 1.48 (s, 3H), 1.42 (m, 2H), 0.93 (t, 3H, J=7.0 Hz). MS [EI+] 499 (M+H)$^+$, [EI−] 497 (M−H)$^+$.

Example 39

2-Butoxy-3-(4-{2-[1-(4-chloro-benzyl)-3-methyl-2-oxo-imidazolidin-4-yl]-ethoxy}-phenyl)-2-methyl-propionic acid

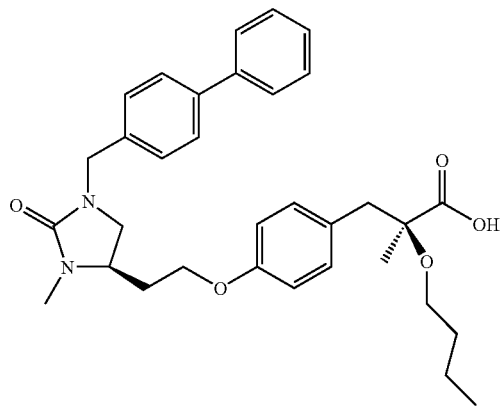

4-Phenylbenzyl chloride (0.031 g, 0.152 mmol) and tetrabutyl ammonium iodide (catalytic amount) are added to a 0° C. suspension of 2-butoxy-2-methyl-3-{4-[2-(3-methyl-2-oxo-imidazolidin-4-yl)-ethoxy]-phenyl}-propionic acid ethyl ester (0.041 g, 00.101 mmol) and sodium hydride (0.010 g, 0.25 mmol, 60% suspension on mineral oil), pre-stirred for 1 h at ambient temperature. The reaction mixture is stirred at ambient temperature 48 h, diluted with ethyl acetate, and washed with 1N HCl and water. The organic layer is dried, concentrated, and purified by LCMS to provide the title compound. $^1$H NMR (400 MHz, CDCl$_3$): δ 7.58-7.53 (m, 5H), 7.43 (t, 2H, J=7.9 Hz), 7.35 (d, 1H, J=7.5 Hz), 7.33 (d, 2H, J=7.9 Hz), 7.05 (d, 2H, J=8.8 Hz), 6.72 (d, 2H, J=8.8 Hz), 4.44, 4.38 (AB$_q$, 2H, J=14.7 Hz), 3.96 (t, 3H, J=6.3 Hz), 3.71-3.64 (m, 1H), 3.58-3.53 (m, 1H), 3.49-3.42 (m, 2H), 3.06, 3.04 (AB$_q$, 2H, J=13.7 Hz), 2.99, 2.93 (AB$_q$, 2H, J=13.7 Hz), 2.86 (s, 3H), 2.27-2.21 (m, 1H), 1.93-1.87 (m, 1H), 1.60-1.53 (m, 2H), 1.47 (s, 3H), 1.40-1.31 (m, 2H), 0.92 (t, 3H, J=7.4 Hz). MS [EI+] 545 (M+H)$^+$, [EI−] 543 (M−H)$^+$.

Example 40

2-Butoxy-2-methyl-3-(4-{2-[3-methyl-2-oxo-1-(3-trifluoromethyl-benzyl)-imidazolidin-4-yl]-ethoxy}-phenyl)-propionic acid

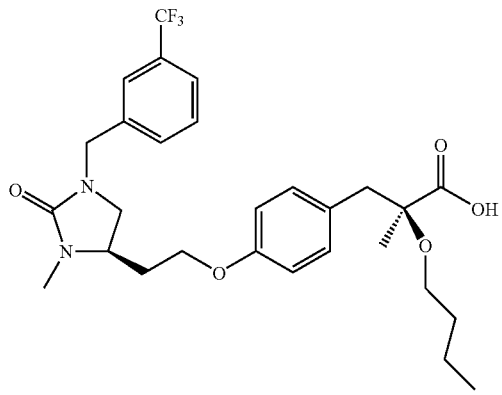

Step A

2-Butoxy-2-methyl-3-(4-{2-[3-methyl-2-oxo-1-(3-trifluoromethyl-benzyl)-imidazolidin-4-yl]-ethoxy}-phenyl)-propionic acid ethyl ester 3-Trifluoromethylbenzyl bromide (0.037 g, 0.157 mmol) and tetrabutyl ammonium iodide (catalytic amount) are added to a 0° C. suspension of 2-Butoxy-2-methyl-3-{4-[2-(3-methyl-2-oxo-imidazolidin-4-yl)-ethoxy]-phenyl}-propionic acid ethyl ester (0.043 g, 0.105 mmol) and sodium hydride (0.010 g, 0.26 mmol, 60% suspension on mineral oil), pre-stirred for 1 h at ambient temperature. The reaction mixture is stirred at ambient temperature for 48 h, diluted with ethyl acetate, and washed with 1N HCl and water. The organic layer is dried over MgSO$_4$, concentrated in vacuo, and used in the next step. MS [EI+] 565 (M+H)$^+$.

Step B

2-Butoxy-2-methyl-3-(4-{2-[3-methyl-2-oxo-1-(3-trifluoromethyl-benzyl)-imidazolidin-4-yl]-ethoxy}-phenyl)-propionic acid: A solution of 2-Butoxy-2-methyl-3-(4-{2-[3-methyl-2-oxo-1-(3-trifluoromethyl-benzyl)-imidazolidin-4-yl]-ethoxy}-phenyl)-propionic acid ethyl ester and 5N NaOH (0.3 mL) in ethanol (3 mL) is refluxed under nitrogen for 1 h, cooled to ambient temperature, and concentrated. The residue is diluted with 1N HCl, extracted with CH$_2$Cl$_2$, dried, concentrated, and purified by LCMS to provide the title compound. $^1$H NMR (400 MHz, CDCl$_3$): δ 7.51-7.38 (m, 4H), 7.04 (d, 2H, J=8.8 Hz), 6.69 (d, 2H, J=8.8 Hz), 4.46, 4.34 (AB$_q$, 2H, J=14.9 Hz), 3.94 (t, 2H, J=5.7 Hz), 3.68-3.60 (m, 1H), 3.57-3.52 (m, 1H), 3.48-3.43 (m, 1H), 3.38 (t, 1H, J=8.8 Hz), 2.98, 2.92 (AB$_q$, 2H, J=14.4 Hz), 2.83 (s, 3H), 2.25-2.18 (m, 1H), 1.91-1.83 (m, 1H), 1.59-1.52 (m, 2H), 1.45 (s, 3H), 1.39-1.30 (m, 2H), 0.91 (t, 3H, J=7.2 Hz). MS [EI+] 537 (M+H)$^+$, [EI−] 535 (M−H)$^+$.

Example 41

2-Butoxy-3-(4-{2-[1-(4-chloro-benzyl)-3-methyl-2-oxo-imidazolidin-4-yl]-ethoxy}-phenyl)-2-methyl-propionic acid: 4-Chlorobenzyl chloride (0.04 g, 0.174 mmol) and tetrabutyl ammonium iodide (catalytic amount) are added to a 0° C. suspension of 2-butoxy-2-methyl-3-{4-[2-(3-methyl-2-oxo-imidazolidin-4-yl)-ethoxy]-phenyl}-propionic acid ethyl ester (0.047 g, 0.116 mmol) and sodium hydride (0.012 g, 0.29 mmol, 60% suspension on mineral oil), pre-stirred for 1 h at ambient temperature. The reaction mixture is stirred at ambient temperature 48 h, diluted with ethyl acetate, and washed with 1N HCl and water. The organic layer is dried, concentrated, and purified by LCMS to provide the title compound. $^1$H NMR (400 MHz, CDCl$_3$): δ 7.27 (d, 2H, J=8.7 Hz), 7.17 (d, 2H, J=8.7 Hz), 7.07 (d, 2H, J=8.7 Hz), 7.71 (d, 2H, J=8.7 Hz), 4.34, 4.32 (AB$_q$, 2H, J=15.0 Hz), 3.95 (t, 3H, J=5.9 Hz), 3.69-3.62 (m, 1H), 3.61-3.55 (m, 1H), 3.51-3.45 (m, 1H), 3.38 (t, 1H, J=8.7 Hz), 3.04-2.93 (m, 3H), 2.84 (s, 3H), 2.26-2.18 (m, 1H), 1.92-1.84 (m, 1H), 1.62-1.54 (m, 2H), 1.49 (s, 3H), 1.42-1.33 (m, 3H), 0.93 (t, 3H, J=7.3 Hz). MS [EI+] 503 (M+H)$^+$, [EI−] 501 (M−H)$^+$.

Example 42

2-Butoxy-3-(4-{2-[1-(4-methoxy-benzyl)-3-methyl-2-oxo-imidazolidin-4-yl]-ethoxy}-phenyl)-2-methyl-propionic acid: A solution of 2-Butoxy-2-methyl-3-{4-[2-(3-methyl-2-oxo-imidazolidin-4-yl)-ethoxy]-phenyl}-propionic acid ethyl ester and 5N NaOH (0.2 mL) in ethanol (2 mL) is refluxed under nitrogen for 1 h, cooled to ambient temperature, and concentrated. The residue is diluted with 1N HCl, extracted with CH$_2$Cl$_2$, dried, concentrated, and purified by LCMS to provide the title compound (0.024 g, 84%). $^1$H NMR (400 MHz, CDCl$_3$): δ 7.16 (d, 2H, J=140.1 Hz), 7.08 (d, 2H, J=8.4 Hz), 6.83 (d, 2H, J=10.1 Hz), 6.70 (d, 2H, J=8.4 Hz), 4.32, 4.28 (AB$_q$, 2H, J=14.7 Hz), 3.92 (t, 2H, J=6.1 Hz), 3.78 (s, 3H), 3.61-3.44 (m, 3H), 3.31 (t, 1H, J=8.5 Hz), 3.00, 2.92 (AB$_q$, 2H, J=14.0 Hz), 2.93 (t, 1H, J=8.5 Hz), 2.82 (s, 3H), 2.23-2.16 (m, 1H), 1.89-1.81 (m, 1H), 1.61-1.54 (m 2H), 1.43 (s, 3H), 1.41-1.32 (m, 2H), 0.91 (t, 3H, J=7.3 Hz). MS [EI+] 499 (M+H)$^+$, [EI−] 497 (M−H)$^+$.

Example 43

2-Ethoxy-3-(4-{2-[1-(4-methoxy-benzyl)-3-methyl-2-oxo-imidazolidin-4-yl]-ethoxy}-phenyl)-2-methyl-propionic acid Step A 2-Ethoxy-3-(4-{2-[1-(4-methoxy-benzyl)-3-methyl-2-oxo-imidazolidin-4-yl]-ethoxy}-phenyl)-2-methyl-propionic acid ethyl ester: A slurry of 22-Hydroxy-3-(4-{2-[1-(4-methoxy-benzyl)-3-methyl-2-oxo-imidazolidin-4-yl]-ethoxy}-phenyl)-2-methyl-propionic acid ethyl ester (3.75 g, 7.97 mmol) and sodium hydride (1.28 g, 31.88 mmol, 60% dispersion on mineral oil) in DMF (30 mL) is stirred for 45 minutes, then cooled to 0° C. Iodoethane (12.75 mL, 159.38 mmol, d=1.95) and 18-crown-6 (8.43 g, 31.88 mmol) are added, then the reaction mixture is stirred 18 h at ambient temperature, then diluted with ethyl acetate. The organic layer is washed, dried, concentrated, and purified by flash chromatography (20% acetone in hexanes) to provide the title compound (3.23 g, 80%). $^1$H NMR (400 MHz, CDCl$_3$): δ 7.17(d, 2H, J=8.6 Hz), 7.08 (d, 2H, J=8.6 Hz), 6.83 (d, 2H, J=9.1 Hz), 6.70 (d, 2H, J=9.1 Hz), 4.31, 4.27 (AB$_q$, 2H, J=14.5 Hz), 4.17-4.11 (m, 2H), 3.93 (t, 2H, J=6.4 Hz), 3.77 (s, 3H), 3.60-3.53 (m, 1H), 3.48-3.39 (m, 2H), 3.32 (t, 1H, J=8.6 Hz), 2.98-2.89 (m, 3H), 2.81(s, 3H), 2.24-2.16 (m, 1H), 1.88-1.80 (m, 1H), 1.29 (s, 3H), 1.25-1.15 (m, 6H). R$_f$=0.54 in 50% acetone in hexanes.

Step B

2-Ethoxy-3-(4-{2-[i-(4-methoxy-benzyl)-3-methyl-2-oxo-imidazolidin-4-yl]-ethoxy}-phenyl)-2-methyl-propionic acid: A solution of 2-ethoxy-3-(4-{2-[1-(4-methoxy-benzyl)-3-methyl-2-oxo-imidazolidin-4-yl]-ethoxy}-phenyl)-2-methyl-propionic acid ethyl ester (0.038 g, 0.076 mmol) and 5N NaOH (0.2 mL) is refluxed for 1 h, cooled to ambient temperature, and concentrated. The residue is diluted with CH$_2$Cl$_2$, washed, dried, and concentrated in vacuo to provide the title compound (0.027 g, 77%). $^1$H NMR (400 MHz, CDCl$_3$): δ 7.16 (d, 2H, J=8.7 Hz), 7.07 (d, 2H, J=8.1 Hz), 6.83 (d, 2H, J=8.7 Hz), 6.70 (d, 2H, J=8.1 Hz), 4.31, 4.27 (Ab$_q$, 2H, J=14.9 Hz), 3.92 (t, 2H, J=6.2 Hz), 3.78 (s, 3H), 3.59-3.52 (m, 3H), 3.33 (t, 1H, J=8.2 Hz), 3.03-2.91 (m, 3H), 2.81 (s, 3H), 2.21-2.17 (m, 1H), 1.90-1.81 (m, 1H), 1.43 (s, 3H), 1.20 (t, 3H, J=7.0 Hz). MS [ES+] m/z exact mass calcd for C$_{26}$H$_{35}$N$_2$O$_6$ 471.2495, found 471.2507.

Example 44

2-Ethoxy-2-methyl-3-(4-{2-[3-methyl-2-oxo-1-(4-trifluoromethyl-benzyl)-imidazolidin-4-yl]-ethoxy}-phenyl)-propionic acid

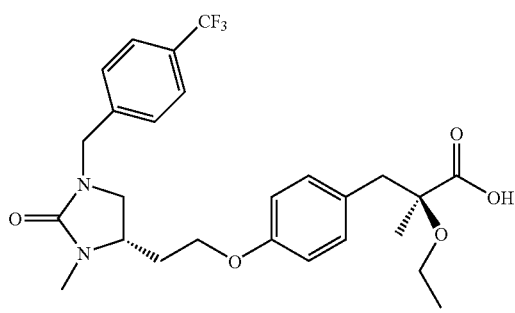

Step A

2-Hydroxy-2-methyl-3-(4-{2-[3-methyl-2-oxo-1-(4-trifluoromethyl-benzyl)-imidazolidin-4-yl]-ethoxy}-phenyl)-propionic acid ethyl ester: Cesium carbonate (8.72 g, 26.76 mmol) is added to a solution of 2-hydroxy-3-(4-{2-[1-(4-methoxy-benzyl)-3-methyl-2-oxo-imidazolidin-4-yl]-ethoxy}-phenyl)-2-methyl-propionic acid ethyl ester (2.0 g, 8.92 mmol) and Toluene-4-sulfonic acid 2-[3-methyl-2-oxo-1-(4-trifluoromethyl-benzyl)-imidazolidin-4-yl]-ethyl ester (4.34 g, 9.51 mmol) in DMF (50 mL). The resultant mixture is stirred at 55° C. under an atmosphere of nitrogen for 18 h, then diluted with ethyl acetate. The organic layer is washed, dried, concentrated, and purified by flash chromatography (25% acetone in hexanes) to provide the title compound. $^1$H NMR (400 MHz, CDCl$_3$): δ 7.95 (s, 1H), 7.50 (d, 2H, J=8.2 Hz), 7.32 (d, 2H, J=8.2 Hz), 7.03 (d, 2H, J=8.2 Hz), 6.65 (d, 2H, J=8.2 Hz), 4.40, 4.32 (AB$_q$, 2H, J=14.7 Hz), 4.14-4.07 (m, 2H), 3.91 (t, 2H, J=5.7 Hz), 3.61-3.55 (m, 1H), 3.33 (t, 1H, J=8.2 Hz), 2.96-2.79 (m, 6H), 2.22-2.15 (m, 1H), 1.87-1.80 (m, 1H), 1.40 (s, 3H), 1.21 (t, 3H, J=7.4 Hz). R$_f$=0.38 in 50% acetone in hexanes.

Step B

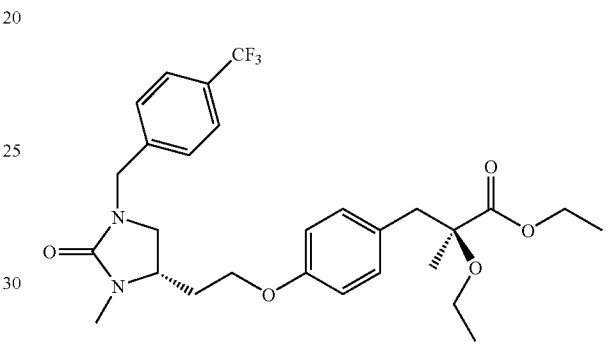

2-Ethoxy-2-methyl-3-(4-{2-[3-methyl-2-oxo-1-(4-trifluoromethyl-benzyl)-imidazolidin-4-yl]-ethoxy}-phenyl)-propionic acid ethyl ester: A slurry of 2-hydroxy-3-(4-hydroxy-phenyl)-2-methyl-propionic acid ethyl ester (0.509 g, 1.00 mmol) and sodium hydride (0.16 g, 4.00 mmol, 60% dispersion on mineral oil) in DMF (3 mL) is stirred for 45 minutes, then cooled to 0° C. Iodoethane (1.60 mL, 20.02 mmol, d=1.95) and 18-crown-6 (1.06 g, 4.00 mmol) are added, then the reaction mixture is stirred 18 h at ambient temperature, then diluted with ethyl acetate. The organic layer is washed, dried, concentrated, and purified by flash chromatography (20% acetone in hexanes) to provide the title compound (3.23 g, 80%). MS [EI+] 537 (M+H)$^+$. R$_f$=0.44 in 50% acetone in hexanes.

Step C

2-Ethoxy-2-methyl-3-(4-{2-[3-methyl-2-oxo-1-(4-trifluoromethyl-benzyl)-imidazolidin-4-yl]-ethoxy}-phenyl)-propionic acid: A solution of 2-Ethoxy-2-methyl-3-(4-{2-[3-methyl-2-oxo-1-(4-trifluoromethyl-benzyl)-imidazolidin-4-yl]-ethoxy}-phenyl)-propionic acid ethyl ester (0.19 g, 0.347 mmol) and 5N NaOH (0.5 mL) in ethanol (5 mL) is refluxed for 1 h, cooled to ambient temperature, and concentrated. The residue is diluted with CH$_2$Cl$_2$, washed, dried, and concentrated in vacuo to provide the title compound. $^1$H NMR (400 MHz, CDCl$_3$): δ 7.63 (d, 2H, J=8.4 Hz), 7.44 (d, 2H, J=8.4 Hz), 7.08 (d, 2H, J=8.7 Hz), 6.76 (d, 2H, J=8.7 Hz), 4.37, 4.35 (AB$_q$, 2H, J=16.4 Hz), 3.99-3.89 (m, 2H), 3.63-3.53 (m, 1H), 3.43-3.23 (m, 2H), 2.98 (t, 1H, J=8.8 Hz), 2.86, 2.84 (AB$_q$, 2H, J=15.4 Hz), 2.71 (s, 3H), 2.51-2.49 (m, 3H), 2.23-2.13 (m, 1H), 1.86-1.74 (m, 1H), 1.15 (s, 3H), 1.08 (t, 3H, J=6.9 Hz). MS [ES+] m/z exact mass calcd for C$_{26}$H$_{32}$N$_2$O$_5$F$_3$ 509.2263, found 509.2288.

Example 45

2-Methyl-3-(4-{2-[3-methyl-2-oxo-1-(4-trifluoromethyl-benzyl)-imidazolidin-4-yl]-ethoxy}-phenyl)-2-propoxy-propionic acid

The title compound is prepared using procedures substantially as described herein and purified by LCMS to provide the title compound (0.017 g, 34% after two steps). $^1$H NMR (400 MHz, CDCl$_3$): δ 7.48 (d, 2H, J=8.0 Hz), 7.29 (d, 2H, J=7.2 Hz), 7.01 (d, 2H, J=7.2 Hz), 6.63 (d, 2H, J=8.0 Hz), 4.45, 4.39 (AB$_q$, 2H, J=15.4 Hz), 3.96 (t, 2H, J=6.0 Hz), 3.69-3.62 (m, 1H), 3.57-3.52 (m, 1H), 3.46-3.37 (m, 3H), 3.04-2.93 (m, 4H), 2.85 (s, 3H), 2.28-2.20 (m, 1H), 1.93-1.84 (m, 1H), 1.67-1.58 (m, 2H), 1.49 (s, 3H), 0.93 (t, 3H, J=7.4 Hz). MS [EI+] 523 (M+H)$^+$, [EI−] 521 (M−H)$^+$.

Example 46

2-Butoxy-2-methyl-3-(4-{2-[3-methyl-2-oxo-1-(4-trifluoromethyl-benzyl)-imidazolidin-4-yl]-ethoxy}-phenyl)-propionic acid

The title compound is prepared substantially using the procedures described herein and purified by LCMS to provide the title compound (0.022 g, 52% after two steps). $^1$H NMR (400 MHz, CDCl$_3$): δ 7.56 (d, 2H, J=8.3 Hz), 7.36 (d, 2H, J=8.3 Hz), 7.07 (d, 2H, J=9.0 Hz), 6.71 (d, 2H, J=9.0 Hz), 4.46, 4.38 (AB$_q$, 2H, J=15.2 Hz), 3.96 (t, 2H, J=5.5 Hz), 3.67-3.61 (m, 1H), 3.60-3.54 (m, 1H), 3.50-3.45 (m, 1H), 3.39 (t, 1H, J=9.0 Hz), 3.03-2.92 (m, 3H), 2.85 (s, 3H), 2.27-2.20 (m, 1H), 1.93-1.84 (m, 1H), 1.62-1.54 (m, 2H), 1.48 (s, 3H), 1.41-1.32 (m, 2H), 0.92 (t, 3H, J=6.9 Hz). MS [EI+] 537 (M+H)$^+$, [EI−] 535 (M−H)$^+$.

Example 47

2-Ethoxy-2-methyl-3-(4-{2-[3-methyl-2-oxo-1-(4-trifluoromethoxy-benzyl)-imidazolidin-4-yl]-ethoxy}-phenyl)-propionic acid

Trifluoroacetic acid (70 mL) is added dropwise to a solution of 2-Ethoxy-2-methyl-3-{4-[2-(3-methyl-2-oxo-imidazolidin-4-yl)-ethoxy]-phenyl}-propionic acid ethyl ester (3.19 g, 6.40 mmol) and triethylsilane (2.04 mL, 12.8 mmol, d=0.728). The reaction mixture is stirred at ambient temperature for 4 hours, concentrated, and diluted with ethyl acetate. The solution is washed, then dried, and concentrated in vacuo to provide the title compound (2.2 g, 92%). $^1$H NMR (400 MHz, CDCl$_3$): δ 7.11 (d, 2H, J=9.3 Hz), 6.76 (d, 2H, J=9.3 Hz), 4.19-4.10 (m, 2H), 4.04-3.98 (m, 2H), 3.77-3.69 (m, 1H), 3.56 (t, 1H, J=8.8 Hz), 3.51-3.38 (m, 2H), 3.22 (t, 1H, J=8.8 Hz), 2.96, 2.94 (AB$_q$, 2H, J=14.0 Hz), 2.78 (s, 3H), 2.27-2.20 (m, 1H), 1.99-1.92 (m, 1H). MS [EI+] 379 (M+H)$^+$.

Step A

2-Ethoxy-2-methyl-3-(4-{2-[3-methyl-2-oxo-1-(4-trifluoromethoxy-benzyl)-imidazolidin-4-yl]-ethoxy}-phenyl)-propionic acid ethyl ester: 4-(Trifluoromoxy)benzyl bromide (0.03 mL, 0.19 mmol) and tetrabutyl ammonium iodide (catalytic amount) are added to a 0° C. suspension of 2-Ethoxy-2-methyl-3-{4-[2-(3-methyl-2-oxo-imidazolidin-4-yl)-ethoxy]-phenyl}-propionic acid ethyl ester (0.048 g, 0.127 mmol) and sodium hydride (0.013 g, 0.32 mmol, 60% suspension on mineral oil), pre-stirred for 1 h at ambient temperature. The reaction mixture is stirred at ambient temperature for 90 minutes, diluted with ethyl acetate, and washed. The organic layer is dried, concentrated, and used in the next step. MS [EI+] 553 (M+H)$^+$.

Step B

2-Ethoxy-2-methyl-3-(4-{2-[3-methyl-2-oxo-1-(4-trifluoromethoxy-benzyl)-imidazolidin-4-yl]-ethoxy}-phenyl)-propionic acid: A solution of 2-ethoxy-2-methyl-3-(4-{2-[3-methyl-2-oxo-1-(4-trifluoromethoxy-benzyl)-imidazolidin-4-yl]-ethoxy}-phenyl)-propionic acid ethyl ester and 5N NaOH (0.3 mL) in ethanol (3 mL) is refluxed for 1 h, cooled to ambient temperature, and concentrated. The residue is diluted with CH$_2$Cl$_2$, dried, and concentrated in vacuo to provide the title compound (0.022 g, 32% after two steps). $^1$H NMR (400 MHz, CDCl$_3$): δ 7.24-7.19 (m, 1H), 7.09 (d, 2H, J=8.3 Hz), 6.83-6.78 (m, 3H), 6.69 (d, 2H, J=8.3 Hz), 4.38, 4.28 (AB$_q$, 2H, J=14.8 Hz), 3.94-3.91 (m, 3H), 3.77 (s, 3H), 3.60-3.53 (m, 3H), 3.36 (t, 1H, J=9.0 Hz), 3.04-2.92 (m, 1H), 1.89-1.83 (m, 1H), 1.40 (s, 3H), 1.23 (t, 3H, J=6.9 Hz). MS [EI+] 525 (M+H)$^+$, [EI−] 523 (M−H)$^+$. R$_f$=0.27 in 10% CH$_3$OH in CH$_2$Cl$_2$.

Example 48

2-Ethoxy-3-(4-{2-[1-(3-methoxy-benzyl)-3-methyl-2-oxo-imidazolidin-4-yl]-ethoxy}-phenyl)-2-methyl-propionic acid

The title compound is prepared using substantially the procedures described herein, and purified by LCMS to provide the title compound (0.022g, 32% after two steps). $^1$H NMR (400 MHz, CDCl$_3$): δ 7.22 (t, 1H, J=7.7 Hz), 7.06 (d, 2H, J=8.3 Hz), 6.83-6.79 (m, 3H), 6.72 (d, 2H, J=7.1 Hz), 4.37, 4.29 (AB$_q$, 2H, J=14.8 Hz), 3.95 (t, 2H, J=6.3 Hz), 3.68-3.52 (m, 6H), 3.39 (t, 3H, J=8.5 Hz), 3.04-2.93 (m, 3H), 2.84 (s, 3H), 2.26-2.20 (m, 1H), 1.92-1.85 (m, 1H), 1.49 (s, 3H), 1.24 (t, 3H, J=7.1 Hz). MS [EI+] 471 (M+H)$^+$, [EI−] 469 (M−H)$^+$. R$_f$=0.27 in 10% CH$_3$OH in CH$_2$Cl$_2$.

Example 49

2-Ethoxy-2-methyl-3-(4-{2-[3-methyl-2-oxo-1-(3-trifluoromethoxy-benzyl)-imidazolidin-4-yl]-ethoxy}-phenyl)-propionic acid

The title compound is prepared using substantially the procedures described purified by LCMS to provide the title compound (0.022g, 32% after two steps). $^1$H NMR (400 MHz, CDCl$_3$): δ 7.33 (t, 1H, J=8.2 Hz), 7.17 (d, 1H, J=7.5 Hz), 7.13-7.06 (m, 4H), 6.72 (d, 2H, J=8.9 Hz), 4.42, 4.34 (AB$_q$, 2H, J=15.3 Hz), 3.96 (t, 2H, J=5.6 Hz), 3.71-3.52 (m, 3H), 3.41 (t, 1H, J=8.3 Hz), 3.05-2.93 (m, 3H), 2.85 (s, 3H), 2.27-2.20 (m, 1H), 1.94-1.85 (m, 1H), 1.47 (s, 3H), 1.23 (t, 3H, J=7.3 Hz). MS [EI+] 525 (M+H)$^+$, [EI−] 523 (M−H)$^+$.

Example 50

2-Ethoxy-2-methyl-3-(4-{2-[3-methyl-2-oxo-1-(3-trifluoromethyl-benzyl)-imidazolidin-4-yl]-ethoxy}-phenyl)-propionic acid

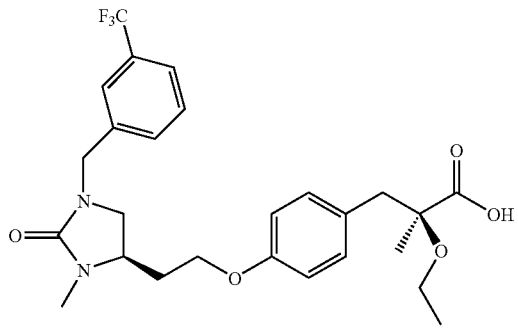

The title compound is prepared using substantially the procedures described herein and purified by LCMS to provide the title compound. $^1$H NMR (400 MHz, CDCl$_3$): δ 7.54-7.42 (m, 4H), 7.07 (d, 2H, J=8.3 Hz), 6.70 (d, 2H, J=9.3 Hz), 4.47, 4.37 (AB$_q$, 2H, J=15.3 Hz), 3.96 (t, 2H, J=6.4 Hz), 3.73-3.65 (m, 1H), 3.64-3.51 (m, 2H), 3.42 (t, 1H, J=8.3 Hz), 3.05 (t, 1H, J=7.2 Hz), 3.01, 2.95 (AB$_q$, 2H, J=14.3 Hz), 2.86 (s, 3H), 2.27-2.20 (m, 1H), 1.94-1.87 (m, 1H), 1.46 (s, 3H), 1.23 (t, 3H, J=7.2 Hz). MS [EI+] 509 (M+H)$^+$, [EI−] 507 (M−H)$^+$.

Example 51

3-{4-[2-(1-Biphenyl-4-ylmethyl-3-methyl-2-oxo-imidazolidin-4-yl)-ethoxy]-phenyl}-2-ethoxy-2-methyl-propionic acid and purified by chromatotron (CH$_3$OH/CH$_2$Cl$_2$ gradient) to provide the title compound (0.033g, 55%). $^1$H NMR (400 MHz, CDCl$_3$): δ 7.58-7.52 (m, 4H), 7.43 (t, 2H, J=7.8 Hz), 7.35-7.31 (m, 3H), 7.05 (d, 2H, J=7.8 Hz), 6.72 (d, 2H, J=8.5 Hz), 4.45, 4.37 (ABqt 2H, J=14.8 Hz), 3.95 (t, 2H, J=5.6 Hz), 3.64-3.52 (m, 3H), 3.40 (t, 1H, J=8.3 Hz), 3.02-2.91 (m, 3H), 2.85 (s, 3H), 2.25-2.20 (m, 1H), 1.91-1.85 (m, 1H), 1.46 (s, 3H), 1.23 (t, 3H, J=7.2 Hz). MS [ES$^+$] m/z exact mass calcd for C$_{31}$H$_{37}$N$_2$O$_5$ 517.2702, found 517.2711. R$_f$=0.31 in 10% CH$_3$OH in CH$_2$Cl$_2$.

Example 52

3-(4-{2-[1-(3,4-Difluoro-benzyl)-3-methyl-2-oxo-imidazolidin-4-yl]-ethoxy}-phenyl)-2-methyl-2-phenoxy-propionic acid and purified by flash chromatography to provide the title compound (0.42g, 63%). $^1$H NMR (400 MHz, CDCl$_3$): δ 7.26-723 (m, 3H), 7.19 (d, 2H, J=8.3 HzO), 7.11-7.04 (m, 3H), 6.91 (d, 2H, J=8.3 Hz), 6.92-6.90 (m, 1H), 6.75 (d, 2H, J=8.3 Hz), 4.21, 4.15 (AB$_q$, 2H, J=14.8 Hz), 3.87 (t, 2H, J=6.6 Hz), 3.59-3.53 (m, 1H), 3.30n (t, 1H, J=8.2 Hz), 3.23, 3.03 (AB$_q$, 2H, J=13.1 Hz), 2.91 (t, 1H, J=8.2 hz), 2.74 (s, 3H), 2.16-2.10 (m, 1H), 1.81-1.76 (m, 1H), 1.42 (s, 3H). MS [EI+] 525 (M+H)$^+$, [EI−] 523 (M−H)$^+$.

Example 53

2-Ethoxy-2-methyl-3-(4-{2-[3-methyl-2-oxo-1-(4-trifluoromethyl-benzyl)-imidazolidin-4-yl]-ethoxy}-phenyl)-propionic acid and concentrated in vacuo to provide the title compound (0.029g, 83%). $^1$H NMR (400 MHz, CDCl$_3$): δ 7.55 (d, 2H, J=8.6 Hz), 7.36 (d, 2H, J=8.6 Hz), 7.07 (d, 2H, J=8.6 Hz), 6.70 (d, 2H, J=8.6 Hz), 4.45, 4.37 (AB$_q$, 2H, J=15.6 Hz), 3.95 (t, 2H, J=6.2 Hz), 3.66-3.51 (m, 3H), 3.37 (t, 1H, J=8.6 Hz), 3.03-2.92 (m, 3H), 2.84 (s, 3H), 2.26-2.19 (m, 1H), 2.26-2.19 (m, 1H), 1.42 (s, 3H), 1.22 (t, 3H, J=7.0 Hz). MS [EI+] 509 (M+H)$^+$, [EI−] 507 (M−H)$^+$.

Example 54

2-Ethoxy-2-methyl-3-(4-{2-[3-methyl-2-oxo-1-(4-trifluoromethyl-benzyl)-imidazolidin-4-yl]-ethoxy}-phenyl)-propionic acid The title compound is prepared using substantially the procedures described herein and concentrated in vacuo to provide the title compound (0.036 g, 88%). $^1$H NMR (400 MHz, CDCl$_3$): δ 7.55 (d, 2H, J=8.6 Hz), 7.36 (d, 2H, J=8.6 Hz), 7.07 (d, 2H, J=8.6 Hz), 6.70 (d, 2H, J=8.6 Hz), 4.45, 4.37 (AB$_q$, 2H, J=15.6 Hz), 3.95 (t, 2H, J=6.2 Hz), 3.66-3.51 (m, 3H), 3.37 (t, 1H, J=8.6 Hz), 3.03-2.92 (s, 3H), 2.26-2.19 (m, 1H), 1.91-1.84 (m, 1H), 1.42 (s, 3H), 1.22 (t, 3H, J=7.0 Hz). MS [EI+] 509 (M+H)$^+$, [EI−] 507 (M−H)$^+$.

Example 55

2-Methyl-3-(4-{2-[3-methyl-2-oxo-1-(4-trifluoromethyl-benzyl)-imidazolidin-4-yl]-ethoxy}-phenyl)-2-phenoxy-propionic acid

Step A 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester: Cesium carbonate (2.18 g, 6.702 mmol) is added to a solution of 3-(4-Hydroxy-phenyl)-2-methyl-2-phenoxy-propionic acid ethyl ester (1.55 g, 5.155 mmol) and Toluene-4-sulfonic acid 2-[3-methyl-2-oxo-1-(4-trifluoromethyl-benzyl)-imidazolidin-4-yl]-ethyl ester (3.19 g, 5.67 mmol) in DMF (30 mL). The resultant mixture is stirred at 55° C. under an atmosphere of nitrogen for 18 h, then diluted with ethyl acetate. The organic layer is washed, then dried, concentrated, and purified by flash chromatography (17% acetone in hexanes) to provide the title compound (3.46 g, 97%). $^1$H NMR (400 MHz, CDCl$_3$): δ 7.57 (d, 2H, J=7.01 Hz), 7.37 (d, 2H, J=7.1 Hz), 7.23-7.19 (m, 4H), 7.13 (d, 2H, J=8.7 Hz), 6.97 (t, 1H, J=7.1 Hz), 6.87-6.80 (m, 4H), 6.67 (d, 2H, J=8.7 Hz), 4.79, 4.07 (AB$_q$, 2H, J=15.0 Hz), 4.47, 4.43 (AB$_q$, 2H, J=15.0 Hz), 4.20 (q, 2H, J=7.1 Hz), 3.92-3.87 (m, 2H), 3.80 (s, 3H), 3.61-3.55 (m, 1H), 3.31 (t, 2H, J=8.7 Hz), 3.24, 3.10 (AB$_q$, 2H, J=14.2 Hz), 3.00 (t, 1H, J=7.9 Hz), 2.21-2.14 (m, 1H), 1.87-1.78 (m, 1H), 1.38 (s, 3H), 1.21 (t, 3H, J=7.1 Hz). MS [EI+] 691 (M+H)$^+$. R$_f$=0.49 in 50% acetone in hexanes.

Step B

2-Methyl-3-(4-{2-[2-oxo-1-(4-trifluoromethyl-benzyl)-imidazolidin-4-yl]-ethoxy}-phenyl)-2-phenoxy-propionic acid ethyl ester: Trifluoroacetic acid (60 mL) is added dropwise to a solution of 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester (3.46 g, 5.01 mmol) and triethylsilane (1.6 mL, 10.0 mmol, d=0.728). The reaction mixture is stirred at ambient temperature for 2 h, concentrated, and diluted with ethyl acetate. The solution is washed, then dried, and concentrated in vacuo to provide the title compound. $^1$H NMR (400 MHz, CDCl$_3$): δ 7.58 (d, 2H, J=8.2 Hz), 7.38 (d, 2H, J=8.2 Hz), 7.23-7.14 (m, 4H), 6.97 (t, 1H, J=7.4 Hz), 6.82 (d, 2H, J=7.4 Hz), 6.78 (d, 2H, J=7.4 Hz), 4.44, 4.38 (AB$_q$, 2H, J=15.6 Hz), 4.20 (q, 2H, J=7.4 Hz), 4.07-3.99 (m, 2H), 3.96-3.89 (m, 1H), 3.47 (t, 1H, J=8.2 Hz), 3.27, 3.09 (AB$_q$, 2H, J=14.1 Hz), 3.04, 3.02 (AB$_q$, 1H, J=6.7 Hz), 2.08-1.99 (m, 1H), 1.98-1.92 (m, 1H), 1.38 (s, 3H), 1.21 (t, 3H, J=6.7 Hz) MS [EI+] 571 (M+H)$^+$, [EI−] 569 (M−H)$^+$. R$_f$=0.07 in 33% acetone in hexanes.

Step C

2-Methyl-3-(4-{2-[3-methyl-2-oxo-1-(4-trifluoromethyl-benzyl)-imidazolidin-4-yl]-ethoxy}-phenyl)-2-phenoxy-propionic acid ethyl ester: A slurry of 2-Methyl-3-(4-{2-[2-oxo-1-(4-trifluoromethyl-benzyl)-imidazolidin-4-yl]-ethoxy}-phenyl)-2-phenoxy-propionic acid ethyl ester (0.544 g, 0.953 mmol) and sodium hydride (0.042 g, 1.05 mmol, 60% dispersion on mineral oil) in DMF (10 mL) is stirred for 1 h, then cooled to 0° C. Iodomethane (0.60 mL, 9.53 mmol, d=2.28) is added, then the reaction mixture is stirred 18 h at ambient temperature and diluted with ethyl acetate. The organic layer is washed, dried, concentrated, and purified by flash chromatography to provide the title compound. $^1$H NMR (400 MHz, CDCl$_3$): δ 7.56 (d, 2H, J=8.0 Hz), 7.37 (d, 2H, J=8.0 Hz), 7.26-7.19 (m, 2H), 7.15 (d, 2H, J=8.9 Hz), 6.97 (t, 1H, J=8.0 Hz), 6.82 (d, 2H, J=8.0 Hz), 6.74 (d, 2H, J=8.9 Hz), 4.46, 4.38 (AB$_q$, 2H, J=15.1 Hz), 4.20 (q, 2H, J=7.1 Hz), 3.97 (t, 2H, J=7.1 Hz), 3.67-3.59 (m, 1H), 3.78 (t, 1H, J=8.9 Hz), 3.26, 3.10 (AB$_q$, 2H, J=14.2 Hz), 2.99 (t, 1H, J=8.9 Hz), 2.85 (s, 3H), 2.28-2.21 (m, 1H), 1.93-1.84 (m, 1H), 1.39 (s, 3H), 1.21 (t, 3H, J=7.1 Hz). MS [EI+]. 585 (M+H)$^+$. R$_f$=0.35 in 50% acetone in hexanes.

Step D

2-Methyl-3-(4-{2-[3-methyl-2-oxo-1-(4-trifluoromethyl-benzyl)-imidazolidin-4-yl]-ethoxy}-phenyl)-2-phenoxy-propionic acid: A solution of 2-methyl-3-(4-{2-[3-methyl-2-oxo-1-(4-trifluoromethyl-benzyl)-imidazolidin-4-yl]-ethoxy}-phenyl)-2-phenoxy-propionic acid ethyl ester and 5N NaOH (0.7 mL) in ethanol (6 mL) is refluxed for 1 h, cooled to ambient temperature, and concentrated. The residue is diluted with CH$_2$Cl$_2$, washed, dried, and concentrated to provide the title compound (0.186 g, 100%). $^1$H NMR (400 MHz, CDCl$_3$): δ 7.54 (d, 2H, J=8.3 Hz), 7.35 (d, 2H, J=8.3 Hz), 7.24-7.17 (m, 4H), 7.00 (t, 1H, J=7.4 Hz), 6.89 (d, 2H, J=7.4 Hz), 6.73 (d, 2H, J=8.3 Hz), 4.45, 4.37 (ABq, 2H, J=15.7 Hz), 3.96 (t, 2H, J=5.5 Hz), 3.68-3.62 (m, 1H), 3.38 (t, 1H, J=8.3 Hz), 3.32, 3.10 (AB$_q$, 2H, J=12.9 Hz), 3.00 (t, 1H, J=8.3 Hz), 2.84 (s, 3H), 2.27-2.19 (m, 1H), 1.92-1.85 (m, 1H), 1.39 (s, 3H). MS [EI+] 557 (M+H)$^+$, [EI−] 555 (M−H)$^+$.

Example 56

3-(4-{2-[3-Ethyl-2-oxo-1-(4-trifluoromethyl-benzyl)-imidazolidin-4-yl]-ethoxy}-phenyl)-2-methyl-2-phenoxy-propionic acid Step A 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester: Cesium carbonate (2.49 g, 7.647 mmol) is added to a solution of 3-(4-Hydroxy-phenyl)-2-methyl-2-phenoxy-propionic acid ethyl ester (1.77 g, 5.88 mmol) and toluene-4-sulfonic acid 2-[3-(4-methoxy-benzyl)-2-oxo-1-(4-trifluoromethyl-benzyl)-imidazolidin-4-yl]-ethyl ester (3.64 g, 6.47 mmol) in DMF (40 mL). The resultant mixture is stirred at 55° C. under an atmosphere of nitrogen for 18 h, then diluted with ethyl acetate. The organic layer is washed, then dried, concentrated, and purified by flash chromatography (acetone/hexanes gradient) to provide the title compound (3.80 g, 94%). $^1$H NMR (400 MHz, CDCl$_3$): δ 7.57 (d, 2H, J=8.4 Hz), 7.37 (d, 2H, J=7.8 Hz), 7.23-7.19 (m, 4H), 7.13 (d, 2H, J=8.4 Hz), 6.97 (t, 1H, J=7.8 Hz), 6.86 (d, 2H, J=8.4 Hz), 6.81 (d, 2H, J=8.4 Hz), 6.67 (d, 2H, J=7.8 Hz), 4.66, 4.20 (AB$_q$, 2H, J=14.9 Hz), 4.47, 4.43 (AB$_q$, 2H, J=15.5 Hz), 4.20 (q, 2H, J=7.1 Hz), 3.89-3.85 (m, 2H), 3.80 (s, 3H), 3.61-3.55 (m, 1H), 3.31 (t, 1H, J=9.1 Hz), 3.26, 3.08 (AB$_q$, 2H, J=13.6 Hz), 3.00 (t, 1H, J=9.1 Hz), 2.20-2.14 (m, 1H), 1.87-1.78 (m, 1H), 1.38 (s, 3H), 1.21 (t, 3H, J=7.1 Hz). MS [EI+] 691 (M+H)$^+$. R$_f$=0.46 in 50% acetone in hexanes.

Step B

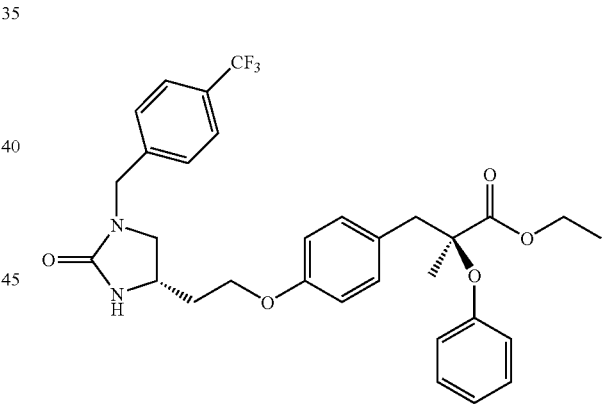

2-Methyl-3-(4-{2-[2-oxo-1-(4-trifluoromethyl-benzyl)-imidazolidin-4-yl -ethoxy]-phenyl}-2-phenoxy-propionic acid ethyl ester: Trifluoroacetic acid (66 mL) is added dropwise to a solution of 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester (3.80 g, 5.50 mmol) and triethylsilane (1.76 mL, 11.0 mmol, d=0.728). The reaction mixture is stirred at ambient temperature for 4 hours, concentrated in vacuo, and diluted with ethyl acetate. The solution is washed, then dried, and concentrated to provide the title compound. $^1$H NMR (400 MHz, CDCl$_3$): δ 7.58 (d, 2H, J=7.7 Hz), 7.38 (d, 2H, J=7.7 Hz), 7.22 (t, 2H, J=9.1 Hz), 7.15 (d, 2H, J=9.1 Hz), 6.97 (t, 1H, J=7.7 Hz), 6.82 (d, 2H, J=7.7 Hz), 6.78 (d, 2H, J=9.1 Hz), 4.41 (q, 2H, J=14.8 Hz), 4.22, 4.18 (AB$_q$, 2H, J=7.0 Hz), 4.04-4.01 (m, 2H), 3.97-3.90 (m, 1H), 3.43 (t, 1H, J=8.4 Hz), 3.26, 3.10 (AB$_q$, 2H, J=14.1 Hz), 3.04, 3.02 (AB$_q$, 1H, J=7.0 Hz), 2.08-1.99 (m, 1H), 1.98-1.90 (m, 1H), 1.38 (s, 3H), 1.21 (t, 3H, J=7.0 Hz). MS [EI+] 571 (M+H)$^+$, [EI−] 569 (M−H)$^+$. R$_f$=0.17 in 33% acetone in hexanes.

Step C

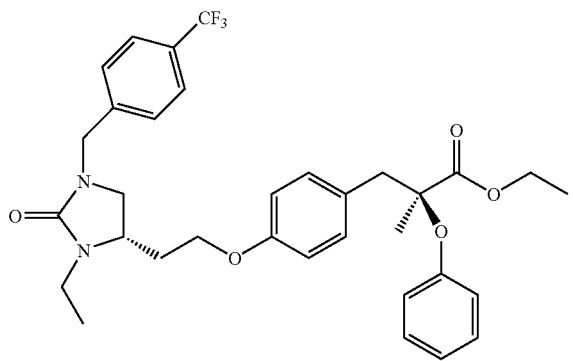

3-(4-{2-[3-Ethyl-2-oxo-1-(4-trifluoromethyl-benzyl)-imidazolidin-4-yl]-ethoxy}-phenyl)-2-methyl-2-phenoxy-propionic acid ethyl ester: A slurry of 2-Methyl-3-(4-{2-[2-oxo-1-(4-trifluoromethyl-benzyl)-imidazolidin-4-yl]-ethoxy}-phenyl)-2-phenoxy-propionic acid ethyl ester (0.500 g, 0.875 mmol) and sodium hydride (0.039 g, 0.96 mmol, 60% dispersion on mineral oil) in DMF (10 mL) is stirred for 1 hour, then cooled to 0° C. Iodoethane (0.70 mL, 8.75 mmol, d=1.975) is added, then the reaction mixture is stirred 18 hours at ambient temperature and diluted with ethyl acetate. The organic layer is washed, dried, and concentrated to provide the title compound. $^1$H NMR (400 MHz, CDCl$_3$): δ 7.55 (d, 2 h, J=8.8 Hz), 7.37 (d, 2H, J=8.0 Hz), 7.21 (t, 2H, J=8.8 Hz), 7.15 (d, 2H, J=8.0 Hz), 6.96 (t, 1H, J=7.2 Hz), 6.82 (d, 2H, J=7.2 Hz), 6.74 (d, 2H, J=8.8 Hz), 4.43, 4.39 (AB$_q$, 2H, J=15.2 Hz), 4.22, 4.17 (AB$_q$, 2H, J=7.2 Hz), 3.96 (t, 1H, J=6.4 Hz), 3.85-3.78 (m, 1H), 3.61-3.55 (m, 1H), 3.35 (t, 1H, J=8.8 Hz), 3.26, 3.12 (AB$_q$, 2H, J=13.6 Hz), 3.16-3.07 (m, 2H), 2.99 (t, 1H, J=8.0 Hz), 2.26-2.19 (m, 1H), 1.90-1.83 (m, 1H), 1.39(s, 3H), 1.21 (t, 3H, J=7.2 Hz), 1.14 (t, 3H, J=7.2 Hz). MS [EI+] 599 (M+H)$^+$.

Step D 3-(4-{2-[3-Ethyl-2-oxo-1-(4-trifluoromethyl-benzyl)-imidazolidin-4-yl]-ethoxy}-phenyl)-2-methyl-2-phenoxy-propionic acid: A solution of 3-(4-{2-[3-Ethyl-2-oxo-1-(4-trifluoromethyl-benzyl)-imidazolidin-4-yl]-ethoxy}-phenyl)-2-methyl-2-phenoxy-propionic acid ethyl ester (0.31 g, 0.518 mmol) and 5N NaOH (1 mL) in ethanol (9 mL) is refluxed for 1 hour, cooled to ambient temperature, and concentrated. The residue is diluted with CH$_2$Cl$_2$, washed, dried, and concentrated in vacuo to provide the title compound (0.256 g, 87%). $^1$H NMR (400 MHz, CDCl$_3$): δ 7.54 (d, 2H, J=7.6 Hz), 7.35 (d, 2H, J=8.4 Hz), 7.21-7.17 (m, 4H), 6.97 (t, 1H, J=7.6 Hz), 6.88 (d, 2H, J=7.6 Hz), 6.72 (d, 2H, J=8.4 Hz), 4.42, 4.38 (AB$_q$, 2H, J=15.1 Hz), 3.94 (t, 2H, J=5.9 Hz), 3.87-3.81 (m, 1H), 3.62-3.53 (m, 1H), 3.36 (t, 1H, J=8.4 Hz), 3.31, 3.08 (AB$_q$, 2H, J=8.4 Hz), 3.15-3.08 (m, 1H), 3.00 (t, 1H, J=8.4 Hz), 2.23-2.19 (m, 1H), 1.89-1.82 (m, 1H), 1.37 (s, 3H), 1.13 (t, 3H, J=6.7 Hz). MS [EI+] 571 (M+H)$^+$, [EI−] 569 (M−H)$^+$.

Example 57

3-(4-{2-[3-(2-Methoxy-ethyl)-2-oxo-1-(4-trifluoromethyl-benzyl)-imidazolidin-4-yl]-ethoxy}-phenyl)-2-methyl-2-phenoxy-propionic acid The title compound is prepared using substantially the procedures described herein, and concentrated in vacuo to provide the title compound (0.139 g, 88%). $^1$H NMR (400 MHz, CDCl$_3$): δ 7.54 (d, 2 h, J=7.5 Hz), 7.35 (d, 2H, J=8.3 Hz), 7.22-7.17 (m, 4H), 6.97 (t, 1H, J=7.5 Hz), 6.88 (d, 2H, J=8.3 Hz), 6.72 (d, 2H, J=8.3 Hz), 4.42, 4.40 (AB$_q$, 2H, J=15.8 Hz), 3.95-3.90 (m, 3H), 3.69-3.63 (m, 1H), 3.55-3.63 (m, 2H), 3.33 (s, 3H), 3.41-3.23 (m, 3H), 3.11-3.01 (m, 2H), 2.73-2.34 (m, 1H), 1.91-1.87 (m, 1H), 1.38(s, 3H). MS [EI+] 601 (M+H)$^+$, [EI−] 599 (M−H)$^+$.

Example 58

2-Butoxy-2-methyl-3-(4-{2-[3-methyl-2-oxo-1-(3-trifluoromethyl-benzyl)-imidazolidin-4-yl]-ethoxy}-phenyl)-propionic acid The title compound is prepared using substantially the procedures described herein and purified by flash chromatography (25% acetone in hexanes) to provide the title compound (0.62 g, 83%). $^1$H NMR (400 MHz, CDCl$_3$): δ 7.51-7.38 (m, 4H), 7.04 (d, 2H, J=8.8 Hz), 6.69 (d, 2H, J=8.8 Hz), 4.46, 4.34 (AB$_q$, 2H, J=14.9 Hz), 3.94 (t, 2H, J=5.7 Hz), 3.68-3.60 (m, 1H), 3.57-3.52 (m, 1H), 3.48-3.43 (m, 1H), 3.38 (t, 1H, J=8.8 Hz), 2.98, 2.92 (AB$_q$, 2H, J=14.4 Hz), 2.83 (s, 3H), 2.25-2.18 (m, 1H), 1.91-1.83 (m, 1H), 1.59-1.52 (m, 2H), 1.45 (s, 3H), 1.39-1.30 (m, 2H), 0.91 (t, 3H, J=7.2 Hz). MS [EI+] 537 (M+H)$^+$, [EI−] 535 (M−H)$^+$.

Example 59

3-{4-[2-(1-Biphenyl-4-ylmethyl-3-methyl-2-oxo-imidazolidin-4-yl)-ethoxy]-phenyl}-2-butoxy-2-methyl-propionic acid The title compound is prepared using substantially the procedures described herein and purified by LCMS to provide the title compound (5.5 mg, 14% over two steps). $^1$H NMR (400 MHz, CDCl$_3$): δ 7.56-7.51 (m, 4H), 7.41 (t, 2H, J=7.8 Hz), 7.33-7.28 (m, 3H), 7.03 (d, 2H, J=8.4 Hz), 6.70 (d, 2H, J=8.4 Hz), 4.43, 4.35 (AB$_q$, 2H, J=15.6 Hz), 3.94 (t, 2H, J=6.0 Hz), 3.66-3.59 (m, 1H), 3.47-3.38 (m, 1H), 3.01 (t, 1H, J=7.8 Hz), 2.97, 2.91 (AB$_q$, 2H, J=13.8 Hz), 2.83 (s, 3H), 2.25-2.18 (m, 1H), 1.91-1.83 (m, 1H), 1.58-1.51 (m, 2H), 1.45 (s, 3H), 1.38-1.29 (m, 2H), 0.89 (t, 3H, J=7.8 Hz). MS [EI+] 545 (M+H)$^+$, [EI−] 543 (M−H)$^+$.

Example 60

3-{4-[2-(1-Benzyl-3-methyl-2-oxo-imidazolidin-4-yl)-ethoxy]-phenyl}-2-butoxy-2-methyl-propionic acid The title compound is prepared using substantially the procedures described herein, and purified by LCMS to provide the title compound (5.5 mg, 14% over two steps). $^1$H NMR (400 MHz, CDCl$_3$): δ 7.31-7.21 (m, 5H), 7.04 (d, 2H, J=8.6 Hz), 6.69 (d, 2H, J=8.6 Hz), 3.38, 3.32 (AB$_q$, 2H, J=15.7 Hz), 3.92 (t, 2H, J=6.3 Hz), 3.62-3.53 (m, 2H), 3.48-3.43 (m, 1H), 3.35 (t, 1H, J=8.6 Hz), 2.99-2.93 (AB$_q$, 2H, J=14.1 Hz), 2.99, 2.93 (AB$_q$ 2H, J=14.1 Hz), 2.95 (t, 2H, J=7.9 Hz), 2.88 (s, 3H), 2.23-2.17 (m, 1H), 1.88-1.82 (m, 1H), 1.60-1.52 (m, 2H), 1.47 (s, 3H), 1.38-1.32 (m, 2H), 1.23 (t, 1H, J=7.1 Hz), 0.91 (t, 3H, J=7.1 Hz). MS [EI+] 469 (M+H)$^+$, [EI−] 467 (M−H)$^+$.

Example 61

2-Methoxy-2-methyl-3-(4-{2-[3-methyl-2-oxo-1-(4-trifluoromethyl-benzyl)-imidazolidin-4-yl]-ethoxy}-phenyl)-propionic acid The title compound is prepared using substantially the procedures described herein, and purified by flash chromatography to provide the title compound (48 mg, 39% over two steps). $^1$H NMR (400 MHz, CDCl$_3$): δ 7.53 (d, 2H, J=8.2 Hz), 7.34 (d, 2H, J=8.2 Hz), 7.07 (d, 2H, J=8.2 Hz), 6.64 (d, 2H, J=8.2 Hz), 4.40, 4.36 (AB$_q$, 2H, J=15.5 Hz), 3.90-3.87 (m, 2H), 3.62-3.56 (m, 1H), 3.35 (t, 1H, J=8.2 Hz), 3.26 (s, 3H), 3.04-2.87 (m, 4H), 2.82 (s, 3H), 2.20-2.16 (m, 1H), 1.87-1.80 (m, 1H), 1.31 (s, 3H). MS [EI+] 495 (M+H)$^+$, [EI−] 493 (M−H)$^+$.

Example 62

2-Methoxy-2-methyl-3-(4-{2-[3-methyl-2-oxo-1-(4-trifluoromethyl-benzyl)-imidazolidin-4-yl]-ethoxy}-phenyl)-propionic acid The title compound is prepared using substantially the procedures described herein, and purified by flash chromatography to provide the title compound (88 mg, 63% over two steps). $^1$H NMR (400 MHz, CDCl$_3$): δ 7.53 (d, 2H, J=8.2 Hz), 7.34 (d, 2H, J=8.2 Hz), 7.07 (d, 2H, J=8.2 Hz), 6.64 (d, 2H, J=8.2 Hz), 4.40, 4.36 (AB$_q$, 2H, J=15.5 Hz), 3.90-3.87 (m, 2H), 3.62-3.56 (m, 1H), 3.35 (t, 1H, J=8.2 Hz), 3.26 (s, 3H), 3.04-2.87 (m, 4H), 2.82 (s, 3H), 2.20-2.16 (m, 1H), 1.87-1.80 (m, 1H), 1.31 (s, 3H). MS [EI+] 495 (M+H)$^+$, [EI−] 493 (M−H)$^+$.

Example 63

2-Methyl-3-(4-{2-[3-methyl-2-oxo-1-(4-trifluoromethyl-benzyl)-imidazolidin-4-yl]-ethoxy}-phenyl)-2-phenoxy-propionic acid

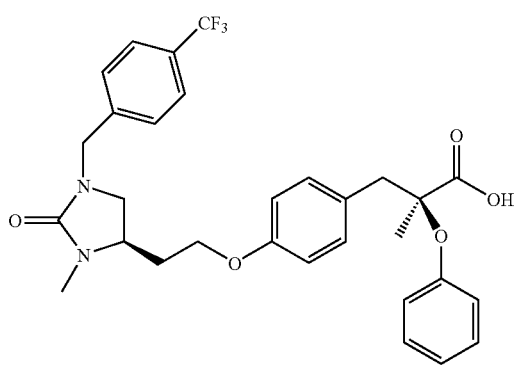

Step A 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester: Cesium carbonate (2.18 g, 6.702 mmol) is added to a solution of 3-(4-Hydroxy-phenyl)-2-methyl-2-phenoxy-propionic acid ethyl ester (1.55 g, 5.155 mmol) and Toluene-4-sulfonic acid 2-[3-methyl-2-oxo-1-(4-trifluoromethyl-benzyl)-imidazolidin-4-yl]-ethyl ester (3.19 g, 5.67 mmol) in DMF (30 mL). The resultant mixture is stirred at 55° C. under an atmosphere of nitrogen for 18 h, then diluted with ethyl acetate. The organic layer is washed, then dried, concentrated, and purified by flash chromatography (17% acetone in hexanes) to provide the title compound (3.46 g, 97%). $^1$H NMR (400 MHz, CDCl$_3$): δ 7.57 (d, 2H, J=7.01 Hz), 7.37 (d, 2H, J=7.1 Hz), 7.23-7.19 (m, 4H), 7.13 (d, 2H, J=8.7 Hz), 6.97 (t, 1H, J=7.1 Hz), 6.87-6.80 (m, 4H), 6.67 (d, 2H, J=8.7 Hz), 4.79, 4.07 (AB$_q$, 2H, J=15.0 Hz), 4.47, 4.43 (AB$_q$, 2H, J=15.0 Hz), 4.20 (q, 2H, J=7.1 Hz), 3.92-3.87 (m, 2H), 3.80 (s, 3H), 3.61-3.55 (m, 1H), 3.31 (t, 2H, J=8.7 Hz), 3.24, 3.10 (AB$_q$, 2H, J=14.2 Hz), 3.00 (t, 1H, J=7.9 Hz), 2.21-2.14 (m, 1H), 1.87-1.78 (m, 1H), 1.38 (s, 3H), 1.21 (t, 3H, J=7.1 Hz). MS [EI+] 691 (M+H)$^+$. R$_f$=0.49 in 50% acetone in hexanes.

Step B

2-Methyl-3-(4-{2-[2-oxo-1-(4-trifluoromethyl-benzyl)-imidazolidin-4-yl]-ethoxy}-phenyl)-2-phenoxy-propionic acid ethyl ester: Trifluoroacetic acid (60 mL) is added dropwise to a solution of 3-(4-{2-[3-(4-Methoxy-benzyl)-2-oxo-1-(4-trifluoromethyl-benzyl)-imidazolidin-4-yl]-ethoxy}-phenyl)-2-methyl-2-phenoxy-propionic acid ethyl ester (3.46 g, 5.0 1mmol) and triethylsilane (1.6 mL, 10.0 mmol, d=0.728). The reaction mixture is stirred at ambient temperature for 2 hours, concentrated, and diluted with ethyl acetate. The solution is washed with a saturated solution of aqueous sodium bicarbonate, water, and brine, then dried over Na$_2$SO$_4$, and concentrated in vacuo to provide the title compound. $^1$H NMR (400 MHz, CDCl$_3$): δ 7.58 (d, 2H, J=8.2 Hz), 7.38 (d, 2H, J=8.2 Hz), 7.23-7.14 (m, 4H), 6.97 (t, 1H, J=7.4 Hz), 6.82 (d, 2H, J=7.4 Hz), 6.78-(d, 2H, J=7.4 Hz), 4.44, 4.38 (AB$_q$, 2H, J=15.6 Hz), 4.20 (q, 2H, J=7.4 Hz), 4.07-3.99 (m, 2H), 3.96-3.89 (m, 1H), 3.47 (t, 1H, J=8.2 Hz), 3.27, 3.09 (AB$_q$, 2H, J=14.1 Hz), 3.04, 3.02 (AB$_q$, 1H, J=6.7 Hz), 2.08-1.99 (m, 1H), 1.98-1.92 (m, 1H), 1.38 (s, 3H), 1.21 (t, 3H, J=6.7 Hz). MS [EI+] 571 (M+H)$^+$, [EI−] 569 (M−H)$^+$. R$_f$=0.07 in 33% acetone in hexanes.

Step C

2-Methyl-3-(4-{2-[3-methyl-2-oxo-1-(4-trifluoromethyl-benzyl)-imidazolidin-4-yl]-ethoxy}-phenyl)-2-phenoxy-propionic acid ethyl ester: A slurry of 2-Methyl-3-(4-{2-[2-oxo-1-(4-trifluoromethyl-benzyl)-imidazolidin-4-yl]-ethoxy}-phenyl)-2-phenoxy-propionic acid ethyl ester (0.544 g, 0.953 mmol) and sodium hydride (0.042 g, 1.05 mmol, 60% dispersion on mineral oil) in DMF (10 mL) was stirred for 1 h, then cooled to 0° C. Iodomethane (0.60 mL, 9.53 mmol, d=2.28) was added, then the reaction mixture is stirred 18 hours at ambient temperature and diluted with ethyl acetate. The organic layer is washed, dried, concentrated, and purified by flash chromatography to provide the title compound. $^1$H NMR (400 MHz, CDCl$_3$): δ 7.56 (d, 2H, J=8.0 Hz), 7.37 (d, 2H, J=8.0 Hz), 7.26-7.19 (m, 2H), 7.15 (d, 2H, J=8.9 Hz), 6.97 (t, 1H, J=8.0 Hz), 6.82 (d, 2H, J=8.0 Hz), 6.74 (d, 2H, J=8.9 Hz), 4.46, 4.38 (AB$_q$, 2H, J=15.1 Hz), 4.20 (q, 2H, J=7.1 Hz), 3.97 (t, 2H, J=7.1 Hz), 3.67-3.59 (m, 1H), 3.78 (t, 1H, J=8.9 Hz), 3.26, 3.10 (AB$_q$, 2H, J=14.2 Hz), 2.99 (t, 1H, J=8.9 Hz), 2.85 (s, 3H), 2.28-2.21 (m, 1H), 1.93-1.84 (m, 1H), 1.39 (s, 3H), 1.21 (t, 3H, J=7.1 Hz). MS [EI+] 585 (M+H)$^+$. R$_f$=0.35 in 50% acetone in hexanes.

Step D

2-Methyl-3-(4-{2-[3-methyl-2-oxo-1-(4-trifluoromethyl-benzyl)-imidazolidin-4-yl]-ethoxy}-phenyl)-2-phenoxy-propionic acid: A solution of 2-methyl-3-(4-{2-[3-methyl-2-oxo-1-(4-trifluoromethyl-benzyl)-imidazolidin-4-yl]-ethoxy}-phenyl)-2-phenoxy-propionic acid ethyl ester and 5N NaOH (0.7 mL) in ethanol (6 mL) is refluxed for 1 h, cooled to ambient temperature, and concentrated in vacuo. The residue is diluted with CH$_2$Cl$_2$, washed, dried, and concentrated to provide the title compound (0.186 g, 100%). $^1$H NMR (400 MHz, CDCl$_3$): δ 7.54 (d, 2H, J=8.3 Hz), 7.35 (d, 2H, J=8.3 Hz), 7.24-7.17 (m, 4H), 7.00 (t, 1H, J=7.4 Hz), 6.89 (d, 2H, J=7.4 Hz), 6.73 (d, 2H, J=8.3 Hz), 4.45, 4.37 (AB$_q$, 2H, J=15.7 Hz), 3.96 (t, 2H, J=5.5 Hz), 3.68-3.62 (m, 1H), 3.38 (t, 1H, J=8.3 Hz), 3.32, 3.10 (AB$_q$, 2H, J=12.9 Hz), 3.00 (t, 1H, J=8.3 Hz), 2.84 (s, 3H), 2.27-2.19 (m, 1H), 1.92-1.85 (m, 1H), 1.39 (s, 3H). MS [EI+] 557 (M+H)$^+$, [EI–] 555 (M–H)$^+$.

Example 64

2,2-Dimethyl-3-(4-{2-[3-methyl-2-oxo-1-(4-trifluoromethyl-benzyl)-imidazolidin-4-yl]-ethoxy}-phenyl)-propionic acid Step A 2,2-Dimethyl-3-(4-{2-[3-methyl-2-oxo-1-(4-trifluoromethyl-benzyl)-imidazolidin-4-yl]-ethoxy}-phenyl)-propionic acid methyl ester To a solution of 3-(4-Hydroxy-phenyl)-2,2-dimethyl-propionic acid methyl ester (31 mg, 0.15 mmol) and Toluene-4-sulfonic acid 2-[3-methyl-2-oxo-1-(4-trifluoromethyl-benzyl)-imidazolidin-4-yl]-ethyl ester (75 mg, 0.16 mmol) in DMF (1 ml) is added Cs$_2$CO$_3$ (64 mg, 0.19 mmol), and the mixture heated at 60° C. for 15 hours. The mixture is cooled, diluted with water (25 ml) and extracted with ethyl acetate (2×25 ml). The combined organic extracts were washed with brine (25 ml), dried (Na$_2$SO$_4$), and concentrated to an oil. Purification by flash chromatography on a Biotage silica cartridge (gradient elution, 2:1 hexanes:ethyl acetate to 1:4 hexanes:ethyl acetate) produced an oil (69 mg, 94%).

MS [EI+] 493 (M+H)$^+$. Structure confirmed by $^1$H-NMR.

Step B 2,2-Dimethyl-3-(4-{2-[3-methyl-2-oxo-1-(4-trifluoromethyl-benzyl)-imidazolidin-4-yl]-ethoxy}-phenyl)-propionic acid To a solution of the ester obtained from Step A (66 mg, 0.13 mmol) in methanol (1.5 ml) is added 5N NaOH (0.3 ml, 1.5 mmol), and the mixture stirred for 20 hours at ambient temperature. The mixture is poured into 1N HCl (20 ml), then extracted with ethyl acetate (2×15 ml). The combined ethyl acetate extracts were washed with water, brine, dried (Na$_2$SO$_4$), and concentrated to a foam (62 mg, 97%.

MS [EI+] 479 (M+H)$^+$. Structure confirmed by $^1$H-NMR.

Example 65

2-methyl-3-(4-{2-[1-(4-methyl-benzyl)-2-oxo-3-propyl-imidazolidin-4-yl]-ethoxy}-phenyl)-2-phenoxy-propionic acid Step A

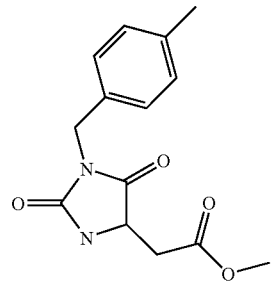

A solution of (2,5-dioxo-imidazolidin-4-yl)-acetic acid, methyl ester (2.35 g, 13.7 mmol) in DMF (100 mL) is treated with p-methyl benzyl bromide (2.90 g, 15.7 mmol), MgSO$_4$ (3.30 g, 27.4 mmol) and then K$_2$CO$_3$ (3.77 g, 27.3 mmol). The resultant mixture is stirred under N$_2$ in an ice bath for 30 minutes and then warmed to room temperature for 16 h. The reaction mixture is then filtered, and then aqueous 1N HCl (150 mL) is added to the filtrate. The filtrate is extracted with EtOAc and the organic layer dried. The solvent is removed to give 4.11 g crude product which is purified by flash chromatography using 100% CH$_2$Cl$_2$ then 97.5:2.5 CH$_2$Cl$_2$:MeOH to give 3.67 g (97%) [1-(4-methyl-benzyl)-2,5-dioxo-imidazolidin-4-yl]-acetic acid methyl ester. $^1$H NMR. MS (ES$^+$) Calc'd for C$_{14}$H$_{17}$N$_2$O$_4$ (M+1) 277. Found m/z 277 (100%).

Step B

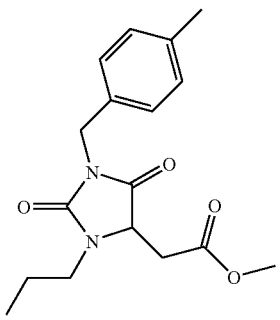

A 0° C. solution of compound [1-(4-methyl-benzyl)-2,5-dioxo-imidazolidin-4-yl]-acetic acid methyl ester (1.60 g, 5.8 mmol) in DMF (28 mL) is treated with sodium hydride (60% dispersion, 0.25 g, 6.4 mmol) and warmed to room temperature and stirred under N$_2$ for 15 minutes. The resultant mixture is cooled to 0° C. and then treated with 1-propyl iodide (1.08 g, 6.4 mmol) and then warmed to room temperature and stirred for 30 minutes. The reaction is quenched with aqueous 1 N HCl (28 mL) and then worked up extractively with EtOAc and water. The organic layer is dried i and the solvent removed to give crude product that is purified by flash chromatography using a gradient of 10:1 to 1:1 hexanes:EtOAc to afford 1.40 g (76%) [1-(4-methyl-benzyl)-2,5-dioxo-3-propyl-imidazolidin-4-yl]-acetic acid methyl ester. $^1$H NMR. MS (ES$^+$) Calc'd for $C_{17}H_{23}N_2O_4$ (M+1) 319. Found m/z 319 (100%).

Step C

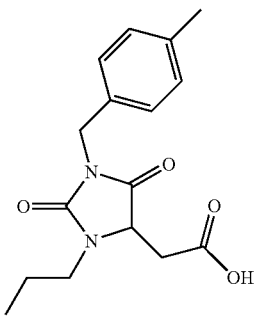

A solution of [1-(4-methyl-benzyl)-2,5-dioxo-3-propyl-imidazolidin-4-yl]-acetic acid methyl ester (1.67 g, 5.20 mmol) in methanol (40 mL) is treated with aqueous 5 N NaOH (4.4 mL) and heated to reflux 1.5 hour. The reaction mixture is cooled, the solvent removed. The resultant residue is acidified and extracted with EtOAc. The organic layer is dried and dried to afford 1.56 g (98%) [1-(4-methyl-benzyl)-2,5-dioxo-3-propyl-imidazolidin-4-yl]-acetic acid. $^1$H NMR. MS (ES$^-$) Calc'd for $C_{16}H_{19}N_2O_4$ (M−1) 303. Found m/z 303 (100%).

Step D

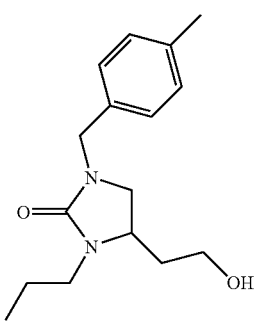

A solution of [1-(4-methyl-benzyl)-2,5-dioxo-3-propyl-imidazolidin-4-yl]-acetic acid (3.23 g, 10.6 mmol) in THF (50 mL) is treated dropwise with 1 M solution of borane-THF complex in THF (53.1 mL, 53.1 mmol) and then stirred at room temperature under $N_2$ for 4 hours. The reaction is quenched with methanol (30 mL) and stirred at room temperature for 16 hour. The solvent is removed to give crude product that is purified by flash chromatography using 97.5/2.5 $CH_2Cl_2$:MeOH to afford 2.46 g (84%) 4-(2-hydroxy-ethyl)-1-(4-methyl-benzyl)-3-propyl-imidazolidin-2-one. $^1$H NMR. MS (ES$^+$) Calc'd for $C_{16}H_{25}N_2O_2$ (M+1) 277. Found m/z 277 (100%).

Step E

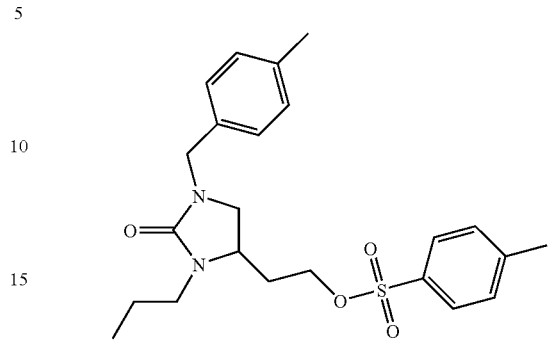

A solution of 4-(2-hydroxy-ethyl)-1-(4-methyl-benzyl)-3-propyl-imidazolidin-2-one (2.46 g, 8.90 mmol), pyridine (2.46 g, 31.1 mmol) and 4-dimethyl amino pyridine (0.33 g, 2.70 mmol) in $CH_2Cl_2$ is treated with p-toluenesulfonic anhydride (4.65 g, 14.2 mmol) and the reaction stirred at room temperature for under $N_2$ for 1.5 hours. The reaction mixture is washed with aqueous 0.5 N HCl (100 mL), the organic layer is dried, and the solvent removed to afford crude product that is purified by flash chromatography using 100% $CH_2Cl_2$ then 97.5:2.5 $CH_2Cl_2$:MeOH to afford 3.31 g (86%) toluene-4-sulfonic acid 2-[1-(4-methyl-benzyl)-2-oxo-3-propyl-imidazolidin-4-yl]-ethyl ester. $^1$H NMR. MS (ES$^+$) Calc'd for $C_{23}H_{31}N_2O_4$ (M+1) 431. Found m/z 431 (100%).

Step F

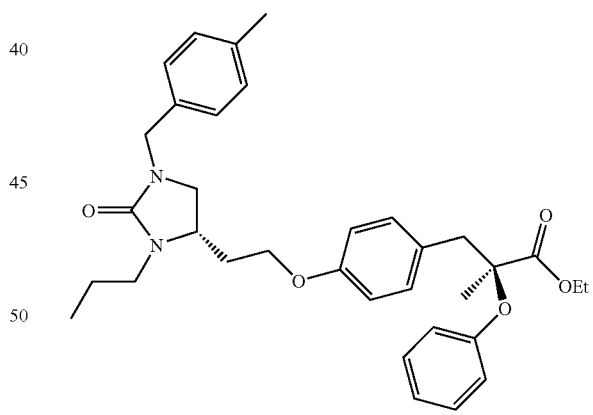

A mixture of 3-(4-hydroxy-phenyl)-2-methyl-2-phenoxy-propionic acid ethyl ester (0.80 g, 2.66 mmol), toluene-4-sulfonic acid 2-[1-(4-methyl-benzyl)-2-oxo-3-propyl-imidazolidin-4-yl]-ethyl ester (1.26 g, 2.93 mmol) and $Cs_2CO_3$ (1.04 g, 3.19 mmol) in DMF (40 mL) is heated to 55° C. under $N_2$ for 17 h. The reaction is cooled and quenched with 1 N HCl (20 mL) and worked up extractively with $Et_2O$ and water. The organic layer is dried and the solvent removed to afford crude product that is purified by flash chromatography using 7:1 hexanes:acetone to afford 1.02 g (68%) 2-methyl-3-(4-{2-[1-(4-methyl-benzyl)-2-oxo-3-propyl-imidazolidin-4-yl]- ethoxy}-phenyl)-2-phenoxy-propionic acid ethyl ester. The diasteriomeric products were separated by chiral HPLC (90:10 heptane:IPA, 280 mL/min, 220 nm,) to give products in >99% de. $R_f$=0.49 (1:1 acetone:hexanes). $^1$H NMR. MS (ES$^+$) Calc'd for $C_{34}H_{43}N_2O_5$ (M+1) 559. Found m/z 559 (100%).

Step G

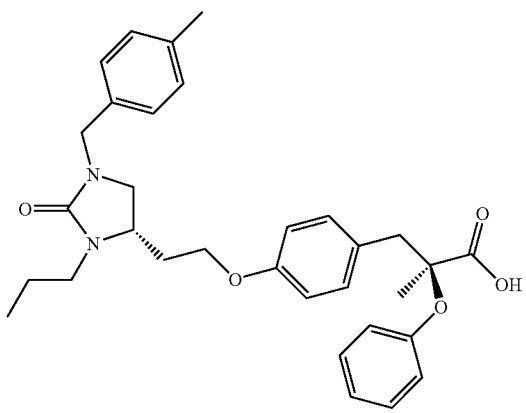

A solution of 2-methyl-3-(4-{2-[1-(4-methyl-benzyl)-2-oxo-3-propyl-imidazolidin-4-yl]-ethoxy}-phenyl)-2-phenoxy-propionic acid ethyl ester (0.456 g, 0.816 mmol) in ethanol (20 mL) is treated with aqueous 5 N NaOH (2 mL) and heated to reflux 1 h. The reaction mixture is cooled, the solvent removed. The resultant residue is acidified and extracted with $CH_2Cl_2$. The organic layer is dried and the solvent removed to afford 0.419 g (97%) 2-methyl-3-(4-{2-[1-(4-methyl-benzyl)-2-oxo-3-propyl-imidazolidin-4-yl]-ethoxy}-phenyl)-2-phenoxy-propionic acid. $^1$H NMR. HRMS (ES$^+$) m/z exact mass calc'd for $C_{32}H_{39}N_2O_5$ (M+1) 531.2859. Found m/z 531.2866.

Example 66

Preparation of 2-methyl-3-{4-[2-(3-methyl-1-naphthalen-2-ylmethyl-2-oxo-imidazolidin-4-yl)-ethoxy]-phenyl}-2-phenoxy-propionic acid Step A

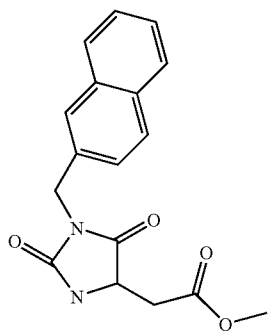

A solution of (2,5-dioxo-imidazolidin-4-yl)-acetic acid methyl ester (6.48 g, 37.6 mmol) in DMF (250 mL) is treated with 2-(bromomethyl)-napthalene (9.15 g, 41.4 mmol), $MgSO_4$ (4.53 g, 37.6 mmol) and then $K_2CO_3$ (15.61 g, 0.113 mol) at 0° C. The resultant mixture is warmed to room temperature and stirred under $N_2$ for 16 hours. The reaction mixture is filtered, and then aqueous 1N HCl (300 mL) is added to the filtrate. The filtrate is extracted with $Et_2O$ and the organic layer dried. The solvent is removed to give a crude oil which is purified by flash chromatography using 2:1 hexanes:acetone to afford 6.27 g of (1-naphthalen-2-ylmethyl-2,5-dioxo-imidazolidin-4-yl)-acetic acid methyl ester (53%). $R_f$=0.32 (1:1 hexanes:acetone). $^1$H NMR.

Step B

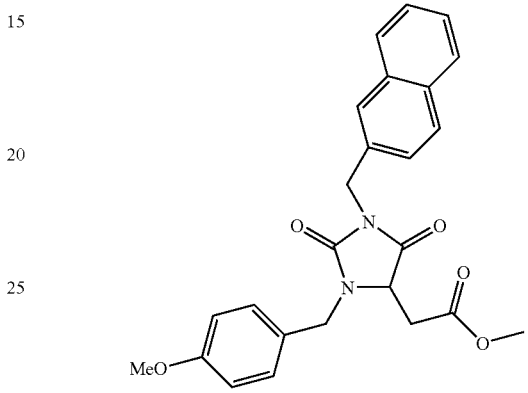

A 0° C. solution of compound (1-naphthalen-2-ylmethyl-2,5-dioxo-imidazolidin-4-yl)-acetic acid methyl ester (6.29 g, 20.1 mmol) in DMF (60 mL) is treated with sodium hydride (60% dispersion, 0.97 g, 24.3 mmol) and warmed to room temperature and stirred under $N_2$ for 20 minutes. The resultant mixture is cooled to 0° C. and then treated with 4-methoxybenzyl, chloride (6.35 g, 40.6 mmol) and then warmed to room temperature and stirred for 16 hours. The reaction is quenched with aqueous 1 N HCl (100 mL) and then worked up extractively with $Et_2O$ and water. The organic layer is dried and the solvent removed to give crude product that is purified by flash chromatography using a gradient of 4:1 hexanes:acetone to afford 8.31 g (95%) [3-(4-methoxy-benzyl)-1-naphthalen-2-ylmethyl-2,5-dioxo-imidazolidin-4-yl]-acetic acid methyl ester. $R_f$=0.44 (1:1 hexanes:acetone). $^1$H NMR.

Step C

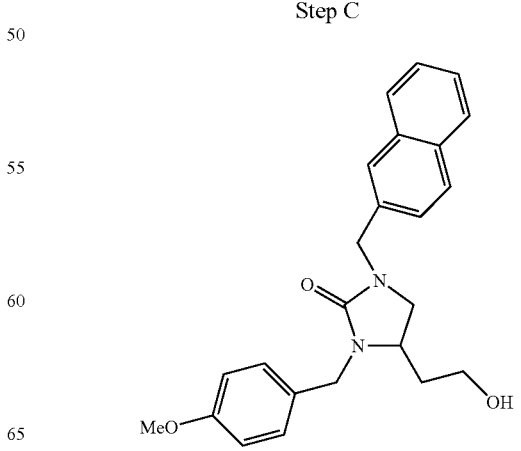

A solution of [3-(4-methoxy-benzyl)-1-naphthalen-2-ylmethyl-2,5-dioxo-imidazolidin-4-yl]-acetic acid methyl ester (8.31 g, 19.2 mmol) in methanol (100 mL) is treated with aqueous 5 N NaOH (40 mL) and heated to reflux 1 hour. The reaction mixture is cooled, the solvent removed in vacuo. The resultant residue is acidified with aqueous 1 N HCl (300 mL) and extracted with Et$_2$O and water. The organic layer is dried and the solvent removed in vacuo to afford 8.08 g (100%) acid that is utilized without purification. A solution of crude acid (8.08 g, assume 19.2 mmol) in THF (100 mL) is treated dropwise with 1 M solution of borane-THF complex in THF (116.0 mL, 0.116 mol) and then stirred at room temperature under N$_2$ for 16 hours. The reaction is quenched with methanol (100 mL) and stirred at room temperature for 1 hour. The solvent is removed to give crude product that is purified by flash chromatography using a gradient of 3:1 to 2:1 hexanes: acetone to afford 5.10 g (68%) 4-(2-hydroxy-ethyl)-3-(4-methoxy-benzyl)-1-naphthalen-2-ylmethyl-imidazolidin-2-one. $^1$H NMR. MS (ES$^+$) Calc'd for C$_{24}$H$_{27}$N$_2$O$_3$ (M+1) 391. Found m/z 391 (100%).

Step D

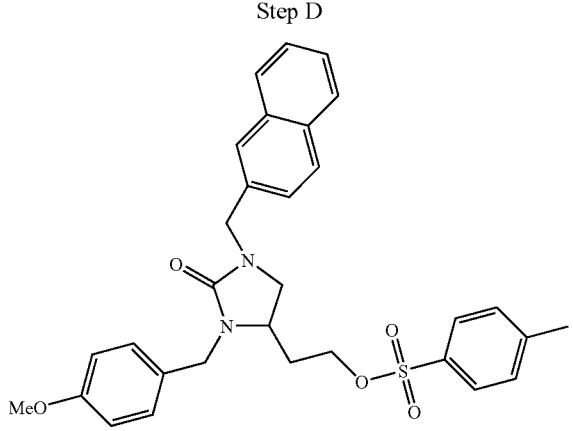

A solution of 4-(2-hydroxy-ethyl)-3-(4-methoxy-benzyl)-1-naphthalen-2-ylmethyl-imidazolidin-2-one (5.10 g, 13.1 mmol), pyridine (3.62 g, 45.7 mmol) and 4-dimethyl amino pyridine (0.48 g, 3.92 mmol) in CH$_2$Cl$_2$ (100 mL) is treated with p-toluenesulfonic anhydride (6.82 g, 20.9 mmol) and the reaction stirred at room temperature for under N$_2$ for 1.5 h. The reaction mixture is washed with aqueous 1 N HCl (100 mL), the organic layer was dried, and the solvent removed in vacuo to afford crude product that is purified by flash chromatography using 3:1 hexanes:acetone to afford 6.74 g (95%) toluene-4-sulfonic acid 2-[3-(4-methoxy-benzyl)-1-naphthalen-2-ylmethyl-2-oxo-imidazolidin-4-yl]-ethyl ester $^1$H NMR. MS (ES$^+$) Calc'd for C$_{31}$H$_{33}$N$_2$O$_5$ (M+1) 545. Found m/z 545 (100%).

Step E

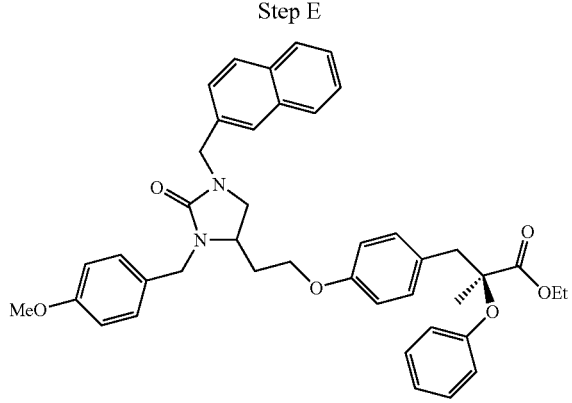

A mixture of 3-(4-hydroxy-phenyl)-2-methyl-2-phenoxy-propionic acid ethyl ester (0.231 g, 0.735 mmol), 2-[3-(4-methoxy-benzyl)-1-naphthalen-2-ylmethyl-2-oxo-imidazolidin-4-yl]-ethyl ester (1.74 g, 3.19 mmol) and Cs$_2$CO$_3$ (1.14 g, 3.5 mmol) in DMF (40 mL) is heated to 65° C. under N$_2$ for 17 h. The reaction is cooled and quenched with 1 N HCl (10 mL) and worked up extractively with Et$_2$O and water. The organic layer is dried and the solvent removed to afford crude product that is purified by flash chromatography using 8:1 then 7:1 hexanes:acetone to afford 1.53 g (78%) 3-(4-{2-[3-(4-methoxy-benzyl)-1-naphthalen-2-ylmethyl-2-oxo-imidazolidin-4-yl]-ethoxy}-phenyl)-2-methyl-2-phenoxy-propionic acid ethyl ester. R$_f$=0.43 (1:1 acetone:hexanes). $^1$H NMR. MS (ES$^+$) Calc'd for C$_{42}$H$_{45}$N$_2$O$_6$ (M+1) 673. Found m/z 673 (100%).

Step F

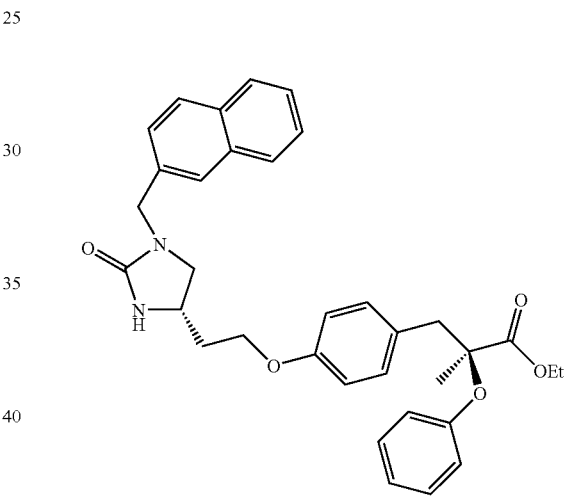

A solution of 3-(4-{2-[3-(4-methoxy-benzyl)-1-naphthalen-2-ylmethyl-2-oxo-imidazolidin-4-yl]-ethoxy}-phenyl)-2-methyl-2-phenoxy-propionic acid ethyl ester (1.54 g, 2.29 mmol) and triethylsilane (0.53 g, 4.56 mmol) in trifluroacetic acid (40 mL) is stirred at room temperature under N$_2$ for 4 hours. The reaction mixture is diluted with water and extracted with EtOAc. The organic layer is dried and the solvent removed in vacuo to afford crude product that is purified by flash chromatography using 3:1 then 1:1 hexanes: acetone to afford 1.25 g (100%) 2-methyl-3-{4-[2-(1-naphthalen-2-ylmethyl-2-oxo-imidazolidin-4-yl]-ethoxy)-phenyl}-2-phenoxy-propionic acid ethyl ester. The diastereomeric mixture could be separated by chiral HPLC (2:3 IPA:heptane mobile phase, 14 mL/min, 225 nm) to afford >99% de 2-methyl-3-{4-[2-(1-naphthalen-2-ylmethyl-2-oxo-imidazolidin-4-yl)-ethoxy]-phenyl}-2-phenoxy-propionic acid ethyl esters. R_f=0.19 (1:1 acetone:hexanes). $^1$H NMR. MS (ES$^+$) Calc'd for $C_{34}H_{37}N_2O_5$ (M+1) 553. Found m/z 553 (100%).

Step G

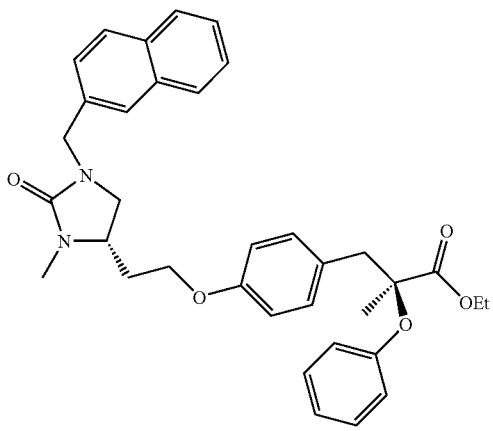

A solution of a diasteriomeric mixture of 2-methyl-3-{4-[2-(1-naphthalen-2-ylmethyl-2-oxo-imidazolidin-4-yl)-ethoxy]-phenyl}-2-phenoxy-propionic acid ethyl ester (0.275 g, 0.498 mmol) in DMF (7 mL) is treated with NaH (60% oil suspension, 0.030 g, 0.750 mmol) and stirred at room temperature under N$_2$ for 30 minutes. The reaction is cooled to 0° C. and treated with iodomethane (0.141 g, 0.996 mmol) and then warmed to room temperature and stirred for 3 hours. The reaction is quenched with 1 N HCl (5 mL) and worked up extractively with Et$_2$O and water. The organic layer is dried and the solvent removed in vacuo to afford crude product that is purified by flash chromatography using 4:1 hexanes:acetone to afford 0.268 g (95%) 2-methyl-3-{4-[2-(3-methyl-1-naphthalen-2-ylmethyl-2-oxo-imidazolidin-4-yl)-ethoxy]-phenyl}-2-phenoxy-propionic acid ethyl ester. The diasteriomeric products are separated by chiral HPLC (8×32 cm Chiralpak AD, 100% IPA, 350 mL/min, 270 nm, to give products in>99% de $^1$H NMR. R_f=0.35 (1:1 acetone: hexanes). MS (ES$^+$) Calc'd for $C_{35}H_{39}N_2O_5$ (M+1) 567. Found m/z 567 (100%).

Step H

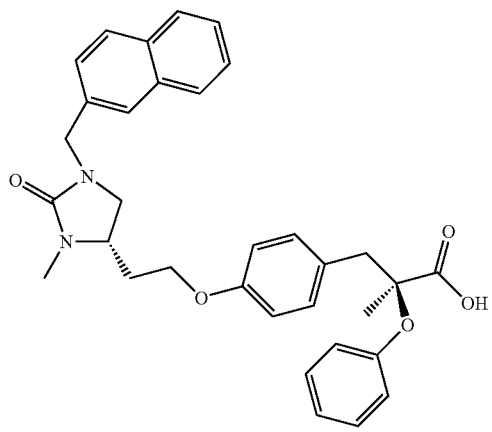

A solution of 2-methyl-3-{4-[2-(3-methyl-1-naphthalen-2-ylmethyl-2-oxo-imidazolidin-4-yl)-ethoxy]-phenyl}-2-phenoxy-propionic acid ethyl ester (0.161 g, 0.284 mmol) in ethanol (8 mL) is treated with aqueous 5 N NaOH (0.75 mL) and heated to reflux 1 h. The reaction mixture is cooled, the solvent removed in vacuo. The resultant residue is acidified with aqueous 1 N HCl (10 mL) and extracted with CH$_2$Cl$_2$. The organic layer is dried (Na$_2$SO$_4$) and the solvent removed in vacuo to afford 0.113 g (74%) 2-methyl-3-{4-[2-(3-methyl-1-naphthalen-2-ylmethyl-2-oxo-imidazolidin-4-yl)-ethoxy]-phenyl}-2-phenoxy-propionic acid. $^1$H NMR. HRMS (ES$^+$) m/z exact mass calc'd for $C_{33}H_{35}N_2O_5$ (M+1) 539.2546. Found m/z 539.2548.

Example 67

2-methyl-3-{4-[2-(1-naphthalen-2-ylmethyl-2-oxo-imidazolidin-4-yl)-ethoxy]-phenyl}-2-phenoxy-propionic acid

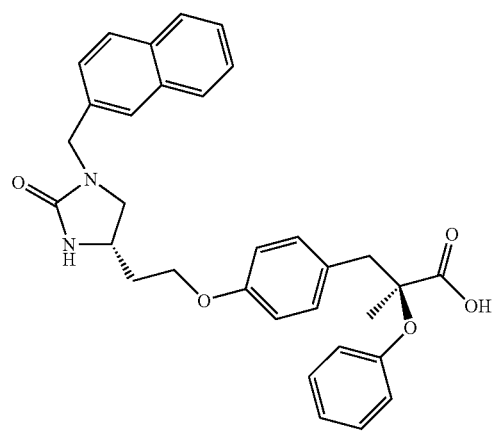

A solution of 2-methyl-3-{4-[2-(1-naphthalen-2-ylmethyl-2-oxo-imidazolidin-4-yl)-ethoxy]-phenyl}-2-phenoxy-propionic acid ethyl esters (0.021 g, 0.040 mmol) in ethanol (8 mL) was treated with aqueous 5 N NaOH (1 mL) and heated to reflux 1 h. The reaction mixture was cooled, the solvent removed in vacuo. The resultant residue was acidified with aqueous 1 N HCl (10 mL) and extracted with CH$_2$Cl$_2$. The organic layer was dried (Na$_2$SO$_4$) and the solvent removed in vacuo to afford 0.021 g (100%) 2-methyl-3-{4-[2-(1-naphthalen-2-ylmethyl-2-oxo-imidazolidin-4-yl)-ethoxy]-phenyl}-2-phenoxy-propionic acid. $^1$H NMR. HRMS (ES$^+$) m/z exact mass calc'd for $C_{32}H_{33}N_2O_5$ (M+1) 525.2389. Found m/z 525.2382.

Example 68

3-(4-{2-[1-(3-methoxy-benzyl)-3-methyl-2-oxo-imidazolidin-4-yl]-ethoxy}-phenyl)-2-methyl-2-phenoxy-propionic acid Step A A solution of 2-methyl-3-{4-[2-(3-methyl-2-oxo-imidazolidin-4-yl)-ethoxy]-phenyl}-2-phenoxy-propionic acid ethyl ester (0.40 g, 0.94 mmol) in DMF (10 mL) is treated with NaH (60% oil suspension, 0.094 g, 2.35 mmol) and stirred at room temperature under N$_2$ for 30 minutes. The reaction is cooled to 0° C. and treated with tetrabutylammonium iodide (0.040 g, 0.11 mmol) and 3-methoxybenzyl bromide (0.29 g, 1.43 mmol) and then warmed to room temperature and stirred for 1.5 h. The reaction is quenched with 1 N HCl (15 mL) and worked up extractively with Et$_2$O and water. The organic layer is dried (MgSO$_4$) and the solvent removed in vacuo to afford crude product that is purified by flash chromatography using 2:1 hexanes:acetone to afford 0.28 g (55%) 3-(4-{2-[1-(3-methoxy-benzyl)-3-methyl-2-oxo-imidazolidin-4-yl]-ethoxy}-phenyl)-2-methyl-2-phenoxy-propionic acid ethyl ester. $^1$H NMR. $R_f$=0.41 (1:1 acetone:hexanes). MS (ES$^+$) Calc'd for $C_{32}H_{39}N_2O_6$ (M+1) 547. Found m/z 547 (100%).

Step B

A solution of 3-(4-{2-[1-(3-methoxy-benzyl)-3-methyl-2-oxo-imidazolidin-4-yl]-ethoxy}-phenyl)-2-methyl-2-phenoxy-propionic acid ethyl ester (0.28 g, 0.51 mmol) in ethanol (20 mL) is treated with aqueous 5 N NaOH (2 mL) and heated to reflux 1 h. The reaction mixture is cooled, the solvent removed in vacuo. The resultant residue is acidified with aqueous 1 N HCl (20 mL) and extracted with $CH_2Cl_2$. The organic layer is dried ($Na_2SO_4$) and the solvent removed in vacuo to afford 0.257 g (97%) 3-(4-{2-[1-(3-methoxy-benzyl)-3-methyl-2-oxo-imidazolidin-4-yl]-ethoxy}-phenyl)-2-methyl-2-phenoxy-propionic acid $^1$H NMR (500 MHz, CDCl$_3$) ☐ 7.28-7.20 (m, 3H), 7.18 (d, 2H, J=8.80 Hz), 7.04 (t, 1H, J=7.34 Hz), 6.91 (d, 2H, J=7.83 Hz), 6.82 (t, 1H, J 7.83 Hz), 6.79-6.78 (m, 2H), 6.73 (d, 2H, J=8.83 Hz), 4.38, 4.28 (AB$_q$, 2H, J=14.92 Hz), 3.95 (t, 2H, J=5.87 Hz), 3.77 (s, 3H), 3.60 (ddd, 1H, J=12.2 Hz, J=8.40 Hz, J=3.42 Hz), 3.36 (t, 1H, J=7.83 Hz), 3.30, 3.10 (AB$_q$, 2H, J=13.69 Hz), 2.96 (t, 1H, J=7.83 Hz), 2.83 (s, 3H), 2.25-2.18 (m, 1H), 1.92-1.84 (m, 1H), 1.42 (s, 3H). HRMS (ES$^+$) m/z exact mass calc'd for $C_{30}H_{35}N_2O_6$ (M+1) 519.2495. Found m/z 519.2504.

Example 69

2-methyl-3-(4-{2-[3-methyl-2-oxo-1-(2-trifluoromethyl-benzyl)-imidazolidin-4-yl]-ethoxy}-phenyl)-2-phenoxy-propionic acid

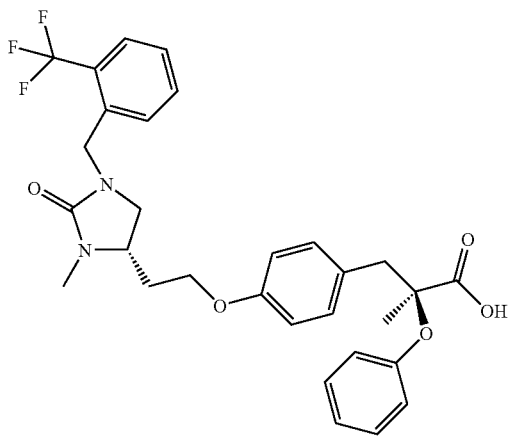

A solution of 2-methyl-3-{4-[2-(3-methyl-2-oxo-imidazolidin-4-yl)-ethoxy]-phenyl}-2-phenoxy-propionic acid ethyl ester (0.109 g, 0.255 mmol) in DMF (7 mL) is treated with NaH (60% oil suspension, 0.021 g, 0.525 mmol) and stirred at room temperature under $N_2$ for 20 minutes. The reaction is treated with 2-trifluoromethyl benzyl bromide (0.092 g, 0.385 mmol) and then warmed to room temperature and stirred for 3 hours. The reaction is quenched with acid and worked up extractively with Et$_2$O and water. The organic layer is dried and the solvent removed to afford crude product that is dissolved in ethanol (20 mL) is treated with aqueous 5 N NaOH (1.5 mL) and heated to reflux 1 hour. The reaction mixture is cooled, the solvent removed. The resultant residue is acidified with aqueous 1 N HCl (20 mL) and extracted with $CH_2Cl_2$. The organic layer is dried and the solvent removed in vacuo to afford crude acid that is purified by preparative HPLC to give 0.096 g (68%) of 2-methyl-3-(4-{2-[3-methyl-2-oxo-1-(2-trifluoromethyl-benzyl)-imidazolidin-4-yl]-ethoxy}-phenyl)-2-phenoxy-propionic acid $^1$H NMR. HRMS (ES$^+$) m/z exact mass calc'd for $C_{30}H_{32}N_2O_5F_3$ (M+1) 557.2263. Found m/z 557.2274.

Example 70

3-(4-{2-[1-(2-methoxy-benzyl)-3-methyl-2-oxo-imidazolidin-4-yl]-ethoxy}-phenyl)-2-methyl-2-phenoxy-propionic acid

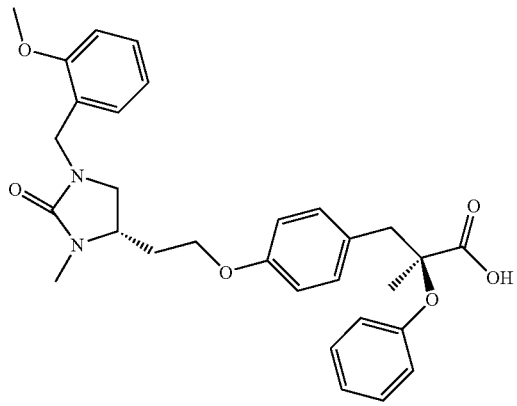

A solution of 2-methyl-3-{4-[2-(3-methyl-2-oxo-imidazolidin-4-yl)-ethoxy]-phenyl}-2-phenoxy-propionic acid ethyl ester (0.12 g, 0.281 mmol) in DMF (7 mL) is treated with NaH (60% oil suspension, 0.023 g, 0.575 mmol) and stirred at room temperature under $N_2$ for 20 minutes. The reaction is treated with 2-methoxybenzyl chloride (0.066 g, 0.421 mmol) and then warmed to room temperature and stirred for 3 h. The reaction is quenched with 1 N HCl (10 mL) and worked up extractively with Et$_2$O and water. The organic layer is dried (MgSO$_4$) and the solvent removed in vacuo to afford crude product that is dissolved in ethanol (20 mL) is treated with aqueous 5 N NaOH (1.5 mL) and heated to reflux 1 h. The reaction mixture is cooled, the solvent removed in vacuo. The resultant residue is acidified with aqueous 1 N HCl (20 mL) and extracted with $CH_2Cl_2$. The organic layer is dried (Na$_2$SO$_4$) and the solvent removed in vacuo to afford crude acid that is purified by preparative HPLC to give 0.077 g (53%) of 3-(4-{2-[1-(2-methoxy-benzyl)-3-methyl-2-oxo-imidazolidin-4-yl]-ethoxy}-phenyl)-2-methyl-2-phenoxy-propionic acid. $^1$H NMR. HRMS (ES$^+$) m/z exact mass calc'd for $C_{30}H_{35}N_2O_6$ (M+1) 519.2495. Found m/z 519.2515.

Example 71

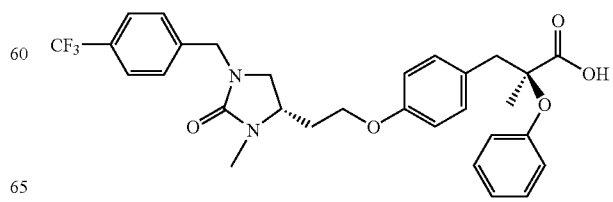

2-Methyl-3-(4-{2-[3-methyl-2-oxo-1-(4-trifluoromethyl-benzyl)-imidazolidin-4-yl]-ethoxy}-phenyl)-2-phenoxy-propionic acid To a mixture of 54 mg of 2-Methyl-3-{4-[2-(3-methyl-2-oxo-imidazolidin-4-yl)-ethoxy]-phenyl}-2-phenoxy-propionic acid ethyl ester in 2 mL of dry DMF at 0° C. under an atmosphere of nitrogen, 10 mg of NaH (0.253 mmol) is added. The resulting solution is allowed to stand at ambient temperature for 20 min. Then 61 mg of 4-trifluoromethylbenzyl bromide is added and resulting mixture is allowed to stand at ambient temperature for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.3 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 35 mg (49%) of the title product. $^1$H NMR (400 MHz, CDCl$_3$): δ 7.56 (d, 2H, J=8.0 Hz), 7.35 (d, 2H, J=8.0 Hz), 7.28-7.18 (m, 4H), 7.05 (t, 1H, J=7.2 Hz), 6.91 (d, 2H, J=8.0 Hz), 6.74 (d, 2H, J=8.0 Hz), 5.49 (bs, 1H), 4.45, 4.39 (ABq, 2H, J=15.4 Hz), 3.98 (t, 2H, J=5.8 Hz), 3.77-3.65 (m, 1H), 3.42 (t, 1H, J=8.5 Hz), 3.28, 3.14 (ABq, 2H, J=14.0 Hz), 3.05 (t, 1H, J=8.5 Hz), 2.86 (s, 3H), 2.28-2.20 (m, 1H), 1.95-1.85 (m, 1H), 1.43 (s, 3H). HRMS (ES$^+$) m/z exact mass calcd for C$_{30}$H$_{32}$N$_2$O$_5$F$_3$ (m+1) 557.2263, found 557.2257.

Example 72

3-(4-{2-[1-(4-tert-Butyl-benzyl)-3-methyl-2-oxo-imidazolidin-4-yl]-ethoxy}-phenyl)-2-(4-fluoro-phenoxy)-2-methyl-propionic acid

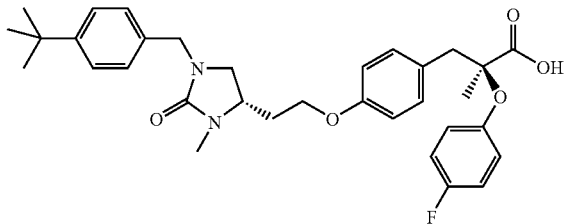

To a mixture of 80 mg of 2-(4-Fluoro-phenoxy)-2-methyl-3-{4-[2-(3-methyl-2-oxo-imidazolidin-4-yl)-ethoxy]-phenyl}-propionic acid ethyl ester in 5 mL of dry DMF at 0° C. under an atmosphere of nitrogen, 18 mg of NaH (0.45 mmol) is added. The resulting solution is allowed to stand at r.t. for 20 min. Then 0.08 mL of 4-tert-butylbenzyl bromide is added and resulting mixture is allowed to stand at r.t. for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.4 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 45 mg (45%) of the title product. $^1$H NMR (400 MHz, CDCl$_3$): δ 7.33 (d, 2H, J=8.4 Hz), 7.18, 7.16 (ABq, 4H, J=8.6 Hz), 6.96-6.92 (m, 2H), 6.88-6.85 (m, 2H), 6.77 (d, 2H, J=8.8 Hz), 4.38, 4.29 (ABq, 2H, J=14.8 Hz), 3.98 (t, 2H, J=6.0 Hz), 3.69 (bs, 1H), 3.73-3.66 (m, 1H), 3.44 (t, 1H, J=8.6 Hz), 3.25, 3.11 (ABq, 2H, J=13.8 Hz), 3.06 (t, 1H, J=8.6 Hz), 2.86 (s, 3H), 2.28-2.19 (m, 1H), 1.97-1.89 (m, 1H), 1.38 (s, 3H), 1.30 (s, 9H). HRMS (ES$^+$) m/z exact mass calcd for C$_{33}$H$_{40}$N$_2$O$_5$F (m+1) 563.2921, found 563.2917.

Example 73

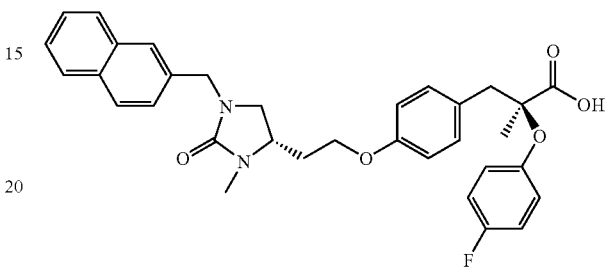

2-(4-Fluoro-phenoxy)-2-methyl-3-{4-[2-(3-methyl-1-naphthalen-2-ylmethyl-2-oxo-imidazolidin-4-yl)-ethoxy]-phenyl}-propionic acid To a mixture of 80 mg of 2-(4-Fluoro-phenoxy)-2-methyl-3-{4-[2-(3-methyl-2-oxo-imidazolidin-4-yl)-ethoxy]-phenyl}-propionic acid ethyl ester in 5 mL of dry DMF at 0° C. under an atmosphere of nitrogen, 18 mg of NaH (0.45 mmol) is added. The resulting solution is allowed to stand at r.t. for 20 min. Then 99 mg of 2-bromomethyl naphthalene is added and resulting mixture is allowed to stand at r.t. for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.4 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 51 mg (51%) of the title product. $^1$H NMR (400 MHz, CDCl$_3$): δ 7.82-7.79 (m, 3H), 7.67 (s, 1H), 7.50-7.44 (m, 2H), 7.35 (d, 1H, J=8.4 Hz), 7.14 (d, 2H, J=8.6 Hz), 6.93 (t, 2H, J=8.4 Hz), 6.87-6.83 (m, 2H), 6.71 (d, 2H, J=8.6 Hz), 5.11 (bs, 1H), 4.53 (s, 2H), 3.95-3.90 (m, 2H), 3.85-3.70 (m, 1H), 3.46 (t, 1H, L=8.7 Hz), 3.23, 3.09 (ABq, 2H, J=14.0 Hz), 3.07 (t, 1H, J=8.7 Hz), 2.89 (s, 3H), 2.26-2.18 (m, 1H), 1.96-1.87 (m, 1H), 1.36 (s, 3H). HRMS (ES$^+$) m/z exact mass calcd for C$_{33}$H$_{34}$N$_2$O$_5$F (m+1) 557.2452, found 557.2439.

Example 74

3-(4-{2-[1-(3,4-Dimethyl-benzyl)-3-methyl-2-oxo-imidazolidin-4-yl]-ethoxy}-phenyl)-2-(4-fluoro-phenoxy)-2-methyl-propionic acid To a mixture of 80 mg of 2-(4-Fluoro-phenoxy)-2-methyl-3-{4-[2-(3-methyl-2-oxo-imidazolidin-4-yl)-ethoxy]-phenyl}-propionic acid ethyl ester in 5 mL of dry DMF at 0° C. under an atmosphere of nitrogen, 18 mg of NaH (0.45 mmol) is added. The resulting solution is allowed to stand at r.t. for 20 min. Then 0.07 mL of 3,4-dimethylbenzyl chloride is added and resulting mixture is allowed to stand at r.t. for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.4 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 54 mg (56%) of the title product. $^1$H NMR (400 MHz, CDCl$_3$): δ 7.18 (d, 2H, J=8.4 Hz), 7.06 (d, 1H, J=7.6 Hz), 7.00 (s, 1H), 6.97-6.85 (m, 5H), 6.75 (d, 2H, J=8.4 Hz), 4.34, 4.25 (ABq, 2H, J=15.0 Hz), 4.31 (bs, 1H), 3.98-3.90 (m, 2H), 3.69-3.61 (m, 1H), 3.39 (t, 1H, J=8.7 Hz), 3.25, 3.11 (ABq, 2H, J=14.0 Hz), 3.00 (t, 1H, J=8.7 Hz), 2.84 (s, 3H), 2.29-2.17 (m, 1H), 2.22 (s, 6H), 1.94-1.87 (m, 1H), 1.37 (s, 3H). HRMS (ES$^+$) m/z exact mass calcd for C$_{31}$H$_{36}$N$_2$O$_5$F (m+1) 535.2608, found 535.2614.

Example 75

3-(4-{2-[1-(4-tert-Butyl-benzyl)-3-methyl-2-oxo-imidazolidin-4-yl]-ethoxy}-phenyl)-2-methyl-2-(4-trifluoromethyl-phenoxy)-propionic acid To a mixture of 80 mg of 2-Methyl-3-{4-[2-(3-methyl-2-oxo-imidazolidin-4-yl)-ethoxy]-phenyl}-2-(4-trifluoromethyl-phenoxy)-propionic acid ethyl ester in 5 mL of dry DMF at 0° C. under an atmosphere of nitrogen, 16 mg of NaH (0.40 mmol) is added. The resulting solution is allowed to stand at r.t. for 20 minute Then 0.07 mL of 4-tert-butylbenzyl bromide is added and resulting mixture is allowed to stand at r.t. for overnight. Reaction mixture is diluted with Et$_2$O and 1N HCl. Organic layer is then washed with 1N HCl. (2×10 mL), brine (2×10 mL), dried over Na$_2$SO$_4$, filtered and concentrated under vacuum. The crude material is in 5 mL of EtOH and 0.5 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 40 mg (40%) of the title product. $^1$H NMR (400 MHz, CDCl$_3$): δ 7.51 (d, 2H, J=8.8 Hz), 7.38-7.32 (m, 2H), 7.16 (t, 4H, J=8.8 Hz), 6.95 (d, 2H, J=8.8 Hz), 6.76 (d, 2H, J=8.8 Hz), 4.37, 4.28 (ABq, 2H, J=14.8 Hz), 4.24 (bs, 1H), 3.97 (t, 2H, J=6.0 Hz), 3.74-3.67 (m, 1H), 3.44 (t, 1H, J=9.2 Hz), 3.31, 3.16 (ABq, 2H, J=13.8 Hz), 3.07 (t, 1H, J=9.2 Hz), 2.85 (s, 3H), 2.27-2.18 (m, 1H), 1.98-1.89 (m, 1H), 1.50 (s, 3H), 1.29 (s, 9H). HRMS (ES$^+$) m/z exact mass calcd for C$_{34}$H$_{40}$N$_2$O$_5$F$_3$ (m+1) 613.2889, found 613.2872.

Example 76

2-Methyl-3-{4-[2-(3-methyl-1-naphthalen-2-ylmethyl-2-oxo-imidazolidin-4-yl)-ethoxy]-phenyl}-2-(4-trifluoromethyl-phenoxy)-propionic acid To a mixture of 80 mg of 2-Methyl-3-{4-[2-(3-methyl-2-oxo-imidazolidin-4-yl)-ethoxy]-phenyl}-2-(4-trifluoromethyl-phenoxy)-propionic acid ethyl ester in 5 mL of dry DMF at 0° C. under an atmosphere of nitrogen, 16 mg of NaH (0.40 mmol) is added. The resulting solution is allowed to stand at r.t. for 20 minute Then 89 mg of 2-bromomethyl naphthalene is added and resulting mixture is allowed to stand at r.t. for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.5 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 mL). Combined organic layer is dried over Na$_2$SO$_4$, filtered and concentrated under vacuum. The crude material is purified by MS/LC to give 51 mg (51%) of the title product. $^1$H NMR (400 MHz, CDCl$_3$): δ 7.81-7.77 (m, 3H), 7.66 (s, 1H), 7.48-7.45 (m, 4H), 7.35 (dd, 1H, J=8.8, 1.6 Hz), 7.12 (d, 2H, J=8.8 Hz), 6.92 (d, 2H, J=8.4 Hz), 6.69 (d, 2H, J=8.4 Hz), 6.20 (bs, 1H), 4.51 (s, 2H), 3.92-3.90 (m, 2H), 3.72-3.64 (m, 1H), 3.41 (t, 1H, J=8.8 Hz), 3.29, 3.13 (AB$_q$, 2H, J=13.8 Hz), 3.03 (t, 1H, J=8.8 Hz), 2.86 (s, 3H), 2.22-2.15 (m, 1H), 1.93-1.84 (m, 1H), 1.46 (s, 3H). HRMS (ES$^+$) m/z exact mass calcd for C$_{34}$H$_{34}$N$_2$O$_5$F$_3$ (m+1) 6072420, found 6072417.

Example 77

3-(4-{2-[1-(3,4-Dimethyl-benzyl)-3-methyl-2-oxo-imidazolidin-4-yl]-ethoxy}-phenyl)-2-methyl-2-(4-trifluoromethyl-phenoxy)-propionic acid To a mixture of 80 mg of 2-Methyl-3-{4-[2-(3-methyl-2-oxo-imidazolidin-4-yl)-ethoxy]-phenyl}-2-(4-trifluoromethyl-phenoxy)-propionic acid ethyl ester in 5 mL of dry DMF at 0° C. under an atmosphere of nitrogen, 16 mg of NaH (0.40 mmol) is added. The resulting solution is allowed to stand at r.t. for 20 min. Then 0.06 mL of 3,4-dimethylbenzyl chloride is added and resulting mixture is allowed to stand at r.t. for overnight. Reaction mixture is diluted with Et$_2$O and 1N HCl. Organic layer is then washed with 1N HCl (2×10 mL), brine (2×10 mL), dried over Na$_2$SO$_4$, filtered and concentrated under vacuum. The crude material is in 5 mL of EtOH and 0.5 mL of 5N NaOH. The mixture is heated to reflux for 1 h. The organic solvent is then removed under vacuum and residue is dissolved in CH$_2$Cl$_2$ and 1N HCl. Aqueous layer is washed with CH$_2$Cl$_2$ (2×10 ml). Combined organic layer is dried over Na$_2$SO$_4$, filtered and concentrated under vacuum. The crude material is purified by MS/LC to give 54 mg (56%) of the title product. $^1$H NMR (400 MHz, CDCl$_3$): δ 7.51 (d, 2H, J=8.6 Hz), 7.16 (d, 1H, J=8.6 Hz), 7.10 (d, 1H, J=8.0 Hz), 7.06 (d, 1H, J=8.0 Hz), 6.99-6.94 (m, 3H), 6.75 (d, 2H, J=8.4 Hz), 4.33, 4.25 (ABq, 2H, J=14.8 Hz), 4.07 (bs, 1H), 3.97-3.93 (m, 2H), 3.70-3.65 (m, 1H), 3.41 (t, 1H, J=8.8 Hz), 3.32, 3.16 (ABq, 2H, J=13.8 Hz), 3.03 (t, 1H, J=8.8 Hz), 2.85 (s, 3H), 2.28-2.20 (m, 1H), 2.22 (s, 3H), 1.96-1.88 (m, 1H), 1.50 (s, 3H). HRMS (ES$^+$) m/z exact mass calcd for C$_{32}$H$_{36}$N$_2$O$_5$F$_3$ (m+1) 585.2576, found 585.2578.

Example 79

2-Methyl-3-(4-{2-[3-methyl-2-oxo-1-(3-phenoxy-benzyl)-imidazolidin-4-yl]-ethoxy}-phenyl)-2-phenoxy-propionic acid The titled compound is prepared, according to the procedures substantially as described herein, yield (0.192 g, 52%).

Mass [EI+] 581 (M+H)$^+$, [EI−] 579 (M−H)$^-$.

Example 80

2-Methyl-3-(4-{2-[3-methyl-2-oxo-1-(3-trifluoromethoxy-benzyl)-imidazolidin-4-yl]-ethoxy}-phenyl)-2-phenoxy-propionic acid The titled compound is prepared, according to the procedures substantially as described herein, yield (0.127 g, 35%). Mass [EI+] 573 (M+H)$^+$, [EI−] 571 (M−H)$^-$.

Example 81

2-Methyl-3-(4-{2-[3-methyl-2-oxo-1-(3-trifluoromethoxy-benzyl)-imidazolidin-4-yl]-ethoxy}-phenyl)-2-phenoxy-propionic acid The titled compound is prepared, according to the procedures substantially as described herein, yield (0.238 g, 63%). Mass [EI+] 573 (M+H)$^+$, [EI−] 571 (M−H)$^-$.

Example 82

2-(2-Fluoro-phenoxy)-2-methyl-3-(4-{2-[3-methyl-2-oxo-1-(4-trifluoromethoxy-benzyl)-imidazolidin-4-yl]-ethoxy}-phenyl)-propionic acid

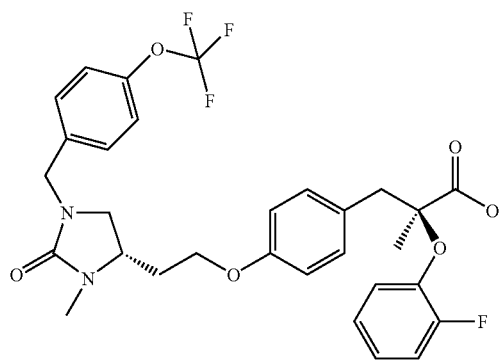

The titled compound is prepared, substantially according to the procedures described herein to produce a white foamy solid (0.087 g, 64%). Mass [EI+] 591 (M+H)$^+$, [EI−] 589 (M−H)$^-$.

Example 83

2-(2-Fluoro-phenoxy)-2-methyl-3-(4-{2-[3-methyl-1-(4-methyl-benzyl)-2-oxo-imidazolidin-4-yl]-ethoxy}-phenyl)-propionic acid The titled compound is prepared, substantially according to the procedures described herein to produce a white foamy solid (0.022 g, 18%). Mass [EI+] 521 (M+H)$^+$, [EI−] 519 (M−H)$^-$.

Example 84

3-(4-{2-[1-(3,4-Dichloro-benzyl)-3-methyl-2-oxo-imidazolidin-4-yl]-ethoxy}-phenyl)-2-(2-fluoro-phenoxy)-2-methyl-propionic acid The titled compound is prepared, substantially according to the procedures described herein to produce a white foamy solid (0.107 g, 80%). Mass [EI+] 574, 577 (M+H)$^+$, [EI−] 573, 575 (M−H)$^-$.

Example 85

3-(4-{2-[11-(3,4-Difluoro-benzyl)-3-methyl-2-oxo-imidazolidin-4-yl]-ethoxy}-phenyl)-2-(2-fluoro-phenoxy)-2-methyl-propionic acid The titled compound is prepared, substantially according to the procedures described herein to produce a white foamy solid (0.107 g, 84%). Mass [EI+] 543 (M+H)$^+$, [EI−] 541 (M−H)$^-$.

Example 86

3-(4-{2-[1-(3,5-Difluoro-benzyl)-3-methyl-2-oxo-imidazolidin-4-yl]-ethoxy}-phenyl)-2-(2-fluoro-phenoxy)-2-methyl-propionic acid The titled compound is prepared, substantially according to the procedures described herein to produce a white foamy solid (0.0824 g, 65%). Mass [EI+] 543 (M+H)$^+$, [EI−] 541 (M−H)$^-$.

Example 87

2-(2-Fluoro-phenoxy)-2-methyl-3-{4-[2-(3-methyl-1-naphthalen-2-ylmethyl-2-oxo-imidazolidin-4-yl)-ethoxy]-phenyl}-propionic acid The titled compound is prepared, substantially according to the procedures described herein to produce a white foamy solid (0.0753 g, 58%). Mass [EI+] 543 (M+H)$^+$, [EI−] 541 (M−H)$^-$.

Example 88

3-{4-[2-(1-Biphenyl-4-ylmethyl-3-methyl-2-oxo-imidazolidin-4-yl)-ethoxy]-phenyl}-2-methyl-2-phenoxy-propionic acid The title compound is prepares substantially according to the procedures described herein, and concentrated to an oil which is purified by MS/LC to yield an oil (25 mg, 25%). MS [EI+]565 (M+H)$^+$. Structure confirmed by $^1$H-NMR.

Example 89

2-Methyl-3-(4-{2-[3-methyl-2-oxo-1-(4-trifluoromethoxy-benzyl)-imidazolidin-4-yl]-ethoxy}-phenyl)-2-phenoxy-propionic acid NaH (8.8 mg, 0.22 mmol, 60% w/w in mineral oil) is added to a cooled (0° C.) solution of 2-Methyl-3-{4-[2-(3-methyl- 2-oxo-imidazolidin-4-yl)-ethoxy]-phenyl}-2-phenoxy-propionic acid ethyl ester (78.5 mg, 0.18 mmol) in DMF (1 ml). After 5 minutes, the reaction mixture is removed from the cooling bath and stirred while warming to ambient temperature over one hour. After the solution is cooled again to 0° C., 4-(trifluoromethoxy)benzyl bromide (59 ul, 0.37 mmol) is added in a single portion, the cooling bath removed, and the mixture stirred for one hour. The reaction mixture is quenched with 1N HCl and extracted with ethyl acetate (2×). The organic extracts were washed with water, brine, dried (Na$_2$SO$_4$), and concentrated to an oil. The crude product is dissolved in methanol (5 ml), treated with 5N NaOH (0.5 ml), and stirred for 14 hours at ambient temperature. After concentration to remove methanol, the residue is partitioned between diethyl ether and water. The aqueous layer is adjusted to pH 2 with conc. HCl, then extracted with ethyl acetate (2×15 ml). The combined ethyl acetate extracts were washed with water, brine, dried (Na$_2$SO$_4$), and concentrated to an oil which is purified by MS/LC to yield an oil (33 mg, 31%).

MS [EI+] 573 (M+H)$^+$. Structure confirmed by $^1$H-NMR.

Example 90

3-(4-{2-[1-(4-Fluoro-3-trifluoromethyl-benzyl)-3-methyl-2-oxo-imidazolidin-4-yl]-ethoxy}-phenyl)-2-methyl-2-phenoxy-propionic acid NaH (9.2 mg, 0.23 mmol, 60% w/w in mineral oil) is added to a cooled (0° C.) solution of 2-Methyl-3-{4-[2-(3-methyl-2-oxo-imidazolidin-4-yl)-ethoxy]-phenyl}-2-phenoxy-propionic acid ethyl ester (82.0 mg, 0.19 mmol) in DMF (1 ml). After 5 minutes, the reaction mixture is removed from the cooling bath and stirred while warming to ambient temperature over one hour. After the solution is cooled again to 0° C., 4-fluoro-3-(trifluoromethyl)benzyl bromide (148 mg, 0.57 mmol) is added in a single portion, the cooling bath removed, and the mixture stirred for one hour. The reaction mixture is quenched with 1N HCl and extracted with ethyl acetate (2×). The organic extracts were washed with water, brine, dried (Na$_2$SO$_4$), and concentrated to an oil. The crude product is dissolved in methanol (5 ml), treated with 5N NaOH (0.5 ml), and stirred for 18 hours at ambient temperature. After concentration to remove methanol, the residue is partitioned between diethyl ether and water. The aqueous layer is adjusted to pH 2 with conc. HCl, then extracted with ethyl acetate (2×15 ml). The combined ethyl acetate extracts were washed with water, brine, dried (Na$_2$SO$_4$), and concentrated to an oil which is purified by MS/LC to yield an oil (41 mg, 37%).

MS [EI+] 575 (M+H)$^+$. Structure confirmed by $^1$H-NMR.

Example 91

3-(4-{2-[1-(3-Fluoro-4-trifluoromethyl-benzyl)-3-methyl-2-oxo-imidazolidin-4-yl]-ethoxy}-phenyl)-2-methyl-2-phenoxy-propionic acid The title compound is prepared substantially as described herein and concentrated to an oil which is purified by MS/LC to yield an oil (45 mg, 41%).

MS [EI+] 575 (M+H)$^+$. Structure confirmed by $^1$H-NMR.

Example 92

2-Methyl-3-(4-{2-[3-methyl-2-oxo-1-(3-trifluoromethyl-benzyl)-imidazolidin-4-yl]-ethoxy}-phenyl)-2-phenoxy-propionic acid Step A 2-Methyl-3-(4-{2-[3-methyl-2-oxo-1-(3-trifluoromethyl-benzyl)-imidazolidin-4-yl]-ethoxy}-phenyl)-2-phenoxy-propionic acid ethyl ester

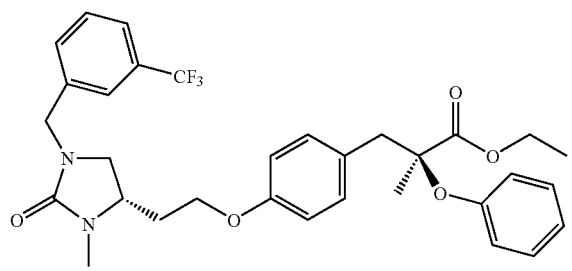

NaH (34 mg, 0.84 mmol, 60% w/w in mineral oil) is added to a cooled (0° C.) solution of 2-Methyl-3-{4-[2-(3-methyl-2-oxo-imidazolidin-4-yl)-ethoxy]-phenyl}-2-phenoxy-propionic acid ethyl ester (300 mg, 0.70 mmol) in DMF (1.5 ml). After 5 minutes, the reaction mixture is removed from the cooling bath and stirred while warming to ambient temperature over 1.5 hours. After the solution is cooled again to 0° C., 3-(trifluoromethyl)benzyl bromide (217 mg, 0.91 mmol) is added in a single portion, the cooling bath removed, and the mixture stirred for 2.5 hours. The reaction mixture is quenched with 1N HCl and extracted with ethyl acetate (2×). The organic extracts were washed with water, brine, dried (Na$_2$SO$_4$), and concentrated to an oil. The crude product is purified by flash chromatography on a Biotage silica cartridge (gradient elution, 5:1 hexanes:ethyl acetate to 1:1 hexanes:ethyl acetate) to provide an oil (273 mg) which is a mixture of the title compound and corresponding substituted-benzyl ester as two closely eluting compounds.

MS [EI+] 585 (M+H)$^+$. Structure confirmed by 1H-NMR.

Step B

2-Methyl-3-(4-{2-[3-methyl-2-oxo-1-(3-trifluoromethyl-benzyl)-imidazolidin-4-yl]-ethoxy}-phenyl)-2-phenoxy-propionic acid

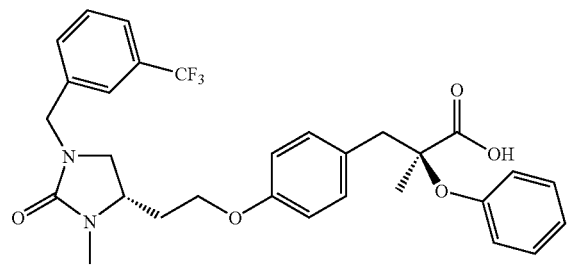

To a solution of the esters obtained from Step A (270 mg) in absolute ethanol (4.5 ml) is added 5N NaOH (1.9 ml, 9.5 mmol), and the mixture stirred for 20 hours at ambient temperature. The mixture is poured into 1N HCl, then extracted with ethyl acetate (2×20 ml). The combined ethyl acetate extracts were washed with water, brine, dried (Na$_2$SO$_4$), and concentrated to an oil which is purified is purified by flash chromatography on a Biotage silica cartridge (gradient elution, 3:1 hexanes:ethyl acetate to 1:2 hexanes:ethyl acetate to yield a foam (78 mg).

MS [EI+]557 (M+H)$^+$. Structure confirmed by $^1$H-NMR.

Example 93

3-(4-{2-[1-(3,4-Dichloro-benzyl)-3-methyl-2-oxo-imidazolidin-4-yl]-ethoxy}-phenyl)-2-methyl-2-phenoxy-propionic acid

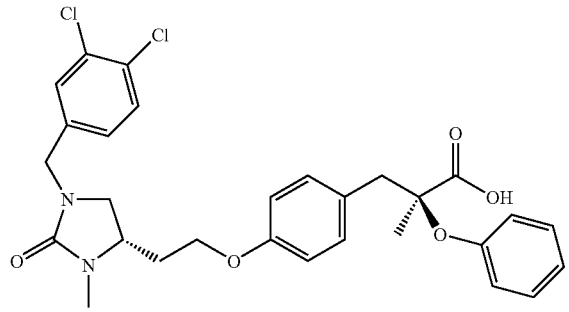

Step A 3-(4-{2-[1-(3,4-Dichloro-benzyl)-3-methyl-2-oxo-imidazolidin-4-yl]-ethoxy}-phenyl)-2-methyl-2-phenoxy-propionic acid ethyl ester NaH (34 mg, 0.84 mmol, 60% w/w in mineral oil) is added to a cooled (0° C.) solution of 2-Methyl-3-{4-[2-(3-methyl-2-oxo-imidazolidin-4-yl)-ethoxy]-phenyl}-2-phenoxy-propionic acid ethyl ester (300 mg, 0.70 mmol) in DMF (1.5 ml). After 5 minutes, the reaction mixture is removed from the cooling bath and stirred while warming to ambient temperature over 1.5 hours. After the solution is cooled again to 0° C., 3,4-dichlorobenzyl bromide (218 mg, 0.91 mmol) is added in a single portion, the cooling bath removed, and the mixture stirred for 2.5 hours. The reaction mixture is quenched with 1N HCl and extracted with ethyl acetate (2×). The organic extracts were washed with water, brine, dried (Na$_2$SO$_4$), and concentrated to an oil. The crude product is purified by flash chromatography on a Biotage silica cartridge (gradient elution, 5:1 hexanes:ethyl acetate to 1:1 hexanes:ethyl acetate) to provide an oil (320 mg) which is a mixture of the title compound and corresponding substituted-benzyl ester as two closely eluting compounds.

MS [EI+] 586 (M+H)$^+$. Structure confirmed by $^1$H-NMR.

Step B 3-(4-{2-[1-(3,4-Dichloro-benzyl)-3-methyl-2-oxo-imidazolidin-4-yl]-ethoxy}-phenyl)-2-methyl-2-phenoxy-propionic acid To a solution of the esters obtained from Step A (320 mg) in absolute ethanol (5.5 ml) is added 5N NaOH (2.2 ml, 10.9 mmol), and the mixture stirred for 20 hours at ambient temperature. The mixture is poured into 1N HCl, then extracted with ethyl acetate (2×20 ml). The combined ethyl acetate extracts were washed with water, brine, dried (Na$_2$SO$_4$), and concentrated to an oil which is purified is purified by flash chromatography on a Biotage silica cartridge (gradient elution, 3:1 hexanes:ethyl acetate to 1:2 hexanes:ethyl acetate to yield a foam (180 mg.)

MS [EI+] 558 (M+H)$^+$. Structure confirmed by $^1$H-NMR.

Example 94

3-(4-{2-[1-(3,5-Bis-trifluoromethyl-benzyl)-3-methyl-2-oxo-imidazolidin-4-yl]-ethoxy}-phenyl)-2-methyl-2-phenoxy-propionic acid The title compound was prepared using substantially the procedures described herein.

Example 95

3-(4-{2-[1-(3,5-Bis-trifluoromethyl-benzyl)-3-methyl-2-oxo-imidazolidin-4-yl]-ethoxy}-phenyl)-2-methyl-2-phenoxy-propionic acid Step A 3-(4-{2-[1-(3,5-Bis-trifluoromethyl-benzyl)-3-methyl-2-oxo-imidazolidin-4-yl]-ethoxy}-phenyl)-2-methyl-2-phenoxy-propionic acid ethyl ester To a cooled (0° C.) suspension of NaH (41 mg, 1.03 mmol, 60% w/w in mineral oil) in DMF (1.0 ml) is added a solution of 2-Methyl-3-{4-[2-(3-methyl-2-oxo-imidazolidin-4-yl)-ethoxy]-phenyl}-2-phenoxy-propionic acid ethyl ester (294 mg, 0.69 mmol) in DMF (1.5 ml). After 5 minutes, the reaction mixture is removed from the cooling bath and stirred while warming to ambient temperature over 45 minutes. After the solution is cooled again to 0° C., 3,5-Bis(trifluoromethyl) benzyl bromide (423 mg, 1.38 mmol) is added in a single portion, the cooling bath removed, and the mixture stirred for 1 hour. The reaction mixture is quenched with 1N HCl and extracted with ethyl acetate (2×). The organic extracts were washed with water, brine, dried (Na$_2$SO$_4$), and concentrated to an oil. The crude product is purified by flash chromatography on a Biotage silica cartridge (gradient elution, 5:1 hexanes:ethyl acetate to 1:1 hexanes:ethyl acetate) to provide an oil (380 mg) which is a mixture of the title compound and corresponding substituted-benzyl ester as two closely eluting compounds.

MS [EI+] 653 (M+H)$^+$. Structure confirmed by 1H-NMR.

Step B 3-(4-{2-[1-(3,5-Bis-trifluoromethyl-benzyl)-3-methyl-2-oxo-imidazolidin-4-yl]-ethoxy}-phenyl)-2-methyl-2-phenoxy-propionic acid To a solution of the esters obtained from Step A (378 mg) in absolute ethanol (4 ml) is added 5N NaOH (1.5 ml, 7.5 mmol), and the mixture stirred for 20 hours at ambient temperature. The mixture is poured into 1N HCl, then extracted with ethyl acetate (2×20 ml). The combined ethyl acetate extracts were washed with water, brine, dried (Na$_2$SO$_4$), and concentrated to an oil which is purified is purified by flash chromatography on a Biotage silica cartridge (gradient elution, 3:1 hexanes:ethyl acetate to 1:2 hexanes:ethyl acetate to yield a foam (266 mg.)

MS [EI+] 625 (M+H)$^+$. Structure confirmed by 1H-NMR.

Example 96

3-(4-{2-[1-(4-Benzoyl-benzyl)-3-methyl-2-oxo-imidazolidin-4-yl]-ethoxy}-phenyl)-2-methyl-2-phenoxy-propionic acid

Step A

3-(4-{2-[1-(4-Benzoyl-benzyl)-3-methyl-2-oxo-imidazolidin-4-yl]-ethoxy}-phenyl)-2-methyl-2-phenoxy-propionic acid ethyl ester To a cooled (0° C.) suspension of NaH (45 mg, 1.1 mmol, 60% w/w in mineral oil) in DMF (0.5 ml) is added a solution of 2-Methyl-3-{4-[2-(3-methyl-2-oxo-imidazolidin-4-yl)-ethoxy]-phenyl}-2-phenoxy-propionic acid ethyl ester (320 mg, 0.75 mmol) in DMF (1.5 ml). After 5 minutes, the reaction mixture is removed from the cooling bath and stirred while warming to ambient temperature over 30 minutes. The solution is cooled again to 0° C., and 4-(bromomethyl)benzophenone (188 mg, 0.68 mmol) is added in a single portion, the cooling bath removed, and the mixture stirred for one hour. The reaction mixture is quenched with 1N HCl and extracted with ethyl acetate (2×). The organic extracts were washed with water, brine, dried (Na$_2$SO$_4$), and concentrated to an oil. The crude product is purified by flash chromatography on a Biotage silica cartridge (gradient elution, 2:1 hexanes:ethyl acetate to 1:2 hexanes:ethyl acetate) to provide an oil (46 mg, 10%).

MS [EI+] 621 (M+H)$^+$. Structure confirmed by 1H-NMR.

Step B

3-(4-{2-[1-(4-Benzoyl-benzyl)-3-methyl-2-oxo-imidazolidin-4-yl]-ethoxy}1-phenyl)-2-methyl-2-phenoxy-propionic acid To a solution of the ester obtained from Step A (46 mg, 0.1 mmol) in absolute ethanol (2 ml) is added 5N NaOH (0.5 ml, 2.5 mmol), and the mixture stirred for 14 hours at ambient temperature. The mixture is poured into 1N HCl, then extracted with ethyl acetate (2×20 ml). The combined ethyl acetate extracts were washed with water, brine, dried (Na$_2$SO$_4$), and concentrated to an oil which is purified is purified by MS/LC to provide a oil (26 mg, 7%).

MS [EI+] 593 (M+H)$^+$. Structure confirmed by $^1$H-NMR.

Example 97

3-(4-{2-[1-(4-Isopropyl-benzyl)-3-methyl-2-oxo-imidazolidin-4-yl]-ethoxy}-phenyl)-2-methyl-2-phenoxy-propionic acid To a cooled (0° C.) suspension of NaH (24 mg, 0.60 mmol, 60% w/w in mineral oil) in DMF (1 ml) is added a solution of 2-Methyl-3-{4-[2-(3-methyl-2-oxo-imidazolidin-4-yl)-ethoxy]-phenyl}-2-phenoxy-propionic acid ethyl ester (128 mg, 0.30 mmol) in DMF (1.5 ml). After 5 minutes, the reaction mixture is removed from the cooling bath and stirred while warming to ambient temperature over 45 minutes. After the solution is cooled again to 0° C., 4-isopropylbenzyl chloride (126 mg, 0.75 mmol) is added in a single portion, the cooling bath removed, and the mixture stirred for 50 minutes. The reaction mixture is quenched with 1N HCl and extracted with ethyl acetate (2×). The organic extracts were washed with water, brine, dried (Na$_2$SO$_4$), and concentrated to an oil. The crude product is dissolved in ethanol (4 ml), treated with 5N NaOH (1.5 ml), and stirred for 24 hours at ambient temperature. The mixture is poured into 1N HCl, then extracted with ethyl acetate (2×20 ml). The combined ethyl acetate extracts were washed with water, brine, dried (Na$_2$SO$_4$), and concentrated to an oil which is purified by MS/LC to provide a foam (110 mg, 69%).

MS [EI+] 531 (M+H)$^+$. Structure confirmed by 1H-NMR.

Example 98

2-Methyl-3-(4-{2-[3-methyl-1-(6-methyl-naphthalen-2-ylmethyl)-2-oxo-imidazolidin-4-yl]-ethoxy}-phenyl)-2-phenoxy-propionic acid The title compound was prepared substantially as described herein and concentrated to an oil which is purified by MS/LC to provide a white solid (83 mg, 50%).

MS [EI+] 553 (M+H)$^+$. Structure confirmed by 1H-NMR.

To a solution of the ester obtained from Step A (69 mg, 0.1 mmol) in methanol (2 ml) is added 5N NaOH (0.2 ml, 1 mmol), and the mixture stirred for 16 hours at ambient temperature. The mixture is poured into 1N HCl (20 ml), then extracted with ethyl acetate (2×15 ml). The combined ethyl acetate extracts were washed with water, brine, dried (Na$_2$SO$_4$), and concentrated to a foam (62 mg, 100%).

MS [EI+] 625 (M+H)$^+$. Structure confirmed by $^1$H-NMR.

Example 99

2-Methyl-3-(3-{2-[3-methyl-2-oxo-1-(4-trifluoromethyl-benzyl)-imidazolidin-4-yl]-ethoxy}-phenyl)-2-phenoxy-propionic acid (Diastereomer 4)

Step A

2-Methyl-3-(3-{2-[3-methyl-2-oxo-1-(4-trifluoromethyl-benzyl)-imidazolidin-4-yl]-ethoxy}-phenyl)-2-phenoxy-propionic acid ethyl ester (Diastereomer 4)

To a solution of 3-(3-Hydroxy-phenyl)-2-methyl-2-phenoxy-propionic acid ethyl ester (Isomer 2) (43 mg, 0.143 mmol,) and Toluene-4-sulfonic acid 2-[3-methyl-2-oxo-1-(4-trifluoromethyl-benzyl)-imidazolidin-4-yl]-ethyl ester (Isomer 2) (72 mg, 0.157 mmol) in DMF (1 ml) at 23° C. is added Cs$_2$CO$_3$ (61 mg, 0.186 mmol) and the suspension heated at 55° C. for 7 hours. The mixture is cooled, filtered, and the filter cake washed with DMF (10 ml). The filtrate is poured into 1N HCl (35 ml) and extracted with ethyl acetate (2×20 ml). The combined organic extracts were washed with water (25 ml), brine (20 ml), dried (Na$_2$SO$_4$) and concentrated to an oil. Purification by flash chromatography on a Biotage silica cartridge (gradient elution, 4:1 hexanes:acetone to 1:1 hexanes:acetone) provided an oil, (72 mg, 87%) (diastereomer 4).

MS [EI+] 585 (M+H)$^+$. Structure confirmed by 1H-NMR.

Step B

2-Methyl-3-(3-{2-[3-methyl-2-oxo-1-(4-trifluoromethyl-benzyl)-imidazolidin-4-yl]-ethoxy}-phenyl)-2-phenoxy-propionic acid (Diasereomer 4)

To a solution of the ester obtained from Step A (72 mg, 0.12 mmol) in methanol (2 ml) is added 5N NaOH (0.5 ml, 2.5 mmol), and the mixture stirred for 20 hours at ambient temperature. The mixture is poured into 1N HCl (20 ml), then extracted with ethyl acetate (2×15 ml). The combined ethyl acetate extracts were washed with water, brine, dried (Na$_2$SO$_4$), and concentrated to an oil (64 mg, 94%) (diastereomer 4).

MS [EI+] 557 (M+H)$^+$. Structure confirmed by 1H-NMR.

Example 100

2-methyl-3-(4-{3-[3-methyl-2-oxo-1-(4-trifluoromethyl-benzyl)-imidazolidin-4-yl]-propyl}-phenyl)-2-phenoxy-propionic acid

Step A

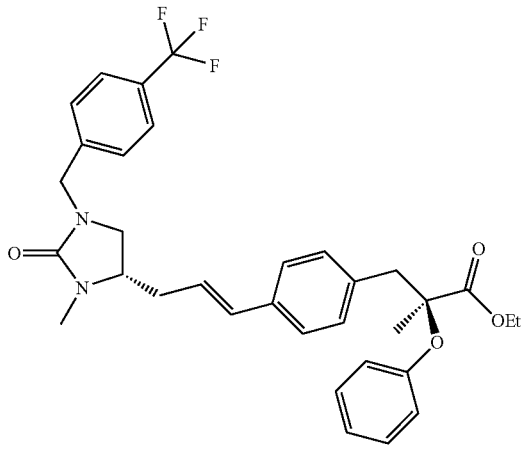

A solution of crude 3-methyl-1-(4-trifluoromethyl-benzyl)-4-[2-(triphenyl-05-phosphanyl)-ethyl]-imidazolidin-2-one iodide (0.65 g, 0.964 mmol) in dry THF (4 mL) is treated with NaH (60% oil suspension, 0.081 g, 2.02 mmol) and stirred at room temperature under $N_2$ for 20 minutes to form the ylide. A solution of 3-(4-formyl-phenyl)-2-methyl-2-phenoxy-propionic acid ethyl ester (0.21 g, 0.672 mmol) in THF (4 mL) is then added to the ylide mixture dropwise at room temperature and the reaction is stirred for 16 h. The reaction is diluted with $Et_2O$ and washed with 1 N HCl and water. The organic layer is dried ($Na_2SO_4$) and the solvent removed in vacuo to afford crude product that is purified by flash chromatography using 6:1 hexanes:acetone to afford 0.070 g (18%) 2-methyl-3-(4-{3-[3-methyl-2-oxo-1-(4-trifluoromethyl-benzyl)-imidazolidin-4-yl]-propenyl}-phenyl)-2-phenoxy-propionic acid ethyl ester. $R_f$=0.22 (1:1 acetone:hexanes). $^1H$ NMR. MS (ES$^+$) Calc'd for $C_{33}H_{36}N_2O_4F_3$ (M+1) 581. Found m/z 581 (100%).

Step B

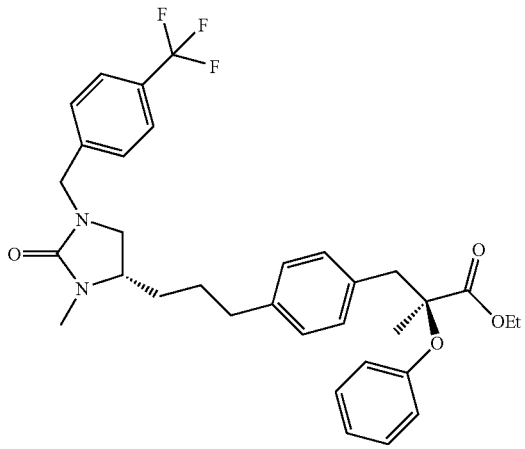

A mixture of 2-methyl-3-(4-{3-[3-methyl-2-oxo-1-(4-trifluoromethyl-benzyl)-imidazolidin-4-yl]-propenyl}-phenyl)-2-phenoxy-propionic acid ethyl ester (0.069 g, 0.119 mmol) and 10% Pd/C (70 mg) in EtOAc (50 mL) is purged with $N_2$ then $H_2$ and then stirred under a $H_2$ balloon at room temperature for 2 h. The reaction mixture is filtered through hyflo and the solvent removed in vacuo to afford 0.069 g (100%) 2-methyl-3-(4-{3-[3-methyl-2-oxo-1-(4-trifluoromethyl-benzyl)-imidazolidin-4-yl]-propyl}-phenyl)-2-phenoxy-propionic acid ethyl ester. $^1H$ NMR. MS (ES$^+$) Calc'd for $C_{33}H_{38}N_2O_4F_3$ (M+1) 583. Found m/z 583 (100%).

Step C

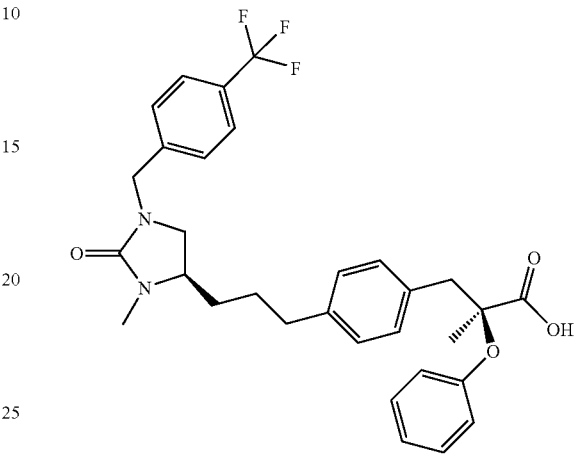

A solution of 2-methyl-3-(4-{3-[3-methyl-2-oxo-1-(4-trifluoromethyl-benzyl)-imidazolidin-4-yl]-propyl}-phenyl)-2-phenoxy-propionic acid ethyl ester (0.062 g, 0.106 mmol) in ethanol (8 mL) is treated with aqueous 5 N NaOH (1 mL) and heated to reflux 1 h. The reaction mixture is cooled, the solvent removed in vacuo. The resultant residue is acidified with aqueous 1 N HCl (20 mL) and extracted with $CH_2Cl_2$. The organic layer is dried ($Na_2SO_4$) and the solvent removed in vacuo to afford 0.062 g (100%) 2-methyl-3-(4-{3-[3-methyl-2-oxo-1-(4-trifluoromethyl-benzyl)-imidazolidin-4-yl]-propyl}-phenyl)-2-phenoxy-propionic acid. $^1H$ NMR. HRMS (ES$^+$) m/z exact mass calc'd for $C_{31}H_{34}N_2O_4F_3$ (M+1) 555.2471. Found m/z 555.2459.

Example 101

3-(2-(1,3-Dioxo-1,3-dihydro-isoindol-2-ylmethyl)-4-{2-[3-methyl-2-oxo-1-(4-trifluoromethyl-benzyl)-imidazolidin-4-yl]-ethoxy}-phenyl)-propionic acid

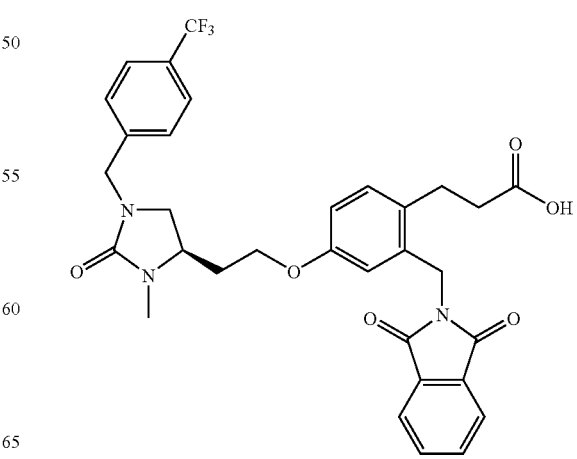

Step A 3-(2-(1,3-Dioxo-1,3-dihydro-isoindol-2-ylmethyl)-4-{2-[3-methyl-2-oxo-1-(4-trifluoromethyl-benzyl)-imidazolidin-4-yl]-ethoxy}-phenyl)-propionic acid tert-butyl ester To a solution of 3-[2-(1,3-Dioxo-1,3-dihydro-isoindol-2-ylmethyl)-4-hydroxy-phenyl]-propionic acid tert-butyl ester (57 mg, 0.15 mmol) and Toluene-4-sulfonic acid 2-[3-methyl-2-oxo-1-(4-trifluoromethyl-benzyl)-imidazolidin-4-yl]-ethyl ester (75 mg, 0.16 mmol) in DMF (1 ml) is added Cs₂CO₃ (64 mg, 0.19 mmol), and the mixture heated at 60° C. for 14 hours. The mixture is cooled, diluted with water (25 ml) and extracted with ethyl acetate (2×25 ml). The combined organic extracts were washed with brine (30 ml), dried (Na₂SO₄), and concentrated to an oil. Purification by flash chromatography on a Biotage silica cartridge (gradient elution, 5:1 to 1:1 hexanes:acetone) produced an oil (72 mg, 73%).

MS [EI+] 666 (M+H)⁺. Structure confirmed by 1H-NMR.

Step B 3-(2-(1,3-Dioxo-1,3-dihydro-isoindol-2-ylmethyl)-4-{2-[3-methyl-2-oxo-1-(4-trifluoromethyl-benzyl)-imidazolidin-4-yl]-ethoxy}-phenyl)-propionic acid A solution of the ester obtained in Step A (70 mg, 0.10 mmol) in trifluoroacetic (1 ml) and methylene chloride (2 ml) is stirred at 23° C. for 7 hours. Concentration of the reaction mixture gave an oil which is partitioned between ethyl acetate (20 ml) and water (25 ml). The ethyl acetate layer is washed with water (15 ml), brine (20 ml), dried (Na₂SO₄), and concentrated to an oil which is purified by chromatography on a Biotage silica cartridge (gradient elution, 100% methylene chloride to 10:1 methylene chloride:methanol) to produce an oil (31 mg, 48%).

MS [EI+] 610 (M+H)⁺. Structure confirmed by 1H-NMR.

Example 102

2,2-Dimethyl-3-(4-{2-[3-methyl-2-oxo-1-(4-trifluoromethyl-benzyl)-imidazolidin-4-yl]-ethoxy}-phenyl)-propionic acid

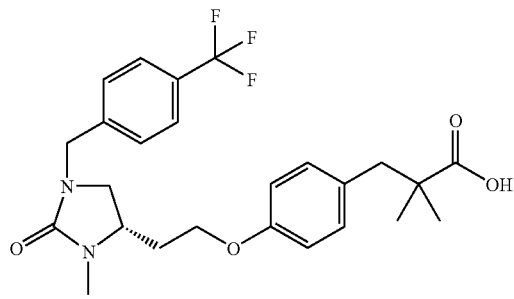

Step A 2,2-Dimethyl-3-(4-{2-[3-methyl-2-oxo-1-(4-trifluoromethyl-benzyl)-imidazolidin-4-yl]-ethoxy}-phenyl)-propionic acid methyl ester To a solution of 3-(4-Hydroxy-phenyl)-2,2-dimethyl-propionic acid methyl ester (31 mg, 0.15 mmol) and Toluene-4-sulfonic acid 2-[3-methyl-2-oxo-1-(4-trifluoromethyl-benzyl)-imidazolidin-4-yl]-ethyl ester (75 mg, 0.16 mmol) in DMF (1 ml) is added Cs₂CO₃ (64 mg, 0.19 mmol), and the mixture heated at 60° C. for 15 hours. The mixture is cooled, diluted with water (25 ml) and extracted with ethyl acetate (2×25 ml). The combined organic extracts were washed with brine (25 ml), dried (Na₂SO₄), and concentrated to an oil. Purification by flash chromatography on a Biotage silica cartridge (gradient elution, 2:1 hexanes:ethyl acetate to 1:4 hexanes:ethyl acetate) produced an oil (64 mg, 88%).

MS [EI+] 493 (M+H)⁺. Structure confirmed by 1H-NMR.

Step B 2,2-Dimethyl-3-(4-{2-[3-methyl-2-oxo-1-(4-trifluoromethyl-benzyl)-imidazolidin-4-yl]-ethoxy}-phenyl)-propionic acid To a solution of the ester obtained from Step A (61 mg, 0.12 mmol) in methanol (1.5 ml) is added 5N NaOH (0.3 ml, 1.5 mmol), and the mixture stirred for 20 hours at ambient temperature. The mixture is poured into 1N HCl (20 ml), then extracted with ethyl acetate (2×15 ml). The combined ethyl acetate extracts were washed with water, brine, dried (Na₂SO₄), and concentrated to a foam (56 mg, 97%.

MS [EI+] 479 (M+H)⁺. Structure confirmed by 1H-NMR.

Example 103

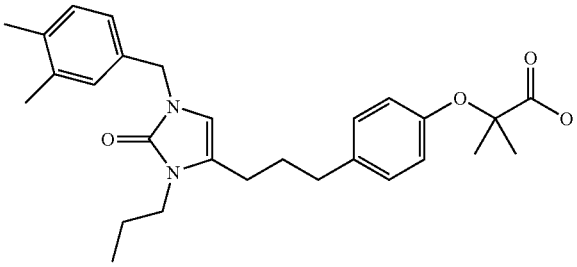

Step A

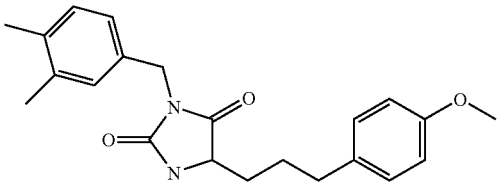

The hydantoin from Example 13 (4.0 g, 16.1 mmol) and 3,4-dimethylbenzyl chloride (2.5 ml, 17.7 mmol) were stirred together in DMF (100 ml). Potassium carbonate (8.9 g, 64.4 mmol) and magnesium sulfate (3.0 g, 25.0 mmol) were added and the resulting mixture was heated to 45° C. for 16 hrs under a drying tube. The reaction was cooled, added slowly to 1 N hydrochloric acid (300 ml) and extracted twice with ethyl acetate. The organic layers were combined, washed with aqueous brine and dried over sodium sulfate. Evaporation of the solvent and subsequent purification by flash chromatography (hexanes:ethyl acetate) gave the desired alkylated hydantoin (1.6 g).

C₂₂H₂₆N₂O₃ (MW=366.5); MS (M+, 367.3, M−365.4)

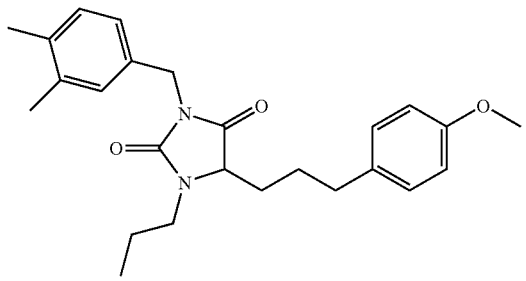

Step B

Sodium hydride (60% dispersion in mineral oil, 0.1 g, 2.4 mmol) was suspended in DMF (25 ml) and cooled to 0° C. under a drying tube. The product from Example 103, Step A (0.8 g, 2.2 mmol), dissolved in DMF (5 ml), was added slowly and allowed to stir at 0° C. for 45 min. Iodopropane (0.23 ml, 2.4 mmol) added to the reaction and allowed to stir for 2.5 hrs. Hydrochloric acid (1N) added slowly, the reaction was added to water and extracted three times with ethyl acetate. The organic layers were combined, washed with aqueous brine and dried over sodium sulfate. Evaporation of the solvent and subsequent purification by flash chromatography (hexanes:ethyl acetate) gave the desired product (0.7 g).

$C_{25}H_{32}N_2O_3$ (MW=408.6); MS (M+, 409.3)

Step C

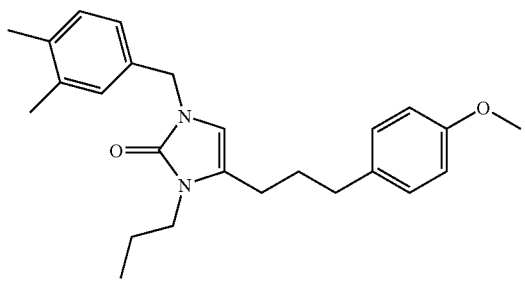

Lithium aluminum hydride (0.084 g, 2.2 mmol) was suspended in THF (10 ml) and cooled to 0° C. under a drying tube. The product from Example 103, Step B (0.7 g, 1.7 mmol), dissolved in THF (5 ml), was added slowly and stirred for 20 min. Hydrochloric acid (5N, 5 ml) added slowly and stirred for 30 min. The reaction mixture was added to water (40 ml) and extracted twice with ethyl acetate. The organic layers were combined, washed with aqueous brine then dried over sodium sulfate. Evaporation of the solvent and subsequent purification by flash chromatography (hexanes:ethyl acetate) gave the desired product (0.53 g).

$C_{25}H_{32}N_2O_2$ (MW=392.6); MS (M+, 393.2)

Step D

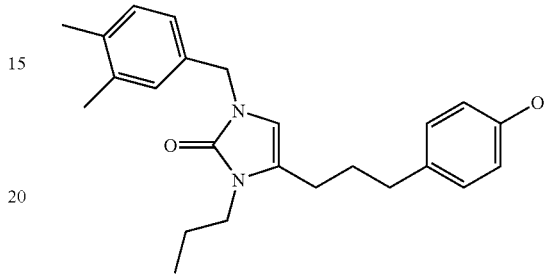

Boron tribromide was stirred in methylene chloride and cooled to 0° C. The product from Example 103, Step C (0.5 g, 1.3 mmol) was added and stirred for 30 min. Methanol (2 ml) slowly added and the mixture added to water which was extracted twice with methylene chloride. The organic layers were combined, washed with aqueous brine then dried over sodium sulfate. Evaporation of the solvent gave the desired crude product (0.5 g).

$C_{24}H_{30}N_2O_2$ (MW=378.5); MS (M+, 379.3)

Step E

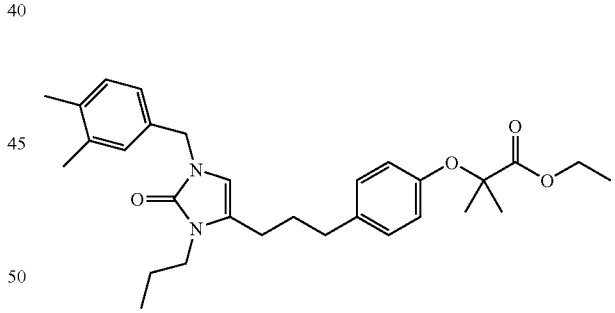

The product from Example 103, Step D (0.5 g, 1.3 mmol) and ethyl 2-bromoisobutyrate (0.57 ml, 3.9 mmol) stirred together in ethanol (15 ml). Potassium carbonate (powdered, Aldrich, 0.72 g, 5.2 mmol) and magnesium sulfate (0.16 g, 1.3 mmol) added and the mixture was stirred at 60° C. overnight. The reaction mixture was cooled and carefully added to 5 N hydrochloric acid (30 ml) and the resulting solution was extracted twice with methylene chloride. The organic layers were combined, washed with aqueous brine then dried over sodium sulfate. Evaporation of the solvent and subsequent purification by flash chromatography (hexanes:ethyl acetate) gave the desired product (0.48 g).

$C_{30}H_{40}N_2O_4$ (MW=492.7); MS (M+, 493.3)

Step F

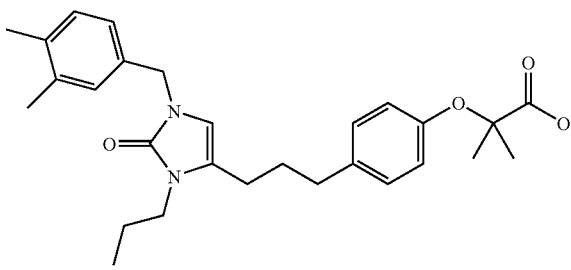

The product from Example 103, Step E (0.45 g, 0.91 mmol) was dissolved in dioxane (8 ml), lithium hydroxide (0.04 g, 1.8 mmol, in 2 ml water) added and stirred at ambient temperature overnight. The reaction was added to water and washed with ether. The aqueous layer was made acidic with the addition of 5 N hydrochloric acid which was then extracted twice with methylene chloride. These organic layers were combined, washed with aqueous brine and dried over sodium sulfate. Evaporation of the solvent and placement under a vacuum gave the desired product (0.37 g)

$C_{28}H_{36}N_2O_4$ (MW=464.6); MS (M+, 465.3, M–, 463.4)

Example 104

Step A

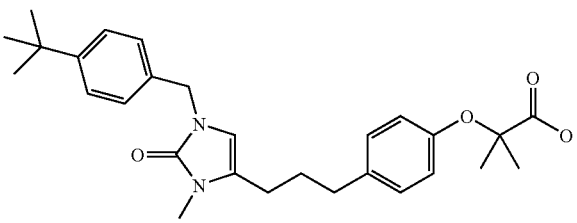

The hydantoin from Example 13 (3.0 g, 12.1 mmol) and p-tert-butylbenzyl bromide (Aldrich, 2.4 ml, 13.3 mmol) were stirred together in DMF (75 ml). Potassium carbonate (powdered, Aldrich, 6.7 g, 48.4 mmol) and magnesium sulfate (1.8 g, 15.0 mmol) were added and the resulting mixture was heated to 50° C. for 4 hrs under a drying tube. The reaction was cooled, added slowly to 5 N hydrochloric acid (100 ml) and extracted three times with ethyl acetate. The organic layers were combined, washed with aqueous brine and dried over sodium sulfate. Evaporation of the solvent and subsequent purification by flash chromatography (hexanes: ethyl acetate) gave the desired alkylated hydantoin (2.8 g).

$C_{24}H_{30}N_2O_3$ (MW=394.5); MS (M+, 395.2, M–,393.3)

Step B

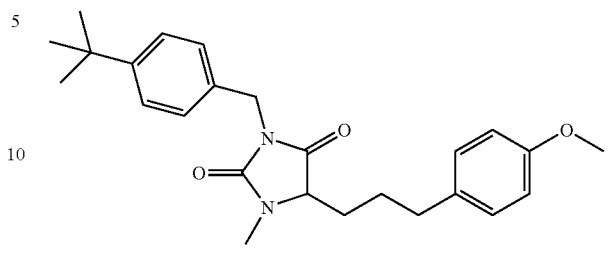

Sodium hydride (60% dispersion in mineral oil, 0.1 g, 2.5 mmol) was suspended in DMF (25 ml) and cooled to 0° C. under a drying tube. The product from Example 104, Step A (0.9 g, 2.3 mmol), dissolved in DMF (5 ml), was added slowly and allowed to stir at 0° C. for 90 min. Iodomethane (0.15 ml, 2.5 mmol) added to the reaction and allowed to stir for 30 min. Hydrochloric acid (5N, 1 ml) added slowly to quench the reaction which was then added to water (75 ml) and extracted twice with ethyl acetate. The organic layers were combined, washed with aqueous brine then dried over sodium sulfate. Evaporation of the solvent and subsequent purification by flash chromatography (hexanes:ethyl acetate) gave the desired product (0.82 g).

$C_{25}H_{32}N_2O_3$ (MW=408.6); MS (M+, 409.2)

Step C

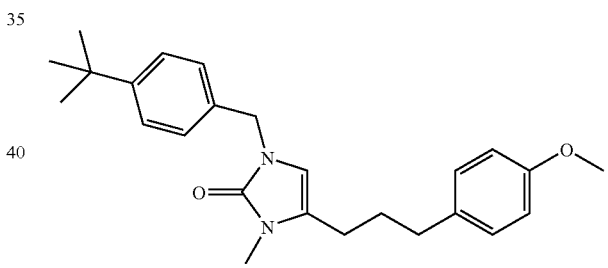

Following the procedure of Example 103, Step C, the product from Example 104, Step B (0.82 g, 2.0 mmol) and lithium aluminum hydride (0.114 g, 3.00 mmol) were used to yield the desired imidazolone as a crude product (0.61 g).

$C_{25}H_{32}N_2O_2$ (MW=392.6); MS (M+, 393.1)

Step D

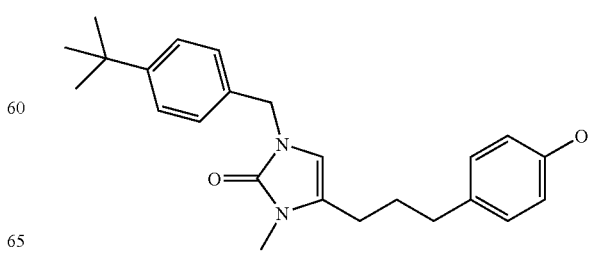

The product from Example 104, Step C (0.6 g, 1.5 mmol) was stirred in methylene chloride (10 ml) and boron tribromide (0.28 ml, 3.0 mmol) added via syringe. The mixture was stirred at ambient temperature for 30 min. then quenched by the slow addition of methanol. The mixture was added to water (50 ml) and extracted twice with methylene chloride. The organic layers were combined, washed with aqueous brine and dried over sodium sulfate. Evaporation of the solvent gave the desired crude product (0.51 g).

$C_{24}H_{30}N_2O_2$ (MW=378.5); MS (M+, 379.2)

Step E

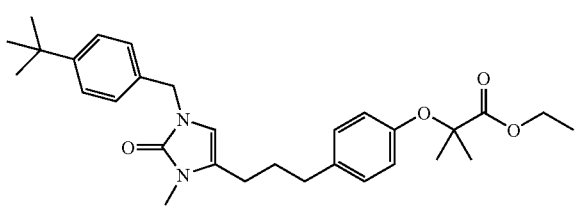

Following the procedure of Example 103, Step E, the product was from Example 104, Step D (0.5 g, 1.3 mmol), ethyl 2-bromoisobutyrate (0.57 ml, 3.9 mmol), potassium carbonate (powdered, Aldrich, 0.72 g, 5.2 mmol) and magnesium sulfate (0.16 g, 1.3 mmol) were used to yield the desired product (0.13 g).

$C_{30}H_{40}N_2O_4$ (MW=492.7); MS (M+, 493.3)

Step F

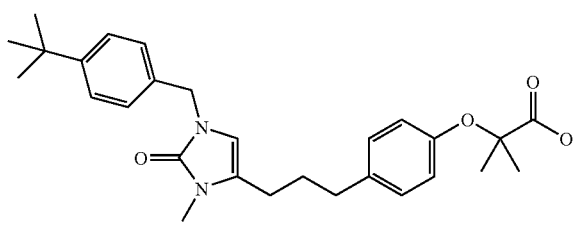

Following the procedure of Example 103, Step F, the product from Example 104, Step E (0.12 g, 0.24 mmol) and lithium hydroxide (0.02 g, 0.72 mmol) were used to yield the desired product after evaporation of the solvent and placement under vacuum (0.089 g).

$C_{28}H_{36}N_2O_4$ (MW=464.6); MS (M+, 465.1, M−, 463.2)

Example 105

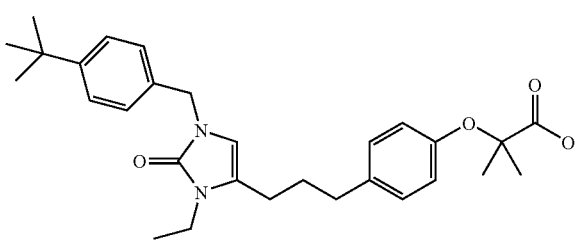

-continued

Step A

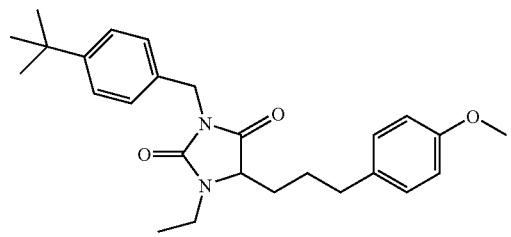

Following the procedure of Example 104, Step B, the product from Example 104, Step A (0.9 g, 2.3 mmol), sodium hydride (60% dispersion in mineral oil, 0.1 g, 2.5 mmol) and iodoethane (0.2 ml, 2.5 mmol) were used to yield the desired product (0.68 g).

$C_{26}H_{34}N_2O_3$ (MW=422.6); MS (M+, 423.2)

Step B

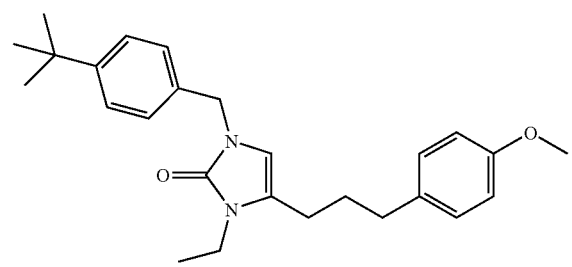

Following the procedure of Example 103, Step C, the product from Example 105, Step A (0.68 g, 1.6 mmol) and lithium aluminum hydride (0.091 g, 2.4 mmol) were used to yield the desired imidazolone as a crude product (0.6 g).

$C_{26}H_{34}N_2O_2$ (MW=406.6); MS (M+, 407.1)

Step C

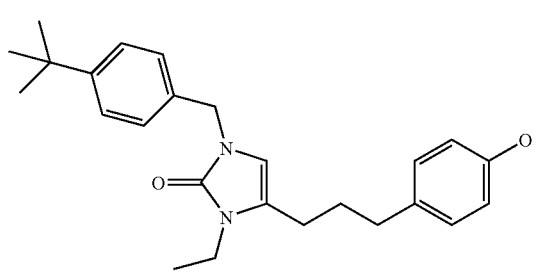

Following the procedure of Example 104, Step D, the product from Example 105, Step B (0.6 g, 1.5 mmol) and boron tribromide (0.28 ml, 3.0 mmol) were used to yield the crude product (0.52 g).

$C_{25}H_{32}N_2O_2$ (MW=392.6); MS (M+, 393.2)

Step D

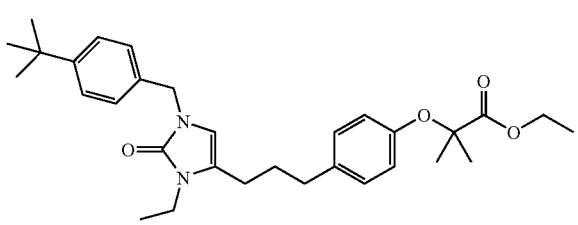

Following the procedure of Example 103, Step E, the product from Example 105, Step C (0.5 g, 1.3 mmol), ethyl 2-bromoisobutyrate (0.57 ml, 3.9 mmol), potassium carbonate (powdered, Aldrich, 0.72 g, 5.2 mmol) and magnesium sulfate (0.16 g, 1.3 mmol) were used to yield the product (0.31 g).

$C_{31}H_{42}N_2O_4$ (MW=506.7); MS (M+, 507.1)

Step E

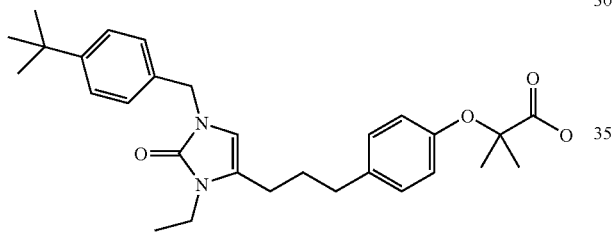

Following the procedure of Example 103, Step F, the product from Example 105, Step D (0.30 g, 0.59 mmol) and lithium hydroxide (0.04 g, 1.7 mmol) were used to yield the desired product as a foam after evaporation of the solvent and placement under vacuum (0.244 g).

$C_{29}H_{38}N_2O_4$ (MW=478.6); MS (M+, 479.1, M−, 477.2)

Example 106

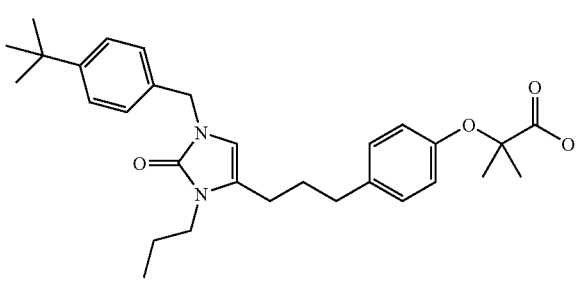

Step A

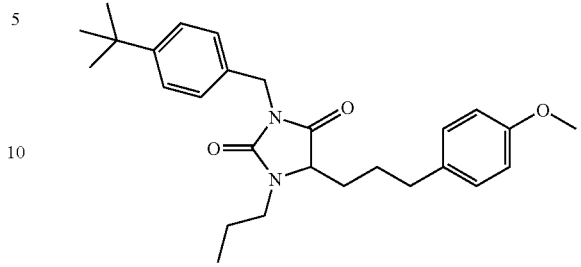

Following the procedure of Example 104, Step B, the product from Example 104, Step A (0.9 g, 2.3 mmol), sodium hydride dispersion in mineral oil, 0.1 g, 2.5 mmol) and iodopropane (0.2 ml, 2.5 nmol) were used to yield the desired product (0.56 g).

$C_{27}H_{36}N_2O_3$ (MW=436.6); MS (M+, 437.2)

Step B

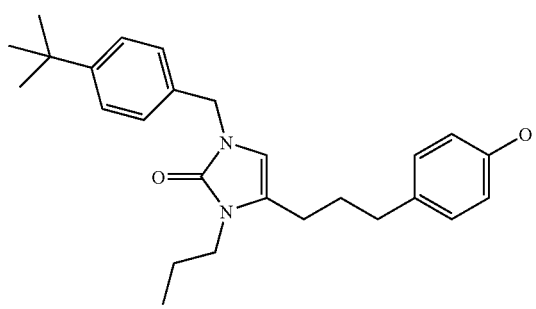

Following the procedure of Example 103, Step C, the product from Example 106, Step A (0.56 g, 1.3 mmol) and lithium aluminum hydride (Aldrich, 0.076 g, 2.0 mmol) were used to yield the desired imidazolone as a crude product (0.51 g).

$C_{27}H_{36}N_2O_2$ (MW=420.6); MS (M+, 421.1)

Step C

Following the procedure of Example 104, Step D, the product from Example 106, Step B (0.5 g, 1.2 mmol) and boron tribromide (0.23 ml, 2.4 mmol) were used to yield the crude product (0.45 g).

$C_{26}H_{34}N_2O_2$ (MW=406.6); MS (M+, 407.3)

Step D

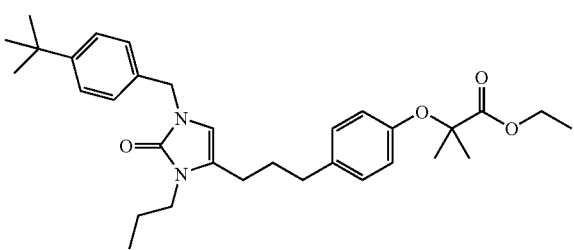

Following the procedure of Example 103, Step E, the product from Example 106, Step C (0.45 g, 1.1 mmol), ethyl 2-bromoisobutyrate (0.57 ml, 3.9 mmol), potassium carbonate (0.72 g, 5.2 mmol) and magnesium sulfate (0.16 g, 1.3 mmol) were used to yield the product (0.26 g).

$C_{32}H_{44}N_2O_4$ (MW=520.7); MS (M+, 521.3)

Step E

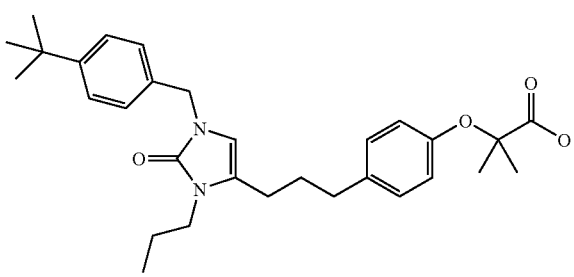

Following the procedure of Example 103, Step F, the product from Example 106, Step D (0.26 g, 0.50 mmol) and lithium hydroxide (0.036 g, 1.5 mmol) were used to yield the desired product after evaporation of the solvent and placement under vacuum (0.184 g).

$C_{30}H_{40}N_2O_4$ (MW 492.7); MS (M+, 493.3, M−, 491.4)

Example 107

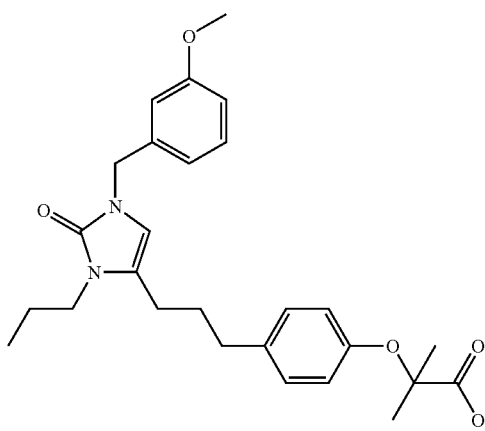

Step A

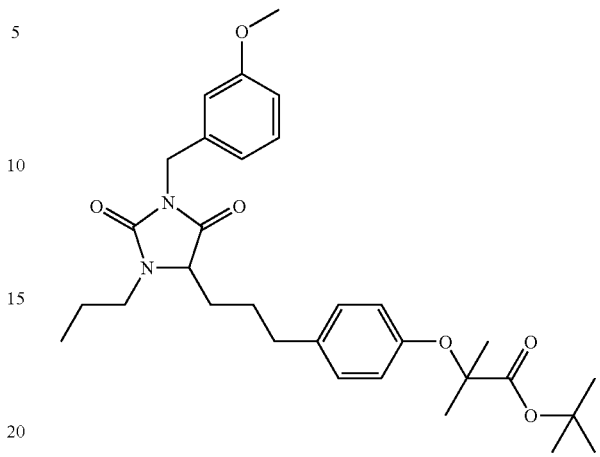

The hydantoin from Example 17, Step A (490.6 mg, 0.988 mmol) was dissolved in DMF (10 mL) and cooled to 0° C. under an atmosphere of $N_2$. The mixture was treated with NaH (60% dispersion in oil, 45.7 mg, 1.14 mmol) and, after 30 minutes, n-propyl iodide (112 µL, 1.15 mmol). The reaction mixture was warmed to room temperature, stirred for 1 hour, then poured into 1 N HCl (50 mL). The resulting solution was extracted with ethyl acetate (2×50 mL). The combined organic extracts were dried over $Na_2SO_4$ and concentrated. Purification by chromatography (4:1 hexanes:ethyl acetate) gave the desired product as a colorless oil (416.1 mg, 78%).

$C_{31}H_{42}N_2O_6$ (MW=538.69); mass spectroscopy: $(M+NH_4^+)=556.3$

Step B

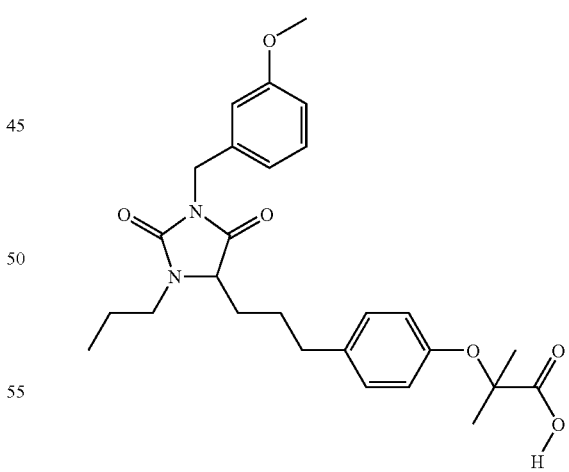

A $CH_2Cl_2$ solution (15 mL) of the ester from Step A (0.411 g, 0.764 mmol) was cooled to 0° C. and treated with TFA (2.0 mL, 26 mmol). The mixture was warmed to room temperature and stirred for 3 hours. The solvent was concentrated to give the crude acid, which was used in the subsequent reaction without further purification.

$C_{27}H_{34}N_2O_6$ (MW=482.58); mass spectroscopy: $(MH^+)=$ 483.2, $(MH^-)=481.3$ Step C

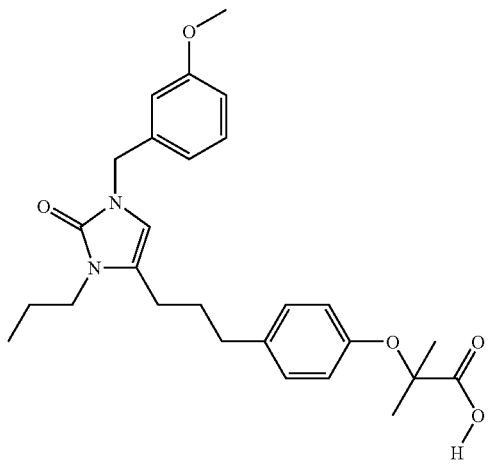

The hydantoin from Step B was dissolved in ethanol (15 mL) and treated with NaBH$_4$ (331 mg, 8.8 mmol). Additional NaBH$_4$ was added to the reaction mixture after 5 hr (150 mg, 4.0 mmol). The resulting mixture was stirred at room temperature overnight then quenched by the careful addition of 5 N HCl (5 mL). The mixture was stirred for 30 minutes then diluted with additional 5 N HCl (50 mL) and extracted with ethyl acetate (3×50 mL). The combined organic extracts were washed with brine, dried over Na$_2$SO$_4$ and concentrated. Purification by chromatography (gradient: 2:1 ethyl acetate: hexane to 100% ethyl acetate to 9:1 ethyl acetate:methanol) gave the desired imidazolone as a white solid (237 mg, 66% for two steps).

C$_{27}$H$_{34}$N$_2$O$_5$ (MW=466.58); mass spectroscopy: (MH$^+$)= 467.3, (MH$^-$)=465.3

Example 108

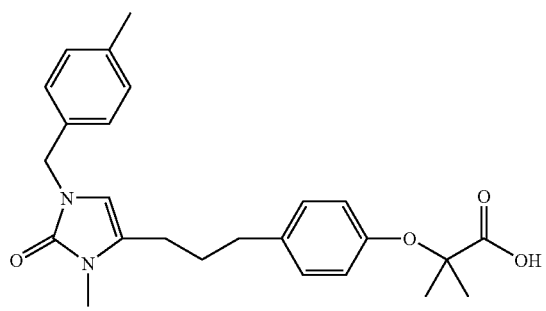

-continued

Step A

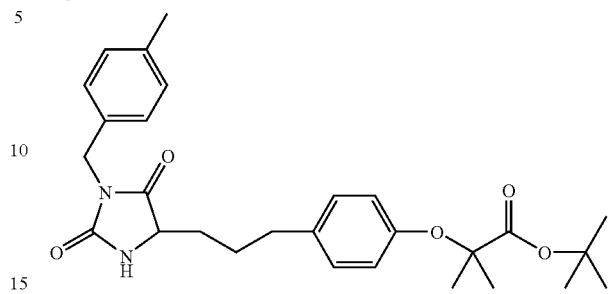

The ester from Example 14, Step F (1.88 g, 0.0050 mol) was dissolved in DMF and treated with α-chloro-p-xylene (0.773 g, 0.0055 mol) and powdered K$_2$CO$_3$. The resulting mixture was stirred at room temperature overnight. The reaction mixture was poured into 1N HCl and combined with ethyl acetate. The organic layer was extracted and washed with brine then dried and concentrated. Purification of the crude material by flash chromatography (4:1 hexanes:ethyl acetate) yielded the desired hydantoin (2.10 g, 88%).

C$_{28}$H$_{36}$N$_2$O$_5$ (MW=480.26); mass spectroscopy (MH$^+$)= 480.1

Step B

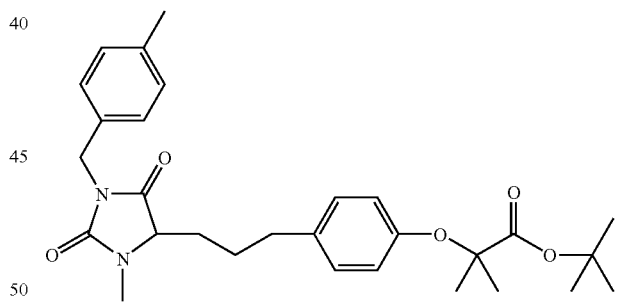

Sodium hydride (0.050 g, 0.0011 mol) was dissolved in DMF (5 ml) and cooled to 0oC. The hydantoin from Step A (0.50 g, 0.0010 mol) was added as a solution in DMF (10 ml). The mixture was stirred for ninety minutes. Iodomethane (0.068 ml, 0.0011 mol) was added and the reaction was stirred for thirty minutes. Hydrochloric acid was added to quench the reaction. The aqueous layer was extracted with ethyl acetate. The organic layer was concentrated. Purification of the resulting material by flash chromatography (10:1 hexanes:ethyl acetate) gave the desired hydantoin (0.247 g, 0.0010 mol).

C$_{29}$H$_{38}$N$_2$O$_5$ (MW=494.28); mass spectroscopy (MH$^+$)= 494.0

Step C

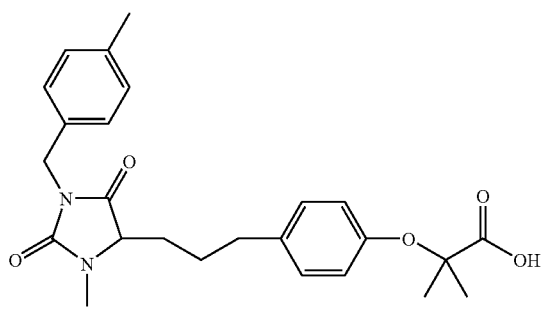

The hydantoin from Step B (0.247 g, 0.00050 mol) was dissolved in methylene chloride (5 ml) and treated with trifluoro acetic acid (0.269 ml, 0.0035 mol) and stirred overnight. The solvent was concentrated and the product was vacuum dried.

$C_{25}H_{30}N_2O_5$ (MW=438.22); mass spectroscopy (MH+)= 439

Step D

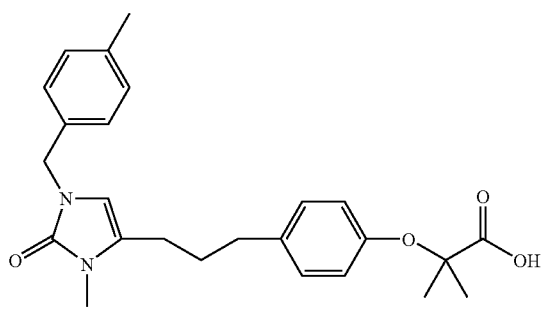

The acid from Step C (0.289, 0.00066 mol) was dissolved in ethanol (10 ml) and treated with sodium borohydride (0.249 g, 0.0066 mol). One hour later, additional sodium borohydride (0.249 g) was added and the reaction was stirred overnight. On the next day, more sodium borohydride (0.249 g) was added to drive the reaction. The reaction was left to stir. On the fifth day, 5N HCl (50 ml) was added to the reaction mixture followed by water (50 ml). The aqueous solution was extracted with ethyl acetate (2×, 50 ml). The organic layer was washed with brine, dried over $Na_2SO_4$, and concentrated. Purification by flash chromatography (100% ethyl acetate) gave the desired acid as a white solid (0.062 g, 23%) $C_{25}H_{30}N_2O_4$ (MW=422.53); mass spectroscopy (MH+)= 423.2

Example 109

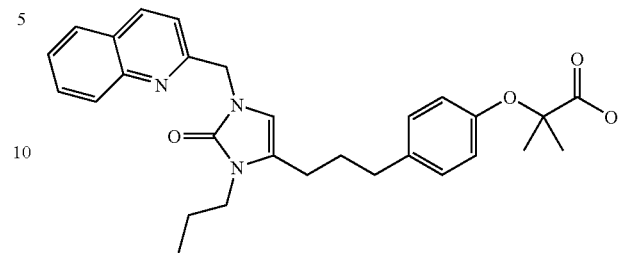

Step A

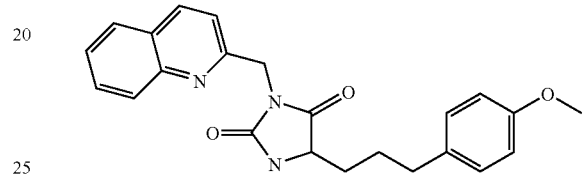

The hydantoin from Example 13 (1.0 g, 4.0 mmol), 2-(chloromethyl)quinoline hydrochloride (0.9 g, 4.4 mmol) and triethylamine (0.4 g, 4.0 mmol) were combined in DMF (25 ml). Potassium carbonate (2.2 g, 16.0 mmol) and magnesium sulfate (0.6 g, 5.0 mmol) added and the mixture was heated to 50° C., under a drying tube, overnight. The reaction mixture was added to hydrochloric acid (1N, 50 ml) and extracted three times with methylene chloride. The organic layers were combined, washed with aqueous brine then dried over sodium sulfate. Evaporation of the solvent and washing with 7:3 hexane/ethyl acetate yielded the desired product as a solid (0.8 g)

$C_{23}H_{23}N_3O_3$ (MW=389.5); MS (M+, 390.2)

Step B

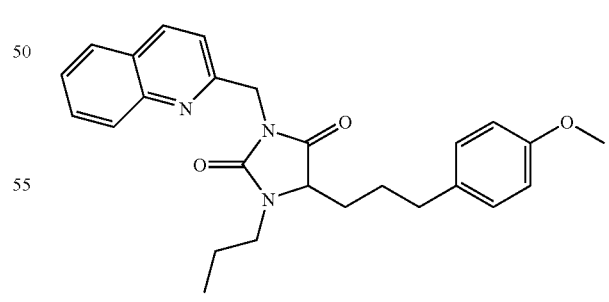

Following the procedure of Example 104, Step B, the product from Example 109, Step A (0.5 g, 1.3 mmol), sodium hydride (Aldrich, 60% dispersion in mineral oil, 0.06 g, 1.4 mmol) and iodopropane (Aldrich, 0.14 ml, 1.4 mmol) were used to yield the desired product (0.41 g).

$C_{26}H_{29}N_3O_3$ (MW=431.5); MS (M+, 432.1)

Step C

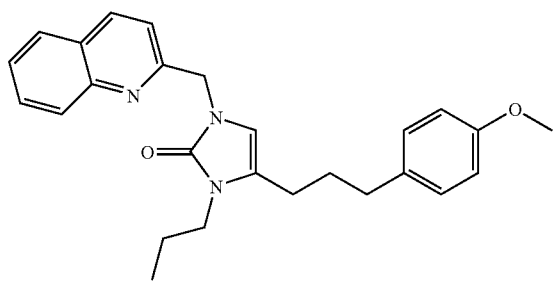

Following the procedure of Example 103, Step C, the product from Example 109, Step B (0.4 g, 0.93 mmol) and lithium aluminum hydride (0.05 g, 1.4 mmol) were used to yield the desired imidazolone as a crude product (0.45 g).

$C_{26}H_{29}N_3O_2$ (MW=415.5); MS (M+, 416.2)

Step D

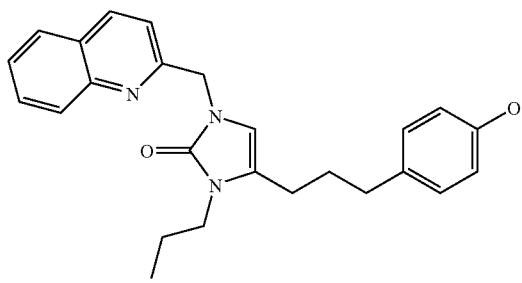

Following the procedure of Example 104, Step D, the product from Example 109, Step C (0.39 g, 0.93 mmol) and boron tribromide (0.19 ml, 2.0 mmol) were used to yield the crude product (0.47 g).

$C_{25}H_{27}N_3O_2$ (MW=401.5); MS (M+, 402.2)

Step E

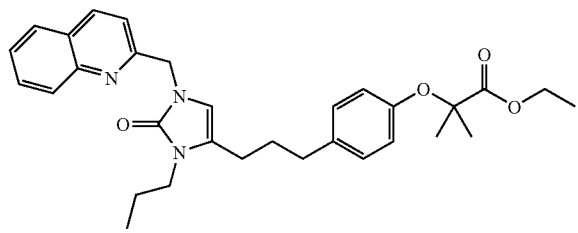

Following the procedure of Example 103, Step E, the product from Example 109, Step D (0.37 g, 0.93 mmol), ethyl 2-bromoisobutyrate (0.48 ml, 3.3 mmol), potassium carbonate (powdered, Aldrich, 0.58 g, 4.2 mmol) and magnesium sulfate (0.18 g, 1.5 mmol) were used to yield the product (0.05 g).

$C_{31}H_{37}N_3O_4$ (MW=515.7); MS (M+, 516.3)

Step F

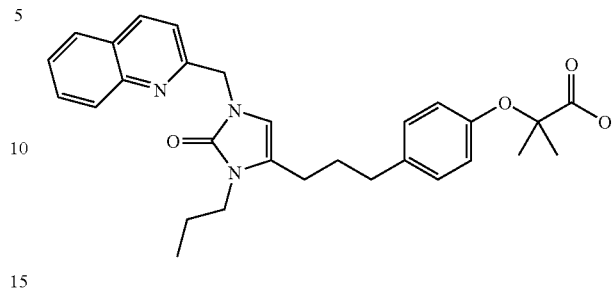

Following the procedure of Example 103, Step F, the product from Example 109, Step E (0.05 g, 0.1 mmol) and lithium hydroxide (0.07 g, 0.3 mmol) were used to yield the desired product (0.022 g).

$C_{29}H_{33}N_3O_4$ (MW=487.6); MS (M+, 488.3, M−, 486.4)

Example 110

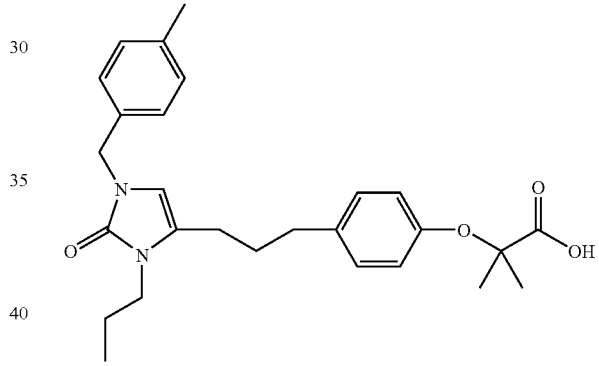

Step A

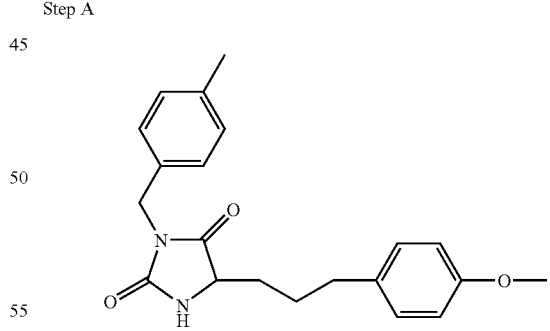

The methoxy ether from Example 13 (3.0 g, 0.012 mol) was dissolved in DMF and treated with p-methyl chlorobenzene (1.87 g, 0.013 mol) and powdered $K_2CO_3$ (6.62 g, 0.048 mol). The resulting mixture was stirred at room temperature overnight. The reaction mixture was poured into 1N HCl and combined with ethyl acetate. The organic layer was extracted and washed with brine then dried and concentrated. Purification of the crude material by flash chromatography (2:1 hexanes:ethyl acetate) yielded the desired hydantoin (3.15 g, 75%). $C_{21}H_{24}N_2O_3$ (MW=352.18); mass spectroscopy (MH+)=353

Step B

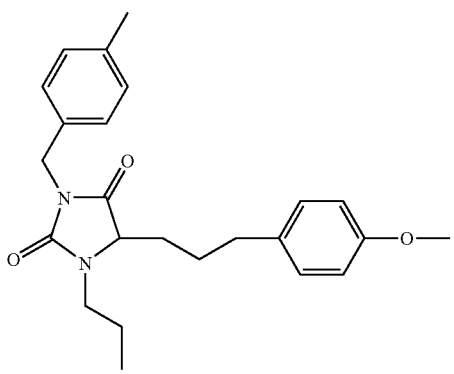

The hydantoin from Step A (0.750 g, 0.0021 mol) was dissolved in DMF (5 ml) and treated with NaH (0.091 g, 0.0023 mol) followed by 1-iodo-propane (0.228 ml, 0.0023 mol). The reaction was stirred overnight under nitrogen. The reaction mixture was poured into 1N HCl and combined with ethyl acetate. The organic layer was extracted and washed with brine then dried and concentrated. Purification of the crude material by flash chromatography (4:1 hexanes:ethyl acetate) yielded the desired product (0.454 g, 55%).

$C_{24}H_{30}N_2O_3$ (MW=394.52); mass spectroscopy (MH+)= 395.2

Step C

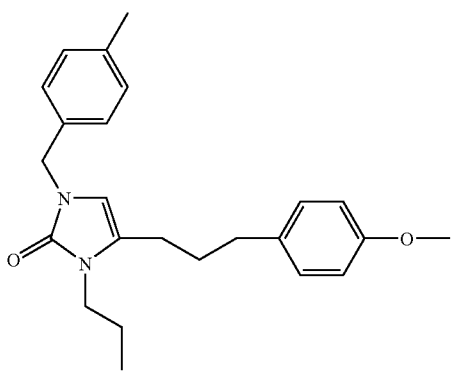

Lithium aluminum hydride (0.0651 g, 0.0017 mol) was dissolved in THF (5 ml). A THF solution of the hydantoin from Step B was added. The reaction was stirred overnight at room temperature. The reaction was quenched by the addition of 5N HCl. After stirring for thirty minutes, water was added and the solution was extracted with ethyl acetate. The organic layer was extracted and washed with brine then dried and concentrated. The crude product was carried forth without further purification (0.400 g, 96%). $C_{24}H_{30}N_2O_2$ (MW=378.23); mass spectroscopy (MH+)=379.2

Step D

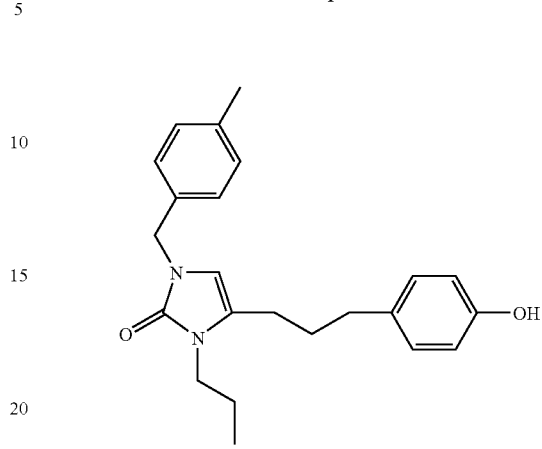

The methoxy ether from Step C (0.400 g, 0.001 mol) was dissolved in methylene chloride (5 ml) and cooled to 0° C. To this solution was added, dropwise, a solution of $BBr_3$ (0.200 ml, 0.002 mol) in methylene chloride (5 ml). After stirring for about thirty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (0.334 g, 92%) was obtained and was carried forth without further purification. $C_{23}H_{28}N_2O_2$ (MW=364.22); mass spectroscopy (MH+)= 365.2

Step E

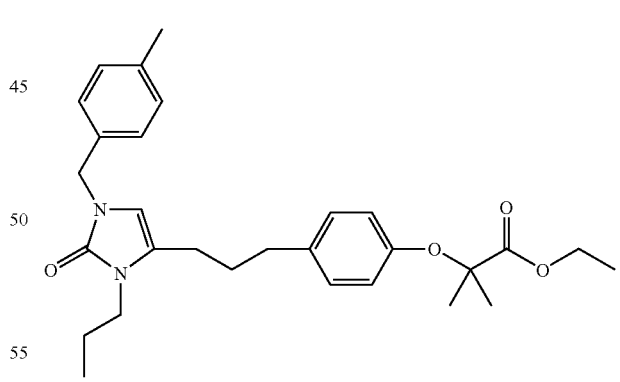

The phenol from Step D (0.334 g, 0.00092 mol) was dissolved in EtOH (5 ml) and treated with ethyl 2-bromoisobutyrate (0.404 ml, 0.0028 mol), powdered $K_2CO_3$ (0.508 g, 0.0037 mol), and $MgSO_4$ (0.110 g, 0.00092 mol). The reaction was stirred overnight at 55° C. Upon cooling, the reaction mixture was poured into 5N HCl and combined with EtOAc. The organic layer was extracted with water followed by brine then concentrated to dryness. Purification by flashed chromatography (1:1 hexanes:ethyl acetate) gave the ester (0.205 g, 46%). $C_{29}H_{38}N_2O_4$ (MW=478.28); mass spectroscopy (MH$^+$)=479.3

Step F

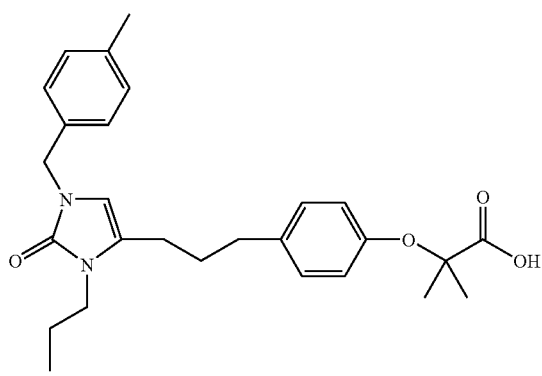

The ester from Step E (0.205 g, 0.00043 mol) was dissolved in methanol (4 ml) and treated with a solution of LiOH in water (1 ml). The reaction was stirred overnight. The reaction was cooled and water (20 ml) was added to the solution. The solution was then acidified using 1N HCl to pH=3 then extracted with ethyl acetate. The organic layer was concentrated to afford the desired carboxylic acid (0.128 g, 66%). $C_{27}H_{34}N_2O_4$ (MW=450.58); mass spectroscopy (MH$^+$)= 451.2

Example 111

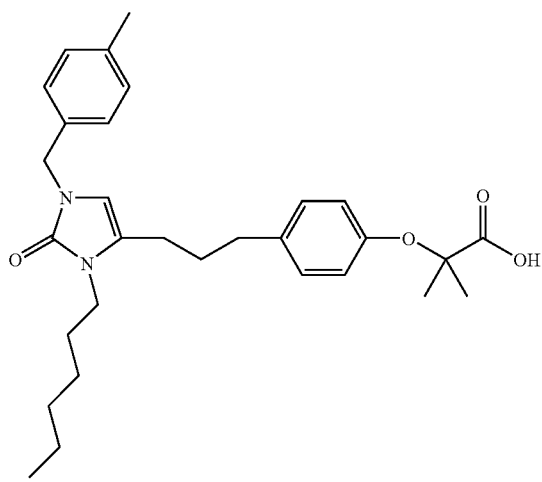

Step A

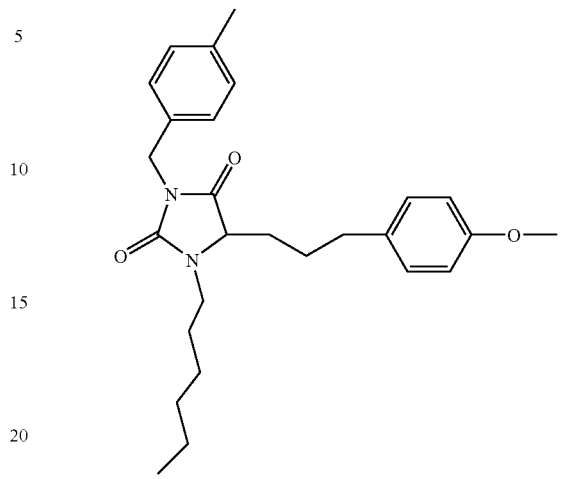

The hydantoin from Example 110; Step A (0.748 g, 0.0021 mol) was dissolved in DMF (5 ml) and treated with NaH (0.091 g, 0.0023 mol) followed by 1-iodo-hexane (0.339 ml, 0.0023 mol). The reaction was stirred overnight under nitrogen. The reaction mixture was poured into 1N HCl and combined with ethyl acetate. The organic layer was extracted and washed with brine then dried and concentrated. Purification of the crude material by flash chromatography (5:1 hexanes:ethyl acetate) yielded the desired product (0.622 g, 68%).
$C_{27}H_{32}F_2N_2O_5$ (MW=502.23); mass spectroscopy (MH+)= 447.1

Step B

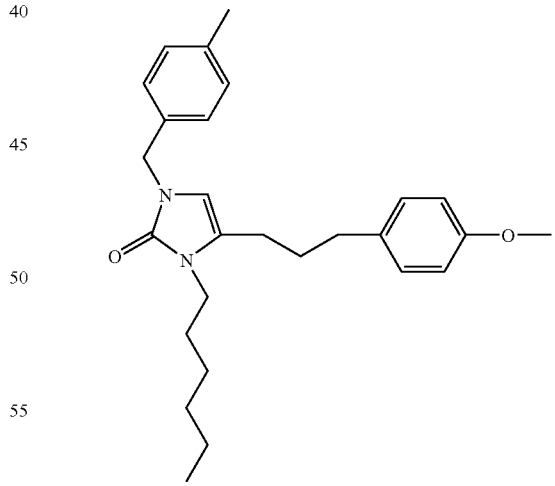

Lithium aluminum hydride (0.622 g, 0.0014 mol) was dissolved in THF (10 ml). A THF solution of the hydantoin from Step A was added. The reaction was stirred for thirty minutes at room temperature. The reaction was quenched by the addition of 5N HCl. After stirring for thirty minutes, water was added and the solution was extracted with ethyl acetate. The organic layer was extracted and washed with brine then dried and concentrated. The crude product was carried forth without further purification (0.556 g, 95%). $C_{27}H_{32}F_2N_2O_5$ (MW=502.23); mass spectroscopy (MH+)=447.1

Step C

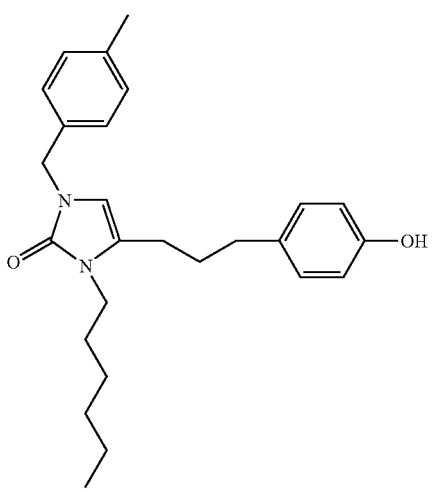

The methoxy ether from Step B (0.556 g, 0.0013 mol) was dissolved in methylene chloride (7 ml) and cooled to 0° C. To this solution was added, dropwise, a solution of BBr$_3$ (0.250 ml, 0.0026 mol) in methylene chloride (5 ml). After stirring for about twenty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (0.465 g, 88%) was obtained and was carried forth without further purification. $C_{22}H_{27}N_3O_2$ (MW=365.48); mass spectroscopy (MH+)= 366.3

Step D

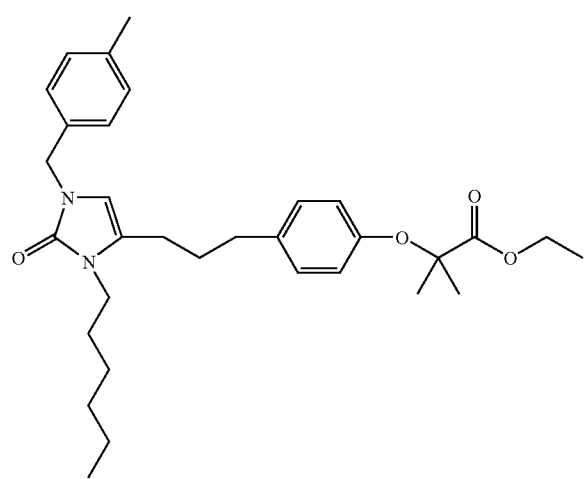

The phenol from Step C (0.465 g, 0.0011 mol) was dissolved in EtOH (10 ml) and treated with ethyl 2-bromoisobutyrate (0.504 ml, 0.0034 mol), powdered K$_2$CO$_3$ (0.607 g, 0.0044 mol), and MgSO$_4$ (0.132 g, 0.0011 mol). The reaction was stirred overnight at 55° C. Upon cooling, the reaction mixture was poured into 5N HCl and combined with EtOAc. The organic layer was extracted with water followed by brine then concentrated to dryness. Purification by flashed chromatography (3:1 hexanes:ethyl acetate; 2:1 hexanes:ethyl acetate) gave the ester (0.241 g, 42%). $C_{28}H_{37}N_3O_4$ (MW=479.62); mass spectroscopy (MH$^+$)=480.3

Step E

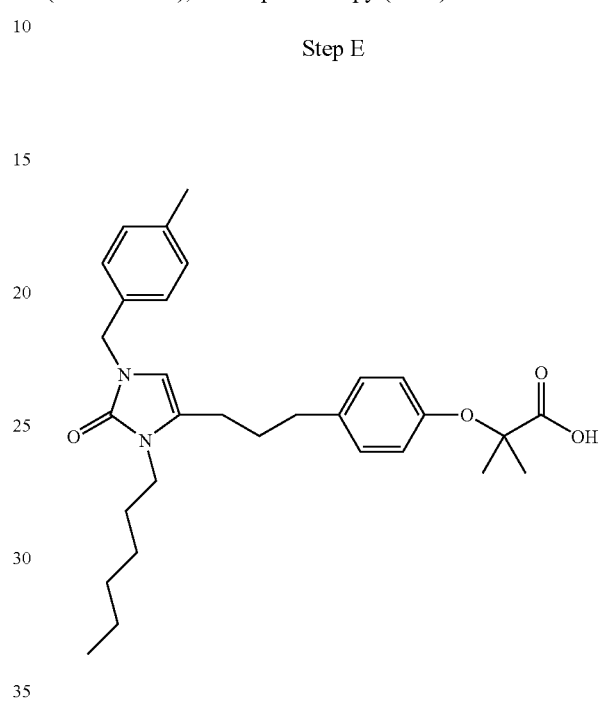

The ester from Step D (0.241 g, 0.00046 mol) was dissolved in methanol (4 ml) and treated with a solution of LiOH in water (1 ml). The reaction was stirred overnight. The reaction was cooled and water (20 ml) was added to the solution. The solution was then acidified using 1N HCl to pH=3 then extracted with ethyl acetate. The organic layer was concentrated to afford the desired carboxylic acid (0.089 g, 40%). $C_{26}H_{33}N_3O_4$ (MW=451.57); mass spectroscopy (MH$^+$)= 452.3

Example 112

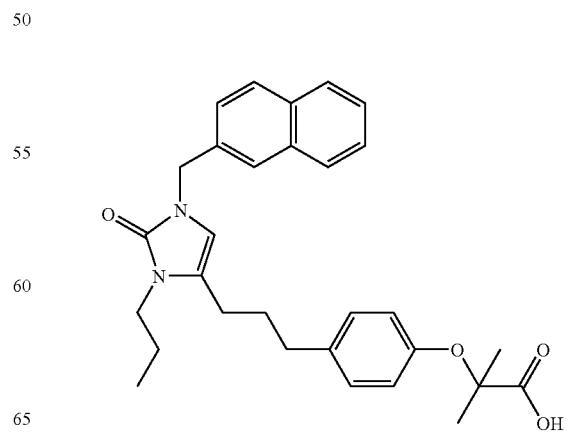

Step A

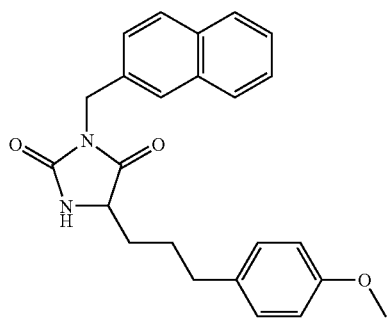

A DMF solution (55 mL) of the hydantoin from Example 13 (1.92 g, 7.73 mmol) was treated sequentially with 2-bromomethyl-1-naphthalene (1.87 g, 8.46 mmol), $K_2CO_3$ (2.2 g, 16 mmol), and $MgSO_4$ (2.3 g, 19 mmol). The resulting mixture was stirred at room temperature overnight. The reaction was quenched by the slow addition of 1 N HCl (150 mL). The resulting mixture was extracted with ethyl acetate (2×100 mL). The combined organic extracts were washed with brine then dried over $Na_2SO_4$ and concentrated. Purification by chromatography (gradient: 3:1 to 1:1 hexanes:ethyl acetate) gave the desired alkylated hydantoin as a white solid (1.47 g, 49%).

$C_{24}H_{24}N_2O_3$ (MW=388.47); mass spectroscopy: $(MH^+)$= 389.2, $(MH^-)$=387.2

Step B

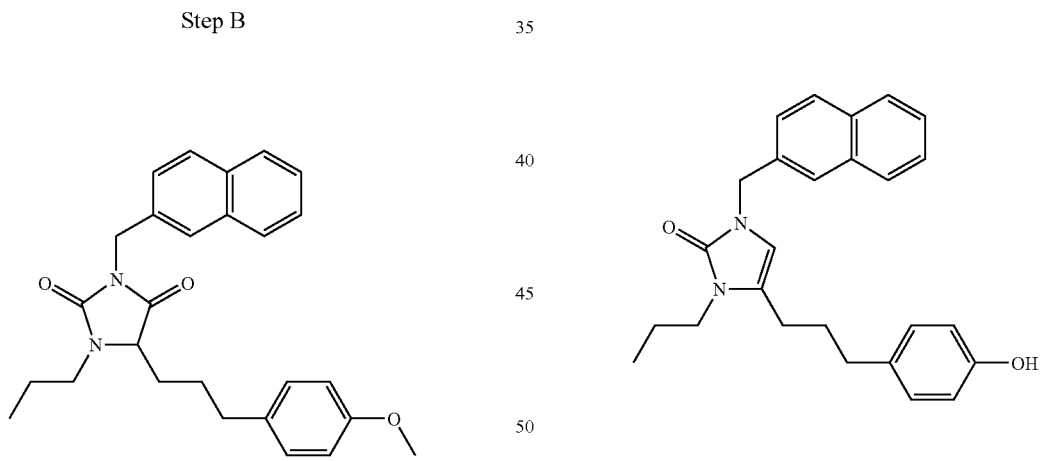

The hydantoin from Step A (637 mg, 1.64 mmol) was dissolved in DMF (20 mL) and cooled to 0° C. under an atmosphere of $N_2$. The mixture was treated with NaH (60% dispersion in oil, 76.3 mg, 1.91 mmol) and, after 15 minutes, n-propyl iodide (192 μL, 1.97 mmol). The reaction mixture was warmed to room temperature, stirred for 1 hour, then poured into 1 N HCl (100 mL). The resulting solution was extracted with ethyl acetate (2×75 mL). The combined organic extracts were dried over $Na_2SO_4$ and concentrated. Purification by chromatography (4:1 hexanes:ethyl acetate) gave the desired product as a yellowish oil (693 mg, 98%).

$C_{27}H_{30}N_2O_3$ (MW=430.55); mass spectroscopy: $(MH^+)$= 431.2

Step C

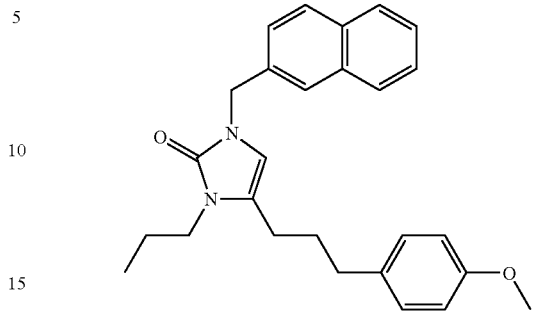

To a slurry of LAH (99.3 mg, 2.6 mmol) in THF (10 mL) at 0° C. under $N_2$ was added the hydantoin from Step B (0.693 g, 1.61 mmol) as a solution in THF (10 mL). After 15 minutes the reaction was quenched by the addition of 5 N HCl (5 mL) in THF (5 mL)., stirred for 30 minutes, then diluted with $H_2O$ (75 mL). The resulting mixture was extracted with ethyl acetate (3×50 mL). The combined organic extracts were washed with brine, dried over $Na_2SO_4$ and concentrated to give the desired imidazolone. The crude product was carried forward without further purification.

$C_{27}H_{30}N_2O_2$ (MW=414.55); mass spectroscopy: $(MH^+)$= 415.2

Step D

The imidazolone from Step C was dissolved in $CH_2Cl_2$ (15 mL) and cooled to 0° C. under an atmosphere of $N_2$. $BBr_3$ (475 μL, 5.0 mmol) was added dropwise, then the reaction mixture was warmed to room temperature. After 1 hr, the solution was again cooled to 0° C. and quenched by the slow addition of a methanol (4 mL) solution in $CH_2Cl_2$ (12 mL). The resulting mixture was extracted with $H_2O$ (50 mL). The aqueous extract was washed with $CH_2Cl_2$ (50 mL) then the combined organic extracts were washed with brine, dried over $Na_2SO_4$, and concentrated to give the desired phenol as an oil. The crude product was carried forward without further purification.

$C_{26}H_{28}N_2O_2$ (MW=400.53); mass spectroscopy: $(MH^+)$= 401.2, $(MH^-)$=399.3

Step E

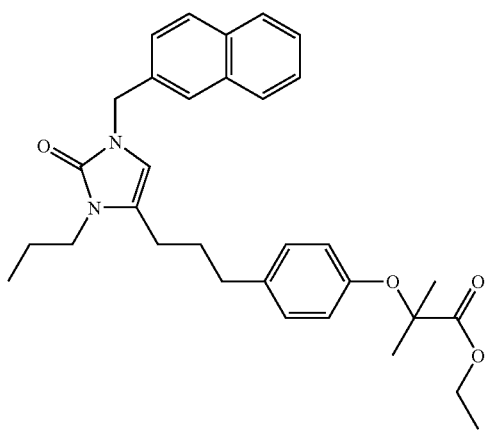

An ethanol solution (15 mL) of the phenol from Step D was treated sequentially with ethyl 2-bromoisobutyrate (900 µL, 6.6 mmol), $K_2CO_3$ (1.0 g, 7.2 mmol), and $MgSO_4$ (1.0 g, 8.3 mmol). The resulting mixture was heated to 55-65° C. overnight. The reaction was quenched by the slow addition of 1 N HCl (5 mL) then poured into additional 1 N HCl (50 mL). The resulting mixture was extracted with $CH_2Cl_2$ (2×50 mL). The combined organic extracts were washed with brine then dried over $Na_2SO_4$ and concentrated. Purification by chromatography (gradient: 2:1 to 1:1 hexanes:ethyl acetate) gave the desired ester as a slightly yellow oil (536.4 mg, 65% for 3 steps).

$C_{32}H_{38}N_2O_4$ (MW=514.67); mass spectroscopy: $(MH^+)$= 515.4

Step F

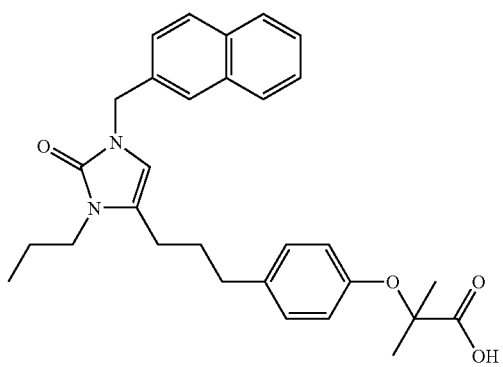

A dioxane solution (10 mL) of the ester from Step E (516.5 mg, 1.0 mmol) was treated with an aqueous solution (5 mL) of LiOH (88 mg, 3.7 mmol). The mixture was heated to 50° C. for 2 hr then the solvent was concentrated and the resulting oil diluted with $H_2O$ (50 mL) and extracted with $Et_2O$ (50 mL). The aqueous extract was acidified with 1 N HCl and extracted with ethyl acetate (2×50 mL). The combined organic extracts were washed with brine, dried over $Na_2SO_4$, and concentrated to give the desired carboxylic acid as a slightly yellow foam-like solid (392.8 mg, 81%)

$C_{30}H_{34}N_2O_4$ (MW=486.62); mass spectroscopy: $(MH^+)$= 487.2, $(MH^-)$=485.4

Example 113

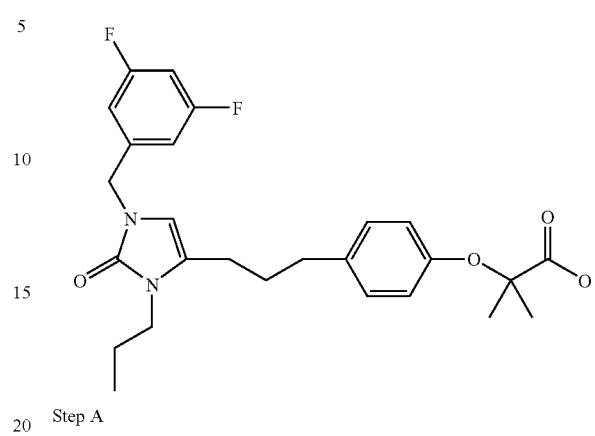

Step A

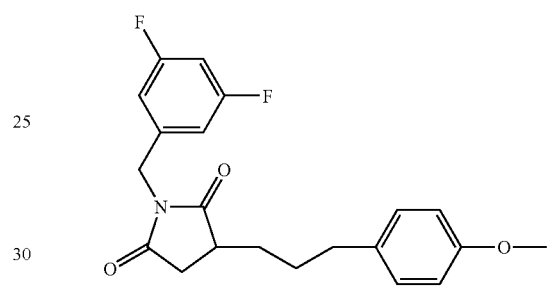

The methoxy ether from Example 13 (1.0 g, 0.0040 mol) was dissolved in DMF and treated with 3, 5 difluoro bromobenezene (0.574 ml, 0.0044 mol) and powdered $K_2CO_3$ (2.20 g, 0.0080 mol). The resulting mixture was stirred at room temperature overnight. The reaction mixture was poured into 1N HCl and combined with ethyl acetate. The organic layer was extracted and washed with brine then dried and concentrated. Purification of the crude material by flash chromatography (4:1 hexanes:ethyl acetate; 4:1 hexanes: ethyl acetate) yielded the desired hydantoin (0.710 g, 46%).

$C_{20}H_{20}F_2N_2O_3$ (MW=3664.14); mass spectroscopy (MH+)= 375.1

Step B

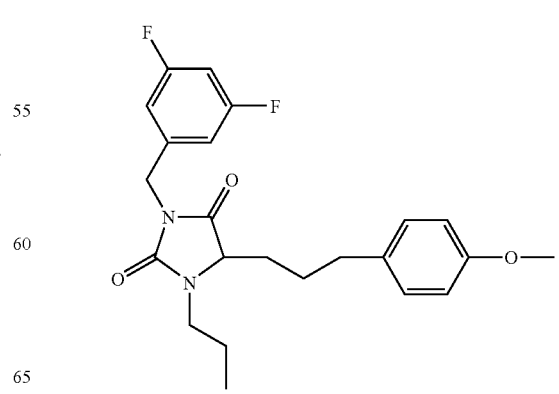

The hydantoin from Step A (0.710 g, 0.0019 mol) was dissolved in DMF (10 ml) and treated with NaH (0.084 g, 0.0021 mol) followed by 1-iodo-propane (0.200 ml, 0.0021 mol). The reaction was stirred overnight under nitrogen. The reaction mixture was poured into 1N HCl and combined with ethyl acetate. The organic layer was extracted and washed with brine then dried and concentrated. Purification of the crude material by flash chromatography (2:1 hexanes:ethyl acetate) yielded the desired product (0.742 g, 94%).

$C_{23}H_{26}F_2N_2O_3$ (MW=416.19); mass spectroscopy (MH+)= 417

Step C

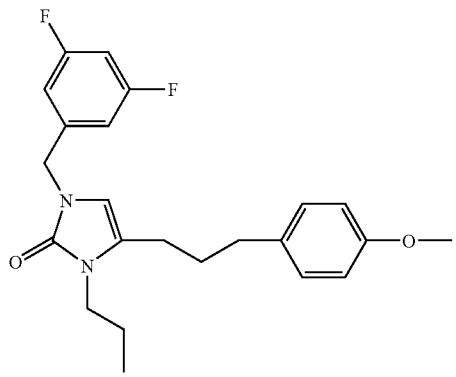

Lithium aluminum hydride (0.742 g, 0.0018 mol) was dissolved in THF (7 ml). A THF solution of the hydantoin from Step B was added. The reaction was stirred for ninety minutes at room temperature. The reaction was quenched by the addition of 5N HCl. After stirring for thirty minutes, water was added and the solution was extracted with ethyl acetate. The organic layer was extracted and washed with brine then dried and concentrated. The crude product was carried forth without further purification (0.690 g, 96%). $C_{23}H_{26}F_2N_2O_2$ (MW=400.20); mass spectroscopy (MH+)=401

Step D

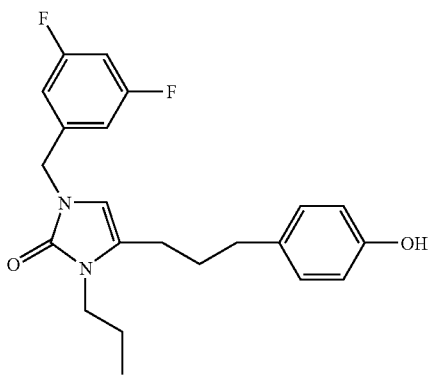

The methoxy ether from Step C (0.690 g, 0.0017 mol) was dissolved in methylene chloride and cooled to 0° C. To this solution was added, dropwise, a solution of BBr$_3$ (0.326 ml, 0.0035 mol) in methylene chloride. After stirring for about thirty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (0.550 g, 84%) was obtained and was carried forth without further purification.

$C_{22}H_{24}F_2N_2O_2$ (MW=386.18); mass spectroscopy (MH+)= 387.2

Step E

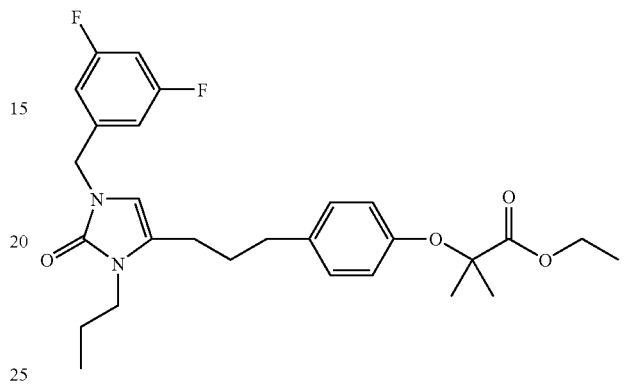

The phenol from Step D (0.055 g, 0.0014 mol) was dissolved in EtOH (7 ml) and treated with ethyl 2-bromoisobutyrate (0.627 ml, 0.0043 mol), powdered K$_2$CO$_3$ (0.773 g, 0.0056 mol), and MgSO$_4$ (0.168 g, 0.0014 mol). The reaction was stirred overnight at 77° C. Upon cooling, the reaction mixture was poured into 5N HCl and combined with EtOAc. The organic layer was extracted with water followed by brine then concentrated to dryness. Purification by flashed chromatography (1:1 hexanes:ethyl acetate) gave the ester (0.135 g, 19%). $C_{28}H_{34}F_2N_2O_4$ (MW=500.25); mass spectroscopy (MH$^+$)=501.2

Step F

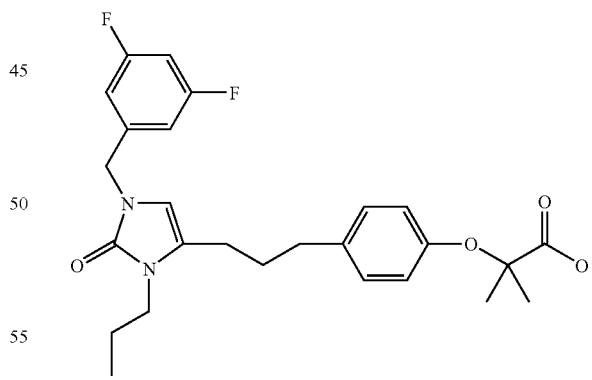

The ester from Step D (0.135 g, 0.00027 mol) was dissolved in methanol (4 ml) and treated with a solution of LiOH in water (1 ml). The reaction was stirred overnight. The reaction was cooled and water (20 ml) was added to the solution. The solution was then acidified using 1N HCl to pH=3 then extracted with ethyl acetate. The organic layer was concentrated to afford the desired carboxylic acid.

$C_{26}H_{30}F_2N_2O_4$ (MW=472.22); mass spectroscopy (MH$^+$)= 473.1

Example 114

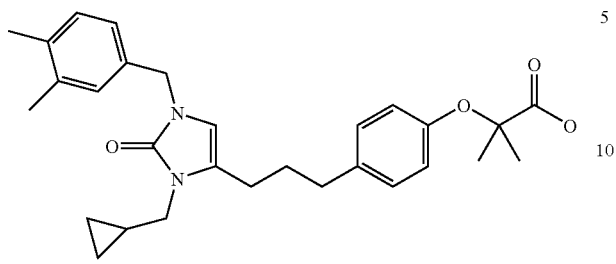

Step A

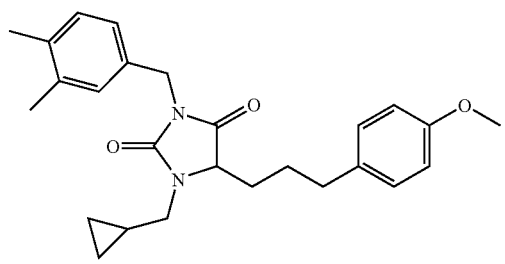

Following the procedure of Example 104, Step B, the product from Example 103, Step A (1.0 g, 2.7 mmol), sodium hydride (Aldrich, 60% dispersion in mineral oil, 0.12 g, 3.0 mmol) and (bromomethyl)cyclopropane (Aldrich, 0.29 ml, 3.0 mmol) were used to yield the desired product (1.05 g).

$C_{26}H_{32}N_2O_3$ (MW=420.6); MS (M+, 421.2)

Step B

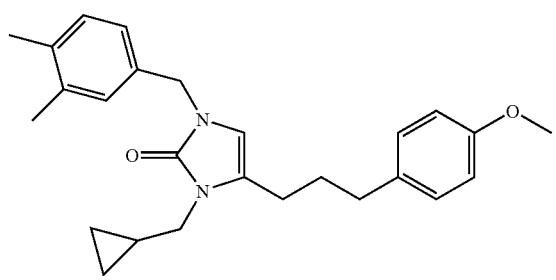

Following the procedure of Example 103, Step C, the product from Example 114, Step A (1.0 g, 2.4 mmol) and lithium aluminum hydride (Aldrich, 0.14 g, 3.6 mmol) were used to yield the desired imidazolone as a crude product (0.94 g).

$C_{26}H_{32}N_2O_2$ (MW=404.6); MS (M+, 405.2)

Step C

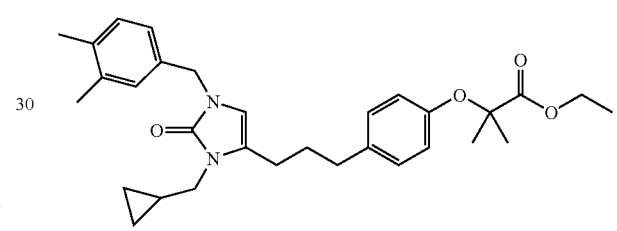

Following the procedure of Example 104, Step D, the product from Example 114, Step B (0.9 g, 2.2 mmol) and boron tribromide (Aldrich, 0.47 ml, 5.0 mmol) were used to yield the crude product (0.9 g).

$C_{25}H_{30}N_2O_2$ (MW=390.5); MS (M+, 391.2, M−, 389.4)

Step D

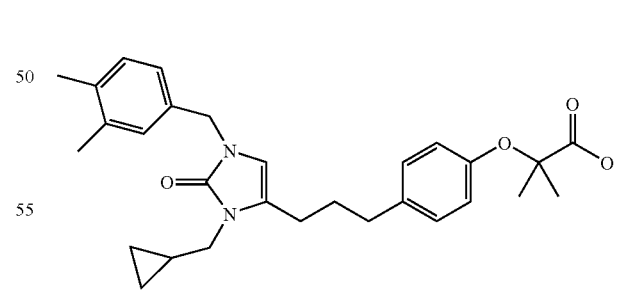

Following the procedure of Example 103, Step E, the product from Example 114, Step C (0.8 g, 2.0 mmol), ethyl 2-bromoisobutyrate (Aldrich, 0.9 ml, 6.0 mmol), potassium carbonate (powdered, Aldrich, 1.1 g, 8.0 mmol) and magnesium sulfate (Mallinkrodt, 0.3 g, 2.5 mmol) were used to yield the product (0.7 g).

$C_{31}H_{40}N_2O_4$ (MW=504.7); MS (M+, 505.4)

Step E

Following the procedure of Example 103, Step F, the product from Example 114, Step D (0.7 g, 1.4 mmol), lithium hydroxide (0.07 g, 2.8 mmol), methanol (8 ml) and water (2 ml) were used to yield the desired product as a foam after evaporation of the solvent and placement under vacuum (0.295 g).

$C_{29}H_{36}N_2O_4$ (MW=476.6); MS (M+, 477.3, M−, 475.2)

Step A

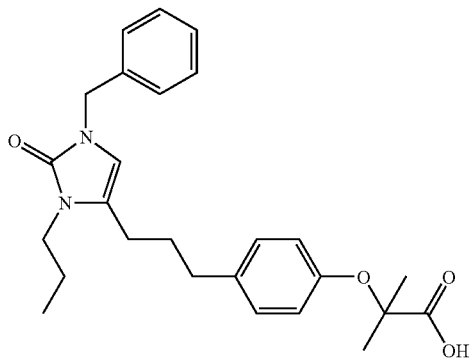

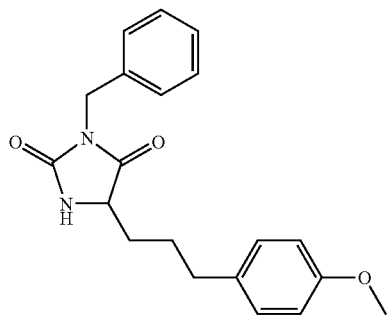

A DMF solution (20 mL) of the hydantoin from Example 13 (960.6 mg, 3.87 mmol) was treated sequentially with benzyl bromide (507 µL, 4.26 mmol), $K_2CO_3$ (1.2 g, 8.7 mmol), and $MgSO_4$ (1.2 g, 10.0 mmol). The resulting mixture was stirred at room temperature overnight. The reaction was quenched by the slow addition of 1 N HCl (55 mL). The resulting mixture was extracted with ethyl acetate (2×50 mL). The combined organic extracts were washed with brine then dried over $Na_2SO_4$ and concentrated. Purification by chromatography (gradient: 3:1 to 2:1 hexanes:ethyl acetate) gave the desired alkylated hydantoin as a white solid (932.3 mg, 71%).

$C_{20}H_{22}N_2O_3$ (MW=338.41); mass spectroscopy: (MH$^+$)=339.1, (MH$^-$)=337.2

Step B

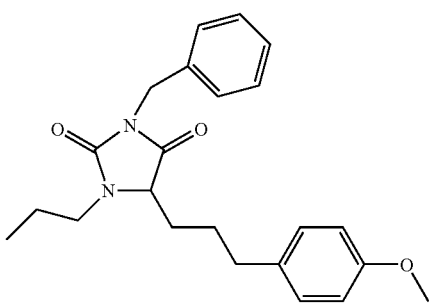

The hydantoin from Step A (897.8 mg, 2.65 mmol) was dissolved in DMF (15 mL) and cooled to 0° C. under an atmosphere of $N_2$. The mixture was treated with NaH (60% dispersion in oil, 125.5 mg, 3.0 mmol) and, after 10 minutes, n-propyl iodide (297 µL, 3.0 mmol). The reaction mixture was warmed to room temperature, stirred for 45 minutes, then quenched by the addition of $H_2O$ (0.5 mL). After stirring overnight, the mixture was poured into 1 N HCl (50 mL). The resulting solution was extracted with ethyl acetate (2×50 mL). The combined organic extracts were dried over $Na_2SO_4$ and concentrated. Purification by chromatography (gradient: 5:1 to 3:1 hexanes:ethyl acetate) gave the desired product as a yellowish oil (951.7 mg, 94%).

$C_{23}H_{28}N_2O_3$ (MW=380.49); mass spectroscopy: (MH$^+$)=381.1

Step C

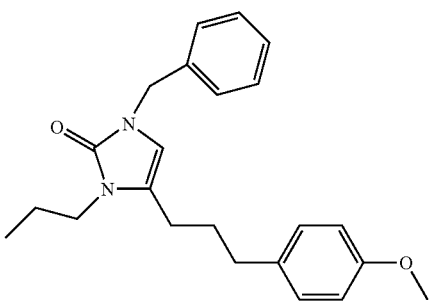

The hydantoin from Step B (938.4 mg, 2.47 mmol) was dissolved in THF (20 mL) and cooled to 0° C. under an atmosphere of $N_2$. LAH (145.7 mg, 3.8 mmol) was added in one portion and, after 30 minutes, the reaction was quenched by the addition of 5 N HCl (5 mL). The resulting mixture was stirred at room temperature for 30 minutes then diluted with $H_2O$ (150 mL) and extracted with ethyl acetate (3×50 mL). The combined organic extracts were washed with brine, dried over $Na_2SO_4$ and concentrated to give the desired imidazolone (871.3 mg, 97%). The crude product was carried forward without further purification.

$C_{23}H_{28}N_2O_2$ (MW=364.49); mass spectroscopy: (MH$^+$)=365.3

Step D

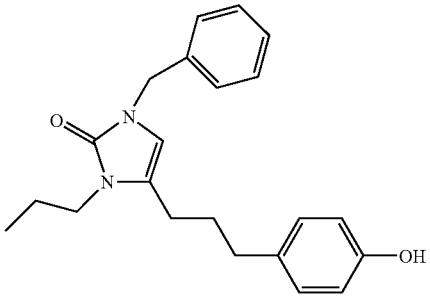

The imidazolone from Step C (845.6 mg, 2.32 mmol) was dissolved in $CH_2Cl_2$ (20 mL) and cooled to 0° C. under an atmosphere of $N_2$. $BBr_3$ (1.0 mL, 10.6 mmol) was added dropwise, then the reaction mixture was warmed to room temperature. After 30 min, the solution was again cooled to 0° C. and quenched by the slow addition of a methanol (1 mL) solution in $CH_2Cl_2$ (10 mL). Additional methanol:$CH_2Cl_2$ (1:1.10 mL) was added and the reaction was warmed to room temperature. The resulting mixture was extracted with $H_2O$ (50 mL). The aqueous extract was washed with $CH_2Cl_2$ (50 mL) then the combined organic extracts were washed with brine, dried over $Na_2SO_4$, and concentrated to give the desired phenol as a foam (782.9 mg, 96%). The crude product was carried forward without further purification.

$C_{22}H_{26}N_2O_2$ (MW=350.46); mass spectroscopy: $(MH^+)$=351.3, $(MH^-)$=349.0

Step E

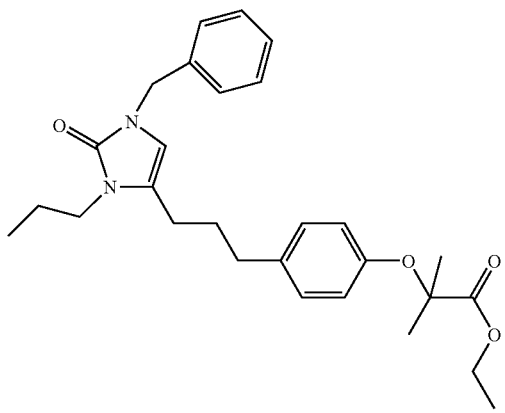

An ethanol solution (20 mL) of the phenol from Step D (775 mg, 2.21 mmol) was treated sequentially with ethyl 2-bromoisobutyrate (900 μL, 6.6 mmol), $K_2CO_3$ (1.5 g, 10.9 mmol), and $MgSO_4$ (1.6 g, 13.3 mmol). The resulting mixture was heated to 55-65° C. overnight. The reaction was quenched by the slow addition of 1 N HCl (10 mL) then poured into additional 1 N HCl (50 mL). The resulting mixture was extracted with ethyl acetate (2×50 mL). The combined organic extracts were washed with brine then dried over $Na_2SO_4$ and concentrated. Purification by chromatography (gradient: 10:1 to 1:1 hexanes:ethyl acetate) gave the desired ester as a slightly yellow oil (659.0 mg, 64%).

$C_{28}H_{36}N_2O_4$ (MW=464.61); mass spectroscopy: $(MH^+)$=465.2

Step F

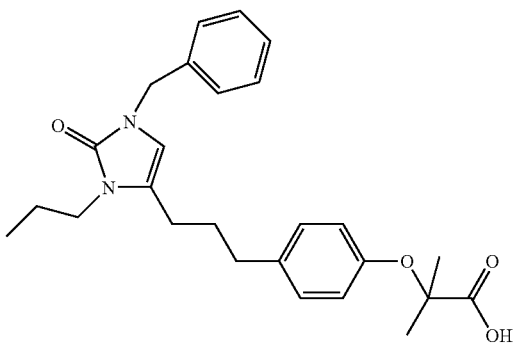

A dioxane solution (15 mL) of the ester from Step E (633.5 mg, 1.4 mmol) was treated with an aqueous solution (5 mL) of LiOH (100 mg, 4.2 mmol). The mixture was stirred at room temperature overnight. The solvent was concentrated and the resulting oil diluted with $H_2O$ (50 mL) and extracted with $Et_2O$ (50 mL). The aqueous extract was acidified with 1 N HCl and extracted with ethyl acetate (2×50 mL). The combined organic extracts were washed with brine, dried over $Na_2SO_4$, and concentrated to give the desired carboxylic acid as a slightly yellow foam-like solid (539.9 mg, 91%)

$C_{26}H_{32}N_2O_4$ (MW 436.56); mass spectroscopy: $(MH^+)$=437.3, $(MH^-)$=435.1

Example 116

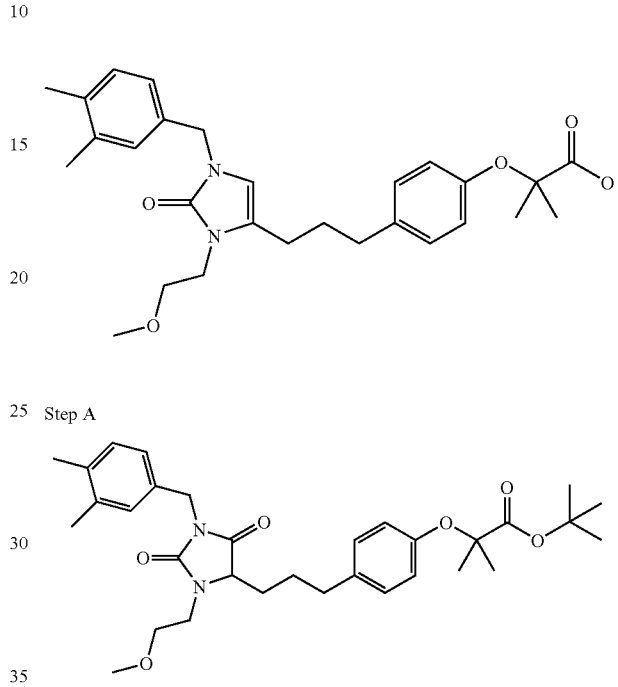

Step A

Following the procedure of Example 104, Step B, the product from Example 16, Step A (0.5 g, 1.0 mmol), sodium hydride (Aldrich, 60% dispersion in mineral oil, 0.05 g, 1.1 mmol) and bromoethylmethyl ether (Aldrich, 0.1 ml, 1.1 mmol) were used to yield the desired product (0.41 g).

$C_{32}H_{44}N_2O_6$ (MW=552.7); $^1H$ NMR

Step B

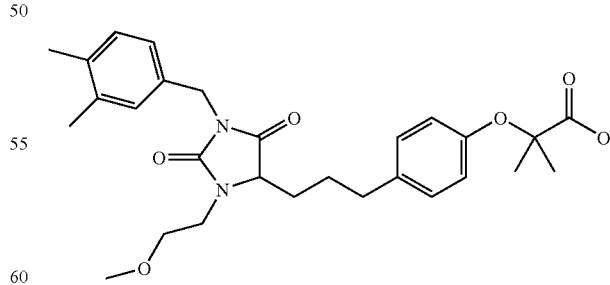

Following the procedure of Example 25, Step B, the product from Example 116, Step A (0.4 g, 0.72 mmol) and trifluoroacetic acid (2 ml) were used to yield the desired product (0.36 g).

$C_{28}H_{36}N_2O_6$ (MW=496.6); MS (M+, 497.3)

Step C

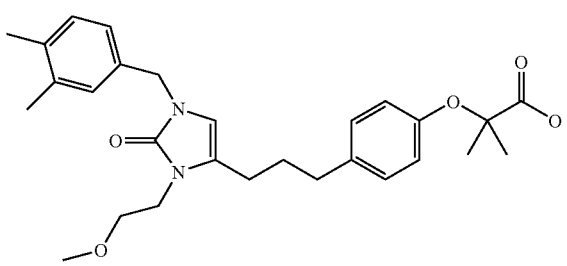

Following the procedure of Example 15, Step B, product from Example 116, Step B (0.36 g, 0.72 mmol) and sodium borohydride (0.54 g, 15.4 mmol) were used to yield the desired product after flash chromatography (methylene chloride:methanol) (0.032 g, 22%).

$C_{28}H_{36}N_2O_5$ (MW=480.6); MS (M+, 481.1, M−, 479.0)

Example 117

Step A

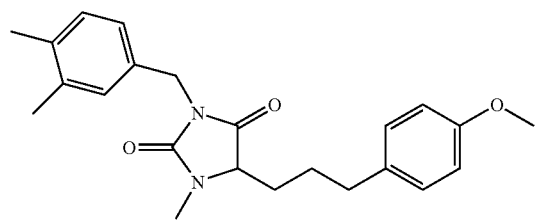

Following the procedure of Example 104, Step B, the product from Example 103, Step A (1.0 g, 2.7 mmol), sodium hydride (60% dispersion in mineral oil, 0.12 g, 3.0 mmol) and iodomethane (0.19 ml, 3.0 mmol) were used to yield the desired product (1.1 g).

$C_{23}H_{28}N_2O_3$ (MW=380.5); MS (M+, 381.2)

Step B

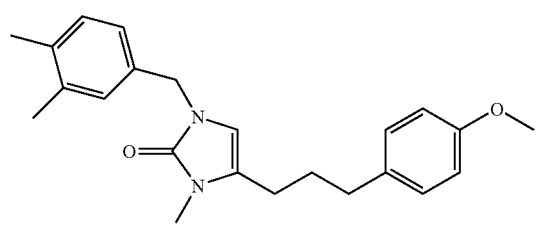

Following the procedure of Example 103, Step C, the product from Example 117, Step A (1.0 g, 2.7 mmol) and lithium aluminum hydride (0.16 g, 4.1 mmol) were used to yield the desired imidazolone as a crude product (0.92 g).

$C_{23}H_{28}N_2O_2$ (MW=364.5); MS (M+, 365.2)

Step C

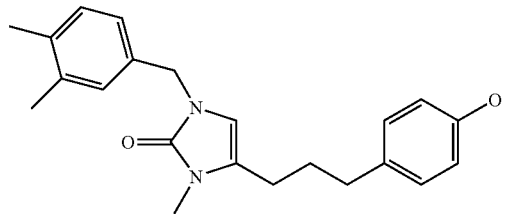

Following the procedure of Example 104, Step D, the product from Example 117, Step B (0.92 g, 2.5 mmol) and boron tribromide (0.47 ml, 5.0 mmol) were used to yield the crude product (0.86 g).

$C_{22}H_{26}N_2O_2$ (MW=350.5); MS (M+, 351.2, M−, 349.3)

Step D

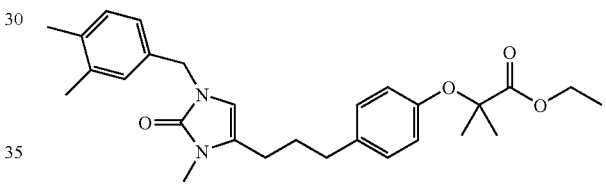

Following the procedure of Example 103, Step E, the product from Example 117, Step C (0.85 g, 2.4 mmol), ethyl 2-bromoisobutyrate (1.1 ml, 7.2 mmol), potassium carbonate (1.3 g, 9.6 mmol) and magnesium sulfate (0.4 g, 3.0 mmol) were used to yield the product (0.75 g).

$C_{28}H_{36}N_2O_4$ (MW=464.6); MS (M+, 465.3)

Step E

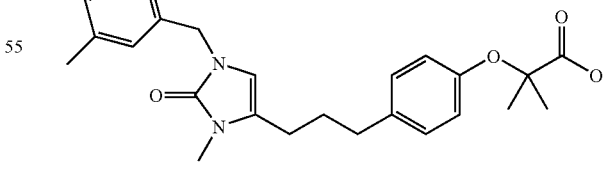

Following the procedure of Example 103, Step F, the product from Example 117, Step D (0.04 g, 0.04 mmol), sodium hydroxide (2N, 1 ml) and methanol (4 ml) were used to yield the desired product after evaporation of the solvent and placement under vacuum (0.0095 g).

$C_{26}H_{32}N_2O_4$ (MW=436.6); MS (M+, 437.3, M−, 435.1)

Example 118

Step A

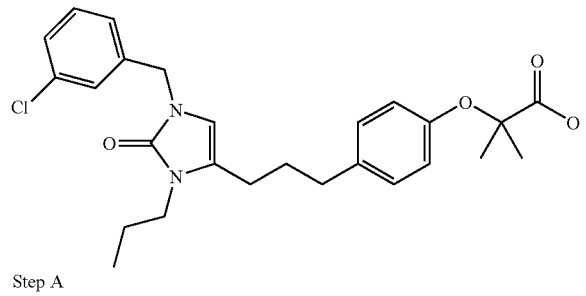

Following the procedure of Example 15, Step A, the hydantoin from Example 13 (1.0 g, 4.0 mmol), 3-chlorobenzylbromide 0.67 ml, 4.4 mmol), potassium carbonate (2.2 g, 16.0 mmol) and magnesium sulfate (0.6 g, 5.0 mmol) were used to yield the desired product (0.8 g).

$C_{20}H_{21}N_2O_3$ cl (MW=372.9); MS (M+, 373.2)

Step B

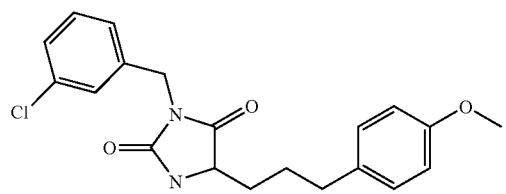

Following the procedure of Example 104, Step B, the product from Example 118, Step A (0.75 g, 2.0 mmol), sodium hydride (0.12 g, 3.0 mmol) and iodopropane (0.29 ml, 3.0 mmol) were used to yield the desired product (0.55 g).

$C_{23}H_{27}N_2O_3Cl$ (MW=414.9); MS (M+, 415.1)

Step C

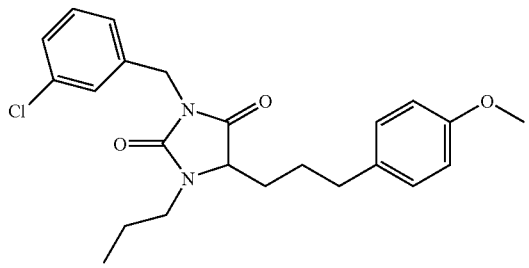

Following the procedure of Example 103, Step C, the product from Example 118, Step B (0.5 g, 1.2 mmol) and lithium aluminum hydride (0.07 g, 1.8 mmol) were used to yield the desired imidazolone as a crude product (0.5 g).

$C_{23}H_{27}N_2O_2Cl$ (MW=389.9); MS (M+, 390.2)

Step D

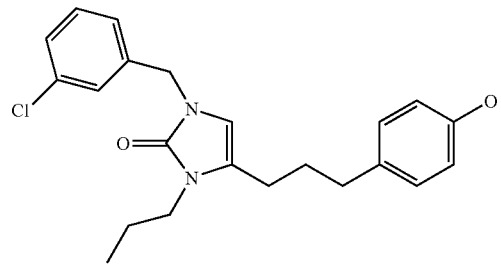

Following the procedure of Example 104, Step D, the product from Example 118, Step C (0.5 g, 1.3 mmol) and boron tribromide (0.34 ml, 3.5 mmol) were used to yield the crude product (0.5 g).

$C_{22}H_{25}N_2O_2Cl$ (MW=384.9); MS (M+, 385.2)

Step E

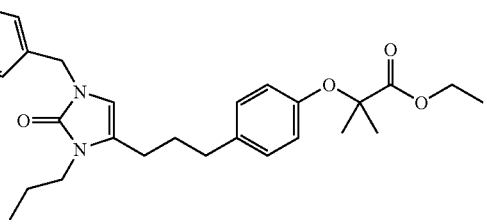

Following the procedure of Example 103, Step E, the product from Example 118, Step D (0.5 g, 1.3 mmol), ethyl 2-bromoisobutyrate (0.57 ml, 3.9 mmol), potassium carbonate (0.7 g, 5.2 mmol) and magnesium sulfate (0.1 g, 1.5 mmol) were used to yield the product (0.21 g).

$C_{28}H_{35}N_2O_4Cl$ (MW=499.1); MS (M+, 499.2)

Step F

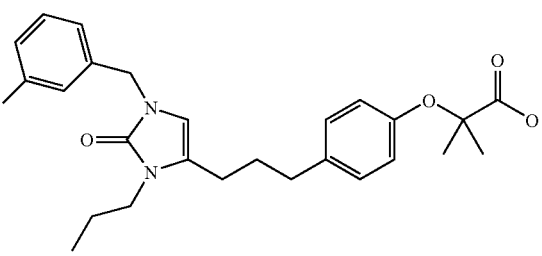

Following the procedure of Example 103, Step F, the product from Example 118, Step E (0.2 g, 0.4 mmol), sodium hydroxide (2N, 4 ml) and methanol (10 ml) were used to yield the desired product after evaporation of the solvent and placement under vacuum (0.163 g).

$C_{26}H_{31}N_2O_4Cl$ (MW=471.0); $^1$H NMR

Example 119

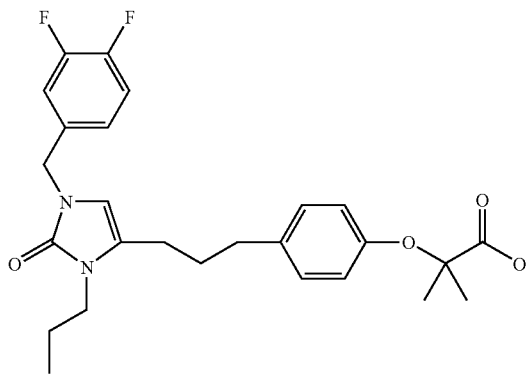

Step A

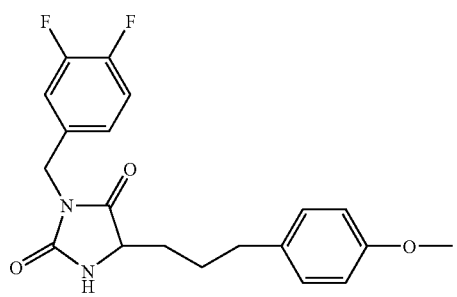

The methoxy ether from Example 13 (1.0 g, 0.004 mol) was dissolved in DMF and treated with 3,4 difluoro bromobenzene (0.568 ml, 0.0044 mol) and powdered $K_2CO_3$ (2.20 g, 0.0080 mol). The resulting mixture was stirred at room temperature overnight. The reaction mixture was poured into 1N HCl and combined with ethyl acetate. The organic layer was extracted and washed with brine then dried and concentrated. Purification of the crude material by flash chromatography (4:1 hexanes:ethyl acetate; 1:1 hexanes:ethyl acetate) yielded the desired hydantoin (0.530 g, 35%). $C_{20}H_{20}F_2N_2O_3$ (MW=374.14); mass spectroscopy (MH+)= 375.2

Step B

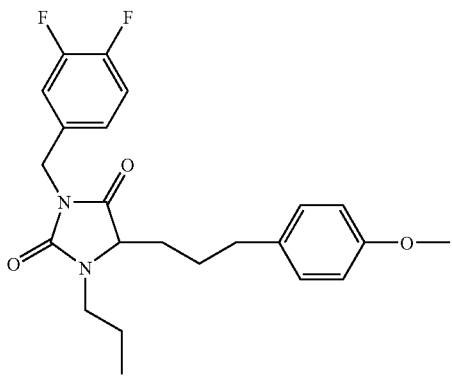

The hydantoin from Step A (0.530 g, 0.00141 mol) was dissolved in DMF (5 ml) and treated with NaH (0.062 g, 0.00156 mol) followed by 1-iodo-propane (0.152 ml, 0.00156 mol). The reaction was stirred overnight under nitrogen. The reaction mixture was poured into 1N HCl and combined with ethyl acetate. The organic layer was extracted and washed with brine then dried and concentrated. Purification of the crude material by flash chromatography (2:1 hexanes:ethyl acetate) yielded the desired product (0.505 g, 86%).
$C_{23}H_{26}F_2N_2O_3$ (MW=416.19); mass spectroscopy (MH+)= 417.2

Step C

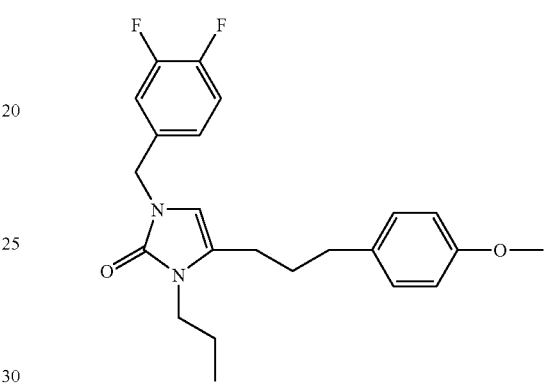

Lithium aluminum hydride (0.0609 g, 0.0018 mol) was dissolved in THF (5 ml). A THF solution of the hydantoin (0.505 g, 0.0012 mol) from Step B was added. The reaction was stirred overnight at room temperature. The reaction was quenched by the addition of 5N HCl. After stirring for thirty minutes, water was added and the solution was extracted with ethyl acetate. The organic layer was extracted and washed with brine then dried and concentrated. The crude product was carried forth without further purification (0.483 g, 100%). $C_{23}H_{26}F_2N_2O_2$ (MW=400.20); mass spectroscopy (MH+)=401

Step D

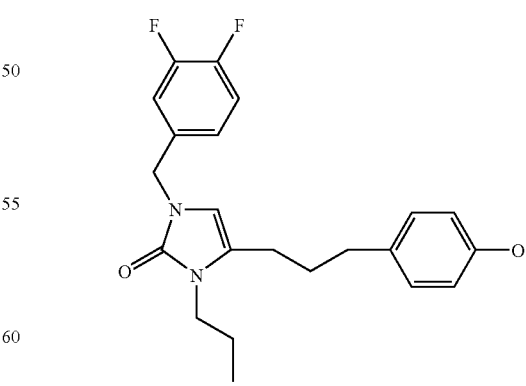

The methoxy ether from Step C (0.483 g, 0.0012 mol) was dissolved in methylene chloride (5 ml) and cooled to 0° C. To this solution was added, dropwise, a solution of $BBr_3$ (0.228 ml, 0.0024 mol) in methylene chloride (5 ml). After stirring for about thirty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (0.438 g, 95%) was obtained and was carried forth without further purification. $C_{22}H_{24}F_2N_2O_2$ (MW=386.18); mass spectroscopy (MH+)=387.2

Step E

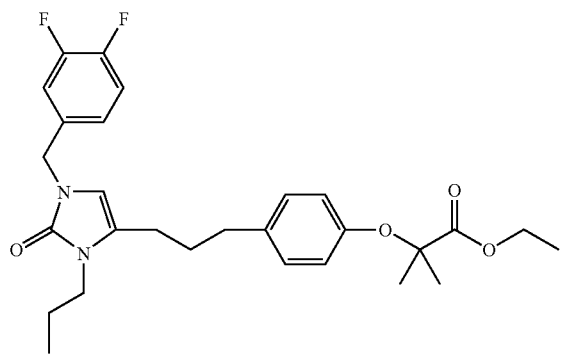

The phenol from Step D (0.438 g, 0.00110 mol) was dissolved in EtOH (7 ml) and treated with ethyl 2-bromoisobutyrate (0.500 ml, 0.0034 mol), powdered $K_2CO_3$ (0.607 g, 0.0044 mol), and $MgSO_4$ (0.132 g, 0.00110 mol). The reaction was stirred overnight at 77.7° C. Upon cooling, the reaction mixture was poured into 5N HCl and combined with EtOAc. The organic layer was extracted with water followed by brine then concentrated to dryness. Purification by flashed chromatography (1:1 hexanes:ethyl acetate) gave the ester (0.267 g, 49%). $C_{28}H_{34}F_2N_2O_4$ (MW=500.59); mass spectroscopy (MH$^+$)=501.3

Step F

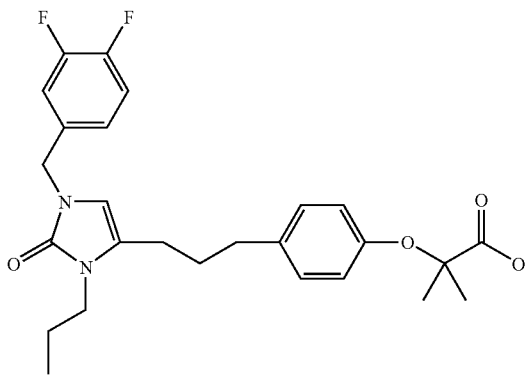

The ester from Step E (0.253 g, 0.00050 mol) was dissolved in methanol (4 ml) and treated with a solution of LiOH in water (1 ml). The reaction was stirred overnight. The reaction was cooled and water (20 ml) was added to the solution. The solution was then acidified using 1N HCl to pH=3 then extracted with ethyl acetate. The organic layer was concentrated to afford the desired carboxylic acid (0.112 g, 47%). $C_{26}H_{30}F_2N_2O_4$ (MW=472.22); mass spectroscopy (MH$^+$)=473.2

Example 120

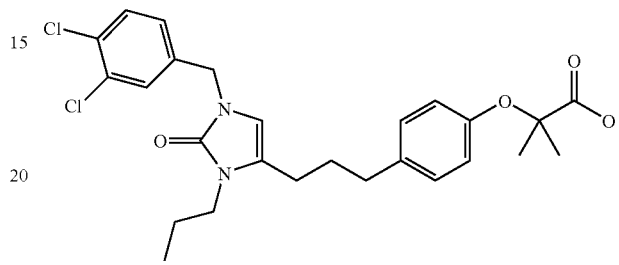

Step A

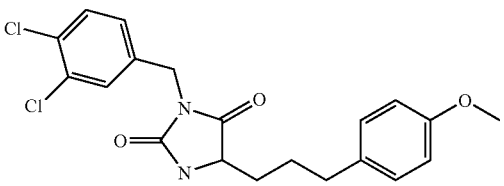

Following the procedure of Example 15, Step A, the hydantoin from Example 13 (1.0 g, 4.0 mmol), 3,4-dichlorobenzylbromide (0.8 ml, 4.4 mmol), potassium carbonate (2.2 g, 16.0 mmol) and magnesium sulfate (0.6 g, 5.0 mmol) were used to yield the desired product (1.03 g).

$C_{20}H_{20}N_2O_3Cl_2$ (MW=407.3); $^1$H NMR

Step B

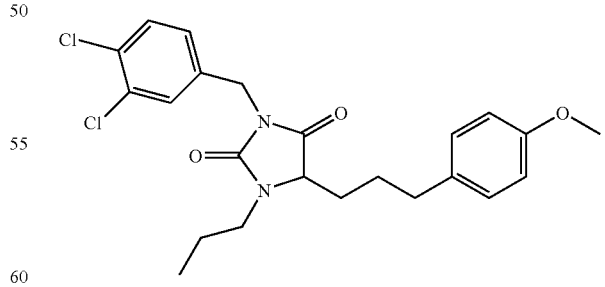

Following the procedure of Example 104, Step B, the product from Example 120, Step A (1.0 g, 2.46 mmol), sodium hydride (0.11 g, 2.7 mmol) and iodopropane (0.26 ml, 2.71 mmol) were used to yield the desired product (0.91 g).

$C_{23}H_{26}N_2O_3Cl_2$ (MW=449.4); MS (M+, 449.1, 451.1)

Step C

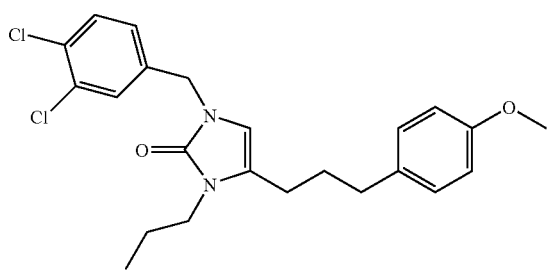

Following the procedure of Example 103, Step C, the product from Example 120, Step B (0.9 g, 2.0 mmol) and lithium aluminum hydride (0.11 g, 3.0 mmol) were used to yield the desired imidazolone as a crude product (0.85 g).

$C_{23}H_{26}N_2O_2Cl_2$ (MW=433.4); MS (M+, 433.1, 435.1)

Step D

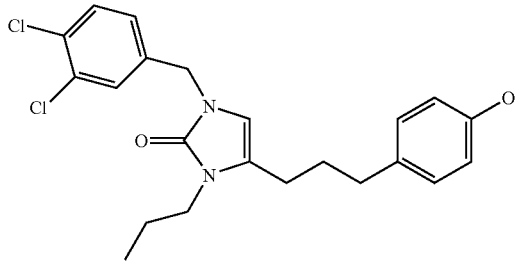

Following the procedure of Example 104, Step D, the product from Example 120, Step C (0.85 g, 2.0 mmol) and boron tribromide (0.6 ml, 6.0 mmol) were used to yield the crude product.

$C_{22}H_{24}N_2O_2Cl_2$ (MW=419.4); MS (M+, 419.1, 421.1)

Step E

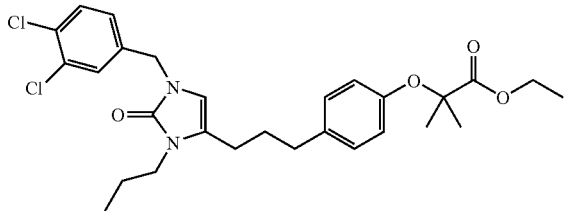

Following the procedure of Example 103, Step E, the product from Example 120, Step D (0.8 g, 1.9 mmol), ethyl 2-bromoisobutyrate (0.83 ml, 5.7 mmol), potassium carbonate (1.0 g, 7.6 mmol) and magnesium sulfate (0.3 g, 2.5 mmol) were used to yield the product (0.48 g).

$C_{28}H_{34}N_2O_4Cl_2$ (MW=533.5); MS (M+, 533.2, 535.2)

Step F

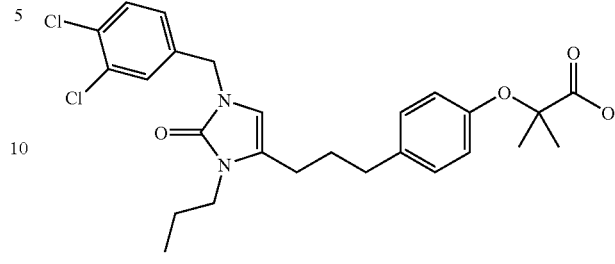

Following the procedure of Example 103, Step F, the product from Example 120, Step E (0.48 g, 0.9 mmol), lithium hydroxide (0.04 g, 1.8 mmol), methanol (8 ml) and water (2 ml) were used to yield the desired product after evaporation of the solvent and placement under vacuum (0.45 g).

$C_{26}H_{30}N_2O_4Cl_2$ (MW=505.5); MS (M+, 505.2, 507.2)

Example 121

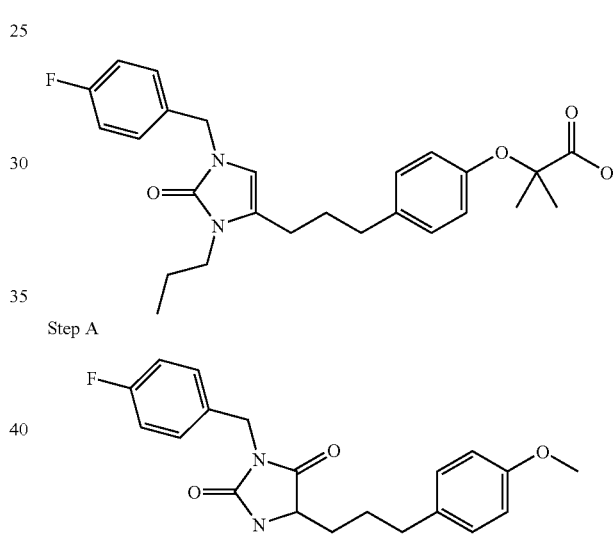

Step A

Following the procedure of Example 15, Step A, the hydantoin from Example 13 (1.0 g, 4.0 mmol), 4-fluorobenzylbromide (0.52 ml, 4.4 mmol), potassium carbonate (2.2 g, 16.0 mmol) and magnesium sulfate (0.6 g, 5.0 mmol) were used to yield the desired product (1.0 g).

$C_{20}H_{21}N_2O_3F$ (MW=356.4); MS (M+, 357.2)

Step B

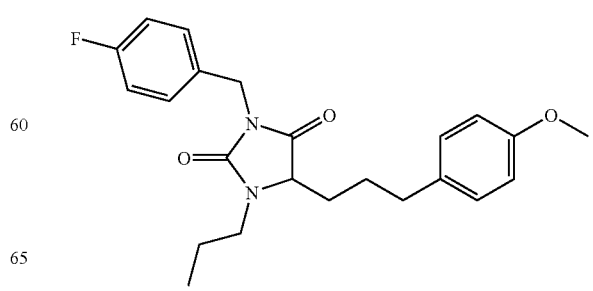

Following the procedure of Example 104, Step B, the product from Example 121, Step A (1.0 g, 2.8 mmol), sodium hydride (0.12 g, 3.1 mmol) and iodopropane (0.3 ml, 3.1 mmol) were used to yield the desired product (0.85 g).

$C_{23}H_{27}N_2O_3F$ (MW=398.5); MS (M+, 399.2)

Step C

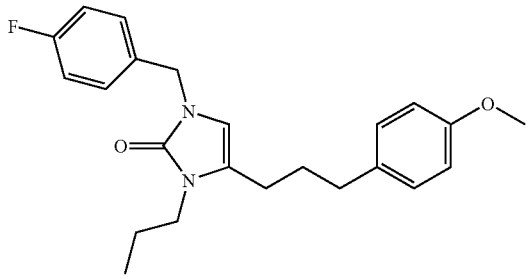

Following the procedure of Example 103, Step C, the product from Example 121, Step B (0.85 g, 2.1 mmol) and lithium aluminum hydride (0.12 g, 3.2 mmol) were used to yield the desired imidazolone as a crude product (0.64 g).

$C_{23}H_{27}N_2O_2F$ (MW=382.5); MS (M+, 383.2)

Step D

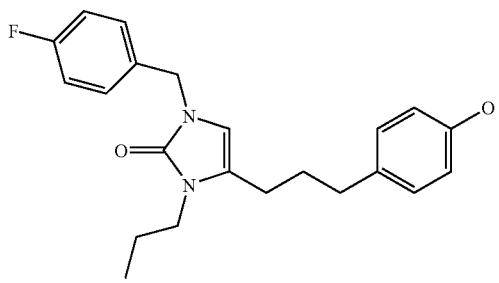

Following the procedure of Example 104, Step D, the product from Example 121, Step C (0.64 g, 1.7 mmol) and boron tribromide (0.49 ml, 5.1 mmol) were used to yield the crude product.

$C_{22}H_{25}N_2O_2F$ (MW=368.5); MS (M+, 369.2)

Step E

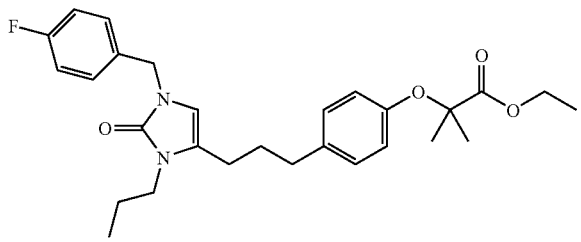

Following the procedure of Example 103, Step E, the product from Example 121, Step D (0.62 g, 1.7 mmol), ethyl 2-bromoisobutyrate (0.74 ml, 5.1 mmol), potassium carbonate (0.9 g, 6.8 mmol) and magnesium sulfate (0.3 g, 2.5 mmol) were used to yield the product (0.49 g).

$C_{28}H_{35}N_2O_4F$ (MW=482.6); MS (M+, 483.3)

Step F

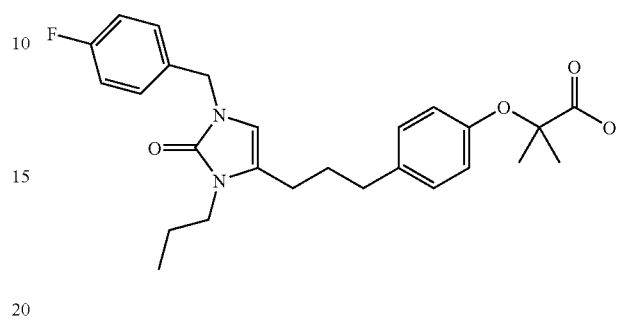

Following the procedure of Example 103, Step F, the product from Example 121, Step E (0.49 g, 1.0 mmol), sodium hydroxide (2N, 2 ml) and methanol (8 ml) were used to yield the desired product after evaporation of the solvent and placement under vacuum (0.4 g).

$C_{26}H_{31}N_2O_4F$ (MW=454.6); MS (M+, 455.3, M−, 453.1)

Example 122

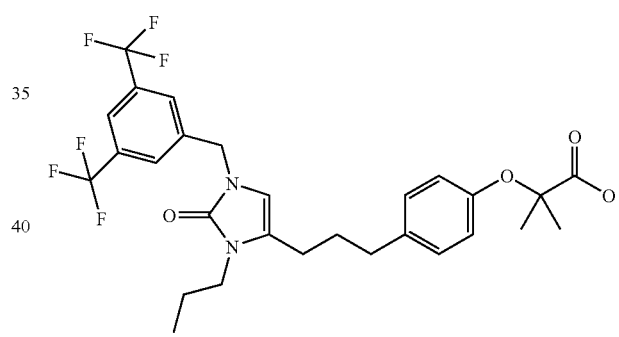

Step A

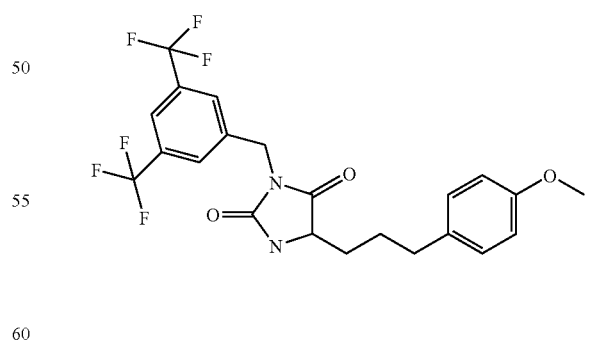

Following the procedure of Example 15, Step A, the hydantoin from Example 13 (1.0 g, 4.0 mmol), 3,5-bistrifluoromethylbenzyl bromide (0.78 ml, 4.4 mmol), potassium carbonate (2.2 g, 16.0 mmol) and magnesium sulfate (0.6 g, 5.0 mmol) were used to yield the desired product (0.85 g).

$C_{22}H_{20}N_2O_3F_6$ (MW=474.4); MS (M+, 475.1)

Step B

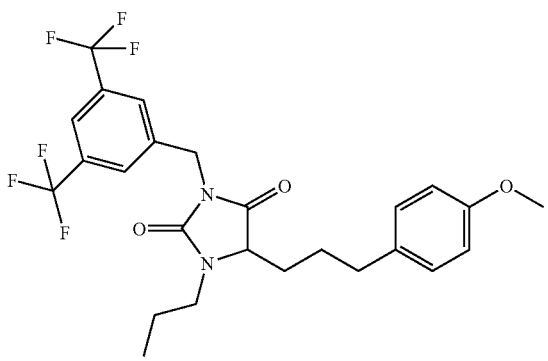

Following the procedure of Example 104, Step B, the product from Example 122, Step A (1.5 g, 3.2 mmol), sodium hydride (0.13 g, 3.5 mmol) and iodopropane (0.34 ml, 3.5 mmol) were used to yield the desired product (1.0 g).

$C_{25}H_{26}N_2O_3F_6$ (MW=516.5); MS (M+, 517.2)

Step C

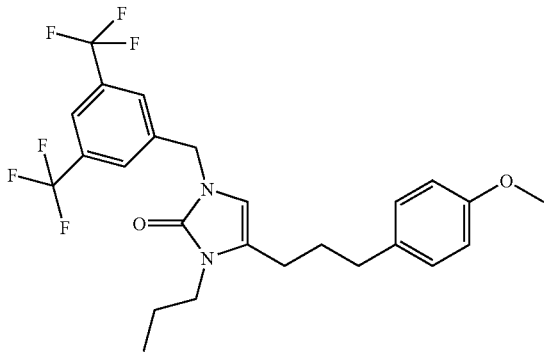

Following the procedure of Example 103, Step C, the product from Example 122, Step B (1.0 g, 1.9 mmol) and lithium aluminum hydride (0.11 g, 2.9 mmol) were used to yield the desired imidazolone as a crude product (0.84 g).

$C_{25}H_{26}N_2O_2F_6$ (MW=500.5); MS (M+, 501.2)

Step D

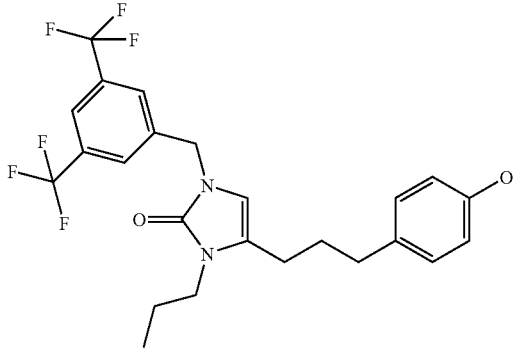

Following the procedure of Example 104, Step D, the product from Example 122, Step C (0.84 g, 1.7 mmol) and boron tribromide (0.49 ml, 5.1 mmol) were used to yield the crude product.

$C_{24}H_{24}N_2O_2F_6$ (MW=486.5); MS (M+, 487.2)

Step E

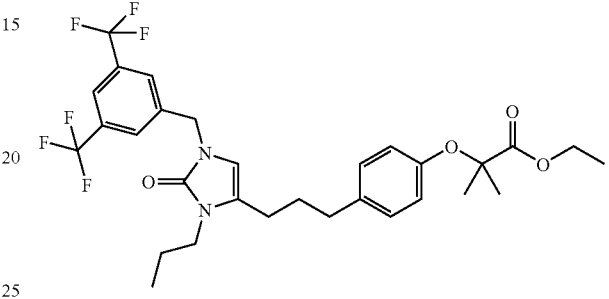

Following the procedure of Example 103, Step E, the product from Example 122, Step D (0.62 g, 1.7 mmol), ethyl 2-bromoisobutyrate (0.74 ml, 5.1 mmol), potassium carbonate (0.9 g, 6.8 mmol) and magnesium sulfate (0.3 g, 2.5 mmol) were used to yield the product (0.57 g).

$C_{30}H_{34}N_2O_4F_6$ (MW=600.6); MS (M+, 601.3)

Step F

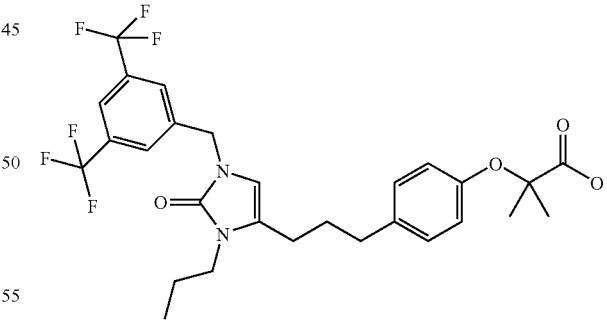

Following the procedure of Example 103, Step F, the product from Example 122, Step E (0.57 g, 0.9 mmol), sodium hydroxide (2N, 2 ml) and methanol (8 ml) were used to yield the desired product after evaporation of the solvent and placement under vacuum (0.54 g).

$C_{28}H_{30}N_2O_4F_6$ (MW=572.6); MS (M+, 573.3, M−, 571.1)

Example 123

Step A

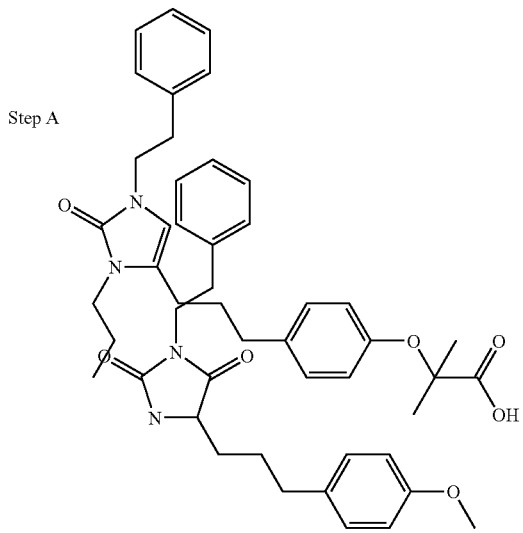

A DMF solution (50 mL) of the hydantoin from Example 13 (1.22 g, 4.2 mmol) was treated sequentially with phenethyl bromide (574 µL, 4.2 mmol), K$_2$CO$_3$ (1.3 g, 9.4 mmol), and MgSO$_4$ (1.8 g, 15 mmol). The resulting mixture was stirred at room temperature overnight. The reaction was quenched with 1 N HCl (200 mL) extracted with diethyl ether (1×200 mL). The organic extract was washed with brine then dried over Na$_2$SO$_4$ and concentrated. Purification by chromatography (gradient: 2:1 to 1:1 hexanes:ethyl acetate) gave the desired alkylated hydantoin as a white solid (766.6 mg, 52%).

C$_{21}$H$_{24}$N$_2$O$_3$ (MW=352.44); mass spectroscopy: (MH$^+$)= 353.2, (MH$^-$)=351.3

Step B

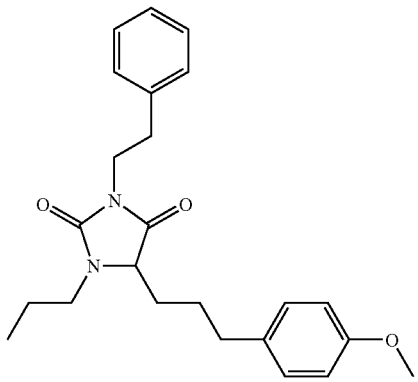

The hydantoin from Step A (761.5 mg, 2.16 mmol) was dissolved in DMF (15 mL) and cooled to 0° C. under an atmosphere of N$_2$. The mixture was treated with NaH (60% dispersion in oil, 101 mg, 2.52 mmol) and, after 15 minutes, n-propyl iodide (243 µL, 2.49 mmol). The reaction mixture was warmed to room temperature, stirred overnight, then poured into 1 N HCl (100 mL). The resulting solution was extracted with diethyl ether and the organic extract was dried over Na$_2$SO$_4$ and concentrated. Purification by chromatography (gradient: 5:1 to 3:1 hexanes:ethyl acetate) gave the desired product as a colorless oil (720.8 mg, 85%).

C$_{24}$H$_{30}$N$_2$O$_3$ (MW=394.52); mass spectroscopy: (MH$^+$)= 395.3

Step C

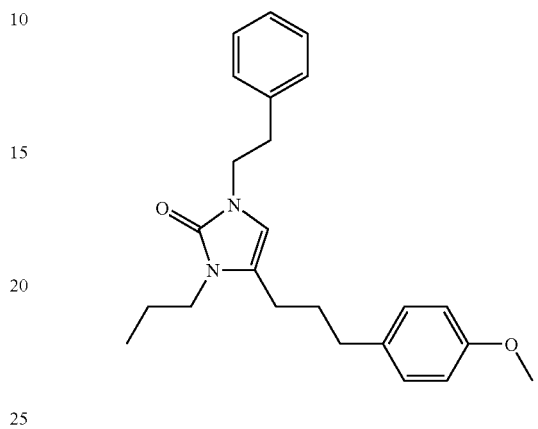

The hydantoin from Step B (704.9 mg, 1.79 mmol) was dissolved in THF (20 mL) and cooled to 0° C. LAH (68 mg, 1.79 mmol) was added in one portion and, after 45 minutes, the reaction was quenched by the addition of 5 N HCl (5 mL). The resulting mixture was stirred at room temperature for 30 minutes then diluted with H$_2$O (100 mL) and extracted with ethyl acetate (2×50 mL). The combined organic extracts were washed with brine, dried over Na$_2$SO$_4$ and concentrated to give the desired imidazolone (667.6 mg, 99%). The crude product was carried forward without further purification.

C$_{24}$H$_{30}$N$_2$O$_2$ (MW=378.52); mass spectroscopy: (MH$^+$)= 379.2

Step D

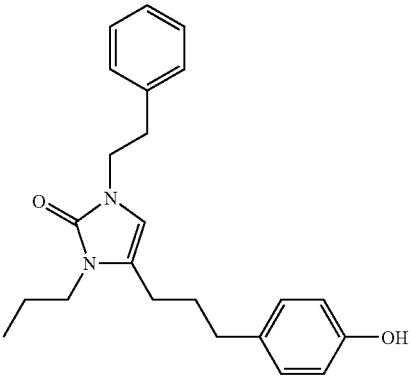

The imidazolone from Step C (659.4 mg, 1.74 nmol) was dissolved in CH$_2$Cl$_2$ (20 mL) and cooled to 0° C. BBr$_3$ (823 µL, 8.70 mmol) was added dropwise, then the reaction mixture was warmed to room temperature. After 1 hour, the solution was again cooled to 0° C. and quenched by the slow addition of a methanol:CH$_2$Cl$_2$ (1:4) solution. The resulting mixture was extracted with H$_2$O (50 mL). The aqueous extract was washed with CH$_2$Cl$_2$ (50 mL) then the combined organic extracts were washed with brine, dried over Na$_2$SO$_4$, and concentrated to give the desired phenol as a foam. The crude product was carried forward without further purification.

$C_{23}H_{28}N_2O_2$ (MW=364.49); mass spectroscopy: (MH$^+$)= 365.3, (MH$^-$)=363.3

Step E

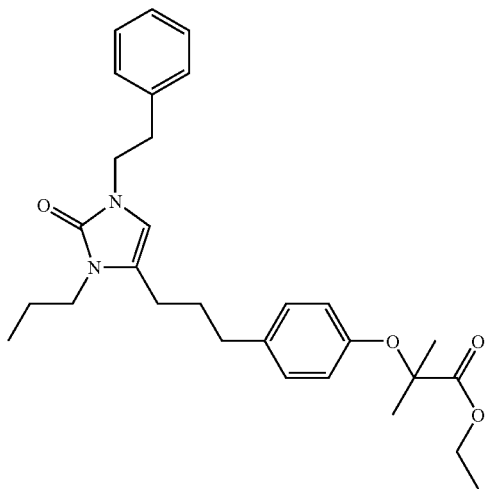

A DMF solution (20 mL) of the phenol from Step D was treated sequentially with ethyl 2-bromoisobutyrate (725 μL, 5.35 mmol), $K_2CO_3$ (1.2 g, 8.7 mmol), and $MgSO_4$ (1.2 g, 10 mmol). The resulting mixture was heated to 55-65° C. for two days. The reaction was quenched with 1 N HCl (100 mL) then extracted with diethyl ether (2×70 mL). The combined organic extracts were washed with brine then dried over $Na_2SO_4$ and concentrated. Purification by chromatography (gradient: 2:1 to 1:1 hexanes:ethyl acetate) gave the desired ester as a slightly yellow oil (325.6 mg, 39% for two steps).

$C_{29}H_{38}N_2O_4$ (MW=478.64); mass spectroscopy: (MH$^+$)= 479.4

Step F

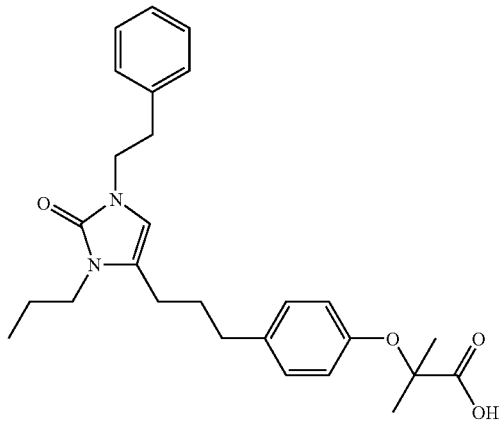

A dioxane solution (10 mL) of the ester from Step E (317.6 mg, 0.66 mmol) was treated with an aqueous solution (5 mL) of LiOH (53 mg, 2.2 mmol). The mixture was stirred at room temperature for two hours. The solvent was concentrated and the resulting oil diluted with $H_2O$ (50 mL) and 1 N NaOH (10 mL), then extracted with $Et_2O$ (50 mL). The aqueous extract was acidified with 1 N HCl and extracted with diethyl ether (2×50 mL). The combined organic extracts were washed with brine, dried over $Na_2SO_4$, and concentrated to give the desired carboxylic acid as a foam-like solid (253.6 mg, 85%) $C_{27}H_{34}N_2O_4$ (MW=450.58); mass spectroscopy: (MH$^+$)= 451.3, (MH$^-$)=449.1

Example 124

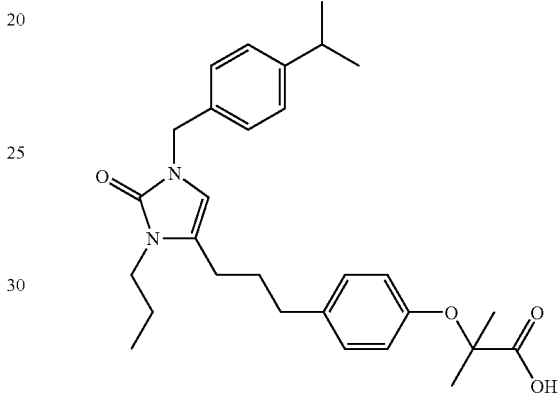

Step A

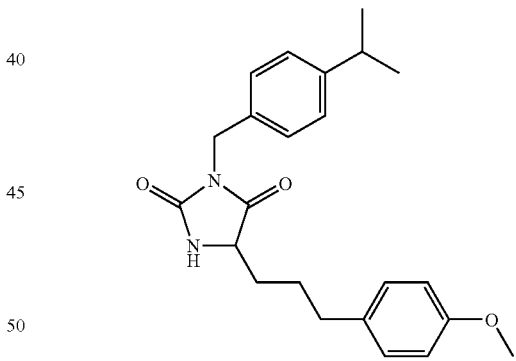

A DMF solution (50 mL) of the hydantoin from Example 13 (1.02 g, 4.1 mmol) was treated with a DMF solution (10 mL) 4-isopropylbenzyl bromide (0.693 g, 4.1 mmol) followed by $K_2CO_3$ (1.2 g, 8.7 mmol), and $MgSO_4$ (1.2 g, 10 mmol). The resulting mixture was stirred at room temperature overnight. The reaction was poured into 1 N HCl (150 mL) then extracted with ethyl acetate (2×100 mL). The combined organic extracts were washed with brine then dried over $Na_2SO_4$ and concentrated. Purification by chromatography (gradient: 3:1 to 1:1 hexanes:ethyl acetate) gave the desired alkylated hydantoin as a white solid (842.5 mg, 54%).

$C_{23}H_{28}N_2O_3$ (MW=380.49); mass spectroscopy: (MH$^+$)= 381.3, (MH$^-$)=379.1

Step B

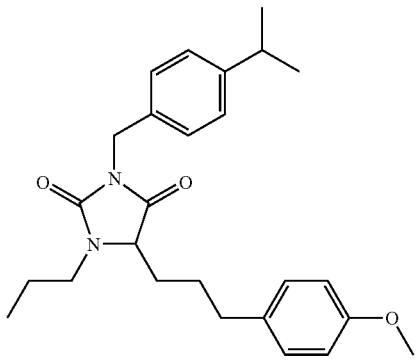

The hydantoin from Step A (827.3 mg, 2.17 mmol) was dissolved in DMF (15 mL) and cooled to 0° C. The mixture was treated with NaH (60% dispersion in oil, 106 mg, 2.65 mmol) and, after 15 minutes, n-propyl iodide (244 µL, 2.50 mmol). The reaction mixture was warmed to room temperature, stirred overnight, then poured into 1 N HCl (100 mL). The resulting solution was extracted with diethyl ether and the organic extract was washed with brine, dried over $Na_2SO_4$ and concentrated. Purification by chromatography (gradient: 5:1 to 3:1 hexanes:ethyl acetate) gave the desired product as a colorless oil (705.3 mg, 77%).

$C_{26}H_{34}N_2O_3$ (MW=422.57); mass spectroscopy: $(MH^+)$= 423.3

Step C

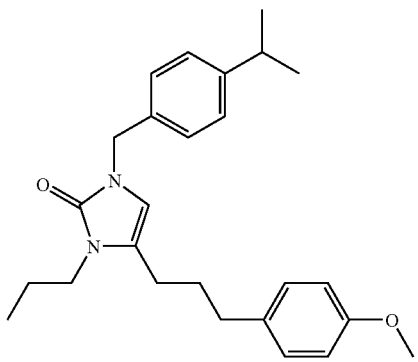

The hydantoin from Step B (687.0 mg, 1.63 mmol) was dissolved in THF (20 mL) and cooled to 0° C. LAH (63 mg, 1.66 mmol) was added in one portion and, after 45 minutes, the reaction was quenched by the addition of 5 N HCl (5 mL) in THF (10 ml). The resulting mixture was stirred at room temperature for 30 minutes then diluted with $H_2O$ (100 mL) and extracted with ethyl acetate (2×50 mL). The combined organic extracts were washed with brine, dried over $Na_2SO_4$ and concentrated to give the desired imidazolone (640.1 mg, 97%). The crude product was carried forward without further purification.

$C_{26}H_{34}N_2O_2$ (MW=406.57); mass spectroscopy: $(MH^+)$= 407.2

Step D

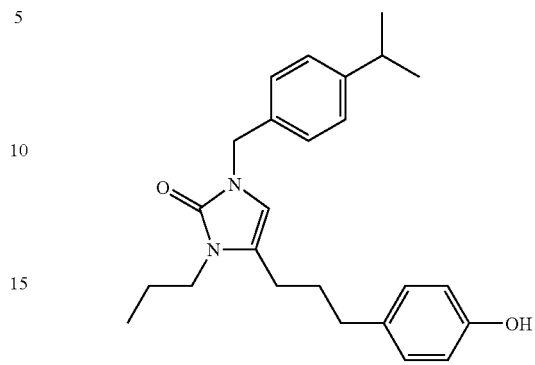

The imidazolone from Step C (630.8 mg, 1.55 mmol) was dissolved in $CH_2Cl_2$ (20 mL) and cooled to 0° C. $BBr_3$ (733 µL, 7.75 mmol) was added dropwise, then the reaction mixture was warmed to room temperature. After 1 hour, the solution was again cooled to 0° C. and quenched by the slow addition of a methanol:$CH_2Cl_2$ (1:4) solution. The resulting mixture was extracted with $H_2O$ (50 mL). The aqueous extract was washed with $CH_2Cl_2$ (50 mL) then the combined organic extracts were washed with brine, dried over $Na_2SO_4$, and concentrated to give the desired phenol as a foam. The crude product was carried forward without further purification.

$C_{25}H_{32}N_2O_2$ (MW 392.55); mass spectroscopy: $(MH^+)$= 393.3, $(MH^-)$=391.4

Step E

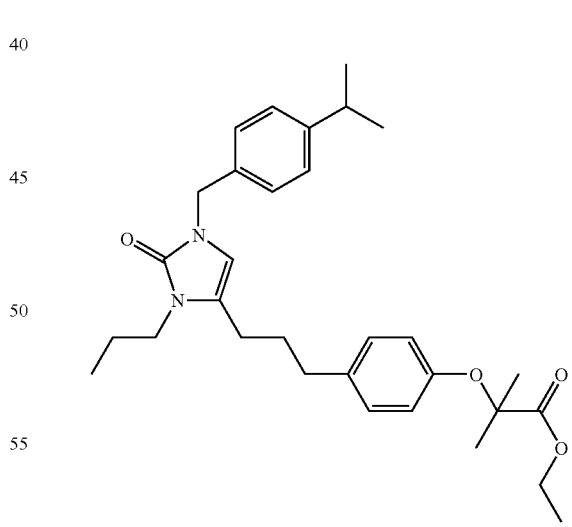

A DMF solution (20 mL) of the phenol from Step D was treated sequentially with ethyl 2-bromoisobutyrate (650 µL, 4.8 mmol), $K_2CO_3$ (1.1 g, 8.0 mmol), and $MgSO_4$ (1.1 g, 9.2 mmol). The resulting mixture was heated to 55-65° C. for two days. The reaction was quenched with 1 N HCl (100 mL) then extracted with diethyl ether (2×75 mL). The combined organic extracts were washed with brine then dried over Na₂SO₄ and concentrated. Purification by chromatography (gradient: 2:1 to 1:1 hexanes:ethyl acetate) gave the desired ester as a slightly yellow oil (202.1 mg, 26% for two steps).

$C_{27}H_{42}N_2O_4$ (MW=506.69); mass spectroscopy: (MH⁺)= 507.4

Step F

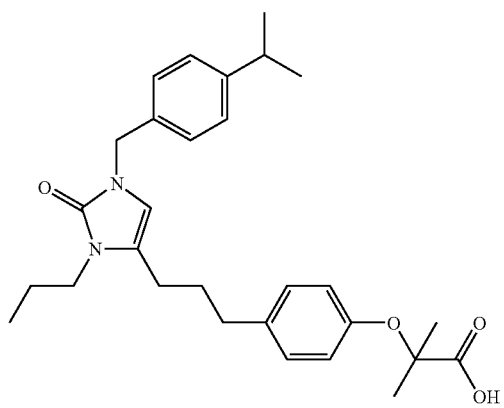

A dioxane solution (10 mL) of the ester from Step E (194.5 mg, 0.43 mmol) was treated with an aqueous solution (5 mL) of LiOH (45 mg, 1.9 mmol). The mixture was stirred at room temperature for two hours. The solvent was concentrated and the resulting oil diluted with H₂O (50 mL) and 1 N NaOH (10 mL), then extracted with Et₂O (50 mL). The aqueous extract was acidified with 1 N HCl and extracted with diethyl ether (2×50 mL). The combined organic extracts were washed with brine, dried over Na₂SO₄, and concentrated to give the desired carboxylic acid as a foam-like solid (163.0 mg, 79%)

$C_{29}H_{38}N_2O_4$ (MW=478.64); mass spectroscopy: (MH⁺)= 479.3, (MH⁻)=477.1

Example 125

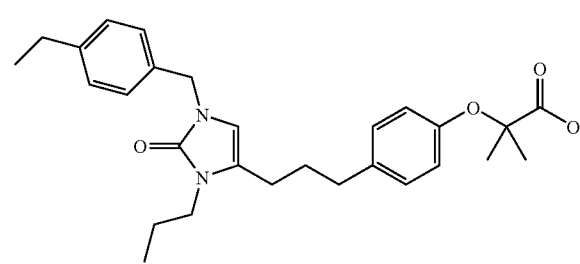

Step A

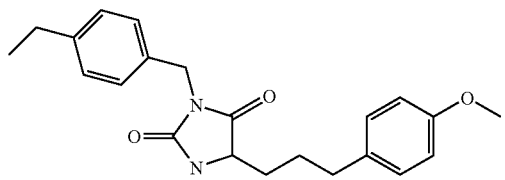

Following the procedure of Example 15, Step A, the hydantoin from Example 13 (1.0 g, 4.0 mmol), 4-ethylbenzyl chloride (0.7 ml, 4.4 mmol), potassium carbonate (2.2 g, 16.0 mmol) and magnesium sulfate (0.6 g, 5.0 mmol) were used to yield the desired product (0.9 g)

$C_{22}H_{26}N_2O_3$ (MW=366.5°); MS (M−, 365.1).

Step B

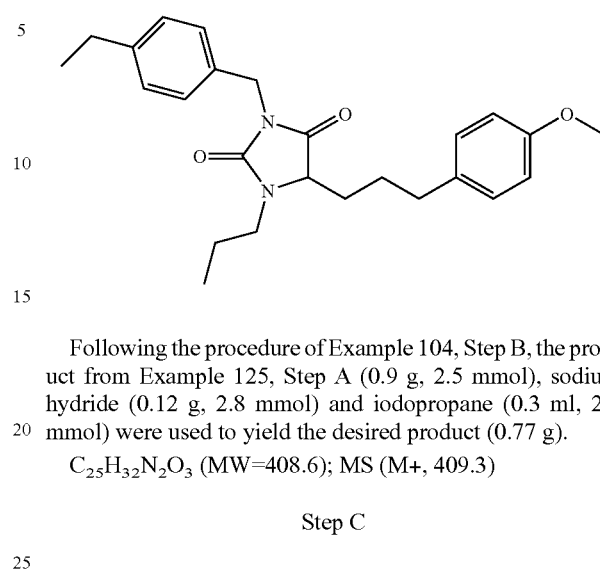

Following the procedure of Example 104, Step B, the product from Example 125, Step A (0.9 g, 2.5 mmol), sodium hydride (0.12 g, 2.8 mmol) and iodopropane (0.3 ml, 2.8 mmol) were used to yield the desired product (0.77 g).

$C_{25}H_{32}N_2O_3$ (MW=408.6); MS (M+, 409.3)

Step C

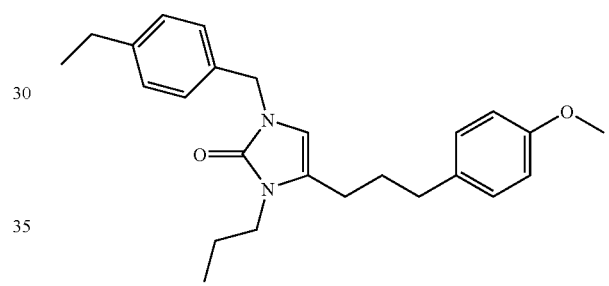

Following the procedure of Example 103, Step C, the product from Example 125, Step B (0.76 g, 1.9 mmol) and lithium aluminum hydride (0.11 g, 2.9 mmol) were used to yield the desired imidazolone as a crude product (0.72 g).

$C_{25}H_{32}N_2O_2$ (MW=392.6); MS (M+, 393.3)

Step D

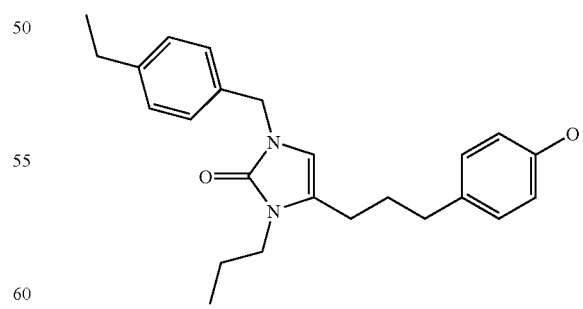

Following the procedure of Example 104, Step D, the product from Example 125, Step C (0.72 g, 1.8 mmol) and boron tribromide (Aldrich, 0.52 ml, 5.4 mmol) were used to yield the crude product.

$C_{24}H_{30}N_2O_2$ (MW=378.5); MS (M+, 379.2)

Step E

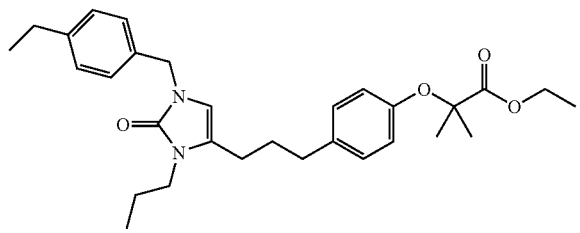

Following the procedure of Example 103, Step E, the product from Example 125, Step D (0.68 g, 1.8 mmol), ethyl 2-bromoisobutyrate (0.83 ml, 5.4 mmol), potassium carbonate (1.0 g, 7.2 mmol) and magnesium sulfate (0.36 g, 3.0 mmol) were used to yield the product (0.29 g).

$C_{30}H_{40}N_2O_4$ (MW=492.7); MS (M+, 493.3)

Step F

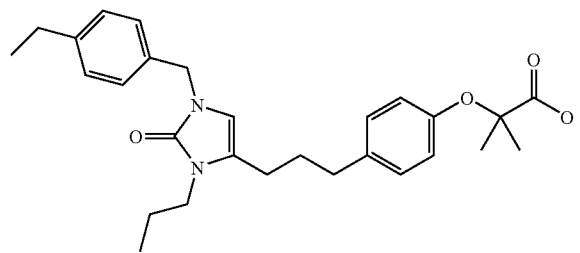

Following the procedure of Example 103, Step F, the product from Example 125, Step E (0.49 g, 1.0 mmol), sodium hydroxide (2N, 1 ml) and methanol (4 ml) were used to yield the desired product after evaporation of the solvent and placement under vacuum.

$C_{28}H_{36}N_2O_4$ (MW=464.6); MS (M+, 465.2, M−, 463.4)

Example 126

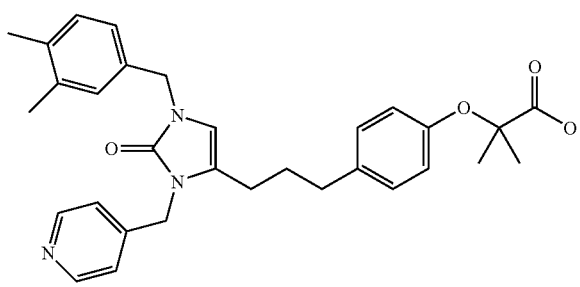

Step A

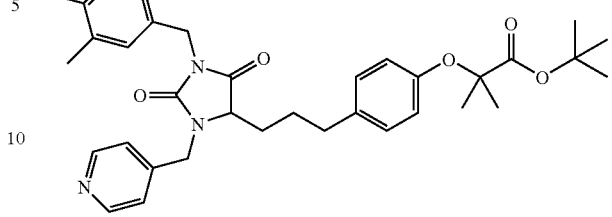

The product from Example 16, Step A (0.6 g, 1.2 mmol) and 4-picolyl chloride hydrochloride (0.2 ml, 1.3 mmol) and triethylamine (0.2 ml) stirred together in DMF (20 ml). Potassium carbonate (0.7 g, 4.8 mmol) and magnesium sulfate (0.2 g, 1.5 mmol) added and the mixture stirred at ambient temperature overnight. The reaction mixture was carefully added to 1 N hydrochloric acid (50 ml) and the resulting solution was extracted twice with ethyl acetate. The organic layers were combined, washed with aqueous brine then dried over sodium sulfate. Evaporation of the solvent and subsequent purification by flash chromatography (hexanes:ethyl acetate) gave the desired product (0.42 g).

$C_{35}H_{43}N_3O_5$ (MW=585.8); MS (M+, 586.3)

Step B

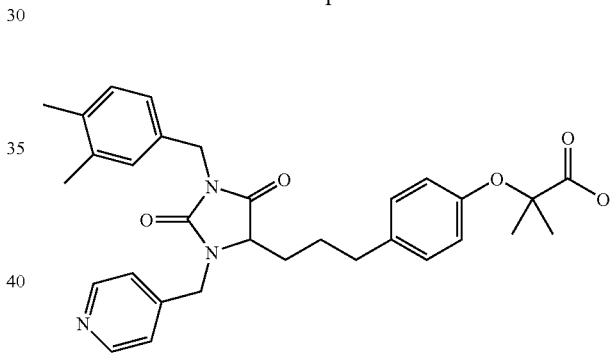

Following the procedure of Example 25, Step B, the product from Example 126, Step A (0.4 g, 0.7 mmol) and trifluoroacetic acid (2 ml) were used to yield the desired product.

$C_{31}H_{35}N_3O_5$ (MW=529.6); MS (M+, 530.4)

Step C

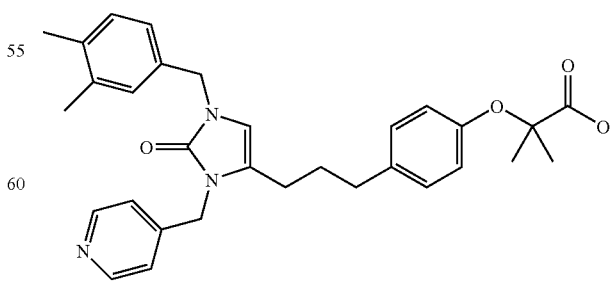

Following the procedure of Example 15, Step B, product from Example 126, Step B (0.35 g, 0.7 mmol) and sodium borohydride (0.28 g, 7.5 mmol) were used to yield the desired product after flash chromatography (methylene chloride: methanol).

$C_{31}H_{35}N_3O_4$ (MW=513.6); MS (M+, 514.4, M−, 512.2)

Example 127

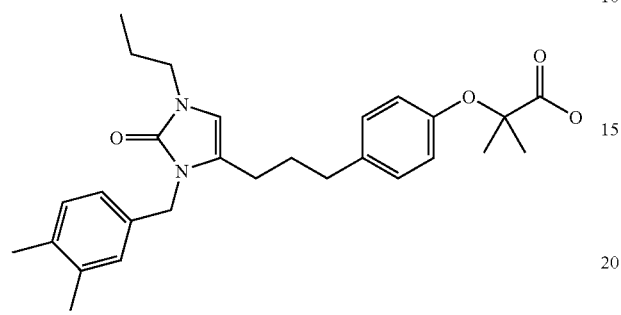

Step A

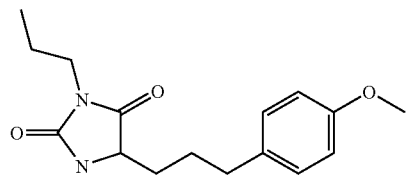

Following the procedure of Example 15, Step A, the hydantoin from Example 13 (1.0 g, 4.0 mmol), iodopropane (0.43 ml, 4.4 mmol), potassium carbonate (2.2 g, 16.0 mmol) and magnesium sulfate (0.6 g, 5.0 mmol) were used to yield the desired product (0.95 g).

$C_{16}H_{22}N_2O_3$ (MW=290.4); MS (M+, 291.2)

Step B

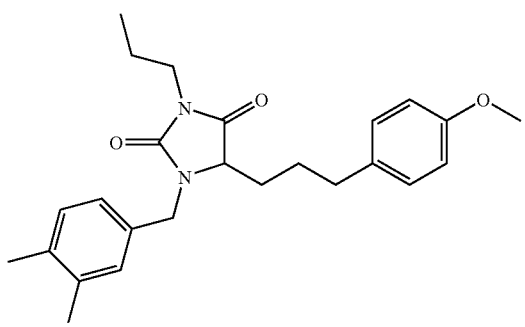

Following the procedure of Example 104, Step B, the product from Example 127, Step A (0.9 g, 3.1 mmol), sodium hydride (0.13 g, 3.4 mmol) and 3,4-dimethylbenzyl chloride (0.5 ml, 3.4 mmol) were used to yield the desired product (1.1 g).

$C_{25}H_{32}N_2O_3$ (MW=408.6); MS (M+, 409.3)

Step C

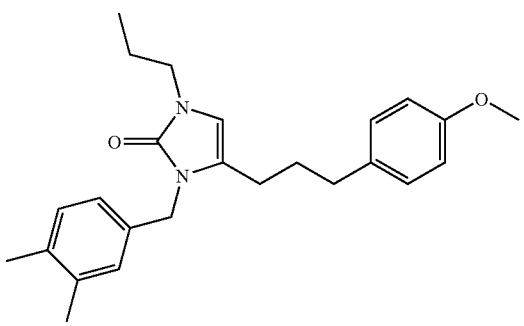

Following the procedure of Example 103, Step C, the product from Example 127, Step B (0.8 g, 1.9 mmol) and lithium aluminum hydride (0.16 g, 4.1 mmol) were used to yield the desired imidazolone as a crude product (0.8 g)

$C_{25}H_{32}N_2O_2$ (MW=392.6); MS (M+, 393.3)

Step D

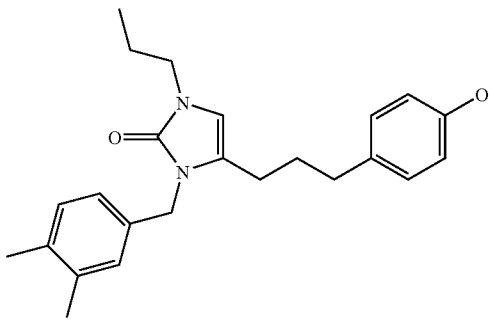

Following the procedure of Example 104, Step D, the product from Example 127, Step C (0.8 g, 2.1 mmol) and boron tribromide (0.6 ml, 6.3 mmol) were used to yield the crude product (0.7 g).

$C_{24}H_{30}N_2O_2$ (MW=378.5); MS (M+, 379.2)

Step E

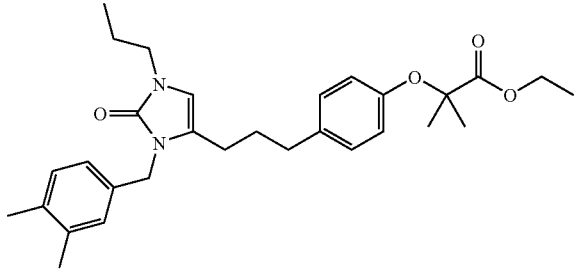

Following the procedure of Example 103, Step E, the product from Example 127, Step D (0.7 g, 1.8 mmol), ethyl 2-bromoisobutyrate (0.8 ml, 5.4 mmol), potassium carbonate (1.0

Step F

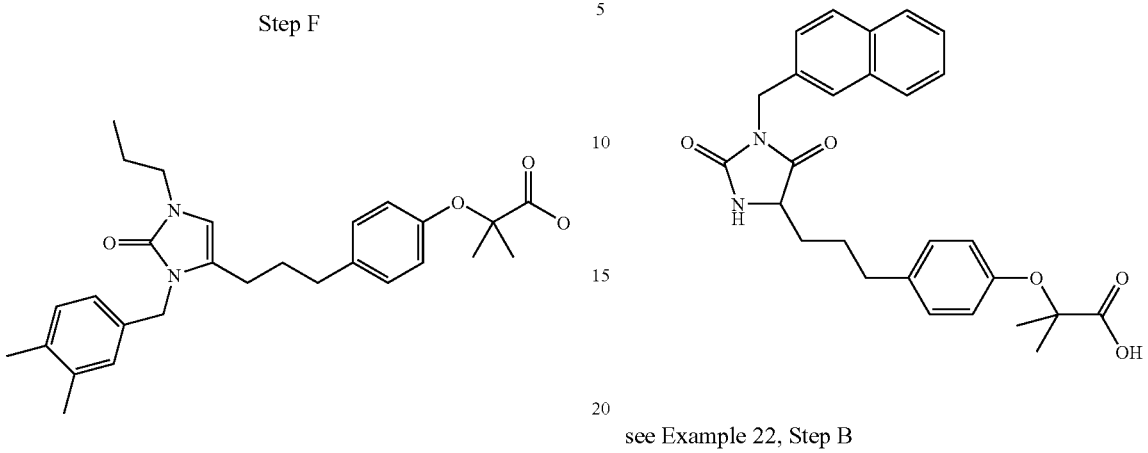

Following the procedure of Example 103, Step F, the product from Example 127, Step E (0.4 g, 1.0 mmol), sodium hydroxide (2N, 1.5 ml) and methanol (5 ml) were used to yield the desired product after evaporation of the solvent and placement under vacuum.

$C_{28}H_{36}N_2O_4$ (MW=464.6); MS (M+, 465.3, M−, 463.1)

Example 128

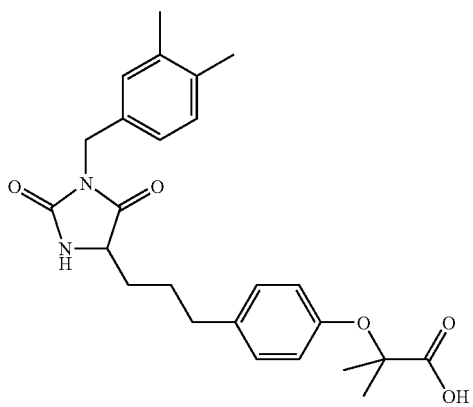

A $CH_2Cl_2$ solution (15 mL) of the ester from Example 16, Step A (279.9 mg, 0.57 mmol) was cooled to 0° C. and treated with TFA (1 mL, 13 mmol). The mixture was warmed to room temperature and stirred for 1.5 hours. The solvent was concentrated to give the crude acid, which was dissolved in 1 N NaOH (25 mL) and washed with diethyl ether (25 mL). The acueous solution was then acidified with 5 N HCl and extracted with diethyl ether (1×25 mL) and ethyl acetate (1×25 mL). The combined organic extracts were dried over $Na_2SO_4$ and concentrated to give the desired caboxylic acid as a white foam (257.3 mg).

$C_{25}H_{30}N_2O_5$ (MW=438.53); mass spectroscopy: (MH+)= 439.1, (MH−)=437.3

Example 129

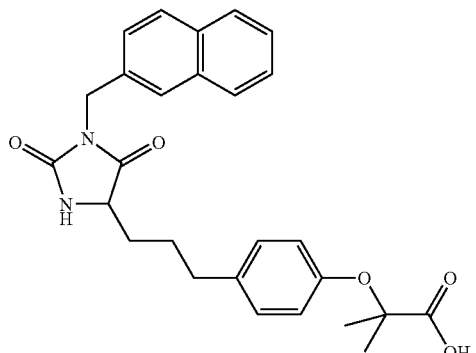

see Example 22, Step B

Example 130

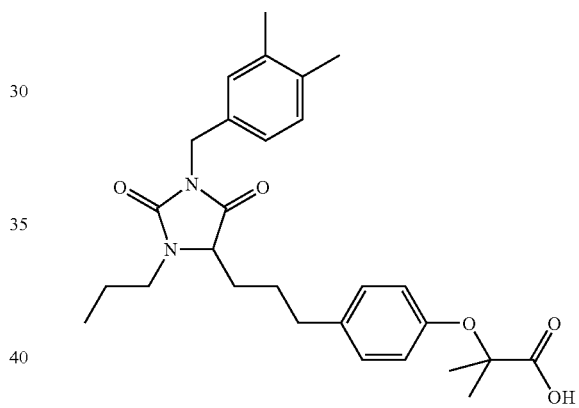

Step A

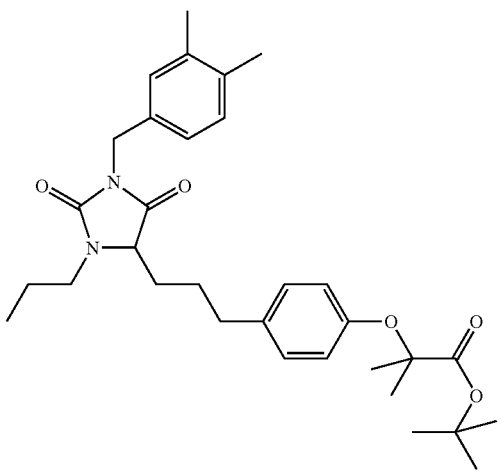

The hydantoin from Example 16, Step A (234.0 mg, 0.47 mmol) was dissolved in DMF (20 mL) and cooled to 0° C. under an atmosphere of $N_2$. The mixturefwas treated with NaH (60% dispersion in oil, 25 mg, 0.63 mmol) and, after 10 minutes, n-propyl iodide (55 µL, 0.56 mmol). The reaction mixture was warmed to room temperature, stirred overnight, then poured into 1 N HCl (100 mL). The resulting solution was extracted with diethyl ether (2×70 mL). The combined organic extracts were dried over $Na_2SO_4$ and concentrated. Purification by chromatography (5:1 hexanes:ethyl acetate) gave the desired product as a colorless oil (70.8 mg, 28%).

$C_{32}H_{44}N_2O_5$ (MW=536.72); mass spectroscopy: ($MH^+$-t-butyl)=481.4, ($M+NH_4^+$)=554.5

Step B

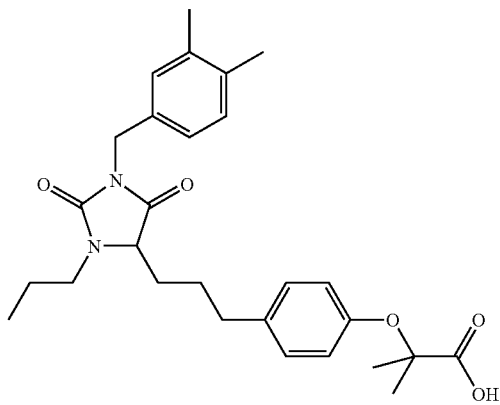

A $CH_2Cl_2$ solution (10 mL) of the ester from Step A (65 mg, 0.12 mmol) was cooled to 0° C. and treated with TFA (0.5 mL, 6.5 mmol). The mixture was warmed to room temperature and stirred for 2 hours. The solvent was concentrated to give the crude acid, which was dissolved in 1 N NaOH (50 mL) and washed with diethyl ether (50 mL). The aqueous solution was then acidified with 5 N HCl and extracted with ethyl acetate (2×25 mL). The combined organic extracts were dried over $Na_2SO_4$ and concentrated to give the desired caboxylic acid as a colorless oil (55.1 mg, 95%).

$C_{28}H_{36}N_2O_5$ (MW=480.61); mass spectroscopy: ($MH^+$)=481.2, ($MH^-$)=479.3

Example 131

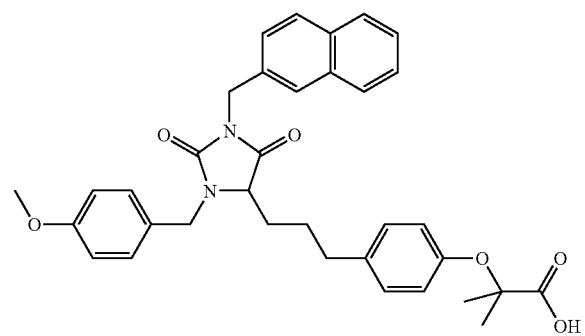

Step A

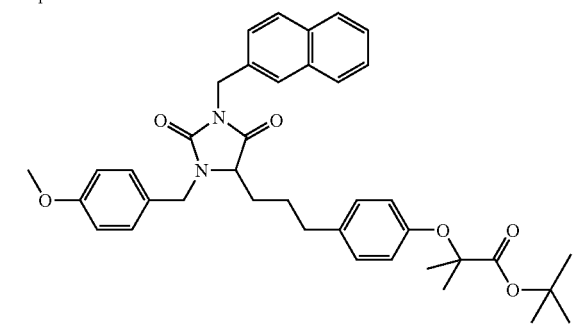

The hydantoin from Example 22, Step A (1.06 g, 2.05 mmol) was dissolved in DMF (25 mL) and cooled to 0° C. under an atmosphere of $N_2$. The mixture was treated with NaH (60% dispersion in oil, 101 mg, 2.5 mmol) and, after 5 minutes, a slight excess of 4-methoxybenzyl chloride. The reaction mixture was warmed to room temperature, stirred for 2 hours, then poured into 1 N HCl (100 mL). The resulting solution was extracted with diethyl ether (2×100 mL). The combined organic extracts were washed with brine, dried over $Na_2SO_4$ and concentrated. Purification by chromatography (2:1 hexanes:ethyl acetate) gave the desired product as a colorless oil (70.8 mg, 28%).

$C_{39}H_{44}N_2O_6$ (MW=636.80); mass spectroscopy: ($M+NH_4^+$)=654.4

Step B

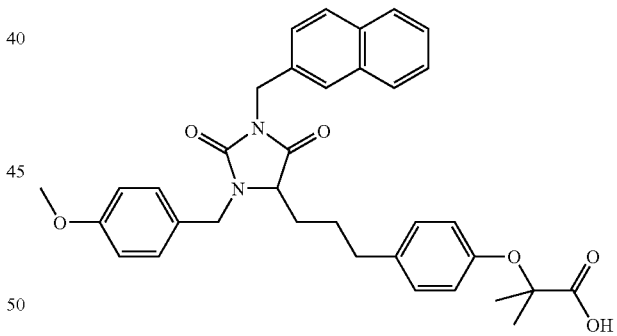

A $CH_2Cl_2$ solution (10 mL) of the ester from Step A (55 mg, 0.086 mmol) was cooled to 0° C. and treated with TFA (0.5 mL, 6.5 mmol). The mixture was warmed to room temperature and stirred for 2 hours. The solvent was concentrated to give the crude acid, which was dissolved in 1 N NaOH (50 mL) and washed with diethyl ether (50 mL). The aqueous solution was then acidified with 5 N HCl and extracted with ethyl acetate (50 mL). The organic extract was dried over $Na_2SO_4$ and concentrated to give the desired caboxylic acid (55.4 mg).

$C_{35}H_{36}N_2O_6$ (MW=580.69); mass spectroscopy: ($MH^+$)=581.2, ($MH^-$)=579.4

Example 132

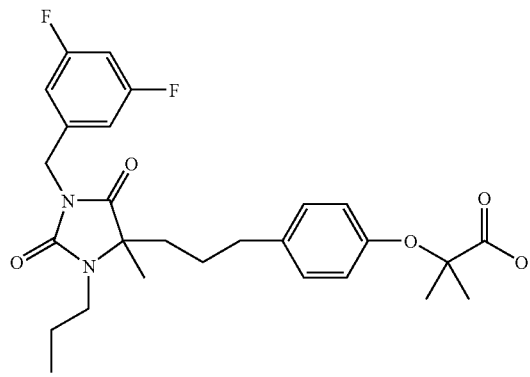

Step A

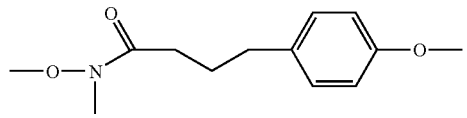

The 4-(4-methoxyphenyl) butyric acid (10.04 g, 0.052 mol) and hydroxylamine (5.04 g, 0.052 mol) were combined in THF and treated with EDAC (11.86 g, 0.062 mol), HOBt (7.0 g, 0.052 mol) and diisopropyl ethyl amine (16.9 ml, 0.124 mol). The reaction was stirred overnight. The reaction was concentrated to one-half its original volume. Ethyl acetate (100 ml) was added and the solution was extracted with 1N HCl. The organic layer was washed with 2N NaOH then concentrated. Purification of the crude material by flash chromatography (2:1 hexanes:ethyl acetate) gave the Weinreb amide (9.77 g, 78%). $C_{13}H_{19}NO_3$ (MW=237.14); mass spectroscopy (MH+)=238.0

Step B

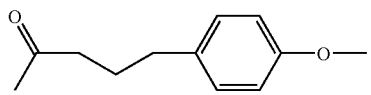

The Weinreb amide from Step A (4.7 g, 0.0198 mol) was dissolved in ether (164 ml) and cooled to 0° C. Methyl magnesium bromide (3.0 M in ether, 33 ml, 99 mmol) was added slowly to the reaction mixture. The reaction was stirred overnight. Hydrochloric acid (1N, 50 ml) was and the mixture was extracted with ether. The organic layer was stripped to afford the methyl ketone as a clear oil (3.66 g, 96%).

$C_{12}H_{16}O_2$ (MW=192.12); mass spectroscopy (MH+)= 192.1

Step C

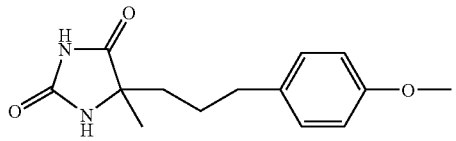

The methyl ketone from Step B (3.66 g, 0.0190 mol) was combined with potassium cyanide (2.73 g, 0.042 mol) and ammonium carbonate (9.13 g, 0.095 mol) in 1:1 methanol: water (35:35 ml) and stirred overnight at 50° C. The reaction mixture was poured into water and extracted with ethyl acetate. The organic layer was washed with brine then concentrated. Purification of the crude material by flash chromatograhy (2:1 hexanes:ethyl acetate) yielded the desired hydantoin as a thick, clear oil. $C_{14}H_{18}N_2O_3$ (MW=262.13); mass spectroscopy (MH+)=263.1

Step D

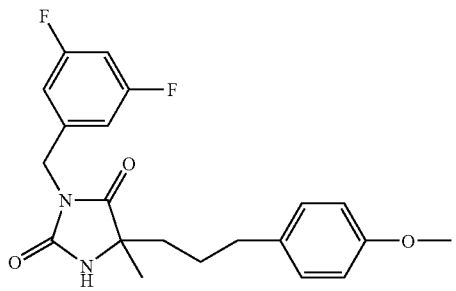

The hydantoin from Step C (1 g, 0.0038 mol) was dissolved in DMF (20 ml) and treated with $K_2CO_3$ (2.09 g, 0.0152 mol) and magnesium sulfate (0.689 g, 0.0057 mol) followed by 3,5 difluoro-bromobenzene (0.543 ml, 0.0042 mol). The reaction was stirred overnight. Hydrochloric acid was added and the mixture was extracted with ethyl acetate. The organic layer was concentrated. Purification of the crude material by flash chromatography (4:1 ethyl acetate:hexanes) give the alkylated hydantoin (1.12 g, 76%).

$C_{21}H_{22}F_2N_2O_3$ (MW=388.16); mass spectroscopy (MH+)= 389.2

Step E

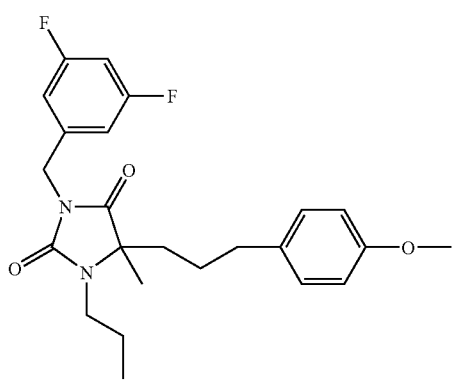

Sodium hydride (0.121 g, 0.0030 mol) was suspended in DMF (5 ml) and cooled to 0° C. The hydantoin from Step D (1.07 g, 0.00276 mol) was added as a solution in DMF (5 ml). Iodopropane (0.295 ml, 0.0030 mol) was syringed into solution and the reaction was stirred overnight at room temperature. The reaction mixture was poured into 1N HCl and extracted with ethyl acetate. Purification of the crude material by flash chromatography (4:1 hexanes:ethyl acetate) gave the desired product as a clear oil (0.951 g, 80%). $C_{24}H_{28}F_2N_2O_3$ (MW=430.21); mass spectroscopy (MH+)=431.2

Step F

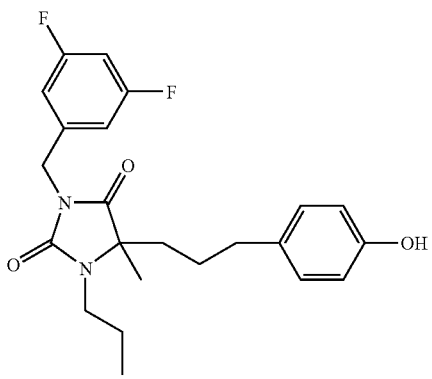

The methoxy ether from Step E (0.951 g, 0.0022 mol) was dissolved in methylene chloride (5 ml) and cooled to 0° C. To this solution was added, dropwise, a solution of $BBr_3$ (0.418 ml, 0.0044 mol) in methylene chloride (5 ml). After stirring for about twenty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (0.910 g, 99%) was obtained and was carried forth without further purification. $C_{23}H_{26}F_2N_2O_3$ (MW=416.19); mass spectroscopy (MH+)=417.2

Step G

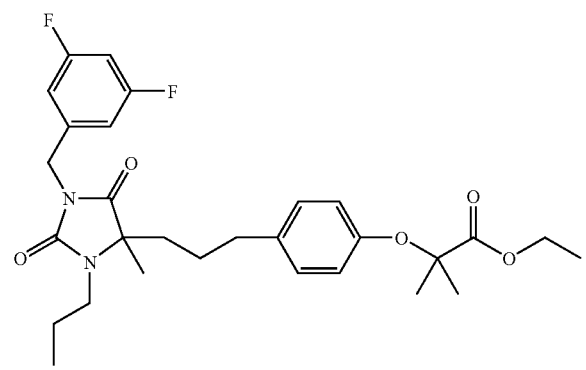

The phenol from Step F (0.910 g, 0.00220 mol) was dissolved in EtOH and treated with ethyl 2-bromoisobutyrate (0.963 ml, 0.0066 mol), powdered $K_2CO_3$ (1.210 g, 0.0088 mol), and $MgSO_4$ (0.264 g, 0.0022 mol). The reaction was stirred overnight at 77.7° C. Upon cooling, the reaction mixture was poured into 5N HCl and combined with EtOAc. The organic layer was extracted with water followed by brine then concentrated to dryness. Purification by flashed chromatography (5:1 hexanes:ethyl acetate) gave the ester (0.850 g, 69%). $C_{29}H_{36}F_2N_2O_5$ (MW=530.26); mass spectroscopy (MH+)=531.3

Step H

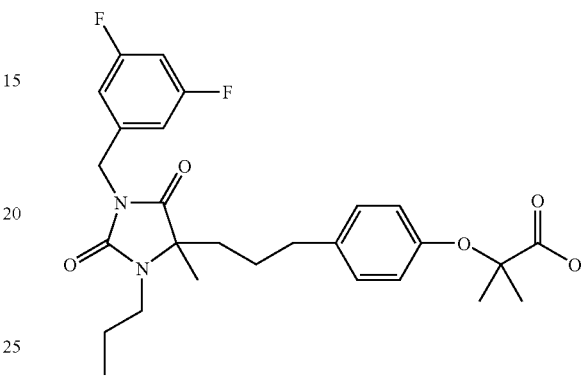

The ester from Step G (0.500 g, 0.00094 mol) was dissolved in methanol (8 ml) and treated with a solution of LiOH in water (2 ml). The reaction was stirred overnight. The reaction was cooled and water was added to the solution. The solution was then acidified using 1N HCl to pH=3 then extracted with ethyl acetate. The organic layer was concentrated to afford the desired carboxylic acid (0.112 g, 47%). Purification of the crude material using reverse phase chromatography (7:3 acetonitrile: water) afforded the desired acid (0.033 mg, 7%) $C_{27}H_{32}F_2N_2O_5$ (MW=502.23); mass spectroscopy (MH+)=503.3

Example 133

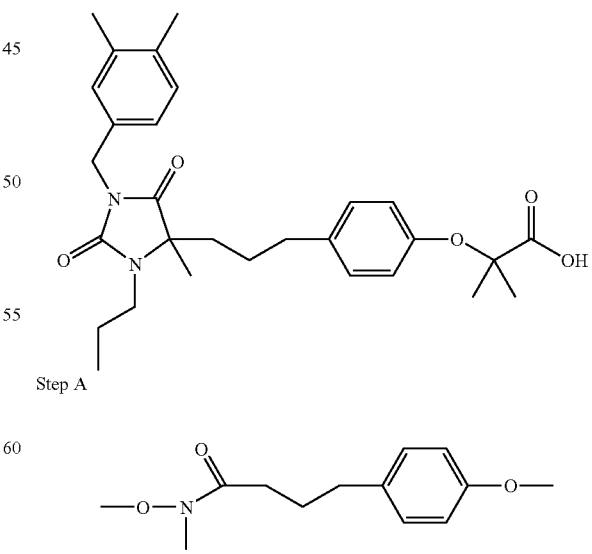

Step A

The 4-(4-methoxyphenyl) butyric acid (10.04 g, 0.052 mol) and hydroxylamine (5.04 g, 0.052 mol) were combined in THF and treated with EDAC (11.86 g, 0.062 mol), HOBt (7.0 g, 0.052 mol) and diisopropyl ethyl amine (16.9 ml, 0.124 mol). The reaction was stirred overnight. The reaction was concentrated to one-half its original volume. Ethyl acetate (100 ml) was added and the solution was extracted with 1N HCl. The organic layer was washed with 2N NaOH then concentrated. Purification of the crude material by flash chromatography (2:1 hexanes:ethyl acetate) gave the Weinreb amide (9.77 g, 78%). $C_{13}H_{19}NO_3$ (MW=237.14); mass spectroscopy (MH+)=238.0

Step B

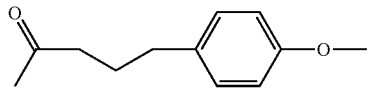

The Weinreb amide from Step A (4.7 g, 0.0198 mol) was dissolved in ether (164 ml) and cooled to 0° C. Methyl magnesium bromide (3.0 M in ether, 33 ml, 99 mmol) was added slowly to the reaction mixture. The reaction was stirred overnight. Hydrochloric acid (1N, 50 ml) was and the mixture was extracted with ether. The organic layer was stripped to afford the methyl ketone as a clear oil (3.66 g, 96%).

$C_{12}H_{16}O_2$ (MW=192.12); mass spectroscopy (MH+)=192.1

Step C

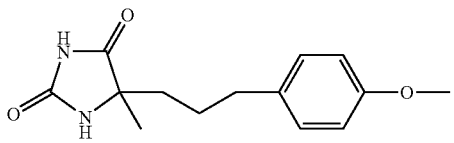

The methyl ketone from Step B (3.66 g, 0.0190 mol) was combined with potassium cyanide (2.73 g, 0.042 mol) and ammonium carbonate (9.13 g, 0.095 mol) in 1:1 methanol:water (35:35 ml) and stirred overnight at 50° C. The reaction mixture was poured into water and extracted with ethyl acetate. The organic layer was washed with brine then concentrated. Purification of the crude material by flash chromatograhy (2:1 hexanes:ethyl acetate) yielded the desired hydantoin as a thick, clear oil. $C_{14}H_{18}N_2O_3$ (MW=262.13); mass spectroscopy (MH+)=263.1

Step D

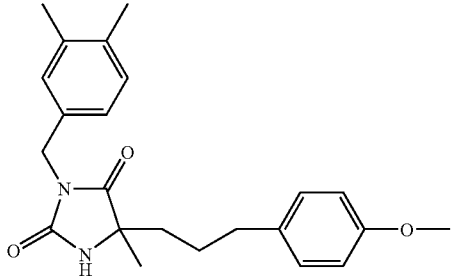

The hydantoin from Step C (1 g, 0.0038 mol) was dissolved in DMF (20 ml) and treated with $K_2CO_3$ (2.09 g, 0.0152 mol) and magnesium sulfate (0.689 g, 0.0057 mol) followed by 3,4 dimethyl-chlorobenzene (0.607 ml, 0.0042 mol). The reaction was stirred overnight. Hydrochloric acid was added and the mixture was extracted with ethyl acetate. The organic layer was concentrated. Purification of the crude material by flash chromatography (2:1 ethyl acetate:hexanes) gave the alkylated hydantoin (1.30 g, 91%). $C_{23}H_{28}N_2O_3$ (MW=380.21); mass spectroscopy (MH+)=381.2

Step E

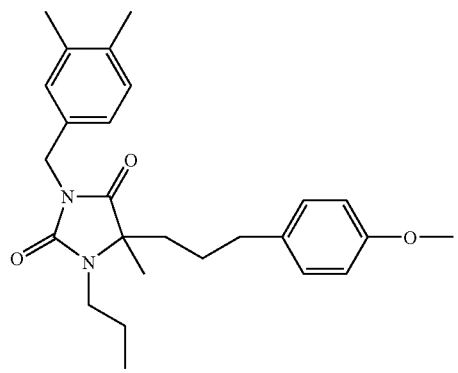

Sodium hydride (0.150 g, 0.0038 mol) was suspended in DMF (5 ml) and cooled to 0° C. The hydantoin from Step D (1.30 g, 0.00340 mol) was added as a solution in DMF (5 ml). Iodopropane (0.367 ml, 0.0038 mol) was syringed into solution and the reaction was stirred overnight at room temperature. The reaction mixture was poured into 1N HCl and extracted with ethyl acetate. Purification of the crude material by flash chromatography (2:1 hexanes:ethyl acetate) gave the desired product as a clear oil (1.27 g, 89%). $C_{26}H_{34}N_2O_3$ (MW=422.26); mass spectroscopy (MH+)=423.2

Step F

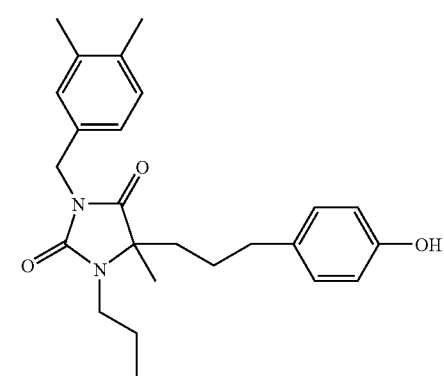

The methoxy ether from Step E (1.27 g, 0.0030 mol) was dissolved in methylene chloride (10 ml) and cooled to 0° C. To this solution was added, dropwise, a solution of $BBr_3$ (0.569 ml, 0.0060 mol) in methylene chloride (5 ml). After stirring for about twenty minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the phenol (1.19 g, 98%) was obtained and was carried forth without further purification. $C_{25}H_{32}N_2O$ (MW=408.24); mass spectroscopy (MH+)=409.2

Step G

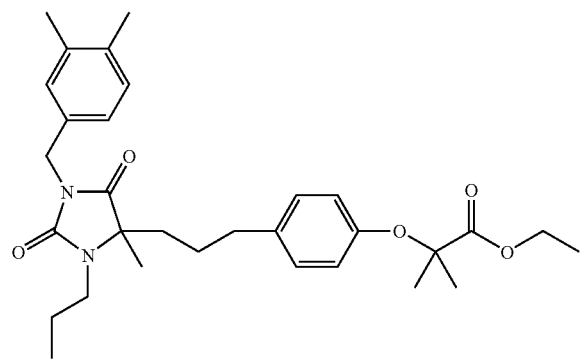

The phenol from Step F (1.19 g, 0.00290 mol) was dissolved in EtOH and treated with ethyl 2-bromoisobutyrate (1.28 ml, 0.0087 mol), powdered $K_2CO_3$ (1.610 g, 0.0117 mol), and $MgSO_4$ (0.348 g, 0.0029 mol). The reaction was stirred overnight at 77.7° C. Upon cooling, the reaction mixture was poured into 5N HCl and combined with EtOAc. The organic layer was extracted with water followed by brine then concentrated to dryness. Purification by flashed chromatography (5:1 hexanes:ethyl acetate) gave the ester (1.26 g, 83%).

$C_{31}H_{42}N_2O_3$ (MW=522.31); mass spectroscopy (MH+)=

Step H

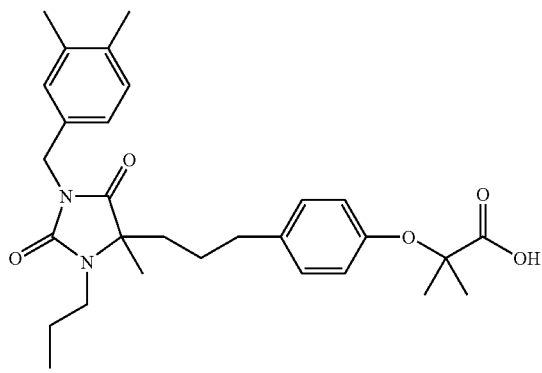

The ester from Step G (0.500 g, 0.00095 mol) was dissolved in methanol (8 ml) and treated with a solution of LiOH in water (2 ml). The reaction was stirred overnight. The reaction was cooled and water was added to the solution. The solution was then acidified using 1N HCl to pH=3 then extracted with ethyl acetate. The organic layer was concentrated to afford the desired carboxylic acid (0.239 g, 51%). Purification of the crude material using reverse phase chromatography (7:3 acetonitrile:water) afforded the desired acid (0.033 mg, 7%). $C_{29}H_{38}N_2O_5$ (MW=494.28); mass spectroscopy (MH+)=495.3

Example 134

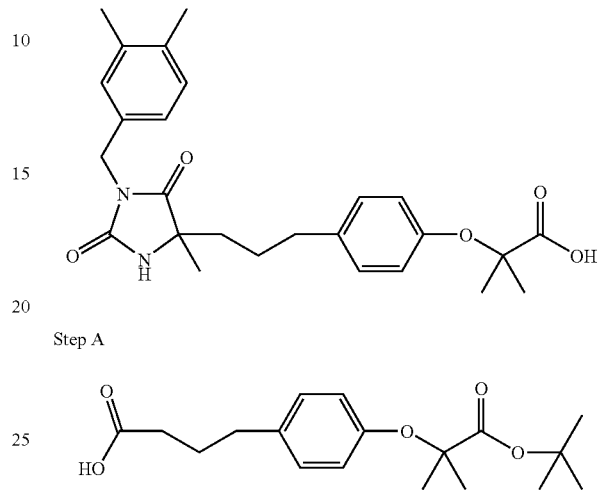

Step A

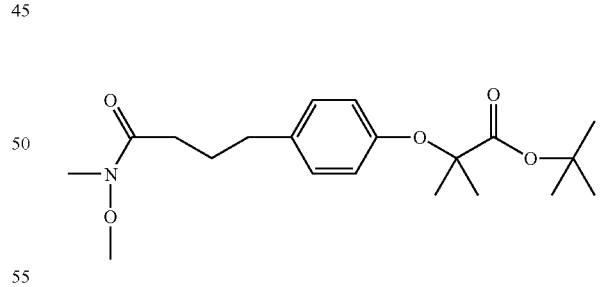

The diester from Example 14, Step B (10 g, 0.032 mol) was dissolved in dioxane. A solution of LiOH in water was added, dropwise, over a period of ten minutes. The reaction was allowed to stir for two hours. The solvent was concentrated and the resulting residue was redisssolved in water then washed with ether. The aqueous solution was acidified with 5N HCl and extracted with ethyl acetate (2×). The combined organic layers were washed with brine, dried over Na2SO4, filtered, and concentrated to afford the desired acid as an yellow oil (9.61 g, 93%). $C_{18}H_{26}O_5$ (MW=322.18); mass spectroscopy (MH+)=321.0

Step B

The acid from Step A (9.60 g, 0.0298 mol) was combined with N-methyl, O-methyl hydroxylamine, EDAC (6.83 g, 0.0358 mol), HOBt (4.02 g, 0.0298 mol), and DIEA (10 ml, 0.075 mol) in THF (80 ml). The reaction was allowed to stir overnight at room temperature. The solvent was concentrated and the resulting material was redissolved in ethyl acetate and extracted with 1N HCl followed by brine. The organic layer was concentrated. Purification by flash chromatography (4:1 hexane:ethyl acetate) gave the Weinreb amide (7.23 g, 66%).

$C_{26}H_{31}NO_5$ (MW=365.22); mass spectroscopy (MH+)=366.22

Step C

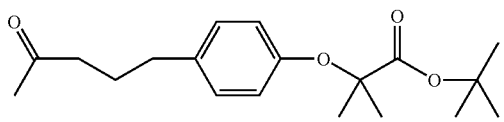

A THF solution (50 ml) of the Weinreb amide from Step B (3.4 g, 0.0093 mol) was cooled to −78° C. and methyl magnesium bromide (3.0 M in ether, 15 ml, 0.046 mol) was added to the solution. After stirring for two hours, 1N HCl was added to quench the reaction. The reaction mixture was extracted with ether. The ethereal layer was concentrated. Purification by flash chromatography (9:1 hexanes:ethyl acetate) yielded the methyl ketone as a colorless oil (1.77 g, 60%). $C_{19}H_{28}O_4$ (MW=320.20); mass spectroscopy (MH+)=321.0

Step D

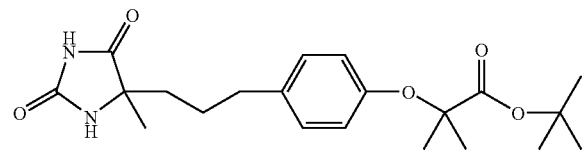

The methyl ketone from Step C (1.77 g, 0.0055 mol) was combined with potassium cyanide (0.792 g, 0.0122 mol) and ammonium carbonate (2.65 g, 0.0277 mol) in 1:1 methanol:water (20:20 ml) and stirred overnight at 50° C. The reaction mixture was poured into water and extracted with ethyl acetate. The organic layer was washed with brine then concentrated to afford the hydantoin as a white solid (2.11 g, 99%) which was carried forth without further purification. $C_{23}H_{30}N_2O_5$ (MW=390.22); mass spectroscopy (MH+)=391.3

Step E

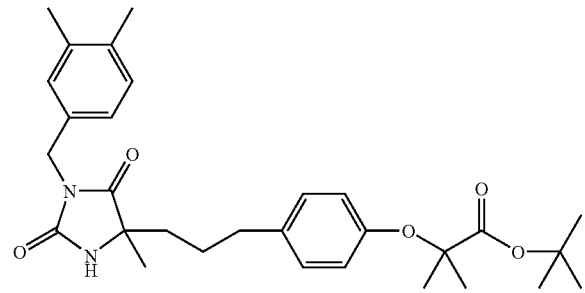

The hydantoin from Step D (0.600 g, 0.0015 mol) was dissolved in DMF (10 ml) and treated with $K_2CO_3$ (0.849 g, 0.0060 mol) and magnesium sulfate (0.271 g, 0.0023 mol) followed by 3,4 dimethyl benzyl chloride (0.245 ml, 0.00169 mol). The reaction was stirred overnight at 45° C. Hydrochloric acid (5N) was added and the mixture was extracted with ethyl acetate (2×). The organic layer was concentrated. Purification of the crude material by flash chromatography (4:1 ethyl acetate:hexanes; 2:1 ethyl acetate:hexanes) give the alkylated hydantoin (0.560 g, 73%). $C_{30}H_{40}N_2O_5$ (MW=508.29); mass spectroscopy (MH+)=509.4

Step F

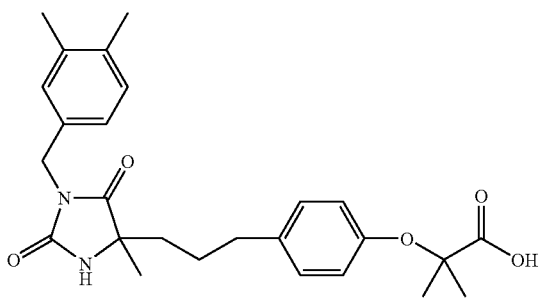

The ester from Step E (0.560 g, 0.0011 mol) was dissolved in dichloromethane (10 ml) and treated with trifluoroacetic acid (0.425 ml). The reaction was stirred overnight. The solution was concentrated and the resulting residue was redissolved in water and extracted with methylene chloride. The organic layer was extracted with 2N NaOH. While allowing the layers to separate, a white precipitate crashed out of solution. The solid was filtered; spectral data indicated that the solid was the desired carboxylic acid (0.170 g, 34%). $C_{26}H_{32}N_2O_5$ (MW=452.23); mass spectroscopy (MH$^+$)=453.3

Example 135

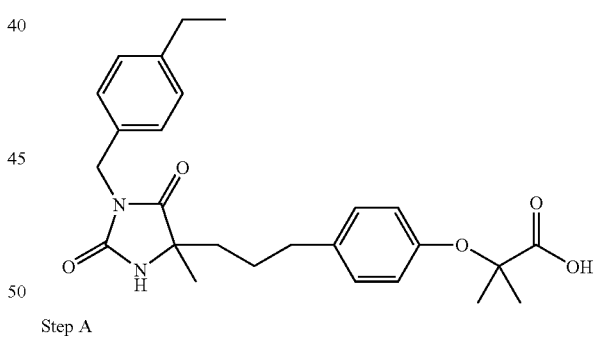

Step A

The diester from Example 14, Step B (10 g, 0.032 mol) was dissolved in dioxane. A solution of LiOH in water was added, dropwise, over a period of ten minutes. The reaction was allowed to stir for two hours. The solvent was concentrated and the resulting residue was redisssolved in water then washed with ether. The aqueous solution was acidified with 5N HCl and extracted with ethyl acetate (2×). The combined organic layers were washed with brine, dried over $Na_2SO_4$, filtered, and concentrated to afford the desired acid as a yellow oil (9.61 g, 93%). $C_{18}H_{26}O_5$ (MW=322.18); mass spectroscopy (MH-)=321.0

Step B

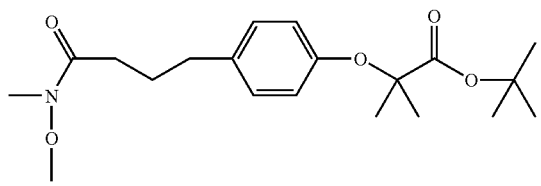

The acid from Step A (9.60 g, 0.0298 mol) was combined with N-methyl, O-methyl hydroxylamine, EDAC (6.83 g, 0.0358 mol), HOBt (4.02 g, 0.0298 mol), and DIEA (10 ml, 0.075 mol) in THF (80 ml). The reaction was allowed to stir overnight at room temperature. The solvent was concentrated and the resulting material was redissolved in ethyl acetate and extracted with 1N HCl followed by brine. The organic layer was concentrated. Purification by flash chromatography (4:1 hexane:ethyl acetate) gave the Weinreb amide (7.23 g, 66%). $C_{20}H_{31}NO_5$ (MW=365.22); mass spectroscopy (MH+)=366.22

Step C

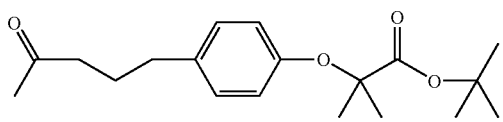

A THF solution (50 ml) of the Weinreb amide from Step B (3.4 g, 0.0093 mol) was cooled to −78° C. and methyl magnesium bromide (3.0 M in ether, 15 ml, 0.046 mol) was added to the solution. After stirring for two hours, 1N HCl was added to quench the reaction. The reaction mixture was extracted with ether. The ethereal layer was concentrated. Purification by flash chromatography (9:1 hexanes:ethyl acetate) yielded the methyl ketone as a colorless oil (1.77 g, 60%). $C_{19}H_{28}O_4$ (MW=320.20); mass spectroscopy (MH+)=321.0

Step D

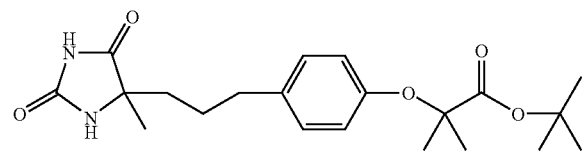

The methyl ketone from Step C (1.77 g, 0.0055 mol) was combined with potassium cyanide (0.792 g, 0.0122 mol) and ammonium carbonate (2.65 g, 0.0277 mol) in 1:1 methanol:water (20:20 ml) and stirred overnight at 50° C. The reaction mixture was poured into water and extracted with ethyl acetate. The organic layer was washed with brine then concentrated to afford the hydantoin as a white solid (2.11 g, 99%) which was carried forth without further purification. $C_{21}H_{30}N_2O_5$ (MW=390.22); mass spectroscopy (MH+)=391.3

Step E

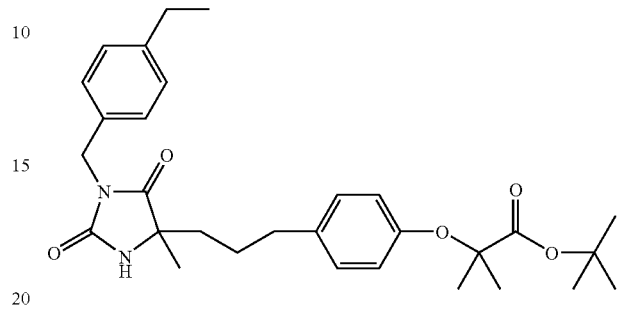

The hydantoin from Step D (0.600 g, 0.0015 mol) was dissolved in DMF (10 ml) and treated with $K_2CO_3$ (0.849 g, 0.0060 mol) and magnesium sulfate (0.271 g, 0.0023 mol) followed by 4-ethyl benzyl chloride (0.252 ml, 0.00169 mol). The reaction was stirred overnight at room temperature. The reaction mixture was poured into 5N HCl and extracted with ethyl acetate (2×). The organic layer was concentrated. Purification of the crude material by flash chromatography (2:1 ethyl acetate:hexanes) gave the alkylated hydantoin as a colorless oil (0.752 g, 98%).

$C_{30}H_{40}N_2O_5$ (MW=508.29); mass spectroscopy (MH+)=509.3

Step F

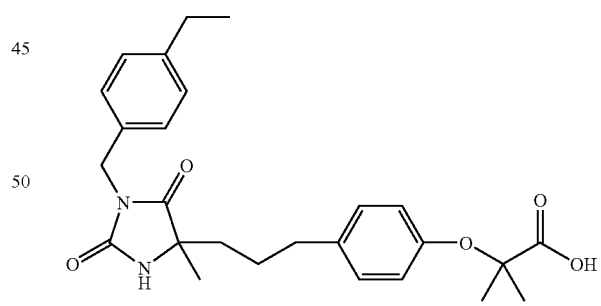

The ester from Step E (0.752 g, 0.00148 mol) was dissolved in dichloromethane (20 ml) and treated with trifluoroacetic acid (0.570 ml, 0.0074 mol). The reaction was stirred overnight. The solution was concentrated. Purification of the crude material by flash chromatography (2:1 hexanes:ethyl acetate) afforded the desired product as a white solid (0.358 g, 54%). $C_{26}H_{32}N_2O_5$ (MW=452.23); mass spectroscopy (MH+)=453.3

Example 136

Step A

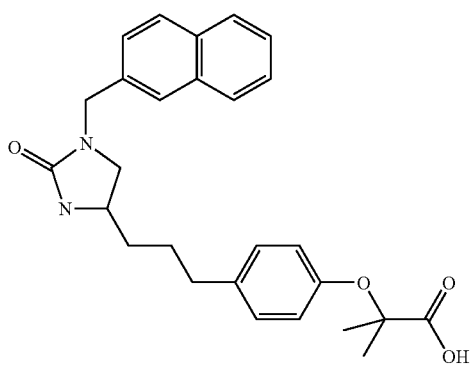

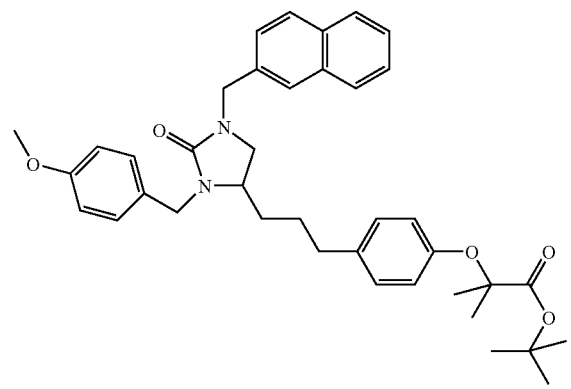

A THF (15 mL) solution of the hydantoin from Example 22, Step A (855.1 mg, 1.34 mmol) under an atmosphere of nitrogen was treated with BH$_3$-THF (1.0 M in THF, 13.5 mL, 13.5 mmol). The reaction mixture was stirred at room temperature for 3 hours then cooled to 0° C. and carefully treated with saturated aqueous sodium bicarbonate (25 mL). After 2 hr additional bicarbonate (20 mL) was added along with H$_2$O (100 mL). The resulting solution was extracted with ethyl acetate (2×100 mL). The combined organic extracts were dried over Na$_2$SO$_4$ and concentrated. Purification by chromatography (2:1 hexanes:ethyl acetate) gave the desired product as a colorless oil (595.4 mg, 71%).

C$_{39}$H$_{46}$N$_2$O$_5$ (MW=622.81); mass spectroscopy: (MH$^+$)=623.3

Step B

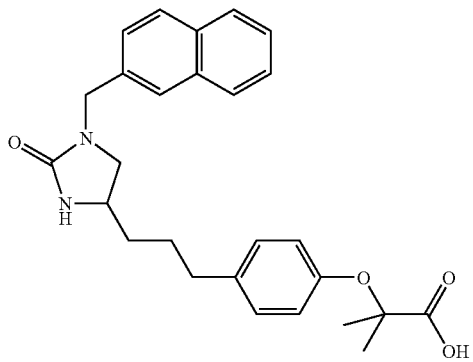

A TFA solution (10 mL) of the product from Step A (595.4 mg, 0.956 mmol) was treated with triethylsilane (618 mL, 3.8 mmol) and stirred at room temperature for 1.5 hour. The reaction mixture was concentrated and the residue diluted with 0.5 N NaOH (50 mL). The aqueous solution was washed with diethyl ether (50 mL), acidified with 5 N HCl, then extracted with ethyl acetate (2×50 mL). The combined organic extracts were dried over Na$_2$SO$_4$ and concentrated to afford the desired carboxylic acid as a foam-like solid (417.8 mg, 98%).

C$_{27}$H$_{30}$N$_2$O$_4$ (MW=446.55); mass spectroscopy: (MH$^+$)=447.2, (MH$^-$)=445.4

Example 137

Step A

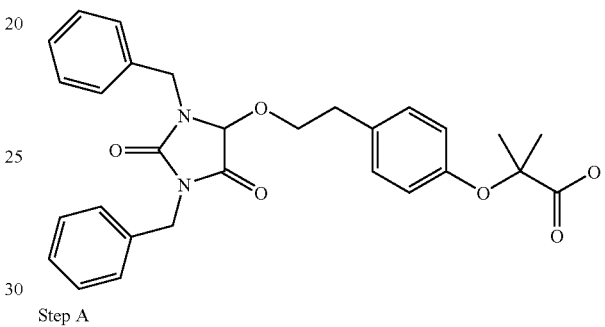

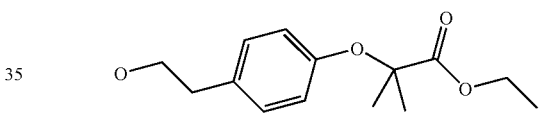

4-Hydroxyphenethyl alcohol (15.0 g, 109 mmol) and ethyl 2-bromoisobutyrate (24 ml, 163.5 mmol) were stirred together in DMF (250 ml). Potassium carbonate (44.9 g, 325 mmol) and magnesium sulfate (13.1 g, 109 mmol) added and the mixture was stirred at 75° C. overnight. The reaction mixture was cooled, filtered over Celite, washing the filter cake with ethyl acetate. The combined filtrates were diluted with ethyl acetate, washed with water and 2N hydrochloric acid, dried over sodium sulfate, filtered and concentrated. The obtained residue was dissolved in ether and washed with 2N sodium hydroxide and aqueous brine, dried over sodium sulfate. Evaporation of the solvent and subsequent purification by flash chromatography (hexanes:ethyl acetate) gave the desired product (11.8 g).

C$_{14}$H$_{20}$O$_4$ (MW=252.3); MS (M+, 253.1)

Step B

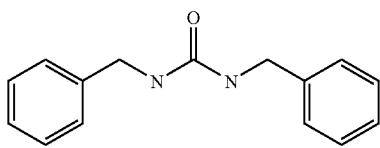

Carbonyldiimidazole (10.0 g, 61.7 nmol) was stirred in methylene chloride (100 ml) and benzylamine (13.5 ml, 23.4 mmol, in $CH_2Cl_2$, 20 ml) was added dropwise. An ice bath was placed under the flask during the addition. After complete addition the mixture was allowed to stir overnight at ambient temperature. The resulting solid was washed with ether and filtered to yield the desired product as a white solid (13.9 g).

$C_{15}H_{16}N_2O$ (MW=240.3); MS (M+, 241.0)

Step C

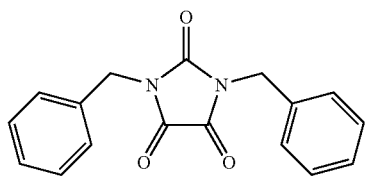

The product from Example 137, Step B (10.0 g, 41.7 mmol) was stirred in dioxane and oxalyl chloride (3.6 ml, 41.7 mmol) was added via syringe. The mixture was heated to 75° C. overnight. Evaporation of the solvent and washing the obtained solid with ether gave the desired product as a white solid (12.1 g).

$C_{17}H_{14}N_2O_3$ (MW=294.3); $^1$NMR

Step D

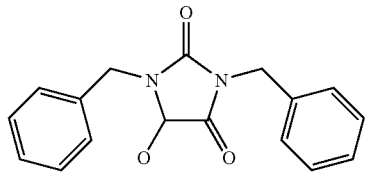

The product from Example 137, Step C (2.0 g, 6.8 mmol) was stirred in THF (50 ml) and methanol (30 ml). Sodium borohydride was added and stirred for 5 minutes. Water (1 ml) and concentrated hydrochloric acid (1 ml) were added then allowed to stand over sodium sulfate overnight. Evaporation of the solvent gave a residue that was dissolved in water and ethyl acetate. Layers were separated and the organic layer was washed with aqueous brine and dried over sodium sulfate. Evaporation of the solvent gave the desired product (2.0 g).

$C_{17}H_{16}N_2O_3$ (MW=296.3); $^1$NMR

Step E

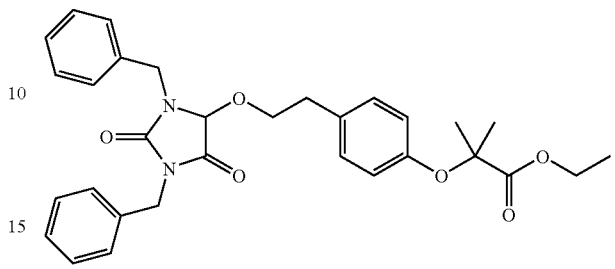

The products from Example 137, Step A (1.7 g, 6.8 mmol) and Step D (1.0 g, 3.4 mmol) were stirred together in acetonitrile (10 ml) with p-toluenesulfonic acid (0.1 g, 0.5 mmol) and heated to 80° C. for 6 hours. The resulting mixture was concentrated and methylene chloride added. This was washed with water and aqueous brine then dried over sodium sulfate. Evaporation of the solvent and subsequent purification by flash chromatography (hexanes/ethyl acetate) gave the desired product (0.8 g).

$C_{31}H_{34}N_2O_6$ (MW 530.6); $^1$NMR

Step F

The product from Example 137, Step E (0.25 g, 0.47 mmol) was dissolved in methanol (2 ml), added to lithium hydroxide (0.02 g, 1.0 mmol, in water, 5 ml) and heated to 50° C. for 1 hour, then stirred over two days at ambient temperature. Hydrolysis completed by heating to reflux for 1 hour. The reaction was added to water and extracted with ether. The aqueous layer was acidified with concentrated hydrochloric acid and extracted twice with ethyl acetate. The organic layers were combined, washed with aqueous brine and dried over sodium sulfate. Evaporation of the solvent gave the desired product (0.19 g).

$C_{29}H_{30}N_2O_6$ (MW=502.6); MS (M−, 501.1)

Example 138

1-Isocyanatomethyl-4-methyl-benzene

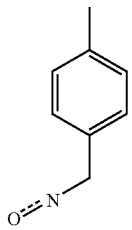

A mixture of p-methyl benzylamine (25 g, 0.21 mol) in CH$_2$Cl$_2$ (200 mL) and aqueous saturated solution of sodium bicarbonate (200 mL) was cooled to 0° C. and then treated dropwise with a 20% solution of phosgene in toluene (100 mL). The reaction was stirred at room temperature for 20 minutes and then the organic layer removed and the aqueous layer back-extracted with CH$_2$Cl$_2$. The organic layer was dried (Na$_2$SO$_4$) and the solvent removed in vacuo to give 20.6 g 1-isocyanatomethyl-4-methyl-benzene that was utilized directly in the next reaction without purification.

Step B 1-(4-Methyl-benzyl)-3-(2-oxo-tetrahydro-furan-3-yl)-urea

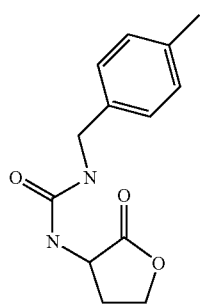

A 0° C. slurry of α-amino-γ-butyrolactone hydrobromide (25 g, 0.137 mol) in THF (200 mL) was combined with 1-isocyanatomethyl-4-methyl-benzene (20.6 g, 0.139 mol) and then treated dropwise with N,N-diisopropylethylamine (19.5 g, 0.151 mol). The reaction mixture was stirred for at room temperature for 2 h. The solvent was removed in vacuo to give 48.5 g crude 1-(4-methyl-benzyl)-3-(2-oxo-tetrahydro-furan-3-yl)-urea that was utilized directly in the next reaction without purification. MS (ES$^{30}$) Calc'd for C$_{13}$H$_{17}$N$_2$O$_3$ (M+1) 249. Found m/z 249 (100%). $^1$H NMR.

Step C 5-(2-Hydroxy-ethyl)-3-(4-methyl-benzyl)-imidazolidine-2,4-dione

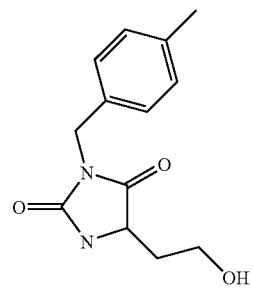

A solution of crude 1-(4-methyl-benzyl)-3-(2-oxo-tetrahydro-furan-3-yl)-urea (48.5 g, assume 0.137 mol) in MeOH (1.5 L) was treated with sodium methoxide (21.1 g, 0.391 mol) and heated to reflux under N$_2$ for 2 h until done by thin layer chromatography (9:1 CH$_2$Cl$_2$:MeOH). The reaction was cooled and the solvent removed in vacuo to give a residue that was combined with aqueous 1 N HCl (640 mL) and extracted with EtOAc. The organic layer was dried (MgSO$_4$) and the solvent removed in vacuo to afford 24.72 g (73%) of crude 5-(2-hydroxy-ethyl)-3-(4-methyl-benzyl)-imidazolidine-2,4-dione as a yellow solid which was carried on in the next step without purification. MS (ES$^+$) Calc'd for C$_{13}$H$_{17}$N$_2$O$_3$ (M+1) 249. Found m/z 249 (100%). $^1$H NMR.

Step D

5-[2-(tert-Butyl-diphenyl-silanyloxy)-ethyl]-3-(4-methyl-benzyl)-imidazolidine-2,4-dione

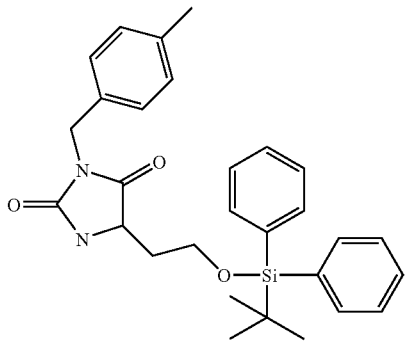

A solution of crude 5-(2-hydroxy-ethyl)-3-(4-methyl-benzyl)-imidazolidine-2,4-dione (24.68 g, 99.4 mmol) and imidazole (10.15 g, 0.149 mol) in DMF (250 mL) was treated dropwise with tert-butyldiphenylsilyl chloride (27.37 g, 99.6 mmol) and then stirred at room temperature under N$_2$ for 7 h. The reaction was worked up extractively with aqueous 1 N HCl (300 mL), diethyl ether and brine and the organic layer was dried (MgSO$_4$) and the solvent removed in vacuo to give crude product which was purified by flash chromatography using a gradient of 5:1 to 2:1 hexanes:EtOAc to afford 23.82 g (49%) of 5-[2-(tert-butyl-diphenyl-silanyloxy)-ethyl]-3-(4- methyl-benzyl)-imidazolidine-2,4-dione. MS (ES$^+$) Calc'd for $C_{29}H_{35}N_2O_3Si$ (M+1) 487. Found m/z 487 (100%). $^1$H NMR.

Step E

5-[2-(tert-Butyl-diphenyl-silanyloxy)-ethyl]-3-(4-methyl-benzyl)-1-propyl-imidazolidine-2,4-dione

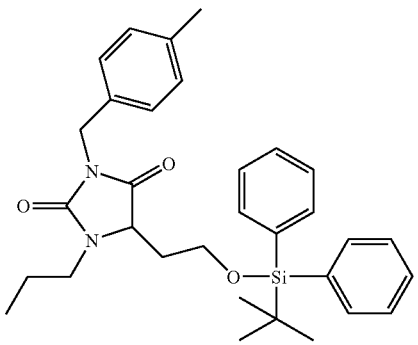

A 0° C. solution of 5-[2-(tert-butyl-diphenyl-silanyloxy)-ethyl]-3-(4-methyl-benzyl)-imidazolidine-2,4-dione (14.26 g, 29.3 mmol) in DMF (250 mL) was treated with sodium hydride (60% dispersion, 1.29 g, 32.2 mmol) and warmed to room temperature and stirred under N$_2$ for 30 minutes. The resultant mixture was cooled to 0° C. and then treated with 1-propyl iodide (5.47 g, 32.2 mmol) and then warmed to room temperature and stirred for 3 h. The reaction was quenched with aqueous 1 N HCl (60 mL) and then worked up extractively with diethyl ether and water. The organic layer was dried (MgSO$_4$) and the solvent removed in vacuo to give crude product that was purified by flash chromatography using 6:1 hexanes:acetone to afford 14.8 g (96%) 5-[2-(tert-butyl-diphenyl-silanyloxy)-ethyl]-3-(4-methyl-benzyl)-1-propyl-imidazolidine-2,4-dione. MS (ES$^+$) Calc'd for $C_{32}H_{40}N_2O_3Si$ (M+1) 529. Found m/z 529 (100%). $^1$H NMR.

Step F 4-(2-Hydroxy-ethyl)-1-(4-methyl-benzyl)-3-propyl-1,3-dihydro-imidazol-2-one

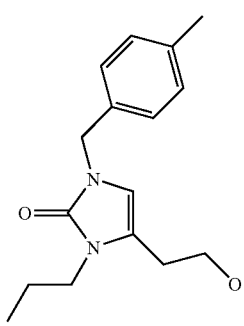

A solution of 5-[2-(tert-butyl-diphenyl-silanyloxy)-ethyl]-3-(4-methyl-benzyl)-1-propyl-imidazolidine-2,4-dione (14.71 g, 27.8 mmol) in EtOH (500 mL) was treated with sodium borohydride (15.78 g, 0.417 mol) in three portions over 6 h and stirred at room temperature under N$_2$ for an additional 16 h. The thick reaction mixture was cooled in an ice bath and slowly quenched with aqueous 1 N HCl (~1 L) over a 1 h period. The reaction mixture was then worked up extractively with EtOAc, water and brine and the organic layer dried (MgSO$_4$) and the solvent removed in vacuo to give 16.79 g crude 4-[2-(tert-butyl-diphenyl-silanyloxy)-ethyl]-1-(4-methyl-benzyl)-3-propyl-1,3-dihydro-imidazol-2-one that was de-silylated immediately.

The 4-[2-(tert-butyl-diphenyl-silanyloxy)-ethyl]-1-(4-methyl-benzyl)-3-propyl-1,3-dihydro-imidazol-2-one (16.79 g, assumed 27.8 mmol) was dissolved in THF (160 mL) and then treated with a 1 M solution of tetrabutylammonium fluoride in THF (55.6 mL, 55.5 mmol) and the reaction stirred at room temperature under N$_2$ for 20 minutes. The reaction was worked up extractively with EtOAc and water and the organic layer dried (MgSO$_4$) and the solvent removed in vacuo to give crude product that was purified by flash chromatography using 3% of MeOH in CH$_2$Cl$_2$ to afford 4.65 g (61%) 4-(2-hydroxy-ethyl)-1-(4-methyl-benzyl)-3-propyl-1,3-dihydro-imidazol-2-one. MS (ES$^+$) Calc'd for $C_{16}H_{23}N_2O_2$ (M+1) 275. Found m/z 275 (100%). $^1$H NMR.

Step G

Toluene-4-sulfonic acid 2-[1-(4-methyl-benzyl)-2-oxo-3-propyl-2,3-dihydro-1H-imidazol-4-yl]-ethyl ester

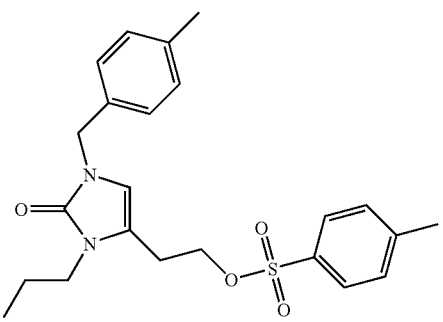

A solution of 4-(2-hydroxy-ethyl)-1-(4-methyl-benzyl)-3-propyl-1,3-dihydro-imidazol-2-one (0.126 g, 0.459 mmol), pyridine (0.146 g, 1.85 mmol) and 4-dimethyl amino pyridine (0.017 g, 0.139 mmol) in CH$_2$Cl$_2$ (10 mL) was treated with p-toluenesulfonic anhydride (0.240 g, 0.735 mmol) and the reaction stirred at room temperature for under N$_2$ for 1.5 h. The reaction mixture was washed with aqueous 1 N HCl (4 mL), the organic layer was dried (MgSO$_4$), and the solvent removed in vacuo to afford crude product that was purified by flash chromatography using 100% CH$_2$Cl$_2$ then 2.5% MeOH in CH$_2$Cl$_2$ to afford 0.194 g (98%) toluene-4-sulfonic acid 2-[1-(4-methyl-benzyl)-2-oxo-3-propyl-2,3-dihydro-1H-imidazol-4-yl]-ethyl ester. MS (ES$^+$) Calc'd for $C_{23}H_{29}N_2O_4S$ (M+1) 429. Found m/z 429 (100%). $^1$H NMR.

Step H

2-Methyl-2-(4-{2-[1-(4-methyl-benzyl)-2-oxo-3-propyl-2,3-dihydro-1H-imidazol-4-yl]-ethoxy}-phenoxy)-propionic acid

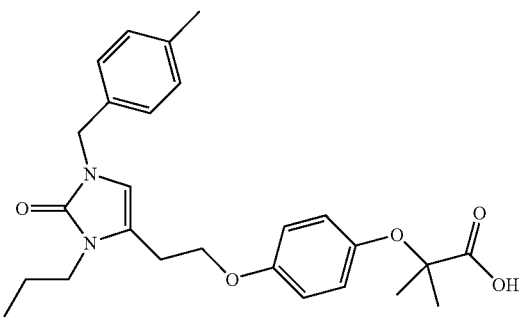

A mixture of toluene-4-sulfonic acid 2-[1-(4-methyl-benzyl)-2-oxo-3-propyl-2,3-dihydro-1H-imidazol-4-yl]-ethyl ester (0.194 g, 1.51 mmol), 2-(4-hydroxy-phenoxy)-2-methyl-propionic acid ethyl ester (0.088 g, 0.392 mmol) and $Cs_2CO_3$ (0.156 g, 0.478 mmol) in DMF (15 mL) was heated at 55° C. for under $N_2$ for 16 h. The reaction mixture was cooled to room temperature, quenched with aqueous 1 N HCl (2 mL), and worked up extractively with EtOAc and water. The organic layer was dried ($MgSO_4$) and the solvent removed in vacuo to afford crude product that was purified by flash chromatography using a gradient of 4:1 to 1:1 hexanes:acetone to afford 0.036 g (19%) 2-methyl-2-(4-{2-[1-(4-methyl-benzyl)-2-oxo-3-propyl-2,3-dihydro-1H-imidazol-4-yl]-ethoxy}-phenoxy)-propionic acid ethyl ester.

The 2-methyl-2-(4-{2-[1-(4-methyl-benzyl)-2-oxo-3-propyl-2,3-dihydro-1H-imidazol-4-yl]-ethoxy}-phenoxy)-propionic acid ethyl ester (0.036 g, 0.075 mmol) was combined with aqueous 5 N NaOH (0.15 mL) in EtOH (5 mL) and heated to reflux under $N_2$ for 1 h. The reaction was cooled and the solvent removed in vacuo to give a residue that was acidified with aqueous 1 N HCl (1 mL). The mixture was extracted with $Et_2O$ and water, the organic layer dried ($MgSO_4$), and the solvent removed in vacuo to afford 0.024 g (71%) 2-methyl-2-(4-{2-[1-(4-methyl-benzyl)-2-oxo-3-propyl-2,3-dihydro-1H-imidazol-4-yl]-ethoxy}-phenoxy)-propionic acid. HRMS (ES$^+$) m/z exact mass calcd for $C_{26}H_{33}N_2O_5$ [M+0.1] 453.2389, found 453.2387. $^1$H NMR.

Example 139

2-Methoxy-2-methyl-3-(4-{2-[1-(4-methyl-benzyl)-2-oxo-3-propyl-2,3-dihydro-1H-imidazol-4-yl]-ethoxy}-phenyl)-propionic acid

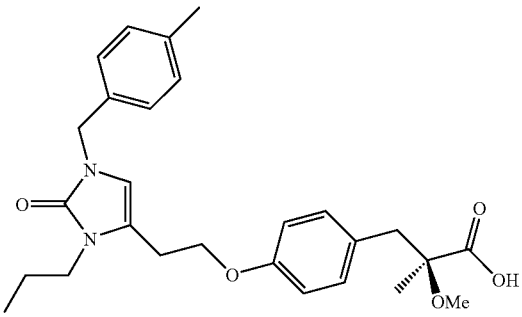

A mixture of toluene-4-sulfonic acid 2-[1-(4-methyl-benzyl)-2-oxo-3-propyl-2,3-dihydro-1H-imidazol-4-yl]-ethyl ester (0.079 g, 0.184 mmol), 3-(4-hydroxy-phenyl)-2-methoxy-2-methyl-propionic acid ethyl ester (0.038 g, 0.169 mmol) and $K_2CO_3$ (0.047 g, 0.340 mmol) in EtOH (8 mL) was heated at 75° C. under $N_2$ for 16 h. The reaction mixture was cooled to room temperature and quenched with aqueous 1 N HCl (1 mL). The solvent was removed in vacuo to give a residue that was diluted with water and extracted with EtOAc. The organic layer was dried ($MgSO_4$) and the solvent removed in vacuo to afford crude product that was purified by flash chromatography using a 2:1 hexanes:acetone to afford 0.036 g (44%) 2-methoxy-2-methyl-3-(4-{2-[1-(4-methyl-benzyl)-2-oxo-3-propyl-2,3-dihydro-1H-imidazol-4-yl]-ethoxy}-phenyl)-propionic acid ethyl ester.

The 2-methoxy-2-methyl-3-(4-{2-[1-(4-methyl-benzyl)-2-oxo-3-propyl-2,3-dihydro-1H-imidazol-4-yl]-ethoxy}-phenyl)-propionic acid ethyl ester (0.015 g, 0.031 mmol) was combined with aqueous 5 N NaOH (0.1 mL) in EtOH (3 mL) and heated to reflux under $N_2$ for 1 h. The reaction was cooled and the solvent removed in vacuo to give a residue that was acidified with aqueous 1 N HCl (3 mL). The mixture was extracted with $Et_2O$ and water, the organic layer dried ($MgSO_4$), and the solvent removed in vacuo to afford 0.015 g (100%) 2-methoxy-2-methyl-3-(4-{2-[1-(4-methyl-benzyl)-2-oxo-3-propyl-2,3-dihydro-1H-imidazol-4-yl]-ethoxy}-phenyl)-propionic acid. MS (ES$^+$) m/z calcd for $C_{26}H_{32}N_2O_5$ [M+1] 453, found 453. $^1$H NMR.

Example 140

2-Methyl-3-(4-{2-[1-(4-methyl-benzyl)-2-oxo-3-propyl-2,3-dihydro-1H-imidazol-4-yl]-ethoxy}-phenyl)-2-phenoxy-propionic acid

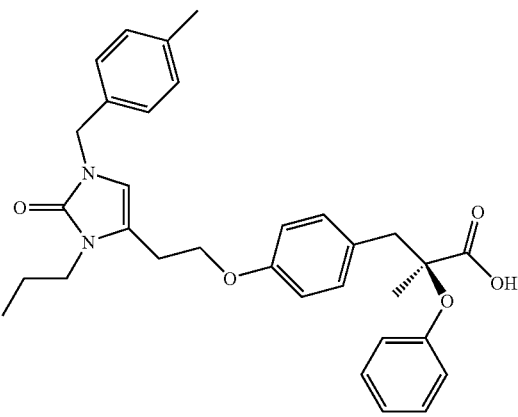

A mixture of toluene-4-sulfonic acid 2-[1-(4-methyl-benzyl)-2-oxo-3-propyl-2,3-dihydro-1H-imidazol-4-yl]-ethyl ester (0.029 g, 0.0677 mmol), 3-(4-Hydroxy-phenyl)-2-methyl-2-phenoxy-propionic acid ethyl ester (0.018 g, 0.0599 mmol) and $Cs_2CO_3$ (0.024 g, 0.0736 mmol) in DMF (3 mL) was heated at 55° C. under $N_2$ for 16 h. The reaction mixture was cooled to room temperature and quenched with aqueous 1 N HCl (0.3 mL) and then was diluted with water and extracted with $Et_2O$. The organic layer was dried ($MgSO_4$) and the solvent removed in vacuo to afford crude product that was purified by flash chromatography using a gradient of 4:1 to hexanes:EtOAc to 2:1 EtOAc:hexanes to afford 0.011 g (32%) 2-methyl-3-(4-{2-[1-(4-methyl-benzyl)-2-oxo-3-propyl-2,3-dihydro-1H-imidazol-4-yl]-ethoxy}-phenyl)-2-phenoxy-propionic acid ethyl ester.

The 2-methyl-3-(4-{2-[1-(4-methyl-benzyl)-2-oxo-3-propyl-2,3-dihydro-1H-imidazol-4-yl]-ethoxy}-phenyl)-2-phenoxy-propionic acid ethyl ester (0.011 g, 0.020 mmol) was combined with aqueous 5 N NaOH (0.2 mL) in EtOH (3 mL) and heated to reflux under $N_2$ for 1 h. The reaction was cooled and the solvent removed in vacuo to give a residue that was acidified with aqueous 1 N HCl (2 mL). The mixture was extracted with $Et_2O$ and water, the organic layer dried ($MgSO_4$), and the solvent removed in vacuo to afford 0.007 g (67%) 2-methyl-3-(4-{2-[1-(4-methyl-benzyl)-2-oxo-3-propyl-2,3-dihydro-1H-imidazol-4-yl]-ethoxy}-phenyl)-2-phenoxy-propionic acid. HRMS ($ES^+$) m/z exact mass calcd for $C_{32}H_{37}N_2O_5$ [M+1] 529.2702, found 529.2715. $^1$H NMR.

Example 141

Step A 1-(3,4-Dimethyl-benzyl)-4-[3-(4-methoxy-phenyl)-propyl]-5-methyl-3-propyl-1,3-dihydro-imidazol-2-one

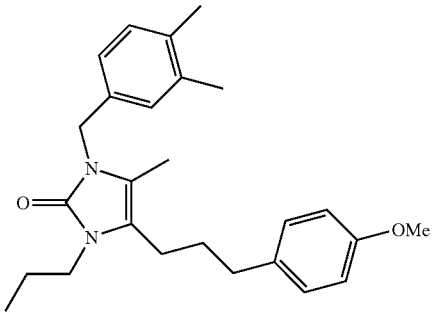

A 0° C. solution of 3-(3,4-dimethyl-benzyl)-5-[3-(4-methoxy-phenyl)-propyl]-1-propyl-imidazolidine-2,4-dione (0.155 g, 0.379 mmol) in THF (6 mL) was treated dropwise with a 3 molar solution of methyl magnesium bromide in $Et_2O$ (0.76 mL, 2.28 mmol) and then stirred at 0° C. under $N_2$ for 1 h. The reaction was quenched with 1 N HCl (5 mL) and stirred at room temperature for 15 minutes to effect elimination and then was worked up extractively with EtOAc and water. The organic layer dried ($MgSO_4$), and the solvent removed in vacuo to afford 0.155 g (100%) 1-(3,4-dimethyl-benzyl)-4-[3-(4-methoxy-phenyl)-propyl]-5-methyl-3-propyl-1,3-dihydro-imidazol-2-one that was utilized without purification. MS ($ES^+$) Calc'd for $C_{26}H_{35}N_2O_2$ (M+1) 407. Found m/z 407 (100%). $^1$H NMR.

Step B 2-(4-{3-[1-(3,4-Dimethyl-benzyl)-5-methyl-2-oxo-3-propyl-2,3-dihydro-1H-imidazol-4-yl]-propyl}-phenoxy)-2-methyl-propionic acid ethyl ester

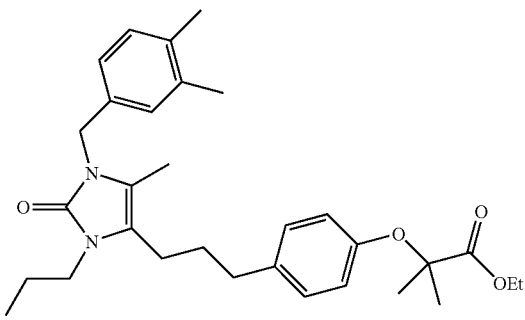

A 0° C. solution of 1-(3,4-dimethyl-benzyl)-4-[3-(4-methoxy-phenyl)-propyl]-5-methyl-3-propyl-1,3-dihydro-imidazol-2-one (0.145 g, 0.357 mmol) in $CH_2Cl_2$ (6 mL) was treated dropwise with $BBr_3$ (0.10 mL, 1.06 mmol) and then stirred at 0° C. under $N_2$ for 30 minutes. The reaction was diluted with $Et_2O$ and then quenched with ice and then water. The organic layer was dried ($MgSO_4$), and the solvent removed in vacuo to afford 0.169 g (100%) 1-(3,4-dimethyl-benzyl)-4-[3-(4-hydroxy-phenyl)-propyl]-5-methyl-3-propyl-1,3-dihydro-imidazol-2-one that was utilized without purification.

The crude 1-(3,4-dimethyl-benzyl)-4-[3-(4-hydroxy-phenyl)-propyl]-5-methyl-3-propyl-1,3-dihydro-imidazol-2-one (0.169 g) was combined with ethyl 2-bromoisobutyrate (0.366 g, 1.87 mmol), $MgSO_4$ (0.043 g, 0.357 mmol) and 325 mesh $K_2CO_3$ (0.197 g, 1.43 mmol) in ethanol (8 mL) and heated a 75° C. for 16 h under $N_2$. The reaction was cooled and the solvent removed in vacuo. The residue was acidified with 1 N HCl (10 mL) and extracted with EtOAc and water. The organic layer was dried ($MgSO_4$), and the solvent removed in vacuo to afford crude product that was purified by flash chromatography using 2:1 to hexanes:acetone to afford 0.124 g (69%) 2-(4-{3-[1-(3,4-dimethyl-benzyl)-5-methyl-2-oxo-3-propyl-2,3-dihydro-1H-imidazol-4-yl]-propyl}-phenoxy)-2-methyl-propionic acid ethyl ester. MS ($ES^+$) Calc'd for $C_{31}H_{43}N_2O_4$ (M+1) 507. Found m/z 507 (100%). $^1$H NMR.

Step C 2-(4-{3-[1-(3,4-Dimethyl-benzyl)-5-methyl-2-oxo-3-propyl-2,3-dihydro-1H-imidazol-4-yl]-propyl}-phenoxy)-2-methyl-propionic acid

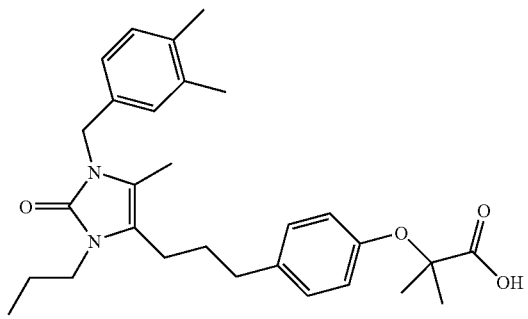

A solution of 2-(4-{3-[1-(3,4-dimethyl-benzyl)-5-methyl-2-oxo-3-propyl-2,3-dihydro-1H-imidazol-4-yl]-propyl}-phenoxy)-2-methyl-propionic acid ethyl ester (0.124 g, 0.244 mmol) in EtOH (10 mL) was treated with aqueous 5 N NaOH (0.5 mL) and heated to reflux under $N_2$ for 1 h. The reaction was cooled and the solvent removed in vacuo to give a residue that was acidified with aqueous 1 N HCl. The mixture was extracted with $Et_2O$ and water, the organic layer dried ($MgSO_4$), and the solvent removed in vacuo to afford 0.104 g (89%) 2-(4-{3-[1-(3,4-dimethyl-benzyl)-5-methyl-2-oxo-3-propyl-2,3-dihydro-1H-imidazol-4-yl]-propyl}-phenoxy)-2-methyl-propionic acid. HRMS ($ES^+$) m/z exact mass calcd for $C_{29}H_{39}N_2O_4$ [M+1] 479.2910, found 479.2917. $^1$H NMR.

Example 142

2-(4-{3-[1-(3,4-Dimethyl-benzyl)-5-ethyl-2-oxo-3-propyl-2,3-dihydro-1H-imidazol-4-yl]-propyl}-phenoxy)-2-methyl-propionic acid

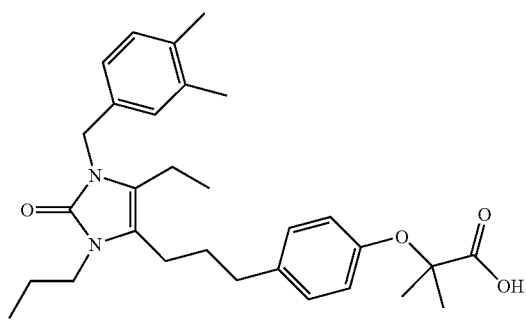

The procedures herein were utilized with ethyl magnesium bromide to afford 2-(4-{3-[1-(3,4-dimethyl-benzyl)-5-ethyl-2-oxo-3-propyl-2,3-dihydro-1H-imidazol-4-yl]-propyl}-phenoxy)-2-methyl-propionic acid. HRMS (ES$^+$) m/z exact mass calcd for $C_{30}H_{41}N_2O_4$ [M+1] 493.3066, found 493.3079. $^1$H NMR.

Cyclic Urea Experimentals

General Procedure

Step A 2-(4-{2-[1-(4-Methoxy-benzyl)-3-methyl-2-oxo-imidazolidin-4-yl]-ethoxy}-phenoxy)-2-methyl-propionic acid ethyl ester

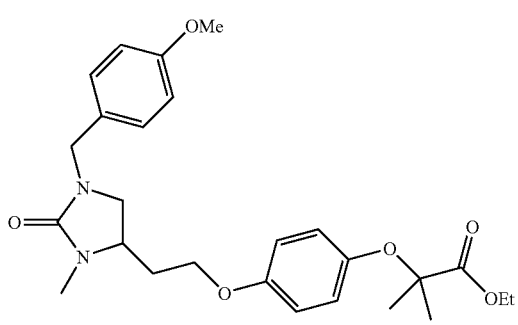

A mixture of toluene-4-sulfonic acid 2-[1-(4-methoxy-benzyl)-3-methyl-2-oxo-imidazolidin-4-yl]-ethyl ester (3.10 g, 7.41 mmol), 2-(4-hydroxy-phenoxy)-2-methyl-propionic acid ethyl ester (1.50 g, 6.69 mmol) and $CS_2CO_3$ (2.62 g, 8.04 mmol) in DMF (70 mL) was heated at 65° C. for under $N_2$ for 16 h. The reaction mixture was cooled to room temperature, quenched with aqueous 1 N HCl (25 mL), and worked up extractively with EtOAc and water. The organic layer was dried (MgSO$_4$) and the solvent removed in vacuo to afford crude product that was purified by flash chromatography using 5:1 hexanes:acetone to afford 2.92 g (93%) 2-(4-{2-[1-(4-methoxy-benzyl)-3-methyl-2-oxo-imidazolidin-4-yl]-ethoxy}-phenoxy)-2-methyl-propionic acid ethyl ester. MS (ES$^+$) Calc'd for $C_{36}H_{47}N_2O_6$ (M+1) 603. Found m/z 603 (100%). $^1$H NMR.

Step B

2-Methyl-2-{4-[2-(3-methyl-2-oxo-imidazolidin-4-yl)-ethoxy]-phenoxy}-propionic acid ethyl ester

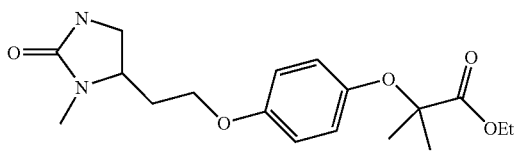

A mixture of 2-(4-{2-[1-(4-methoxy-benzyl)-3-methyl-2-oxo-imidazolidin-4-yl]-ethoxy}-phenoxy)-2-methyl-propionic acid ethyl ester (2.72 g, 5.78 mmol) and triethylsilane (1.34 g, 11.5 mmol) was treated with trifluoroacetic acid (70 mL) and stirred at room temperature under $N_2$ for 5 h. The reaction mixture was diluted with water and then extracted with ethyl acetate. The organic layer was dried (MgSO$_4$) and the solvent removed in vacuo to afford crude product that was purified by flash chromatography using 98:2 $CH_2Cl_2$:MeOH to afford 2.40 g (100%) 2-methyl-2-{4-[2-(3-methyl-2-oxo-imidazolidin-4-yl)-ethoxy]-phenoxy}-propionic acid ethyl ester. R$_f$=0.09 (1:1 hexanes:acetone); MS (ES$^+$) Calc'd for $C_{18}H_{27}N_2O_5$ (M+1) 351. Found m/z 351 (100%). $^1$H NMR.

Step C 2-(4-{2-[1-(4-Methanesulfonyl-benzyl)-3-methyl-2-oxo-imidazolidin-4-yl]-ethoxy}-phenoxy)-2-methyl-propionic acid ethyl ester

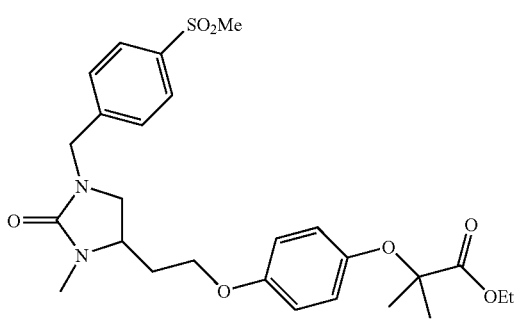

A solution of 2-methyl-2-{4-[2-(3-methyl-2-oxo-imidazolidin-4-yl)-ethoxy]-phenoxy}-propionic acid ethyl ester (0.143 g, 0.408 mmol) in dry DMF (4 mL) was treated a 60% suspension of NaH (0.033 g, 0.825 mmol) and the resultant mixture was stirred at room temperature for 20 minutes under $N_2$. The reaction mixture was cooled to 0° C. and then treated with p-methylsulfonylbenzyl chloride and then warmed to room temperature and stirred for 16 h. The reaction was acidified with aqueous 1 N HCl (4 mL), diluted with water and extracted with Et$_2$O. The organic layer was dried (MgSO$_4$) and the solvent removed in vacuo to afford crude product that was purified by column chromatography using a gradient of 4:1 to 1:1 hexanes:acetone to afford 0.090 g (42%) 2-(4-{2-[1-(4-methanesulfonyl-benzyl)-3-methyl-2-oxoimidazolidin-4-yl]-ethoxy}-phenoxy)-2-methyl-propionic acid ethyl ester. $R_f$=0.40 (1:1 hexanes:acetone) MS (ES$^+$) Calc'd for $C_{26}H_{35}N_2O_7S$ (M+1) 518. Found m/z 518 (100%). $^1$H NMR.

Step D 2-(4-{2-[1-(4-Methanesulfonyl-benzyl)-3-methyl-2-oxo-imidazolidin-4-yl]-ethoxy}-phenoxy)-2-methyl-propionic acid

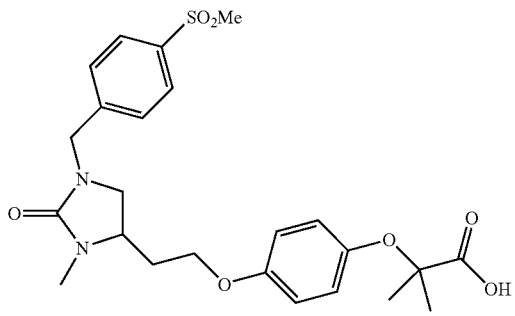

A solution of 2-(4-{2-[1-(4-methanesulfonyl-benzyl)-3-methyl-2-oxo-imidazolidin-4-yl]-ethoxy}-phenoxy)-2-methyl-propionic acid ethyl ester (0.087 g, 0.168 mmol) in ethanol (8 mL) was treated with aqueous 5 N NaOH (1 mL) and heated to reflux 1 h. The reaction mixture was cooled, the solvent removed in vacuo. The resultant residue was acidified with aqueous 1 N HCl (5 mL) and extracted with $CH_2Cl_2$. The organic layer was dried ($MgSO_4$) and the solvent removed in vacuo to afford 0.043 g (52%) 2-(4-{2-[1-(4-methanesulfonyl-benzyl)-3-methyl-2-oxo-imidazolidin-4-yl]-ethoxy}1-phenoxy)-2-methyl-propionic acid. HRMS (ES$^+$) m/z exact mass calcd for $C_{24}H_{31}N_2O_7S$ 491.1852, found 491.1879. $^1$H NMR.

Example 143

2-(4-{2-[1-(4-Methoxy-benzyl)-3-methyl-2-oxo-imidazolidin-4-yl]-ethoxy}-phenoxy)-2-methyl-propionic acid

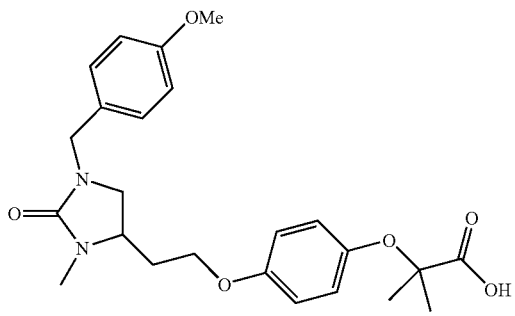

A solution of 2-(4-{2-[1-(4-methoxy-benzyl)-3-methyl-2-oxo-imidazolidin-4-yl]-ethoxy}-phenoxy)-2-methyl-propionic acid ethyl ester (0.198 g, 0.421 mmol) in ethanol (10 mL) was treated with aqueous 5 N NaOH (1 mL) and heated to reflux 1.5 h. The reaction mixture was cooled, the solvent removed in vacuo. The resultant residue was acidified with aqueous 1 N HCl (10 mL) and extracted with $Et_2O$. The organic layer was dried ($MgSO_4$) and the solvent removed in vacuo to afford 0.147 g (79%) 2-(4-{2-[1-(4-methoxy-benzyl)-3-methyl-2-oxo-imidazolidin-4-yl]-ethoxy}-phenoxy)-2-methyl-propionic acid. MS (ES$^+$) Calc'd for $C_{24}H_{31}N_2O_6$ (M+1) 443. Found m/z 443 (100%). $^1$H NMR.

Example 144

(R)-2-Methyl-2-(4-{2-[3-methyl-2-oxo-1-(4-trifluoromethyl-benzyl)-imidazolidin-4-yl]-ethoxy}-phenoxy)-propionic acid

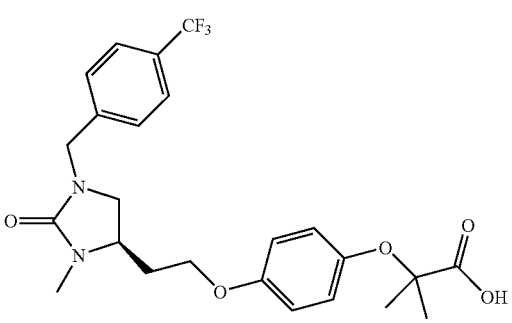

The procedures herein were utilized with 4-trifluoromethylbenzyl bromide to prepare (R)-2-methyl-2-(4-{2-[3-methyl-2-oxo-1-(4-trifluoromethyl-benzyl)-imidazolidin-4-yl]-ethoxy}-phenoxy)-propionic acid. HRMS (ES$^+$) m/z exact mass calcd for $C_{24}H_{28}N_2O_5F_3$ 481.1950, found 481.1960. $^1$H NMR.

Example 145

(R)-2-(4-{2-[1-(3,4-Difluoro-benzyl)-3-methyl-2-oxo-imidazolidin-4-yl]-ethoxy}-phenoxy)-2-methyl-propionic acid

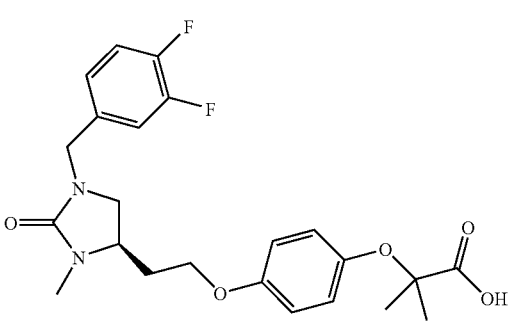

The procedures herein were utilized with 3,4-difluorobenzyl bromide to prepare (R)-2-(4-{2-[1-(3,4-difluoro-benzyl)-3-methyl-2-oxo-imidazolidin-4-yl]-ethoxy}-phenoxy)-2-methyl-propionic acid. HRMS (ES$^+$) m/z exact mass calcd for $C_{23}H_{27}N_2O_5F_2$ 449.1888, found 449.1888. $^1$H NMR.

Example 146

(R)-2-Methyl-2-{4-[2-(3-methyl-2-oxo-1-quinolin-2-ylmethyl-imidazolidin-4-yl)-ethoxy]-phenoxy}-propionic acid

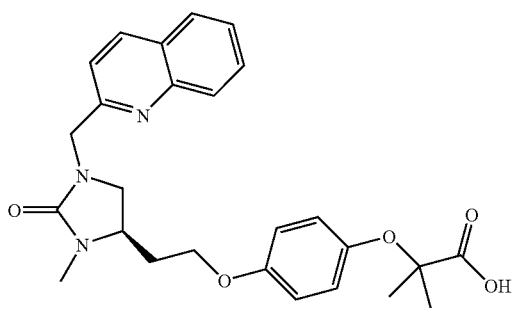

The procedures herein were utilized with 2-(chloromethyl)quinoline to prepare (R)-2-methyl-2-{4-[2-(3-methyl-2-oxo-1-quinolin-2-ylmethyl-imidazolidin-4-yl)-ethoxy]-phenoxy}-propionic acid. HRMS (ES$^+$) m/z exact mass calcd for $C_{26}H_{30}N_3O_5$ 464.2185, found 464.2193. $^1$H NMR.

Example 147

(R)-2-(4-{2-[1-(3,5-Difluoro-benzyl)-3-methyl-2-oxo-imidazolidin-4-yl]-ethoxy}-phenoxy)-2-methyl-propionic acid

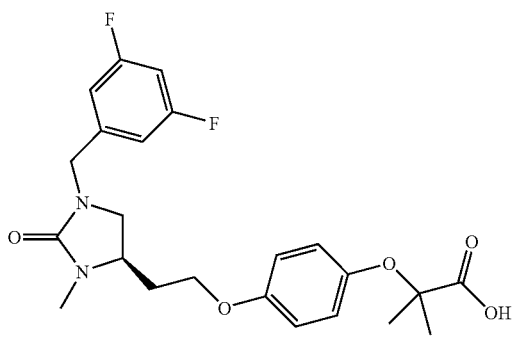

The procedures herein were utilized with 3,5-difluorobenzyl bromide to prepare (R)-2-(4-{2-[1-(3,5-difluoro-benzyl)-3-methyl-2-oxo-imidazolidin-4-yl]-ethoxy}-phenoxy)-2-methyl-propionic acid. HRMS (ES$^+$) m/z exact mass calcd for $C_{23}H_{27}N_2O_5F_2$ 449.1888, found 449.1913. $^1$H NMR.

Example 148

(R)-2-(4-{2-[1-(3-Methoxy-benzyl)-3-methyl-2-oxo-imidazolidin-4-yl]-ethoxy}-phenoxy)-2-methyl-propionic acid

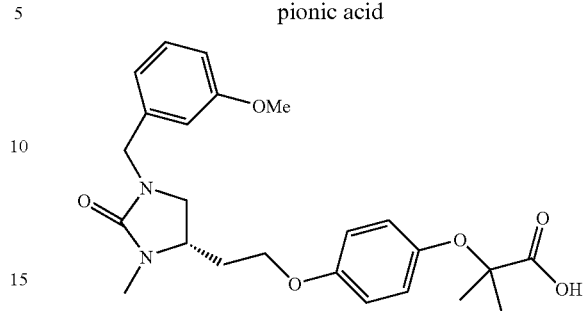

The procedures herein were utilized with 3-methoxybenzyl bromide to prepare (R)-2-(4-{2-[1-(3-methoxy-benzyl)-3-methyl-2-oxo-imidazolidin-4-yl]-ethoxy}-phenoxy)-2-methyl-propionic acid. HRMS (ES$^+$) m/z exact mass calcd for $C_{24}H_{31}N_2O6$ 443.2182, found 443.2182. $^1$H NMR.

Example 149

(R)-2-(4-{2-[1-(4-Chloro-benzyl)-3-methyl-2-oxo-imidazolidin-4-yl]-ethoxy}-phenoxy)-2-methyl-propionic acid

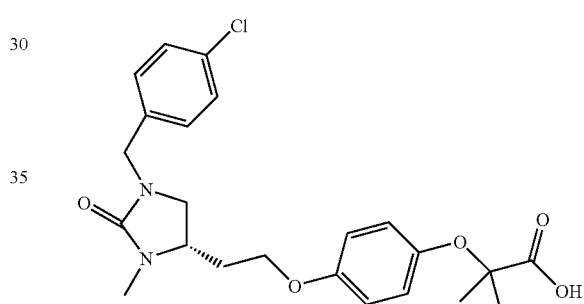

The procedures herein were utilized with 4-chlorobenzyl bromide to prepare (R)-2-(4-{2-[1-(4-chloro-benzyl)-3-methyl-2-oxo-imidazolidin-4-yl]-ethoxy}-phenoxy)-2-methyl-propionic acid. HRMS (ES$^+$) m/z exact mass calcd for $C_{23}H_{28}N_2O_5Cl$ 447.1687, found 447.1667. $^1$H NMR.

Example 150

(R)-2-Methyl-2-{4-[2-(3-methyl-2-oxo-1-pyridin-2-ylmethyl-imidazolidin-4-yl)-ethoxy]-phenoxy}-propionic acid

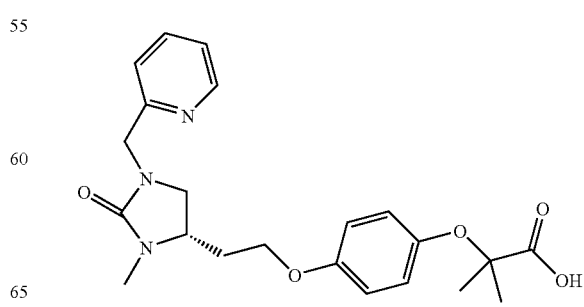

The procedures herein were utilized with 2-picolyl chloride hydrochloride to prepare (R)-2-methyl-2-{4-[2-(3-methyl-2-oxo-1-pyridin-2-ylmethyl-imidazolidin-4-yl)-ethoxy]-phenoxy}-propionic acid. HRMS (ES+) m/z exact mass calcd for $C_{22}H_{28}N_3O_5$ 414.2029, found 414.2028. $^1$H NMR.

Example 151

Step A

[1-(3,4-Dimethyl-benzyl)-2,5-dioxo-imidazolidin-4-yl]-acetic acid methyl ester

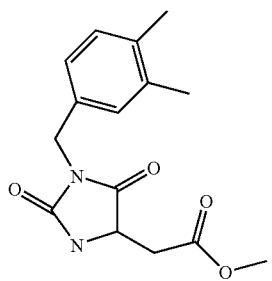

A solution of (2,5-dioxo-imidazolidin-4-yl)-acetic acid methyl ester (6.0 g, 34.8 mmol) in DMF (240 mL) was treated with 3,4-dimethyl benzyl bromide (5.93 g, 38.3 mmol), $MgSO_4$ (8.40 g, 60.8 mmol) and then 325 mesh $K_2CO_3$ (9.15 g, 66.2 mmol) at 0° C. The resultant mixture was warmed to room temperature under $N_2$ and then heated at 50° C. for 5 h. The reaction mixture was cooled to room temperature then filtered, and then aqueous 1N HCl (140 mL) was added to the filtrate. The filtrate was extracted with EtOAc and the organic layer dried ($MgSO_4$). The solvent was removed in vacuo to give 11.43 g crude product which was purified by flash chromatography using 3:1 hexanes:acetone to give 6.35 g of product that was triturated in $Et_2O$/hexanes and filtered to give 2.24 g (22%) [1-(3,4-dimethyl-benzyl)-2,5-dioxo-imidazolidin-4-yl]-acetic acid methyl ester. MS (ES+) Calc'd for $C_{15}H_{19}N_2O_4$ (M+1) 291. Found m/z 291 (100%). $^1$H NMR.

Step B

[1-(3,4-Dimethyl-benzyl)-3-(4-methoxy-benzyl)-2,5-dioxo-imidazolidin-4-yl]-acetic acid methyl ester

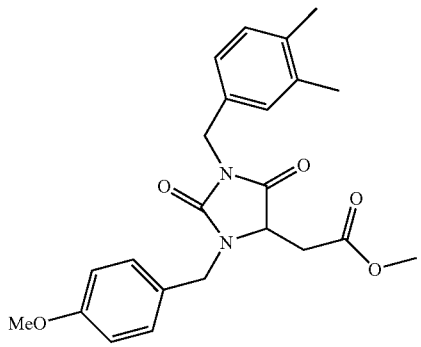

A 0° C. solution of compound [1-(3,4-dimethyl-benzyl)-2,5-dioxo-imidazolidin-4-yl]-acetic acid methyl ester (2.24 g, 7.71 mmol) in DMF (30 mL) was treated with sodium hydride (60% dispersion, 0.37 g, 9.25 mmol) and warmed to room temperature and stirred under $N_2$ for 20 minutes. The resultant mixture was cooled to 0° C. and then treated with 4-methoxybenzyl chloride (2.41 g, 15.4 mmol) and then warmed to room temperature and stirred for 16 h. The reaction was quenched with 25 mL of aqueous 1 N HCl and then worked up extractively with $Et_2O$ and water. The organic layer was dried ($MgSO_4$) and the solvent removed in vacuo to give crude product that was purified by flash chromatography using a gradient of 5:1 hexanes:acetone to afford 3.23 g (100%) [1-(3,4-dimethyl-benzyl)-3-(4-methoxy-benzyl)-2,5-dioxo-imidazolidin-4-yl]-acetic acid methyl ester. MS (ES+) Calc'd for $C_{23}H_{26}N_2O_5$ (M+1) 411. Found m/z. 411 (100%). $^1$H NMR.

Step C 1-(3,4-Dimethyl-benzyl)-4-(2-hydroxy-ethyl)-3-(4-methoxy-benzyl)-imidazolidin-2-one

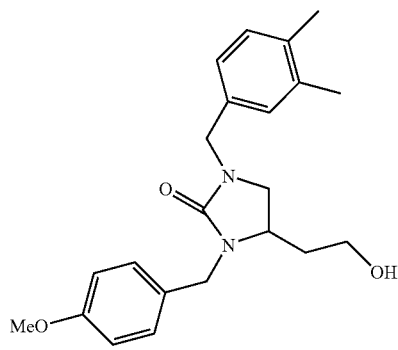

A solution of [1-(3,4-dimethyl-benzyl)-3-(4-methoxy-benzyl)-2,5-dioxo-imidazolidin-4-yl]-acetic acid methyl ester (3.22 g, 7.84 mmol) in methanol (50 mL) was treated with aqueous 5 N NaOH (25.7 mL) and heated to reflux 1.5 h. The reaction mixture was cooled, the solvent was removed in vacuo. The resultant residue was acidified with aqueous 1 N HCl (200 mL) and extracted with $Et_2O$ and water. The organic layer was dried ($MgSO_4$) and the solvent was removed in vacuo to afford 3.18 g (100%) of acid that was utilized without purification. A solution of crude acid (3.18 g, assume 7.84 mmol) in THF (50 mL) was treated dropwise with 1 M solution of borane-THF complex in THF (47 mL, 47 mmol) and then stirred at room temperature under $N_2$ for 16 h. The reaction was quenched with methanol (30 mL) and stirred at room temperature for 30 minutes. The solvent was removed in vacuo to give crude product that was purified by flash chromatography using 3:1 hexanes:acetone to afford 1.89 g (65%) 1-(3,4-dimethyl-benzyl)-4-(2-hydroxy-ethyl)-3-(4-methoxy-benzyl)-imidazolidin-2-one. MS (ES+) Calc'd for $C_{22}H_{28}N_2O_3$ (M+1) 369. Found m/z 369 (100%). $^1$H NMR.

Step D

Toluene-4-sulfonic acid 2-[1-(3,4-dimethyl-benzyl)-3-(4-methoxy-benzyl)-2-oxo-imidazolidin-4-yl]-ethyl ester

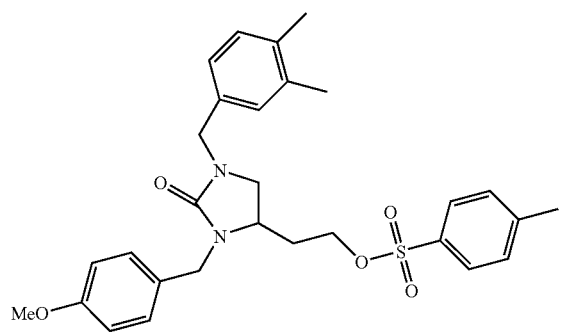

A solution of 1-(3,4-dimethyl-benzyl)-4-(2-hydroxy-ethyl)-3-(4-methoxy-benzyl)-imidazolidin-2-one (1.89 g, 5.13 mmol), pyridine (1.42 g, 17.9 mmol) and 4-dimethyl amino pyridine (0.188 g, 1.54 mmol) in $CH_2Cl_2$ was treated with p-toluenesulfonic anhydride (2.68 g, 8.21 mmol) and the reaction stirred at room temperature for under $N_2$ for 1.5 h. The reaction mixture was washed with aqueous 0.5 N HCl (100 mL), the organic layer was dried ($MgSO_4$), and the solvent removed in vacuo to afford crude product that was purified by flash chromatography using 3:1 hexanes:acetone to afford 2.57 g (96%) toluene-4-sulfonic acid 2-[1-(3,4-dimethyl-benzyl)-3-(4-methoxy-benzyl)-2-oxo-imidazolidin-4-yl]-ethyl ester. MS ($ES^+$) Calc'd for $C_{29}H_{34}N_2O_5S$ (M+1) 523. Found m/z 523 (100%). $^1$H NMR.

Step E 2-(4-{2-[1-(3,4-Dimethyl-benzyl)-3-(4-methoxy-benzyl)-2-oxo-imidazolidin-4-yl]-ethoxy}-phenoxy)-2-methyl-propionic acid ethyl ester

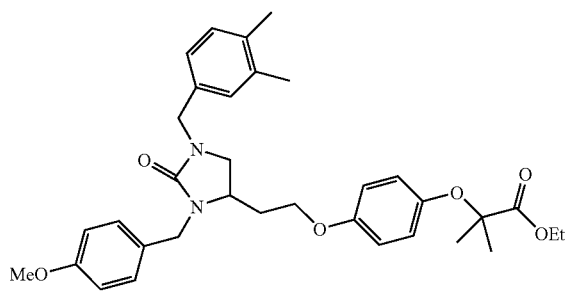

A mixture of toluene-4-sulfonic acid 2-[1-(3,4-dimethyl-benzyl)-3-(4-methoxy-benzyl)-2-oxo-imidazolidin-4-yl]-ethyl ester (2.54 g, 4.86 mmol), 2-(4-hydroxy-phenoxy)-2-methyl-propionic acid ethyl ester (0.99 g, 4.01 mmol) and $CS_2CO_3$ (1.73 g, 5.31 mmol) in DMF (60 mL) was heated at 55° C. for under $N_2$ for 16 h. The reaction mixture was cooled to room temperature, quenched with aqueous 1 N HCl (25 mL), and worked up extractively with EtOAc and water. The organic layer was dried ($MgSO_4$) and the solvent removed in vacuo to afford crude product that was purified by flash chromatography using 4:1 hexanes:acetone to afford 2.51 g (99%) 2-(4-{2-[1-(3,4-dimethyl-benzyl)-3-(4-methoxy-benzyl)-2-oxo-imidazolidin-4-yl]-ethoxy}-phenoxy)-2-methyl-propionic acid ethyl ester. MS ($ES^+$) Calc'd for $C_{34}H_{43}N_2O_6$ (M+1) 575. Found m/z 575 (100%). $^1$H NMR.

Step F 2-(4-{2-[1-(3,4-Dimethyl-benzyl)-2-oxo-imidazolidin-4-yl]-ethoxy}-phenoxy)-2-methyl-propionic acid ethyl ester

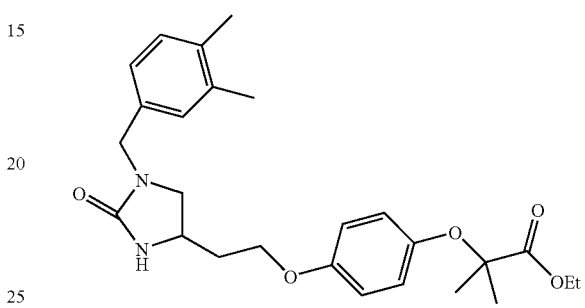

A solution of 2-(4-{2-[1-(3,4-dimethyl-benzyl)-3-(4-methoxy-benzyl)-2-oxo-imidazolidin-4-yl]-ethoxy}-phenoxy)-2-methyl-propionic acid ethyl ester (2.51 g, 4.36 mmol) in trifluoroacetic acid (70 mL) was stirred at room temperature under $N_2$ for 1 h. The reaction was diluted with water, and extracted with $Et_2O$. The organic layer was dried ($MgSO_4$) and the solvent removed in vacuo to afford crude product that was purified by flash chromatography using 98:2 $CH_2Cl_2$:MeOH to afford 1.20 g (60%) 2-(4-{2-[1-(3,4-dimethyl-benzyl)-2-oxo-imidazolidin-4-yl]-ethoxy}-phenoxy)-2-methyl-propionic acid ethyl ester. MS ($ES^+$) Calc'd for $C_{26}H_{35}N_2O_5$ (M+1) 455. Found m/z 455 (100%). $^1$H NMR.

Step G 2-(4-{2-[1-(3,4-Dimethyl-benzyl)-2-oxo-imidazolidin-4-yl]-ethoxy}-phenoxy)-2-methyl-propionic acid

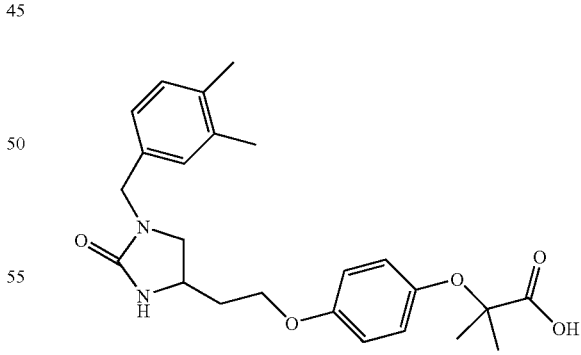

A solution of 2-(4-{2-[1-(3,4-dimethyl-benzyl)-2-oxo-imidazolidin-4-yl]-ethoxy}-phenoxy)-2-methyl-propionic acid ethyl ester (0.087 g, 0.191 mmol) in ethanol (8 mL) was treated with aqueous 5 N NaOH (0.4 mL) and heated to reflux 1.5 h. The reaction mixture was cooled, the solvent removed in vacuo. The resultant residue was acidified with aqueous 1 N HCl (5 mL) and extracted with $Et_2O$. The organic layer was dried ($MgSO_4$) and the solvent removed in vacuo to afford 0.059 g (72%) 2-(4-{2-[1-(3,4-dimethyl-benzyl)-2-oxo-imidazolidin-4-yl]-ethoxy}-phenoxy)-2-methyl-propionic acid. HRMS (ES+) m/z exact mass calcd for $C_{24}H_{31}N_2O_5$ [M+1] 427.2233, found 427.2232. $^1$H NMR.

Example 152

Step A 2-(4-{2-[1-(3,4-Dimethyl-benzyl)-3-methyl-2-oxo-imidazolidin-4-yl]-ethoxy}-phenoxy)-2-methyl-propionic acid ethyl ester

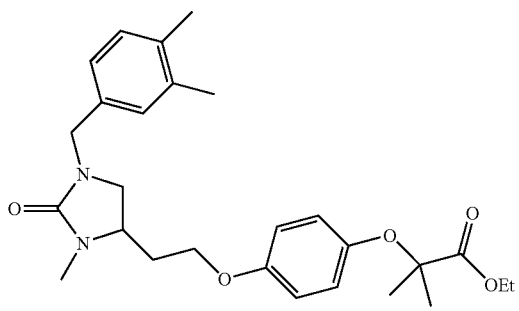

A solution of 2-(4-{2-[1-(3,4-dimethyl-benzyl)-2-oxo-imidazolidin-4-yl]-ethoxy}-phenoxy)-2-methyl-propionic acid ethyl ester (0.128 g, 0.280 mmol) in DMF (4 mL) was treated with 60% oil suspension of NaH (0.028 g, 0.70 mmol) and stirred at room temperature under $N_2$ for 15 minutes. The reaction was cooled to 0° C. and treated with iodomethane (0.16 g, 1.13 mmol) and then warmed to room temperature and stirred for 1 h. The reaction was quenched with 1 N HCl (3 mL) and worked up extractively with $Et_2O$ and water. The organic layer was dried ($MgSO_4$) and the solvent removed in vacuo to afford crude product that was purified by flash chromatography using 5:1 hexanes:acetone to afford 0.098 g (74%) 2-(4-{2-[1-(3,4-dimethyl-benzyl)-3-methyl-2-oxo-imidazolidin-4-yl]-ethoxy}-phenoxy)-2-methyl-propionic acid ethyl ester. MS (ES+) Calc'd for $C_{27}H_{37}N_2O_5$ (M+1) 469. Found m/z 469 (100%). $^1$H NMR.

Step B 2-(4-{2-[1-(3,4-Dimethyl-benzyl)-3-methyl-2-oxo-imidazolidin-4-yl]-ethoxy}-phenoxy)-2-methyl-propionic acid

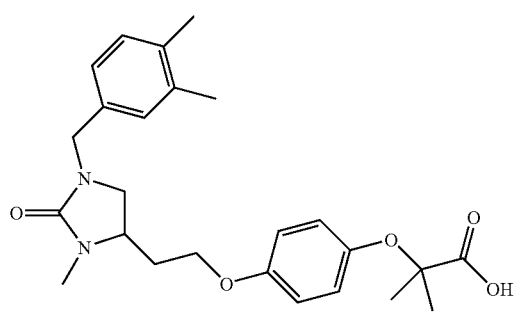

A solution of 2-(4-{2-[1-(3,4-dimethyl-benzyl)-3-methyl-2-oxo-imidazolidin-4-yl]-ethoxy}-phenoxy)-2-methyl-propionic acid ethyl ester (0.098 g, 0.209 mmol) in ethanol (8 mL) was treated with aqueous 5 N NaOH (0.5 mL) and heated to reflux 1 h. The reaction mixture was cooled, the solvent removed in vacuo. The resultant residue was acidified with aqueous 1 N HCl (5 mL) and extracted with $Et_2O$. The organic layer was dried ($MgSO_4$) and the solvent removed in vacuo to afford 0.050 g (54%) 2-(4-{2-[1-(3,4-dimethyl-benzyl)-3-methyl-2-oxo-imidazolidin-4-yl]-ethoxy}-phenoxy)-2-methyl-propionic acid. HRMS (ES+) m/z exact mass calcd for $C_{25}H_{33}N_2O_5$ [M+1] 4.41.2389, found 441.2390. $^1$H NMR.

Example 153

2-(4-{2-[1-(3,4-Dimethyl-benzyl)-3-ethyl-2-oxo-imidazolidin-4-yl]-ethoxy}-phenoxy)-2-methyl-propionic acid

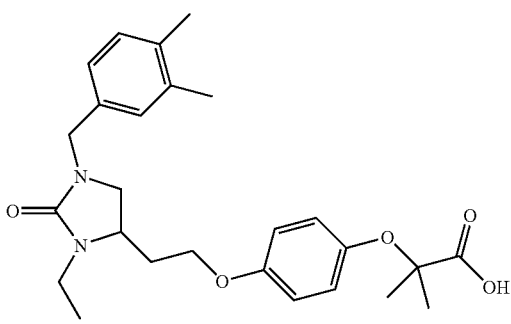

The procedures herein utilized with ethyl iodide to afford 2-(4-{2-[1-(3,4-dimethyl-benzyl)-3-ethyl-2-oxo-imidazolidin-4-yl]-ethoxy}-phenoxy)-2-methyl-propionic acid. MS (ES+) Calc'd for $C_{26}H_{35}N_2O_5$ (M+1) 455. Found m/z 455 (100%). $^1$H NMR.

Example 154

2-(4-{2-[1-(3,4-Dimethyl-benzyl)-2-oxo-3-propyl-imidazolidin-4-yl]-ethoxy}-phenoxy)-2-methyl-propionic acid

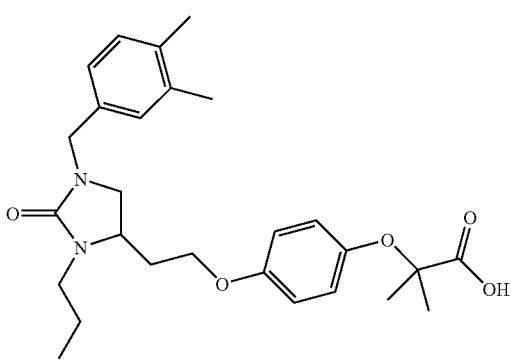

The procedures herein utilized with propyl iodide to afford 2-(4-{2-[1-(3,4-dimethyl-benzyl)-2-oxo-3-propyl-imidazolidin-4-yl]-ethoxy}-phenoxy)-2-methyl-propionic acid. MS (ES+) Calc'd for $C_{27}H_{37}N_2O_5$ (M+1) 469. Found m/z 469 (100%). $^1$H NMR.

Example 155

(R)-2-Methyl-2-(4-{2-[1-(4-methyl-benzyl)-2-oxo-3-propyl-imidazolidin-4-yl]-ethoxy}-phenoxy)-propionic acid

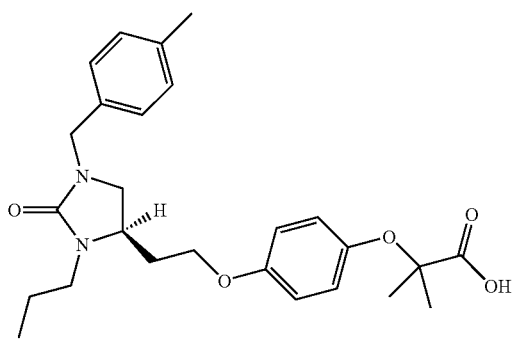

The procedures herein were utilized to prepare 2-methyl-2-(4-{2-[1-(4-methyl-benzyl)-2-oxo-3-propyl-imidazolidin-4-yl]-ethoxy}-phenoxy)-propionic acid. HRMS (ES+) m/z exact mass calcd for $C_{26}H_{35}N_2O_5$ [M+1] 455.2546, found 455.2565. $^1$H NMR.

Example 156

(R)-2-Methyl-2-(4-{2-[3-methyl-1-(4-methyl-benzyl)-2-oxo-imidazolidin-4-yl]-ethoxy}-phenoxy)-propionic acid

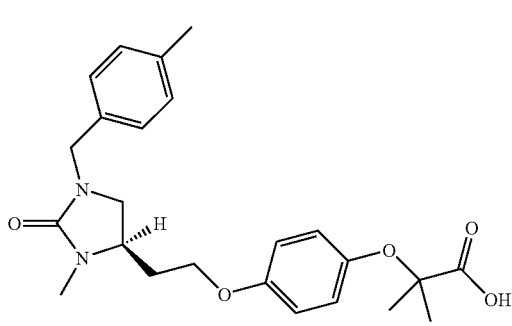

The procedures herein were utilized to prepare 2-methyl-2-(4-{2-[3-methyl-1-(4-methyl-benzyl)-2-oxo-imidazolidin-4-yl]-ethoxy}-phenoxy)-propionic acid. HRMS (ES+) m/z exact mass calcd for $C_{24}H_{31}N_2O_5$ [M+1] 427.2233, found 427.2233. $^1$H NMR.

Example 157

2-(4-{2-[1-(4-tert-Butyl-benzyl)-2-oxo-imidazolidin-4-yl]-ethoxy}-phenoxy)-2-methyl-propionic acid

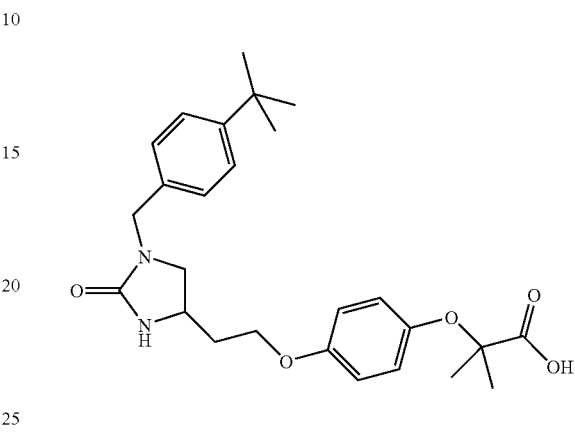

The procedures herein were utilized to prepare 2-(4-{2-[1-(4-tert-butyl-benzyl)-2-oxo-imidazolidin-4-yl]-ethoxy}-phenoxy)-2-methyl-propionic acid. HRMS (ES+) m/z exact mass calcd for $C_{26}H_{35}N_2O_5$ [M+1] 455.2546, found 455.2538. $^1$H NMR.

Example 158

2-(4-{2-[1-(4-tert-Butyl-benzyl)-3-methyl-2-oxo-imidazolidin-4-yl]-ethoxy}-phenoxy)-2-methyl-propionic acid

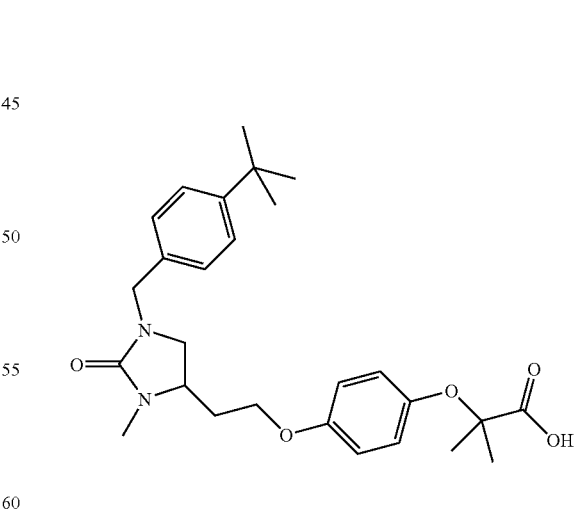

The procedures herein were utilized to prepare 2-(4-{2-[1-(4-tert-Butyl-benzyl)-3-methyl-2-oxo-imidazolidin-4-yl]-ethoxy}-phenoxy)-2-methyl-propionic acid. HRMS (ES+) m/z exact mass calcd for $C_{27}H_{37}N_2O_5$ [M+1] 469.2702, found 469.2690. $^1$H NMR.

Example 159

2-(4-{2-[1-(4-tert-Butyl-benzyl)-3-ethyl-2-oxo-imidazolidin-4-yl]-ethoxy}-phenoxy)-2-methyl-propionic acid

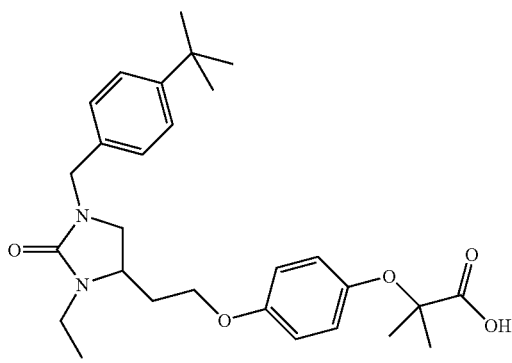

The procedures herein were utilized to prepare 2-(4-{2-[1-(4-tert-butyl-benzyl)-3-ethyl-2-oxo-imidazolidin-4-yl]-ethoxy}-phenoxy)-2-methyl-propionic acid. MS (ES+) Calc'd for $C_{28}H_{39}N_2O_5$ (M+1) 483. Found m/z 483 (100%). $^1$H NMR.

Example 160

2-(4-{2-[1-(4-tert-Butyl-benzyl)-2-oxo-3-propyl-imidazolidin-4-yl]-ethoxy}-phenoxy)-2-methyl-propionic acid

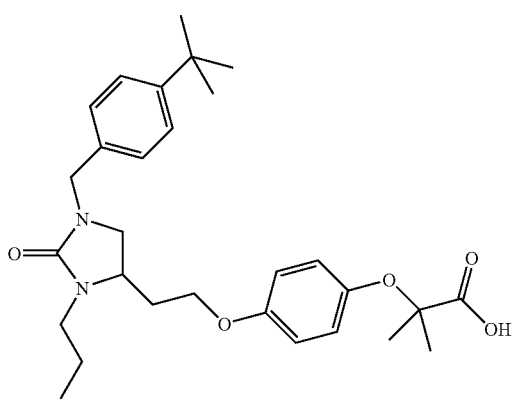

The procedures herein were utilized to prepare 2-(4-{2-[1-(4-tert-butyl-benzyl)-2-oxo-3-propyl-imidazolidin-4-yl]-ethoxy}-phenoxy)-2-methyl-propionic acid. MS (ES+) Calc'd for $C_{29}H_{41}N_2O_5$ (M+1) 497. Found m/z 497 (100%). $^1$H NMR.

Example 161

2-Methyl-2-{4-[2-(1-naphthalen-2-ylmethyl-2-oxo-imidazolidin-4-yl)-ethoxy]-phenoxy}-propionic acid

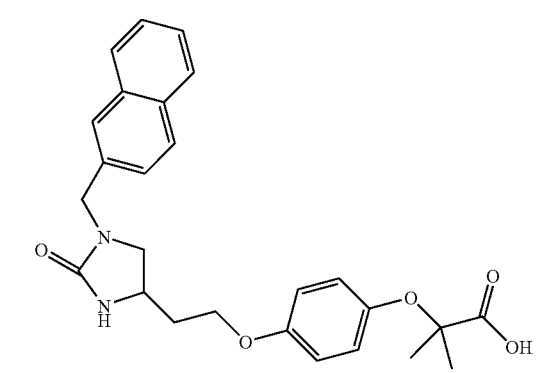

The procedures herein were utilized to prepare 2-methyl-2-{4-[2-(1-naphthalen-2-ylmethyl-2-oxo-imidazolidin-4-yl)-ethoxy]-phenoxy}-propionic acid. MS (ES+) Calc'd for $C_{26}H_{29}N_2O_5$ (M+1) 449. Found m/z 449 (100%). $^1$H NMR.

Example 162

2-Methyl-2-{4-[2-(3-methyl-1-naphthalen-2-ylmethyl-2-oxo-imidazolidin-4-yl)-ethoxy]-phenoxy}-propionic acid

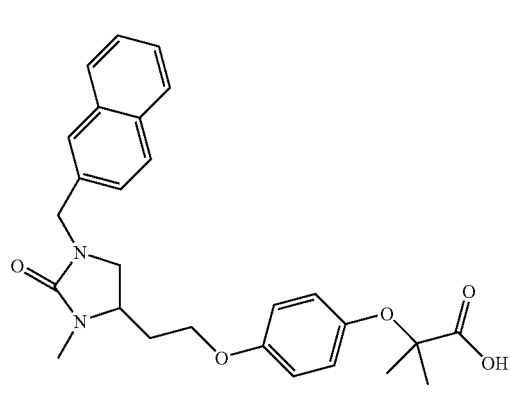

The procedures herein were utilized to prepare 2-methyl-2-{4-[2-(3-methyl-1-naphthalen-2-ylmethyl-2-oxo-imidazolidin-4-yl)-ethoxy]-phenoxy}-propionic acid. MS (ES+) Calc'd for $C_{27}H_{31}N_2O_5$ (M+1) 463. Found m/z 463 (100%). $^1$H NMR.

Example 163

2-Methyl-2-{4-[2-(1-naphthalen-2-ylmethyl-2-oxo-3-propyl-imidazolidin-4-yl)-ethoxy]-phenoxy}-propionic acid

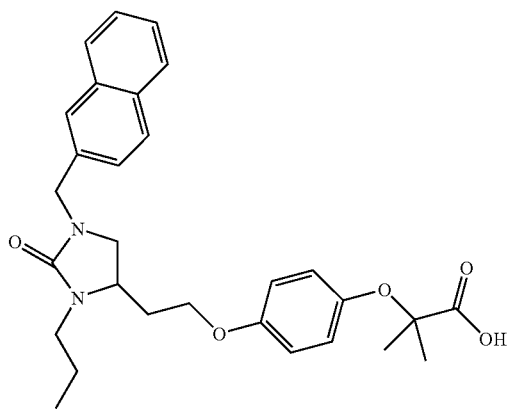

The procedures herein were utilized to prepare 2-methyl-2-{4-[2-(1-naphthalen-2-ylmethyl-2-oxo-3-propyl-imidazolidin-4-yl)-ethoxy]-phenoxy}-propionic acid. MS (ES$^+$) Calc'd for $C_{29}H_{35}N_2O_5$ (M+1) 491. Found m/z 491 (100%). $^1$H NMR.

Example 164

2,2-Dimethyl-3-(4-{2-[1-(4-methyl-benzyl)-2-oxo-3-propyl-imidazolidin-4-yl]-ethoxy}-phenyl)-propionic acid

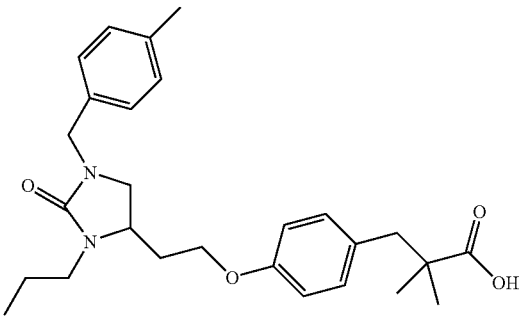

The procedures herein were utilized to prepare 2,2-dimethyl-3-(4-{2-[1-(4-methyl-benzyl)-2-oxo-3-propyl-imidazolidin-4-yl]-ethoxy}-phenyl)-propionic acid. HRMS (ES$^+$) m/z exact mass calcd for $C_{27}H_{37}N_2O_4$ [M+1] 453.2753, found 453.2754. $^1$H NMR.

Example 165

2-Methyl-2-(3-{2-[1-(4-methyl-benzyl)-2-oxo-3-propyl-imidazolidin-4-yl]-ethoxy}-phenoxy)-propionic acid

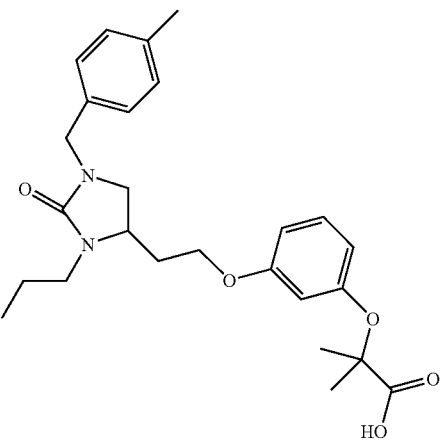

The procedures herein were utilized to prepare 2-methyl-2-(3-{2-[1-(4-methyl-benzyl)-2-oxo-3-propyl-imidazolidin-4-yl]-ethoxy}-phenoxy)-propionic acid. HRMS (ES$^+$) m/z exact mass calcd for $C_{26}H_{34}N_2O_5$ [M+1] 455.2546, found 455.2549. $^1$H NMR.

Example 166

2-Methoxy-2-methyl-3-(4-{2-[1-(4-methyl-benzyl)-2-oxo-3-propyl-imidazolidin-4-yl]-ethoxy}-phenyl)-propionic acid

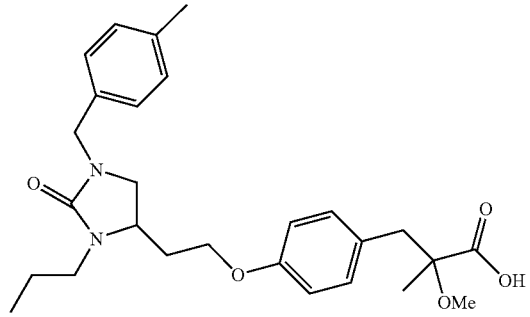

The procedures herein were utilized to prepare 2-methoxy-2-methyl-3-(4-{2-[1-(4-methyl-benzyl)-2-oxo-3-propyl-imidazolidin-4-yl]-ethoxy}-phenyl)-propionic acid. HRMS (ES$^+$) m/z exact mass calcd for $C_{27}H_{36}N_2O_5$ [M+1] 469.2702, found 469.2709. $^1$H NMR.

Example 167

2-(4-{2-[1-(4-Methyl-benzyl)-2-oxo-3-propyl-imidazolidin-4-yl]-ethoxy}-benzyl)-butyric acid

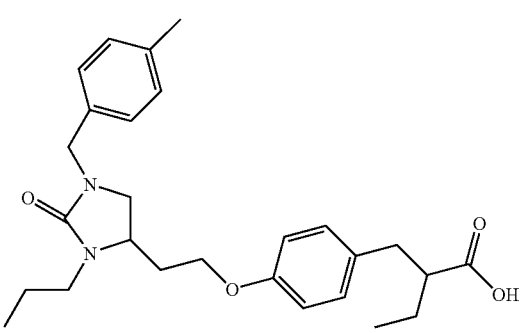

The procedures herein were utilized to prepare 2-(4-{2-[1-(4-methyl-benzyl)-2-oxo-3-propyl-imidazolidin-4-yl]-ethoxy}-benzyl)-butyric acid. HRMS (ES$^+$) m/z exact mass calcd for $C_{27}H_{36}N_2O_4$ [M+1] 453.2753, found 453.2749. $^1$H NMR.

Example 168

4-{2-[1-(4-Methyl-benzyl)-2-oxo-3-propyl-imidazolidin-4-yl]-ethoxy}-benzoic acid

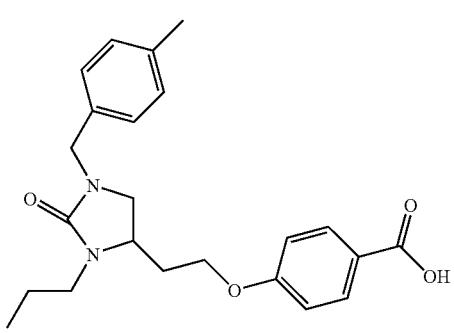

The procedures herein were utilized to prepare 4-{2-[1-(4-methyl-benzyl)-2-oxo-3-propyl-imidazolidin-4-yl]-ethoxy}-benzoic acid. HRMS (ES$^+$) m/z exact mass calcd for $C_{23}H_{29}N_2O_4$ [M+1] 397.2127, found 397.2112. $^1$H NMR.

Example 169

(4-{2-[1-(4-Methyl-benzyl)-2-oxo-3-propyl-imidazolidin-4-yl]-ethoxy}-phenyl)-acetic acid

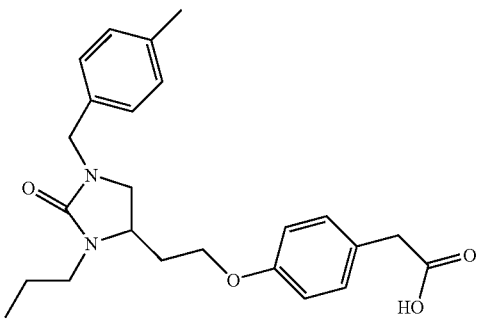

The procedures herein were utilized to prepare (4-{2-[1-(4-methyl-benzyl)-2-oxo-3-propyl-imidazolidin-4-yl]-ethoxy}-phenyl)-acetic acid. HRMS (ES$^+$) m/z exact mass calcd for $C_{24}H_{31}N_2O_4$ [M+1] 411.2284, found 411.2269. $^1$H NMR.

Example 170

3-(4-{2-[-(4-Methyl-benzyl)-2-oxo-3-propyl-imidazolidin-4-yl]-ethoxy}-phenyl)-propionic acid The procedures herein were utilized to prepare 3-(4-{2-[1-(4-methyl-benzyl)-2-oxo-3-propyl-imidazolidin-4-yl]-ethoxy}-phenyl)-propionic acid. HRMS (ES$^+$) m/z exact mass calcd for $C_{25}H_{33}N_2O_4$ [M+1] 425.2440, found 425.2427. $^1$H NMR.

Example 171

3-{2-[1-(4-Methyl-benzyl)-2-oxo-3-propyl-imidazolidin-4-yl]-ethoxy}-benzoic acid

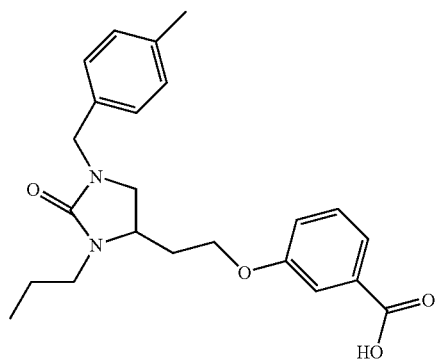

The procedures herein were utilized to prepare 3-{2-[1-(4-methyl-benzyl)-2-oxo-3-propyl-imidazolidin-4-yl]-ethoxy}-benzoic acid. HRMS (ES⁺) m/z exact mass calcd for $C_{23}H_{29}N_2O_4$ [M+1] 397.2127, found 397.2118. ¹H NMR.

Example 172

Step A 1-(4-Hydroxy-phenyl)-cyclopentanecarboxylic acid ethyl ester

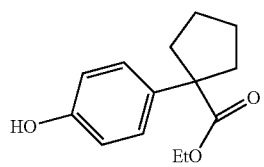

A solution of 1-(p-methoxyphenyl)-cyclopentanecarboxylic acid 093909 (5.0 g, 22.7 mmol) in ethanol (50 mL) was treated with conc. $H_2SO_4$ (4.40 g, 44.9 mmol) and heated to reflux under $N_2$ for 12 h. The reaction was cooled and the solvent removed in vacuo to give a residue that was extracted with EtOAc and water. The organic layer was dried ($MgSO_4$) and the solvent removed in vacuo to 5.93 g crude ester (100%) that was utilized without purification. The ester (5.93 g, assume 22.7 mmol) was dissolved in dry $CH_2Cl_2$ (75 mL), cooled to −78° C. and then treated dropwise with $BBr_3$ (11.4 g, 45.6 mmol). The reaction was warmed to 0° C. for 15 minutes and then quenched with methanol then water. The reaction mixture was extracted with $CH_2Cl_2$ and water, the organic layer was dried ($MgSO_4$), and the solvent removed in vacuo to give crude product that was purified by flash chromatography using 6:1 hexanes:EtOAc to afford 4.34 g (79%) 1-(4-hydroxy-phenyl)-cyclopentanecarboxylic acid ethyl ester. MS (ES⁺) Calc'd for $C_{14}H_{19}O_3$ (M+1) 235. Found m/z 235 (100%). ¹H NMR.

Step B 1-(4-{2-[1-(4-Methyl-benzyl)-2-oxo-3-propyl-imidazolidin-4-yl]-ethoxy}-phenyl)-cyclopentanecarboxylic acid

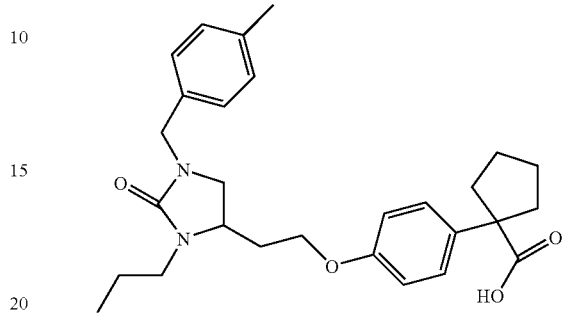

A mixture of 1-(4-hydroxy-phenyl)-cyclopentanecarboxylic acid ethyl ester (0.042 g, 0.179 mmol), toluene-4-sulfonic acid 2-[1-(4-methyl-benzyl)-2-oxo-3-propyl-imidazolidin-4-yl]-ethyl ester (0.085 g, 0.197 mmol) and 325 mesh $K_2CO_3$ (0.050 g, 0.362 mmol) in ethanol (5 mL) was heated at reflux for under $N_2$ for 16 h. The reaction was then treated with aqueous 5 N NaOH (0.5 mL) and heated to reflux 1.5 h. The reaction mixture was cooled, the solvent removed in vacuo. The resultant residue was acidified with aqueous 1 N HCl (10 mL) and extracted with $Et_2O$. The organic layer was dried ($MgSO_4$) and the solvent removed in vacuo to afford 0.058 g crude acid that was purified by preparative HPLC to afford 0.033 g (40%) 1-(4-{2-[1-(4-methyl-benzyl)-2-oxo-3-propyl-imidazolidin-4-yl]-ethoxy}-phenyl)-cyclopentanecarboxylic acid. MS (ES⁺) Calc'd for $C_{28}H_{37}N_2O_4$ (M+1) 465. Found m/z 465 (100%). ¹H NMR.

Example 173

2-Methyl-2-(4-{2-[1-(4-methyl-benzyl)-2-oxo-3-propyl-imidazolidin-4-yl]-ethoxy}-phenoxy)-3-phenyl-propionic acid

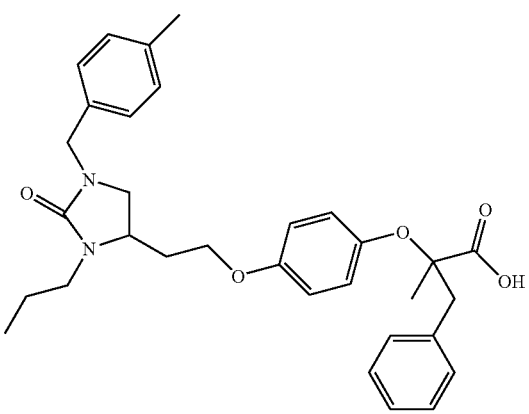

The procedures herein were utilized to prepare 2-methyl-2-(4-{2-[1-(4-methyl-benzyl)-2-oxo-3-propyl-imidazolidin-4-yl]-ethoxy}-phenoxy)-3-phenyl-propionic acid. HRMS (ES⁺) m/z exact mass calcd for $C_{32}H_3BN_2O_5$ [M+1] 531.2859, found 531.2855. ¹H NMR.

Example 174

2-Methoxy-3-(4-{2-[1-(4-methyl-benzyl)-2-oxo-3-propyl-imidazolidin-4-yl]-ethoxy}-phenyl)-propionic acid

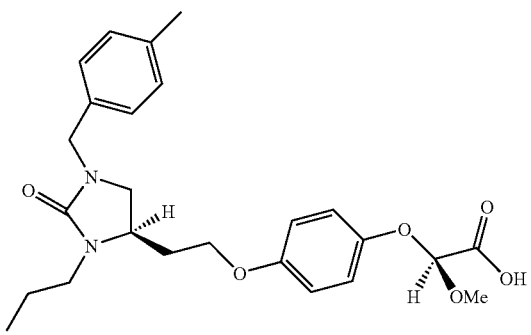

The procedures herein were utilized to prepare 2-Methoxy-3-(4-{2-[1-(4-methyl-benzyl)-2-oxo-3-propyl-imidazolidin-4-yl]-ethoxy}-phenyl)-propionic acid. MS (ES⁺) Calc'd for $C_{26}H_{35}N_2O_5$ (M+1) 455. Found m/z 455 (100%). ¹H NMR.

Example 175

Step A

5-[3-(4-Methoxy-phenyl)-propyl]-3-(4-methyl-benzyl)-imidazolidine-2,4-dione

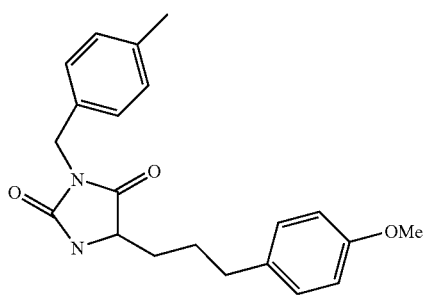

A solution of 5-[3-(4-methoxy-phenyl)-propyl]-imidazolidine-2,4-dione (2.00 g, 8.05 mmol) in DMF (80 mL) was treated with p-methyl benzyl bromide (1.64 g, 8.86 mmol), MgSO₄ (1.94 g, 16.1 mmol) and then 325 mesh K₂CO₃ (2.12 g, 15.3 mmol). The resultant mixture was stirred under N₂ in an ice bath for 30 minutes and then warmed to room temperature for 16 h. The reaction mixture was then filtered, and then aqueous 1N HCl (40 mL) was added to the filtrate. The filtrate was extracted with EtOAc and the organic layer dried (MgSO₄). The solvent was removed in vacuo to give a crude product which was purified by flash chromatography using 3:1 hexanes:EtOAc to afford 2.41 g (85%) 5-[3-(4-methoxy-phenyl)-propyl]-imidazolidine-2,4-dione. MS (ES⁺) Calc'd for $C_{21}H_{25}N_2O_3$ (M+1) 353. Found m/z 353 (100%). ¹H NMR.

Step B

5-[3-(4-Methoxy-phenyl)-propyl]-3-(4-methyl-benzyl)-1-propyl-imidazolidine-2,4-dione

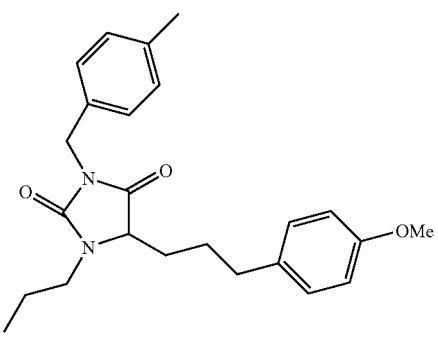

A 0° C. solution of compound 5-[3-(4-methoxy-phenyl)-propyl]-imidazolidine-2,4-dione (2.41 g, 6.84 mmol) in DMF (35 mL) was treated with sodium hydride (60% dispersion, 0.23 g, 5.75 mmol) and warmed to room temperature and stirred under N₂ for 15 minutes. The resultant mixture was cooled to 0° C. and then treated with 1-propyl iodide (0.96 g, 5.64 mmol) and then warmed to room temperature and stirred for 1 h. The reaction was quenched with 1 N HCl (20 mL) and then worked up extractively with Et₂O and water. The organic layer was dried (MgSO₄) and the solvent removed in vacuo to give crude product that was purified by flash chromatography using a 6:1 hexanes:EtOAc to afford 1.58 g (71%) 5-[3-(4-methoxy-phenyl)-propyl]-3-(4-methyl-benzyl)-1-propyl-imidazolidine-2,4-dione. MS (ES⁺) Calc'd for $C_{24}H_{31}N_2O_3$ (M+1) 395. Found m/z 395 (100%). ¹H NMR.

Step C

4-[3-(4-Methoxy-phenyl)-propyl]-1-(4-methyl-benzyl)-3-propyl-imidazolidin-2-one

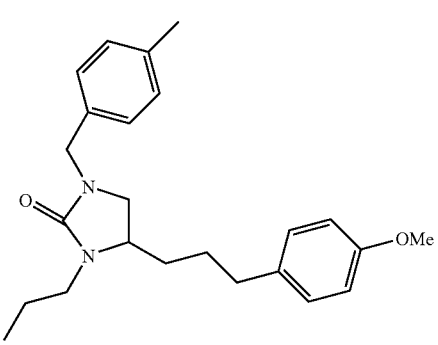

A solution of 5-[3-(4-methoxy-phenyl)-propyl]-3-(4-methyl-benzyl)-1-propyl-imidazolidine-2,4-dione (1.26 g, 3.19 mmol) in THF (20 ml) was treated dropwise with 1 M solution of borane-THF complex in THF (16 mL, 16 mmol) and then stirred at room temperature under N₂ for 22 h. The reaction was quenched with methanol (20 mL) and stirred at room temperature for 2 hr. The solvent was removed in vacuo to give 1.25 g (100%) crude 4-[3-(4-methoxy-phenyl)-propyl]-1-(4-methyl-benzyl)-3-propyl-imidazolidin-2-one that was carried on without purification. MS (ES$^+$) Calc'd for $C_{24}H_{33}N_2O_2$ (M+1) 381. Found m/z 381 (100%). $^1$H NMR.

Step D

4-[3-(4-Hydroxy-phenyl)-propyl]-1-(4-methyl-benzyl)-3-propyl-imidazolidin-2-one

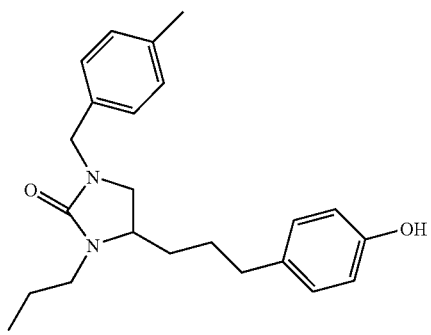

A solution of 4-[3-(4-methoxy-phenyl)-propyl]-1-(4-methyl-benzyl)-3-propyl-imidazolidin-2-one (1.22 g, assume 3.21 mmol) was dissolved in dry $CH_2Cl_2$ (25 mL), cooled to 0° C. and then treated dropwise with $BBr_3$ (2.41 g, 9.63 mmol). The reaction was stirred at 0° C. for 1 h. The reaction mixture was diluted with $Et_2O$ and water, the organic layer was dried (MgSO$_4$), and the solvent removed in vacuo to give crude product that was purified by flash chromatography using 1:1 hexanes:EtOAc to afford 0.687 g (68%) 4-[3-(4-hydroxy-phenyl)-propyl]-1-(4-methyl-benzyl)-3-propyl-imidazolidin-2-one. MS (ES$^+$) Calc'd for $C_{23}H_{31}N_2O_2$ (M+1) 367. Found m/z 367 (100%). $^1$H NMR.

Step E

2-Methyl-2-(4-{3-[1-(4-methyl-benzyl)-2-oxo-3-propyl-imidazolidin-4-yl]-propyl}-phenoxy)-propionic acid ethyl ester

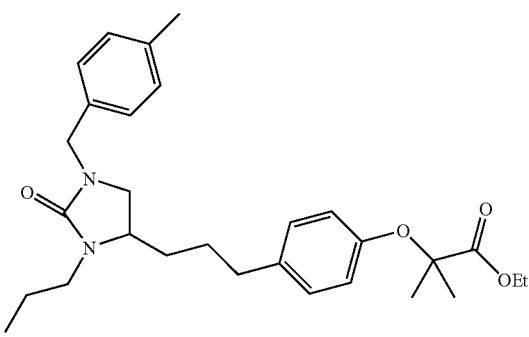

A mixture of 4-[3-(4-hydroxy-phenyl)-propyl]-1-(4-methyl-benzyl)-3-propyl-imidazolidin-2-one (0.687 g, 1.87 mmol), ethyl 2-bromoisobutyrate (2.55 g, 13.1 mmol), MgSO$_4$ (0.22 g, 1.83 mmol) and 325 mesh K$_2$CO$_3$ (0.77 g, 5.57 mmol) in ethanol (60 mL) was heated at 70° C. for under N$_2$ for 16 h. The reaction mixture was cooled and the solvent removed in vacuo to give a residue that was acidified with 1 N HCl (20 mL). The reaction was diluted with EtOAc and washed with water. The organic layer was dried (MgSO$_4$) and the solvent removed in vacuo to give crude product that was purified by flash chromatography using 5:1 hexanes:acetone to afford 0.648 g (72%) 2-methyl-2-(4-{3-[1-(4-methyl-benzyl)-2-oxo-3-propyl-imidazolidin-4-yl]-propyl}-phenoxy)-propionic acid ethyl ester. MS (ES$^+$) Calc'd for $C_{29}H_{41}N_2O_4$ (M+1) 481. Found m/z 481 (100%). $^1$H NMR.

Step F

2-Methyl-2-(4-{3-[1-(4-methyl-benzyl)-2-oxo-3-propyl-imidazolidin-4-yl]-propyl}-phenoxy)-propionic acid

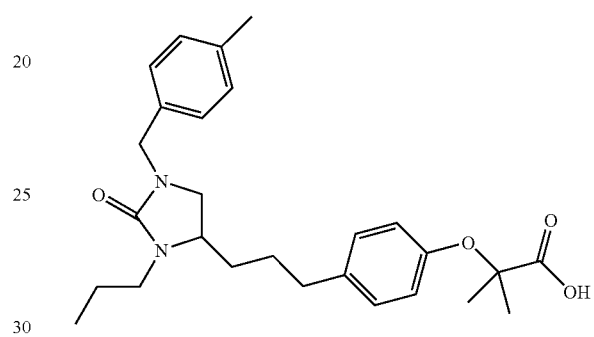

A solution of 2-methyl-2-(4-{3-[(1-(4-methyl-benzyl)-2-oxo-3-propyl-imidazolidin-4-yl]-propyl}-phenoxy)-propionic acid ethyl ester (0.191 g, 0.397 mmol) in ethanol (10 mL) was treated with aqueous 5 N NaOH (0.8 mL) and heated to reflux 1.5 h. The reaction mixture was cooled, the solvent removed in vacuo. The resultant residue was acidified with aqueous 1 N HCl (10 mL) and extracted with Et$_2$O. The organic layer was dried (MgSO$_4$) and the solvent removed in vacuo to afford 0.178 g (99%) 2-methyl-2-(4-{3-[1-(4-methyl-benzyl)-2-oxo-3-propyl-imidazolidin-4-yl]-propyl}-phenoxy)-propionic acid. HRMS (ES$^+$) m/z exact mass calcd for $C_{27}H_{37}N_2O_4$ [M+1] 453.2753, found 453.2751. $^1$H NMR.

Example 176

(R)-2-Methyl-2-(4-{3-[1-(4-methyl-benzyl)-2-oxo-3-propyl-imidazolidin-4-yl]-propyl}-phenoxy)-propionic acid

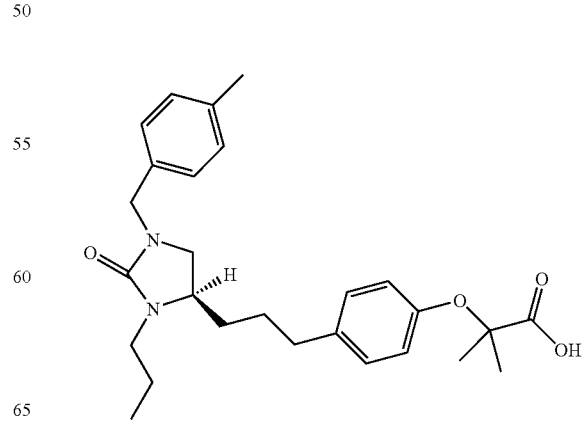

The procedures herein were utilized to prepare (R)-2-methyl-2-(4-{3-[1-(4-methyl-benzyl)-2-oxo-3-propyl-imidazolidin-4-yl]-propyl}-phenoxy)-propionic acid. HRMS (ES⁺) m/z exact mass calcd for $C_{27}H_{37}N_2O_4$ [M+1] 453.2753, found 453.2757. ¹H NMR.

Example 177

Step A 2-(4-{3-[1-(3,4-Dimethyl-benzyl)-2,5-dioxo-imidazolidin-4-yl]-propyl}-phenoxy)-2-methyl-propionic acid tert-butyl ester

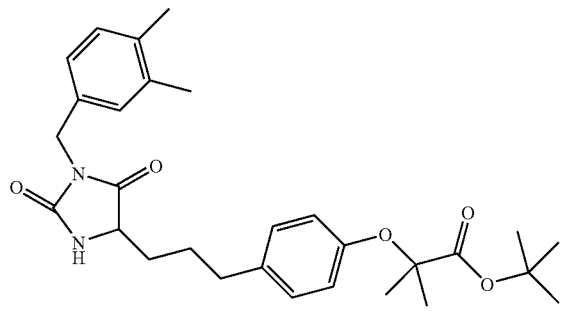

Compound 2-{4-[3-(2,5-dioxo-imidazolidin-4-yl)-propyl]-phenoxy}-2-methyl-propionic acid tert-butyl ester (0.29 g, 0.770 mmol) in DMF (10 mL) was treated with 3,4-dimethyl benzyl chloride (0.131 g, 0.847 mmol), MgSO₄ (0.185 g, 1.54 mmol) and then 325 mesh K₂CO₃ (0.213 g, 1.54 mmol). The resultant mixture was heated to 50° C. under N₂ for 4 h. The reaction mixture was cooled and quenched with 1N HCl (8 mL) and then extracted with EtOAc and water. The organic layer was dried (MgSO₄) and the solvent was removed in vacuo to give a crude product which was purified by flash chromatography using a gradient of 4:1 then 1:1 hexanes:EtOAc to afford 0.202 g (53%) 2-(4-{3-[1-(3,4-dimethyl-benzyl)-2,5-dioxo-imidazolidin-4-yl]-propyl}-phenoxy)-2-methyl-propionic acid tert-butyl ester. MS (ES⁺) Calc'd for $C_{29}H_{39}N_2O_5$ (M+1) 495. Found m/z 495 (100%). ¹H NMR.

Step B 2-(4-{3-[1-(3,4-Dimethyl-benzyl)-2-oxo-imidazolidin-4-yl]-propyl}-phenoxy)-2-methyl-propionic acid tert-butyl ester

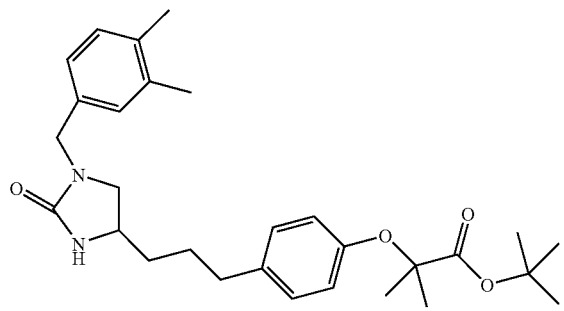

A solution of 2-(4-{3-[1-(3,4-dimethyl-benzyl)-2,5-dioxo-imidazolidin-4-yl]-propyl}-phenoxy)-2-methyl-propionic acid tert-butyl ester (0.113 g, 0.228 mmol) in THF (6 mL) was treated dropwise with 1 M solution of borane-THF complex in THF (4.4 mL, 4.4 mmol) and then stirred at room temperature under N₂ for 32 h. The reaction was quenched with methanol (6 mL) and stirred at room temperature for 2 hr. The solvent was removed in vacuo to give crude product that was purified by flash chromatography using 97:3 CH₂Cl₂:MeOH to afford 0.051 g (47%) 2-(4-{3-[1-(3,4-dimethyl-benzyl)-2-oxo-imidazolidin-4-yl]-propyl}-phenoxy)-2-methyl-propionic acid tert-butyl ester. MS (ES⁺) Calc'd for $C_{29}H_{41}N_2O_4$ (M+1) 481. Found m/z 481 (100%). ¹H NMR.

Step C 2-(4-{3-[1-(3,4-Dimethyl-benzyl)-2-oxo-imidazolidin-4-yl]-propyl}-phenoxy)-2-methyl-propionic acid

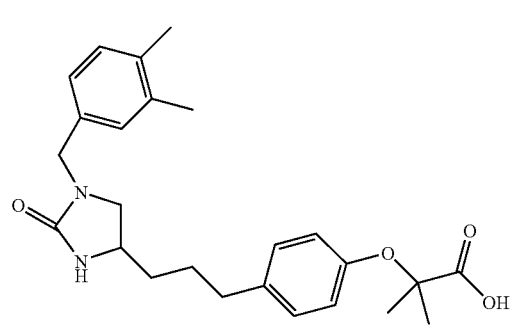

A solution of 2-(4-{3-[1-(3,4-dimethyl-benzyl)-2-oxo-imidazolidin-4-yl]-propyl}-phenoxy)-2-methyl-propionic acid tert-butyl ester (0.051 g, 0.106 mmol) in CH₂Cl₂ (3 mL) was treated with trifluoroacetic acid (0.5 mL) and stirred at room temperature under N₂ for 5 h. The solvent removed in vacuo to give crude acid that was purified by flash chromatography using 94:6 CH₂Cl₂:MeOH to afford 0.011 g (24%) 2-(4-{3-[1-(3,4-dimethyl-benzyl)-2-oxo-imidazolidin-4-yl]-propyl}-phenoxy) -2-methyl-propionic acid. MS (ES⁺) Calc'd for $C_{25}H_{33}N_2O_4$ (M+1) 425. Found m/z 425 (100%). ¹H NMR.

Example 178

2-(4-{3-[1-(4-tert-Butyl-benzyl)-2-oxo-imidazolidin-4-yl]-propyl}-phenoxy)-2-methyl-propionic acid

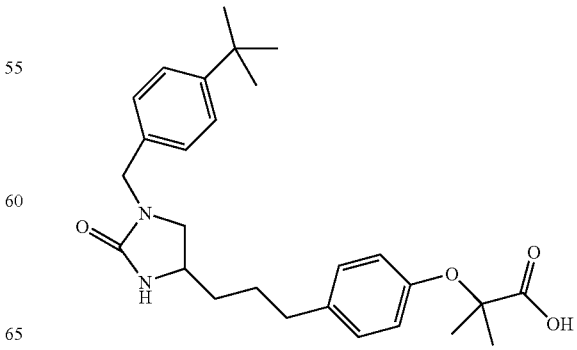

The procedures herein were utilized to prepare 2-(4-{3-[1-(4-tert-butyl-benzyl)-2-oxo-imidazolidin-4-yl]-propyl}-phenoxy)-2-methyl-propionic acid. MS (ES+) Calc'd for $C_{27}H_{37}N_2O_4$ (M+1) 453. Found m/z 453 (100%). $^1$H NMR.

Example 179

2-(4-{3-[1-(4-Chloro-benzyl)-2-oxo-imidazolidin-4-yl]-propyl}-phenoxy)-2-methyl-propionic acid

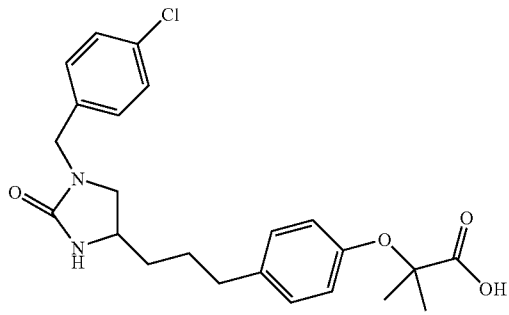

The procedures herein were utilized to prepare 2-(4-{3-[1-(4-chloro-benzyl)-2-oxo-imidazolidin-4-yl]-propyl}-phenoxy)-2-methyl-propionic acid. MS (ES+) Calc'd for $C_{23}H_{28}ClN_2O_4$ (M+1) 431. Found m/z 431 (100%).

Example 180

2-(4-{3-[1-(4-Chloro-benzyl)-3-methyl-2-oxo-imidazolidin-4-yl]-propyl}-phenoxy)-2-methyl-propionic acid

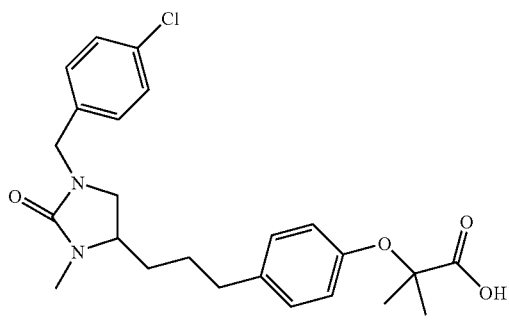

The procedures herein were utilized to prepare 2-(4-{3-[1-(4-chloro-benzyl)-3-methyl-2-oxo-imidazolidin-4-yl]-propyl}-phenoxy)-2-methyl-propionic acid. MS (ES+) Calc'd for $C_{24}H_{30}ClN_2O_4$ (M+1) 445. Found m/z 445 (100%).

Example 181

2-Methyl-2-{4-[3-(3-methyl-1-naphthalen-2-ylmethyl-2-oxo-imidazolidin-4-yl)-propyl]-phenoxy}-propionic acid

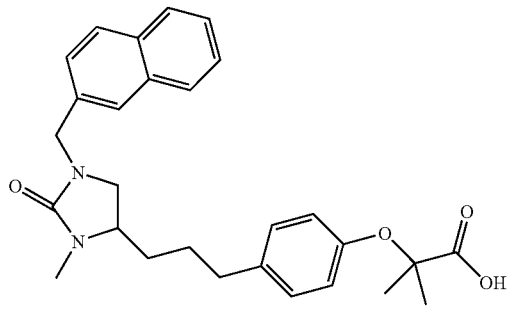

The procedures herein were utilized to prepare 2-methyl-2-{4-[3-(3-methyl-1-naphthalen-2-ylmethyl-2-oxo-imidazolidin-4-yl)-propyl]-phenoxy}-propionic acid. MS (ES+) Calc'd for $C_{28}H_{33}N_2O_4$ (M+1) 461. Found m/z 461 (100%).

Example 182

2-{4-[3-(3-Ethyl-1-naphthalen-2-ylmethyl-2-oxo-imidazolidin-4-yl)-propyl]-phenoxy}-2-methyl-propionic acid

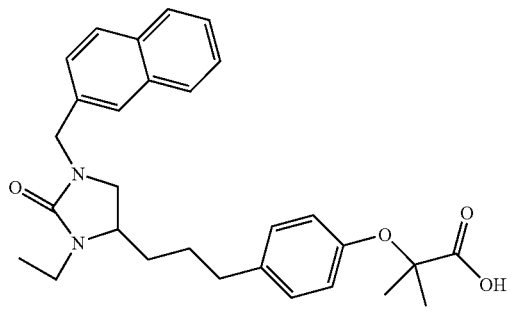

The procedures herein were utilized to prepare 2-{4-[3-(3-ethyl-1-naphthalen-2-ylmethyl-2-oxo-imidazolidin-4-yl)-propyl]-phenoxy}-2-methyl-propionic acid. MS (ES+) Calc'd for $C_{29}H_{35}N_2O_4$ (M+1) 475. Found m/z 475 (100%).

Example 183

2-Methyl-2-{4-[3-(1-naphthalen-2-ylmethyl-2-oxo-3-propyl-imidazolidin-4-yl)-propyl]-phenoxy}-propionic acid

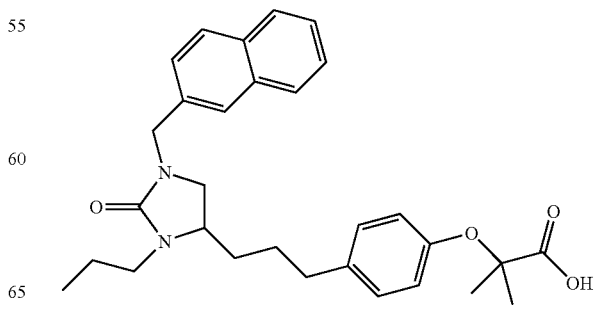

The procedures herein were utilized to prepare 2-methyl-2-{4-[3-(1-naphthalen-2-ylmethyl-2-oxo-3-propyl-imidazolidin-4-yl)-propyl]-phenoxy}-propionic acid. MS (ES+) Calc'd for $C_{30}H_{37}N_2O_4$ (M+1) 489. Found m/z 489 (100%).

Example 184

2-(4-{3-[1-(4-tert-butyl-benzyl)-3-methyl-2-oxo-imidazolidin-4-yl]-propyl}-phenoxy)-2-ethyl-butyric acid

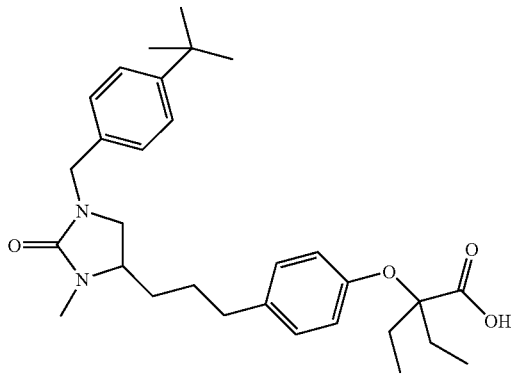

A mixture of 1-(4-tert-butyl-benzyl)-4-[3-(4-hydroxyphenyl)-propyl]-3-methyl-imidazolidin-2-one (0.077 g, 0.202 mmol), potassium tert-butoxide (0.091 g, 0.745 mmol) and ethyl α-bromodiethylacetate (0.361 g, 1.61 mmol) in 2-methyl-2-propanol (8 mL) was heated to 100° C. under $N_2$ for 16 h. Aqueous 5 N NaOH (1.5 mL) was added to the reaction mixture and it was heated at reflux an additional 1 h. The reaction mixture was cooled and quenched with 1 N HCl. The mixture was then diluted with water and extracted with $CH_2Cl_2$. The organic layer was dried ($Na_2SO_4$) and the solvent removed in vacuo to afford 0.288 g of crude product that was purified by preparative HPLC to give 0.014 g (14%) 2-(4-{3-[1-(4-tert-butyl-benzyl)-3-methyl-2-oxo-imidazolidin-4-yl]-propyl}-phenoxy)-2-ethyl-butyric acid. $^1$H NMR. HRMS (ES+) m/z exact mass calcd for $C_{30}H_{43}N_2O_4$ [M+1] 495.3223, found 495.3252.

Example 185

1-(4-{3-[1-(4-tert-butyl-benzyl)-3-methyl-2-oxo-imidazolidin-4-yl]-propyl}-phenoxy)-cyclohexanecarboxylic acid

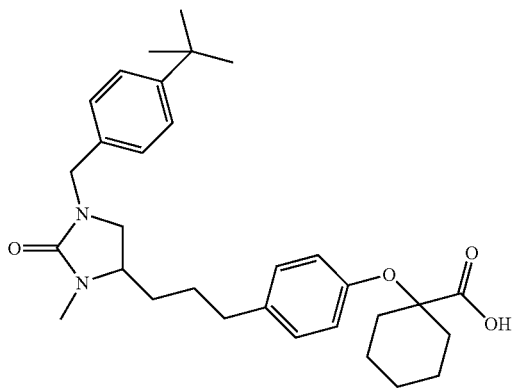

A mixture of 1-(4-tert-butyl-benzyl)-4-[3-(4-hydroxyphenyl)-propyl]-3-methyl-imidazolidin-2-one (0.074 g, 0.194 mmol) and potassium tert-butoxide (0.044 g, 0.392 nmol) in 2-methyl-2-propanol (8 mL) was heated to 60° C. under $N_2$ and then and methyl 1-bromocyclohexanecarboxylate (0.274 g, 1.16 mmol) was added dropwise to the to 60° C. solution. Additional potassium tert-butoxide (0.044 g, 0.392 mmol) and methyl 1-bromocyclohexanecarboxylate (0.274 g, 1.16 mmol) was added to the reaction and it was stirred for 2 h. The reaction mixture was cooled and quenched with 1 N HCl. The mixture was then diluted with water and extracted with $CH_2Cl_2$. The organic layer was dried ($Na_2SO_4$) and the solvent removed in vacuo to afford 0.400 g of crude product that was purified by preparative HPLC to give 0.059 g (60%) 1-(4-{3-[1-(4-tert-butyl-benzyl)-3-methyl-2-oxo-imidazolidin-4-yl]-propyl}-phenoxy)-cyclohexanecarboxylic acid. $^1$H NMR. HRMS (ES+) m/z exact mass calcd for $C_{31}H_{43}N_2O_4$ [M+1] 507.3223, found 507.3237.

Example 186

2-(4-{3-[1-(4-tert-butyl-benzyl)-3-methyl-2-oxo-imidazolidin-4-yl]-propyl}-phenoxy)-2-ethyl-hexanoic acid

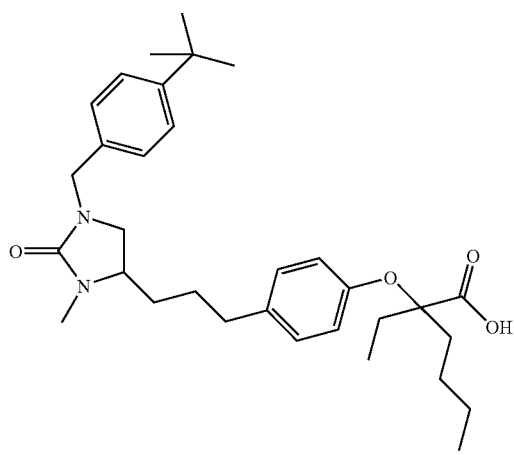

The procedures herein were utilized to prepare 2-(4-{3-[1-(4-tert-butyl-benzyl)-3-methyl-2-oxo-imidazolidin-4-yl]-propyl}-phenoxy)-2-ethyl-hexanoic acid $^1$H NMR. HRMS (ES+) m/z exact mass calcd for $C_{32}H_{47}N_2O_4$ [M+1] 523.3536, found 523.3555.

Example 187

2-(4-{3-[1-(4-tert-butyl-benzyl)-3-methyl-2-oxo-imidazolidin-4-yl]-propyl}-phenoxy)-pentanoic acid

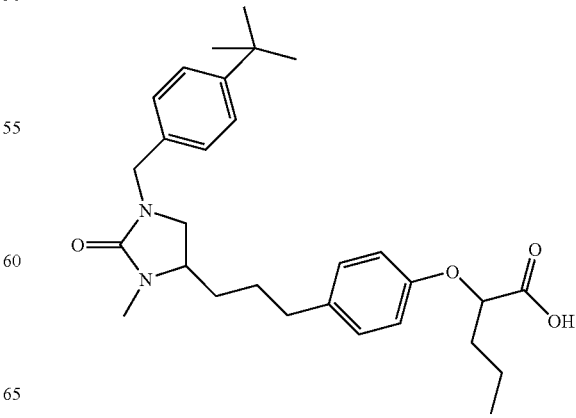

The procedures herein were utilized to prepare 2-(4-{3-[1-(4-tert-butyl-benzyl)-3-methyl-2-oxo-imidazolidin-4-yl]-propyl}-phenoxy)-pentanoic acid. ¹H NMR. HRMS (ES⁺) m/z exact mass calcd for $C_{29}H_{42}N_2O_4$ [M+1] 481.3066, found 481.3062.

Example 188

2-(4-{3-[1-(4-tert-butyl-benzyl)-3-methyl-2-oxo-imidazolidin-4-yl]-propyl}-phenoxy)-4-methyl-pentanoic acid

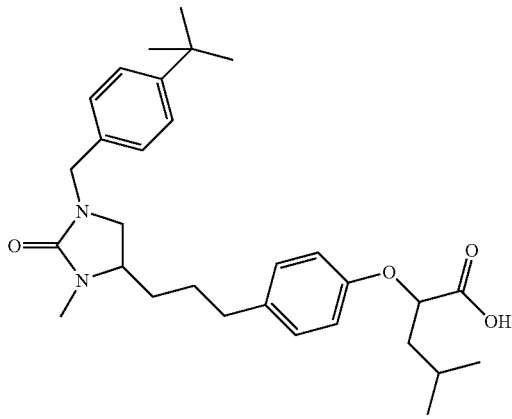

The procedures herein were utilized to prepare 2-(4-{3-[1-(4-tert-butyl-benzyl)-3-methyl-2-oxo-imidazolidin-4-yl]-propyl}-phenoxy)-4-methyl-pentanoic acid. ¹H NMR. HRMS (ES⁺) m/z exact mass calcd for $C_{30}H_{43}N_2O_4$ [M+1] 495.3223, found 495.3244.

Example 189

Step A 2-bromo-2-methyl-pentanoic acid

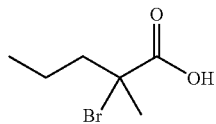

A mixture of 2-methylpentoic acid (10.0 g, 86.1 mmol), N-bromosuccinimide (22.98 g, 129 mmol) and conc. $H_2SO_4$ (2.5 mL) in trifluoroacetic acid (50 mL) was heated to reflux under $N_2$ for 16 h. The reaction was cooled and the solvent removed in vacuo and the crude oil was purified via vacuum distillation (1 mm, 135-140° C.) to give a slowly crystallizing oil that was diluted with $CH_2Cl_2$ and then filtered to remove solids. The solvent was removed in vacuo to afford 9.08 g (54%) of 2-bromo-2-methyl-pentanoic acid. ¹H NMR.

Step B

4-[3-(4-hydroxy-phenyl)-propyl]-3-methyl-1-(4-trifluoromethyl-benzyl)-imidazolidin-2-one

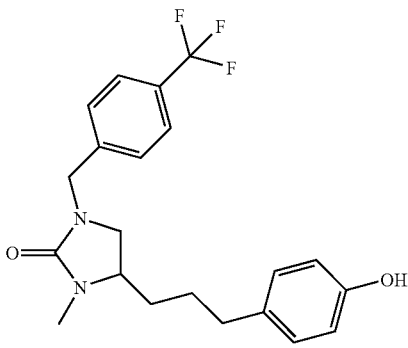

A solution of 4-[3-(4-methoxy-phenyl)-propyl]-3-methyl-1-(4-trifluoromethyl-benzyl)-imidazolidin-2-one (3.51 g, 8.63 mmol) in dry $CH_2Cl_2$ (60 mL), cooled to −78° C. and then treated dropwise with $BBr_3$ (6.49 g, 25.9 mmol). The reaction was warmed 0° C. and stirred for 2 h under $N_2$. The reaction mixture was diluted with water and extracted with $CH_2Cl_2$. The organic layer was dried ($MgSO_4$), and the solvent removed in vacuo to give crude product that was purified by flash chromatography using 2:1 hexanes:acetone to afford 3.01 g (89%) 4-[3-(4-hydroxy-phenyl)-propyl]-3-methyl-1-(4-trifluoromethyl-benzyl)-imidazolidin-2-one. ¹H NMR. MS (ES³⁰) Calc'd for $C_{21}H_{24}N_2O_2F_3$ (M+1) 393. Found m/z 393 (100%).

Step C 2-methyl-2-(4-{3-[3-methyl-2-oxo-1-(4-trifluoromethyl-benzyl)-imidazolidin-4-yl]-propyl}-phenoxy)-pentanoic acid ethyl ester

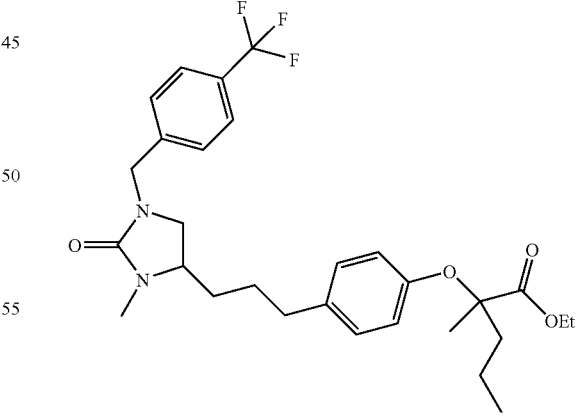

A mixture of 4-[3-(4-hydroxy-phenyl)-propyl]-3-methyl-1-(4-trifluoromethyl-benzyl)-imidazolidin-2-one (0.51 g, 1.30 mmol) and 2-bromo-2-methyl-pentanoic acid (2.54 g, 13.0 mmol) in 2-methyl-2-propanol (10 mL) was heated to 45° C. under $N_2$ and then a solution of 1 M potassium tert-butoxide in 2-methyl-2-propanol (27.3 mL, 27.3 mmol) was added dropwise and the reaction was stirred at 45° C. for 40 minutes. The reaction mixture was cooled and quenched with 1 N HCl (50 mL). The mixture was then diluted with water and extracted with Et₂O. The organic layer was dried (Na₂SO₄) and the solvent removed in vacuo to afford crude product that was combined with EtOH (50 mL) and conc. H₂SO₄ (6 mL). The mixture was heated to reflux for 3 h. The reaction mixture was cooled and the solvent removed in vacuo. The residue was diluted with water and extracted with EtOAc and the organic layer was dried (Na₂SO₄). The solvent was removed in vacuo to give crude product that was purified by flash chromatography using 5:1 hexanes:acetone to afford 0.491 g (71%) 2-methyl-2-(4-{3-[3-methyl-2-oxo-1-(4-trifluoromethyl-benzyl)-imidazolidin-4-yl]-propyl}-phenoxy)-pentanoic acid ethyl ester. This material could be purified by chiral preparative HPLC (conditions,) $^1$H NMR. MS (ES$^+$) m/z calcd for $C_{29}H_{38}N_2O_4F_3$ [M+1] 535. Found 535 (100%).

Step D 2-methyl-2-(4-{3-[3-methyl-2-oxo-1-(4-trifluoromethyl-benzyl)-imidazolidin-4-yl]-propyl}-phenoxy)-pentanoic acid

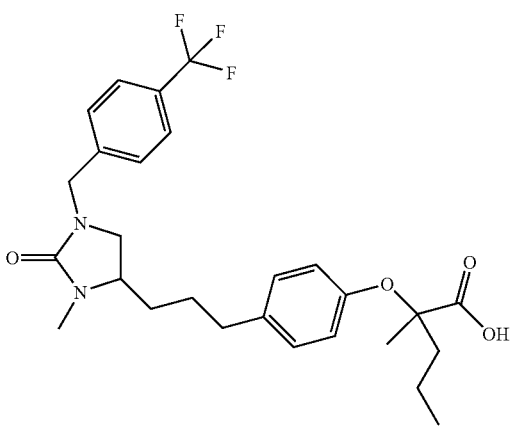

A mixture of 2-methyl-2-(4-{3-[3-methyl-2-oxo-1-(4-trifluoromethyl-benzyl)-imidazolidin-4-yl]-propyl}-phenoxy)-pentanoic acid ethyl ester (0.020 g, 0.040 mmol) and 5 N NaOH (0.5 mL) in EtOH (6 mL) was heated at reflux for 1 h. The reaction mixture was cooled and quenched with 1 N HCl. The mixture was then diluted with water and extracted with CH₂Cl₂. The organic layer was dried (Na₂SO₄) and the solvent removed in vacuo to afford 0.010 g (53%) 2-methyl-2-(4-{3-[3-methyl-2-oxo-1-(4-trifluoromethyl-benzyl)-imidazolidin-4-yl]-propyl}-phenoxy)-pentanoic acid. $^1$H NMR. HRMS (ES$^+$) m/z exact mass calcd for $C_{27}H_{34}N_2O_4F_3$ [M+1] 507.2471, found 507.2459.

Example 190

Step A 2-methoxy-3-(4-{2-[3-methyl-2-oxo-1-(4-trifluoromethyl-benzyl)-imidazolidin-4-yl]-ethoxy}-phenyl)-propionic acid ethyl ester

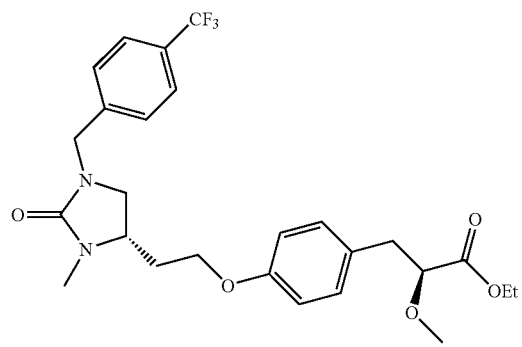

A mixture of 3-(4-hydroxy-phenyl)-2-methoxy-propionic acid ethyl ester 0.027 g, 0.120 mmol), toluene-4-sulfonic acid 2-[3-methyl-2-oxo-1-(4-trifluoromethyl-benzyl)-imidazolidin-4-yl]-ethyl ester (0.061 g, 0.133 mmol) and Cs₂CO₃ (0.059 g, 0.181 mmol) in DMF (4 mL) was heated to 55° C. under N₂ for 16 h. The reaction was cooled and quenched with 1 N HCl (10 mL) and worked up extractively with Et₂O and water. The organic layer was dried (MgSO₄) and the solvent removed in vacuo to afford crude product that was purified by flash chromatography using 4:1 then 3:1 hexanes:acetone to afford 0.040 g (64%) 2-methoxy-3-(4-{2-[3-methyl-2-oxo-1-(4-trifluoromethyl-benzyl)-imidazolidin-4-yl]-ethoxy}-phenyl)-propionic acid ethyl ester. $^1$H NMR. MS (ES$^+$) Calc'd for $C_{26}H_{32}N_2O_5F_3$ (M+1) 509. Found m/z 509 (100%).

Step B 2-methoxy-3-(4-{2-[3-methyl-2-oxo-1-(4-trifluoromethyl-benzyl)-imidazolidin-4-yl]-ethoxy}-phenyl)-propionic acid

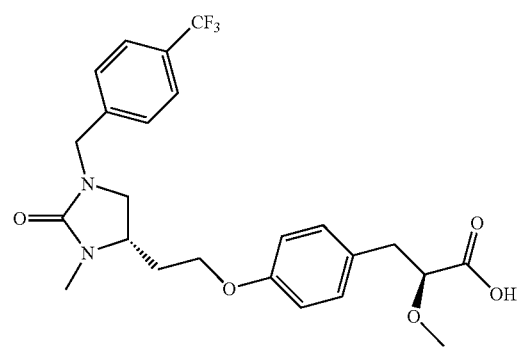

A solution of 2-methoxy-3-(4-{2-[3-methyl-2-oxo-1-(4-trifluoromethyl-benzyl)-imidazolidin-4-yl]-ethoxy}-phenyl)-propionic acid ethyl ester (0.040 g, 0.079 mmol) in ethanol (5 mL) was treated with aqueous 5 N NaOH (0.5 mL) and stirred at room temperature for 2 h. The solvent removed in vacuo. The resultant residue was acidified with aqueous 1 N HCl (10 mL) and extracted with CH$_2$Cl$_2$. The organic layer was dried (Na$_2$SO$_4$) and the solvent removed in vacuo to afford 0.026 g (68%) 2-methoxy-3-(4-{2-[3-methyl-2-oxo-1-(4-trifluoromethyl-benzyl)-imidazolidin-4-yl]-ethoxy}-phenyl)- propionic acid. $^1$H NMR. MS (ES$^+$) m/z calc'd for C$_{24}$H$_{28}$N$_2$O$_5$F$_3$ (M+1) 481. Found m/z 481.

Example 191

2-ethoxy-3-(4-{2-[3-methyl-2-oxo-1-(4-trifluoromethyl-benzyl)-imidazolidin-4-yl]-ethoxy}-phenyl)-propionic acid

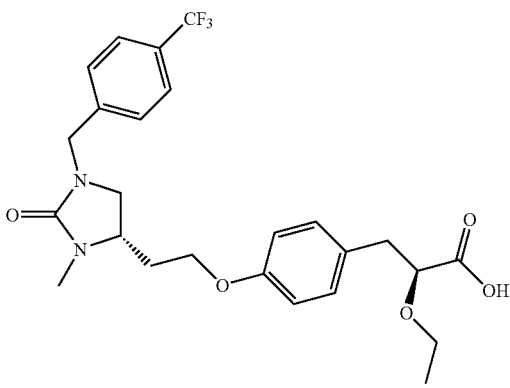

The procedures herein were utilized to prepare 2-ethoxy-3-(4-{2-[3-methyl-2-oxo-1-(4-trifluoromethyl-benzyl)-imidazolidin-4-yl]-ethoxy}-phenyl)-propionic acid. $^1$H NMR. MS (ES$^+$) m/z calc'd for C$_{25}$H$_{30}$N$_2$O$_5$F$_3$ (M+1) 495. Found m/z 495.

Example 192

3-(4-{2-[3-methyl-2-oxo-1-(4-trifluoromethyl-benzyl)-imidazolidin-4-yl]-ethoxy}-phenyl)-2-propoxy-propionic acid

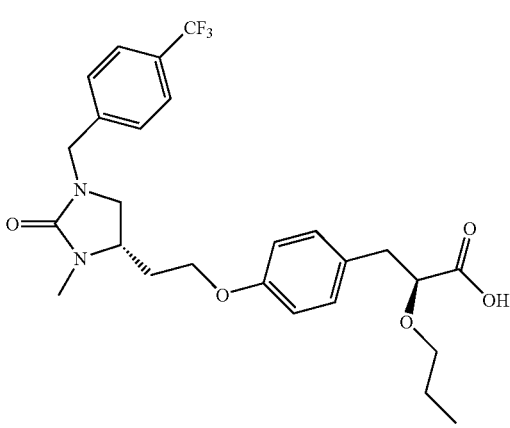

The procedures herein were utilized to prepare 3-(4-{2-[3-methyl-2-oxo-1-(4-trifluoromethyl-benzyl)-imidazolidin-4-yl]-ethoxy}-phenyl)-2-propoxy-propionic acid. $^1$H NMR. HRMS (ES$^+$) m/z exact mass calc'd for C$_{26}$H$_{32}$N$_2$O$_5$F$_3$ (M+1) 509.2263. Found m/z 509.2268.

Example 193

Step A 3-(4-benzyloxy-phenyl)-2-cyclopentyloxy-propionic acid cyclopentyl ester

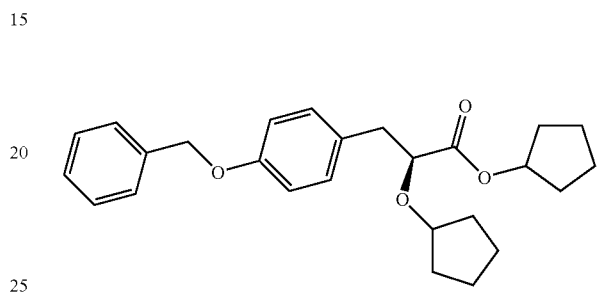

A mixture of 3-(4-benzyloxy-phenyl)-2-hydroxy-propionic acid (1.0 g, 3.67 mmol), cyclopentyl iodide (7.2 g, 36.7 mmol) and silver (I) oxide (4.25 g, 18.3 mmol) in DMF (15 mL) was heated at 55° C. under N$_2$ for 72 h. The reaction mixture was cooled, diluted with Et$_2$O and filtered through hyflo. The filtrate was extracted with water and the organic layer was dried (MgSO$_4$) and the solvent removed in vacuo to afford crude product that was purified by flash chromatography using 10:1 hexanes:acetone to afford 0.255 g (17%) 3-(4-benzyloxy-phenyl)-2-cyclopentyloxy-propionic acid cyclopentyl ester. R$_f$=0.67 (1:1 hexanes:acetone). $^1$H NMR.

Step B 2-cyclopentyloxy-3-(4-hydroxy-phenyl)-propionic acid cyclopentyl ester

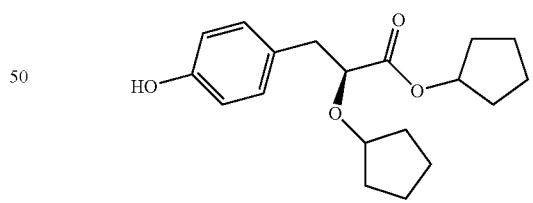

A mixture of 3-(4-benzyloxy-phenyl)-2-cyclopentyloxy-propionic acid cyclopentyl ester (0.137 g, 0.335 mmol) and 10% Pd/C (0.14 g) in EtOAc (70 mL) was purged with N$_2$ then H$_2$ and then stirred under a H$_2$ balloon atmosphere for 3 h at room temperature. Upon reaction completion, MgSO$_4$ was added and the mixture filtered through hyflo. The solvent was removed in vacuo to afford 0.090 g (84%) 2-cyclopentyloxy-3-(4-hydroxy-phenyl)-propionic acid cyclopentyl ester. $^1$H NMR. MS (ES$^-$) Calc'd for C$_{19}$H$_{25}$O$_4$ (M−1) 317. Found m/z 317 (100%).

Step C 2-cyclopentyloxy-3-(4-{2-[3-methyl-2-oxo-1-(4-trifluoromethyl-benzyl)-imidazolidin-4-yl]-ethoxy}-phenyl)-propionic acid cyclopentyl ester

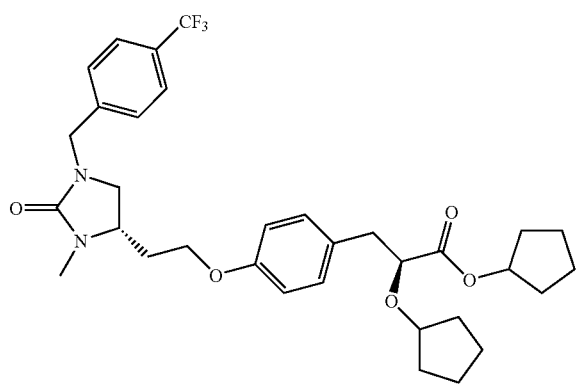

A mixture of 2-cyclopentyloxy-3-(4-hydroxy-phenyl)-propionic acid cyclopentyl ester (0.090 g, 0.283 mmol), toluene-4-sulfonic acid 2-[3-methyl-2-oxo-1-(4-trifluoromethyl-benzyl)-imidazolidin-4-yl]-ethyl ester (0.140 g, 0.307 mmol) and $Cs_2CO_3$ (0.138 g, 0.423 mmol) in DMF (10 mL) was heated to 65° C. under $N_2$ for 16 h. The reaction was cooled and quenched with 1 N HCl (10 mL) and worked up extractively with $Et_2O$ and water. The organic layer was dried ($MgSO_4$) and the solvent removed in vacuo to afford crude product that was purified by flash chromatography using 3:1 hexanes:acetone to afford 0.108 g (64%) 2-cyclopentyloxy-3-(4-{2-[3-methyl-2-oxo-1-(4-trifluoromethyl-benzyl)-imidazolidin-4-yl]-ethoxy}-phenyl)-propionic acid cyclopentyl ester. $^1$H NMR. MS (ES$^+$) Calc'd for $C_{33}H_{42}N_2O_5F_3$ (M+1) 603. Found m/z 603 (100%).

Step D 2-cyclopentyloxy-3-(4-{2-[3-methyl-2-oxo-1-(4-trifluoromethyl-benzyl)-imidazolidin-4-yl]-ethoxy}-phenyl)-propionic acid

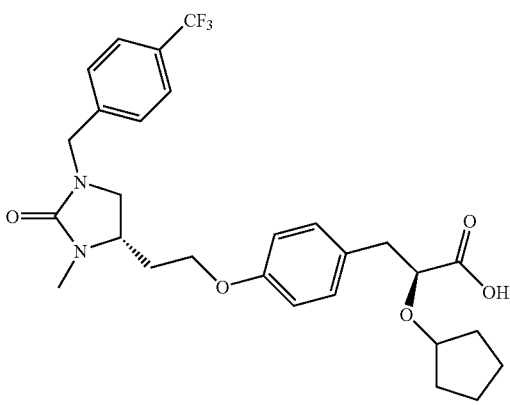

A solution of 2-cyclopentyloxy-3-(4-{2-[3-methyl-2-oxo-1-(4-trifluoromethyl-benzyl)-imidazolidin-4-yl]-ethoxy}-phenyl)-propionic acid cyclopentyl ester (0.108 g, 0.179 mmol) in ethanol (10 mL) was treated with aqueous 5 N NaOH (1 mL) and stirred at room temperature for 3 h. The solvent removed in vacuo. The resultant residue was acidified with aqueous 1 N HCl (10 mL) and extracted with $CH_2Cl_2$. The organic layer was dried ($Na_2SO_4$) and the solvent removed in vacuo to afford 0.106 g of crude acid that was purified by chiral HPLC (20×250 nm Chiralpak AD, 3:2 heptane:IPA with 0.1% trifluoroacetic acid mobile phase, 14 mL/min, 225 nm) to give 0.080 g (83%) of 100% de 2-cyclopentyloxy-3-(4-{2-[3-methyl-2-oxo-1-(4-trifluoromethyl-benzyl)-imidazolidin-4-yl]-ethoxy}-phenyl)-propionic acid. $^1$H NMR. HRMS (ES$^+$) m/z exact mass calc'd for $C_{28}H_{34}N_2O_5F_3$ (M+1) 535.2420. Found m/z 535.2408.

Example 194

Step A 5-(4-benzyloxy-benzyl)-2,2-dimethyl-[1,3]dioxolan-4-one

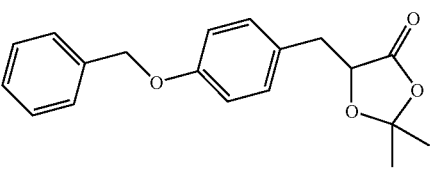

A mixture of 3-(4-benzyloxy-phenyl)-2-hydroxy-propionic acid (2.0 g, 7.34 mmol), 2,2-dimethoxypropane (18.63 g, 179 mmol) and pyridinium p-toluene sulfonate (0.92 g, 3.66 mmol) in $CHCl_3$ (80 mL) was heated to reflux for 40 minutes under $N_2$. The reaction was cooled and worked up extractively with $CH_2Cl_2$ and water. The organic layer was dried ($Na_2SO_4$) and the solvent removed in vacuo to afford crude product that was purified by flash chromatography using 10:1 hexanes:acetone to afford 2.01 g (88%) 5-(4-benzyloxy-benzyl)-2,2-dimethyl-[1,3]dioxolan-4-one. $R_f$=0.53 (1:1 hexanes:acetone). $^1$H NMR (500 MHz, $CDCl_3$) δ 7.43-7.35 (m, 4H), 7.34-7.29 (m, 1H), 7.16 (d, 2H, J=8.80 Hz), 6.91 (d, 2H, J=8.80 Hz), 5.04 (s, 2H), 4.61 (dd, 1H, J=6.36 Hz, J=4.40 Hz), 3.13 (dd, 1H, J=14.67 Hz, J=4.40 Hz), 2.99 (dd, 1H, J=14.67 Hz, J=4.40 Hz), 1.50 (s, 3H), 1.36 (s, 3H); MS (ES$^+$) Calc'd for $C_{19}H_{20}O_4$ (M+NH$_4$) 330. Found m/z 330 (100%).

Step B 5-(4-hydroxy-benzyl)-2,2-dimethyl-[1,3]dioxolan-4-one

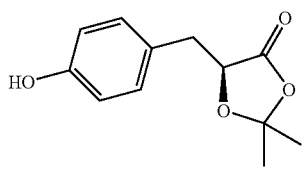

A mixture of 5-(4-benzyloxy-benzyl)-2,2-dimethyl-[1,3]dioxolan-4-one (1.0 g, 3.20 mmol) and 10% Pd/C (0.75 g) in EtOAc (40 mL) was purged with $N_2$ then $H_2$ and then stirred under a $H_2$ balloon atmosphere for 3 h at room temperature. Upon reaction completion, $Na_2SO_4$ was added and the mixture filtered through hyflo. The solvent was removed in vacuo to afford 0.747 g (100%) 5-(4-hydroxy-benzyl)-2,2-dimethyl-[1,3]dioxolan-4-one. ¹H NMR (500 MHz, CDCl₃) δ 7.11 (d, 2H, J=8.31 Hz), 6.76 (d, 2H, J=8.31 Hz), 4.92 (bs, 1H), 4.61 (dd, 1H, J=6.36 Hz, J=4.40 Hz), 3.11 (dd, 1H, J=14.67 Hz, J=4.40 Hz), 2.98 (dd, 1H, J=14.67 Hz, J=4.40 Hz), 1.50 (s, 3H), 1.36 (s, 3H); MS (ES⁻) Calc'd for C₁₂H₁₃O₄ (M−1) 221. Found m/z 221 (100%).

Step C 3-(4-hydroxy-phenyl)-2-isopropoxy-propionic acid ethyl ester

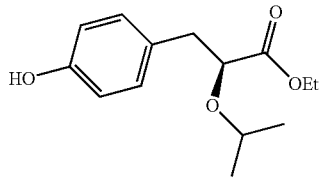

A 0° C. solution of 5-(4-hydroxy-benzyl)-2,2-dimethyl-[1,3]dioxolan-4-one (0.20 g, 0.900 mmol) and triethylsilane (1.05 g, 9.0 mmol) in dry CH₂Cl₂ (10 mL) was treated dropwise with a 1 molar solution of TiCl₄ in CH₂Cl₂ (0.90 mL, 0.900 mmol) under N₂. The resultant red slurry was stirred at 0° C. for 15 minutes and then warmed to room temperature for 45 minutes. The reaction mixture was quenched with water and extracted with EtOAc. The organic layer was dried (Na₂SO₄) and the solvent removed in vacuo to afford 0.320 g of crude acid that was carried on as is. The oil was dissolved in EtOH (25 mL) and treated with conc. H₂SO₄ (1 mL) and then stirred at room temperature for 17 h under N₂. The solvent was removed in vacuo and the oil extracted with EtOAc and water. The organic layer was dried (Na₂SO₄) and the solvent removed in vacuo to afford crude product that was purified by flash chromatography using 5:1 hexanes:acetone to give 0.158 g (70%) 3-(4-hydroxy-phenyl)-2-isopropoxy-propionic acid ethyl ester. R$_f$=0.48 (1:1 hexanes:acetone). ¹H NMR (500 MHz, CDCl₃) δ 7.10 (d, 2H, J=8.80 Hz), 6.73 (d, 2H, J=8.31 Hz), 4.79 (bs, 1H) 4.20-4.12 (m, 2H), 3.99 (dd, 1H, J=8.31 Hz, J=4.89 Hz), 3.49 (hp, 1H, J=5.87 Hz), 2.95-2.83 (m, 2H), 1.23 (t, 3H, J=6.85 Hz), 1.14 (d, 3H, J=6.36 Hz), 0.97 (d, 3H, J=6.36 Hz); MS (ES⁻) Calc'd for C₁₄H₁₉O₄ (M−1) 251. Found m/z 251 (100%). 97.6% ee by chiral HPLC assay (Chiralcel OJ, 4.6×250 mm, 90/10 heptane/IPA eluent, 1 mL/min, 266 nm).

Step D 3-(4-{2-[1-(4-hydroxy-benzyl)-3-methyl-2-oxo-imidazolidin-4-yl]-ethoxy}-phenyl)-2-isopropoxy-propionic acid ethyl ester

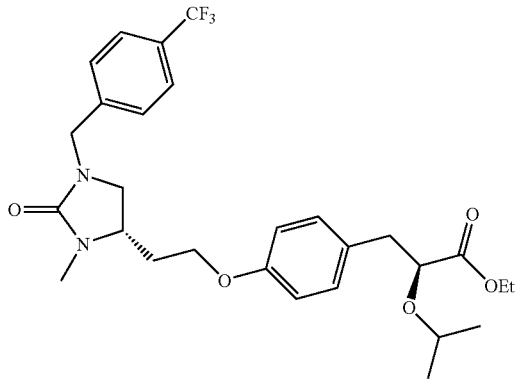

A mixture of 3-(4-hydroxy-phenyl)-2-isopropoxy-propionic acid ethyl ester (0.034 g, 0.134 mmol), toluene-4-sulfonic acid 2-[3-methyl-2-oxo-1-(4-trifluoromethyl-benzyl)-imidazolidin-4-yl]-ethyl ester (0.068 g, 0.149 mmol) and Cs₂CO₃ (0.066 g, 0.202 mmol) in DMF (6 mL) was heated to 65° C. under N₂ for 16 h. The reaction was cooled and quenched with 1 N HCl (10 mL) and worked up extractively with Et₂O and water. The organic layer was dried (MgSO₄) and the solvent removed in vacuo to afford crude product that was purified by flash chromatography using 4:1 hexanes:acetone to afford 0.048 g (67%) 3-(4-{2-[1-(4-hydroxy-benzyl)-3-methyl-2-oxo-imidazolidin-4-yl]-ethoxy}-phenyl)-2-isopropoxy-propionic acid ethyl ester. R$_f$=0.36 (1:1 hexanes:acetone). ¹H NMR (500 MHz, CDCl₃) δ ¹H NMR (500 MHz, CDCl₃) □ 7.56 (d, 2H, J=8.07 Hz), 7.36 (d, 2H, J=8.07 Hz), 7.13 (d, 2H, J=8.80 Hz), 6.72 (d, 2H, J=8.80 Hz), 4.47, 4.36 (AB$_q$, 2H, J=15.16 Hz), 4.20-4.12 (m, 2H), 4.00-3.94 (m, 3H), 3.66-3.59 (m, 1H), 3.48 (hp, 1H, J=5.87 Hz), 3.37 (t, 1H, J=8.80 Hz), 2.98 (t, 1H, J=8.80 Hz), 2.90-2.85 (m, 2H), 2.84 (s, 3H), 2.27-2.23 (m, 1H), 1.93-1.84 (m, 1H), 1.23 (t, 3H, J=6.85 Hz), 1.14 (d, 3H, J=5.87 Hz), 0.97 (d, 3H, J=5.87 Hz). MS (ES⁺) Calc'd for C₂₈H₃₆N₂O₅F₃ (M+1) 537. Found m/z 537 (100%).

Step E 3-(4-{2-[1-(4-hydroxy-benzyl)-3-methyl-2-oxo-imidazolidin-4-yl]-ethoxy}-phenyl)-2-isopropoxy-propionic acid

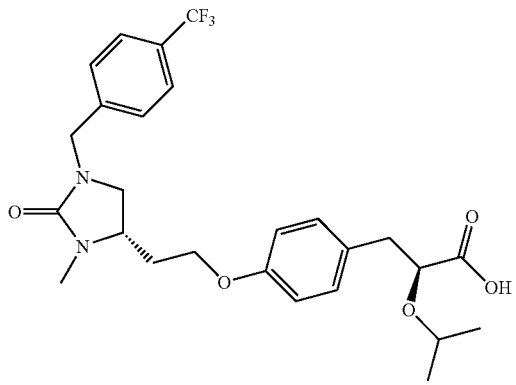

A solution of 3-(4-{2-[1-(4-hydroxy-benzyl)-3-methyl-2-oxo-imidazolidin-4-yl]-ethoxy}-phenyl)-2-isopropoxy-propionic acid ethyl ester (0.048 g, 0.089 mmol) in ethanol (8 mL) was treated with aqueous 5 N NaOH (1.5 mL) and stirred at room temperature for 2 h. The solvent removed in vacuo. The resultant residue was acidified with aqueous 1 N HCl (15 mL) and extracted with CH₂Cl₂. The organic layer was dried (Na₂SO₄) and the solvent removed in vacuo to afford 0.038 g (84%) 3-(4-{2-[1-(4-hydroxy-benzyl)-3-methyl-2-oxo-imidazolidin-4-yl]-ethoxy}-phenyl)-2-isopropoxy- propionic acid. ¹H NMR (500 MHz, CDCl₃) δ 7.49 (d, 2H, J=8.07 Hz), 7.30 (d, 2H, J=8.07 Hz), 7.06 (d, 2H, J=8.31 Hz), 6.66 (d, 2H, J=8.31 Hz), 4.40, 4.31 (AB$_q$, 2H, J=15.65 Hz), 4.03-4.01 (m, 1H), 3.90 (t, 2H, J=5.87 Hz), 3.59-3.53 (m, 1H), 3.48 (hp, 1H, J=5.87 Hz), 3.31 (t, 1H, J=8.80 Hz), 3.12-2.96 (m, 1H), 2.95 (t, 1H, J=8.80 Hz), 2.90-2.79 (m, 1H), 2.78 (s, 3H), 2.27-2.23 (m, 1H), 1.93-1.84 (m, 1H), 1.14 (d, 3H, J=5.87 Hz), 0.97 (d, 3H, J=5.87 Hz). HRMS (ES⁺) m/z exact mass calc'd for C₂₆H₃₂N₂O₅F₃ (M+1) 509.2274. Found m/z 509.2263.

Example 195

2-(1-ethyl-propoxy)-3-(4-{2-[1-(4-hydroxy-benzyl)-3-methyl-2-oxo-imidazolidin-4-yl]-ethoxy}-phenyl)-propionic acid

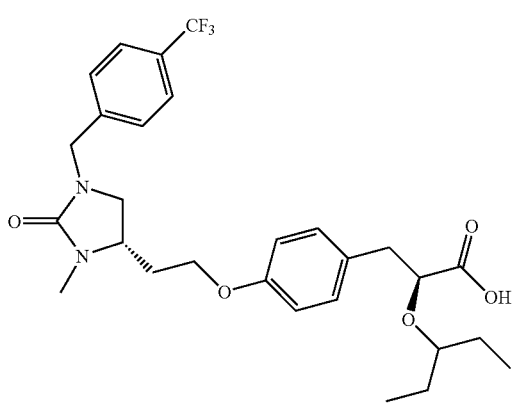

The procedures herein were utilized to prepare 2-(1-ethyl-propoxy)-3-(4-{2-[1-(4-hydroxy-benzyl)-3-methyl-2-oxo-imidazolidin-4-yl]-ethoxy}-phenyl)-propionic acid. $^1$H NMR. MS (ES$^+$) m/z calc'd for $C_{28}H_{35}N_2O_5F_3$ (M+1) 537. Found m/z 537.

Example 196

2-methoxy-3-(4-{3-[3-methyl-2-oxo-1-(4-trifluoromethyl-benzyl)-imidazolidin-4-yl]-propyl}-phenyl)-propionic acid

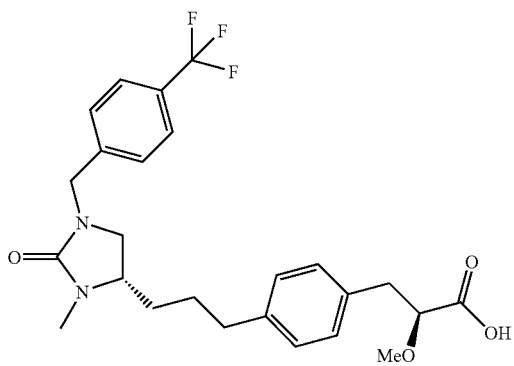

The procedures herein were utilized to prepare 2-methoxy-3-(4-{3-[3-methyl-2-oxo-1-(4-trifluoromethyl-benzyl)-imidazolidin-4-yl]-propyl}-phenyl)-propionic acid. $^1$H NMR. HRMS (ES$^+$) m/z exact mass calc'd for $C_{25}H_{30}N_2O_4F_3$ (M+1) 479.2158. Found m/z 479.2171.

Example 197

2-methoxy-2-methyl-3-(4-{3-[3-methyl-2-oxo-1-(4-trifluoromethyl-benzyl)-imidazolidin-4-yl]-propyl}-phenyl)-propionic acid

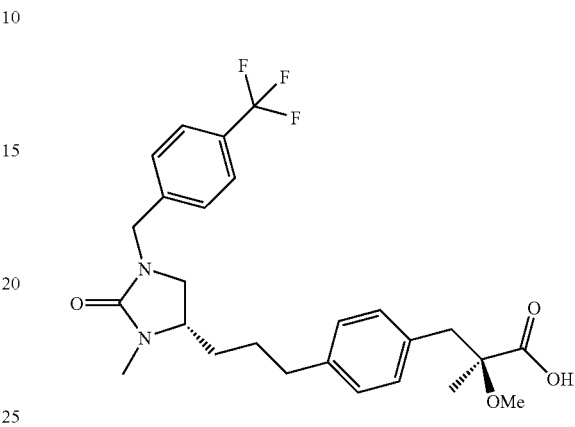

The procedures herein were utilized to prepare 2-methoxy-2-methyl-3-(4-{3-[3-methyl-2-oxo-1-(4-trifluoromethyl-benzyl)-imidazolidin-4-yl]-propyl}-phenyl)-propionic acid. $^1$H NMR. HRMS (ES$^+$) m/z exact mass calc'd for $C_{26}H_{32}N_2O_4F_3$ (M+1) 493.2314. Found m/z 493.2321.

Example 198

Step A 2-(4-trifluoromethyl-phenoxy)-propionic acid ethyl ester

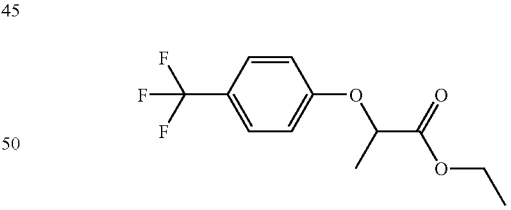

A mixture of trifluromethyl-p-cresol (9.74 g, 60.1 mmol), ethyl 2-bromopropionate (10.9 g, 60.1 mmol) and Cs$_2$CO$_3$ (39.15 g, 120 mmol) in DMF (450 mL) was heated at 90° C. under N$_2$ for 16 h. The reaction was cooled and filtered using Et$_2$O to rinse the solids. The filtrate was washed with 1 N HCl (200 mL) and water. The organic layer was dried (Na$_2$SO$_4$) and the solvent removed in vacuo to afford 19.03 g of crude product that was purified by flash chromatography using 6:1 hexanes:acetone to afford 13.96 g (89%) 2-(4-trifluoromethyl-phenoxy)-propionic acid ethyl ester. $R_f$=0.63 (1:1 hexanes:acetone). $^1$NMR.

Step B

3-(3-benzyloxy-phenyl)-3-hydroxy-2-methyl-2-(4-trifluoromethyl-phenoxy)-propionic acid ethyl ester

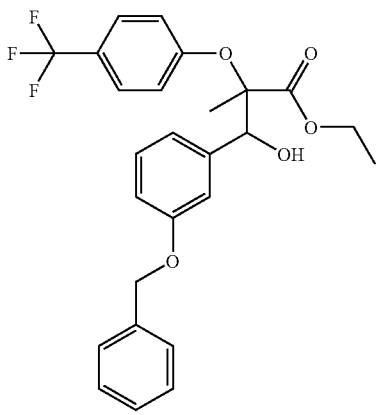

A −78° C. solution of 2-(4-trifluoromethyl-phenoxy)-propionic acid ethyl ester (10.0 g, 38.1 mmol) in THF (80 mL) was transferred via cannula to a −78° C. solution of 1.5 M LDA-THF complex (45.8 mL, 68.7 mmol) in THF (80 mL). The resultant mixture was stirred for 5 minutes at −78° C. and then 3-benzyloxybenzaldehyde (7.3 g, 34.4 mmol) was added in one portion and the reaction mixture stirred at −78° C. for 5 minutes and was then was quenched with a −78° C. THF solution of acetic acid (6.82 g, 113.5 mmol). The reaction mixture was diluted with aqueous saturated $NH_4Cl$ and extracted with $Et_2O$. The organic layer was dried ($Na_2SO_4$) and the solvent removed in vacuo to afford 19.84 g of crude product that was purified by flash chromatography using 8:1 then 4:1 hexanes:acetone to afford 7.88 g (44%) 3-(3-benzyloxy-phenyl)-3-hydroxy-2-methyl-2-(4-trifluoromethyl-phenoxy)-propionic acid ethyl ester as a mixture of diastereomers. $R_f$=0.55 (1:1 hexanes:acetone). $^1$NMR.

Step C

3-(3-hydroxy-phenyl)-2-methyl-2-(4-trifluoromethyl-phenoxy)-propionic acid ethyl ester

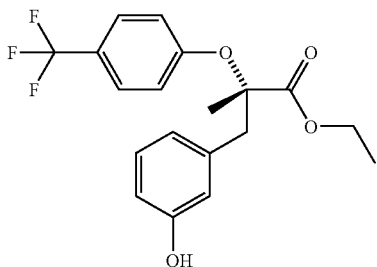

Trifluoroacetic anhydride (6.99 g, 33.3 mmol) was added dropwise to a 0° C. solution of 3-(3-benzyloxy-phenyl)-3-hydroxy-2-methyl-2-(4-trifluoromethyl-phenoxy)-propionic acid ethyl ester (7.88 g, 16.6 mmol) and pyridine (13.10 g, 0.166 mol) in $CH_2Cl_2$ (150 mL). The reaction solution was warmed to room temperature and stirred under $N_2$ for 3 h. The reaction solution was washed twice with aqueous 1 N HCl (175 mL each) and the organic layer dried ($MgSO_4$). The solvent was removed in vacuo to give 9.03 g (95%) of crude 3-(3-benzyloxy-phenyl)-2-methyl-3-(2,2,2-trifluoro-acetoxy)-2-(4-trifluoromethyl-phenoxy)-propionic acid ethyl ester which was carried on immediately.

The 3-(3-benzyloxy-phenyl)-2-methyl-3-(2,2,2-trifluoro-acetoxy)-2-(4-trifluoromethyl-phenoxy)-propionic acid ethyl ester (9.03 g, 15.8 mmol) was combined with 10% Pd/C (9.0 g) in ethyl acetate (200 mL). The mixture was purged with $N_2$ then $H_2$ and then stirred at room temperature under a $H_2$ balloon for approximately 48 h. The reaction mixture was filtered through hyflo to remove the catalyst and the resultant filtrate dried ($MgSO_4$). The solvent was removed in vacuo to give crude product that was purified by flash chromatography using 3:1 hexanes:acetone to afford 1.96 g (32%) 3-(3-hydroxy-phenyl)-2-methyl-2-(4-trifluoromethyl-phenoxy)-propionic acid ethyl ester. The racemic phenol was purified by preparative chiral HPLC (Chiralcel OD, 5×37 cm, 95:5 heptane:IPA mobile phase, 150 ml/min, 285 nm, GK8-A015150-031). $R_f$=0.32 (1:1 hexanes:acetone). 1 NMR. MS (ES$^-$) Calc'd for $C_{19}H_{18}O_4F_3$ (M−1) 367. Found m/z 367 (100%).

Step D

2-methyl-3-(3-{2-[3-methyl-2-oxo-1-(4-trifluoromethyl-benzyl)-imidazolidin-4-yl]-ethoxy}-phenyl)-2-(4-trifluoromethyl-phenoxy)-propionic acid ethyl ester

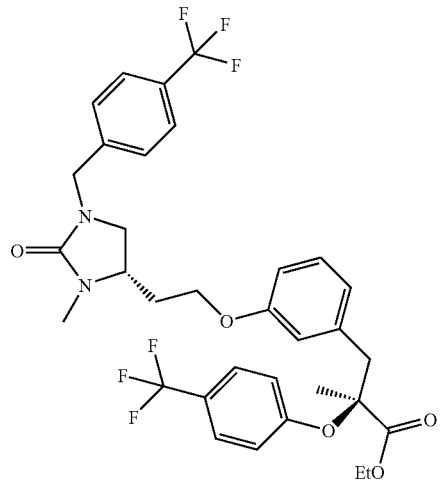

A mixture of 3-(3-hydroxy-phenyl)-2-methyl-2-phenoxy-propionic acid ethyl ester (0.100 g, 0.271 mmol), toluene-4-sulfonic acid 2-[3-methyl-2-oxo-1-(4-trifluoromethyl-benzyl)-imidazolidin-4-yl]-ethyl ester (0.136 g, 0.298 mmol) and $Cs_2CO_3$ (0.133 g, 0.408 mmol) in DMF (8 mL) was heated to 65° C. under $N_2$ for 17 h. The reaction was cooled and quenched with 1 N HCl (10 mL) and worked up extractively with $Et_2O$ and water. The organic layer was dried ($MgSO_4$) and the solvent removed in vacuo to afford crude product that was purified by flash chromatography using 4:1 hexanes:acetone to afford 0.113 g (64%) 2-methyl-3-(3-{2-[3-methyl-2-oxo-1-(4-trifluoromethyl-benzyl)-imidazolidin-4-yl]-ethoxy}-phenyl)-2-(4-trifluoromethyl-phenoxy)-propionic acid ethyl ester. $^1$H NMR. MS (ES$^+$) Calc'd for $C_{33}H_{35}N_2O_5F_6$ (M +1) 653. Found m/z 653 (100%).

Step E 2-methyl-3-(3-{2-[3-methyl-2-oxo-1-(4-trifluoromethyl-benzyl)-imidazolidin-4-yl]-ethoxy}-phenyl)-2-(4-trifluoromethyl-phenoxy)-propionic acid

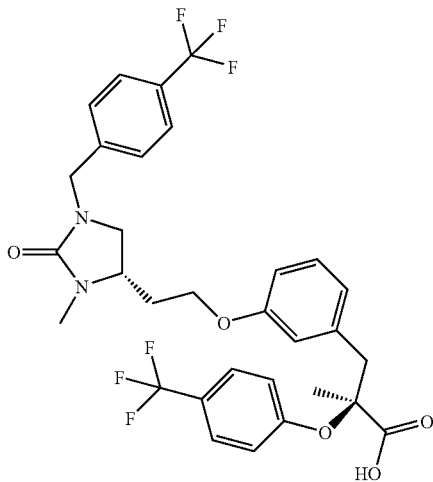

A solution of 2-methyl-3-(3-{2-[3-methyl-2-oxo-1-(4-trifluoromethyl-benzyl)-imidazolidin-4-yl]-ethoxy}-phenyl)-2-(4-trifluoromethyl-phenoxy)-propionic acid ethyl ester (0.113 g, 0.173 mmol) in ethanol (12 mL) was treated with aqueous 5 N NaOH (2 mL) and heated to reflux 1 h. The reaction mixture was cooled, the solvent removed in vacuo. The resultant residue was acidified with aqueous 1 N HCl (15 mL) and extracted with $CH_2Cl_2$. The organic layer was dried ($Na_2SO_4$) and the solvent removed in vacuo to afford 0.108 g (100%) 2-methyl-3-(3-{2-[3-methyl-2-oxo-1-(4-trifluoromethyl-benzyl)-imidazolidin-4-yl]-ethoxy}-phenyl)-2-(4-trifluoromethyl-phenoxy)-propionic acid. $^1$H NMR. HRMS (ES$^+$) m/z exact mass calc'd for $C_{31}H_{31}N_2O_5F_6$ (M+1) 625.2137. Found m/z 625.2134.

Example 199

2-methyl-3-(3-{2-[3-methyl-2-oxo-1-(4-trifluoromethyl-benzyl)-imidazolidin-4-yl]-ethoxy}-phenyl)-2-(3-trifluoromethyl-phenoxy)-propionic acid

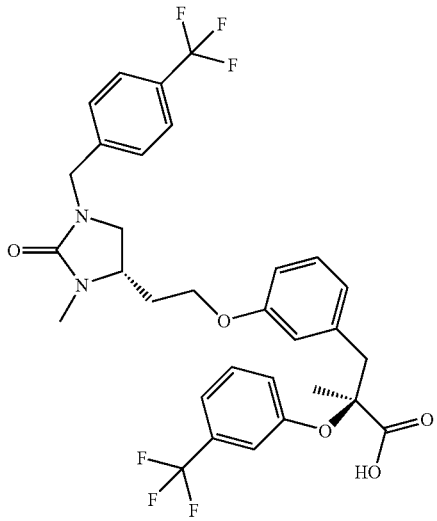

The procedures herein were utilized to prepare 2-methyl-3-(3-{2-[3-methyl-2-oxo-1-(4-trifluoromethyl-benzyl)-imidazolidin-4-yl]-ethoxy}-phenyl)-2-(3-trifluoromethyl-phenoxy)-propionic acid. $^1$H NMR. HRMS (ES$^+$) m/z exact mass calc'd for $C_{31}H_{31}N_2O_5F_6$ (M+1) 625.2137. Found m/z 625.2128.

Example 200

3-{4-[2-(1-hexyl-3-methyl-2-oxo-imidazolidin-4-yl)-ethoxy]-phenyl}-2-methyl-2-phenoxy-propionic acid

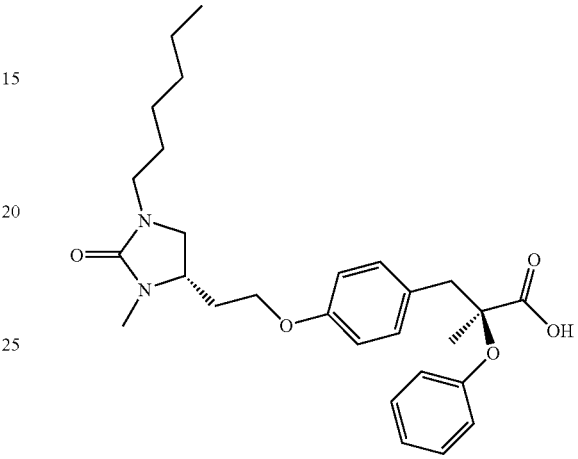

The procedures herein were utilized to prepare 3-{4-[2-(1-hexyl-3-methyl-2-oxo-imidazolidin-4-yl)-ethoxy]-phenyl}-2-methyl-2-phenoxy-propionic acid. $^1$H NMR. HRMS (ES$^+$) m/z exact mass calc'd for $C_{28}H_{39}N_2O_5$ (M+1) 483.2859. Found m/z 483.2882.

Example 201

3-{4-[2-(1-benzo[1,3]dioxol-5-ylmethyl-3-methyl-2-oxo-imidazolidin-4-yl)-ethoxy]-phenyl}-2-methyl-2-phenoxy-propionic acid

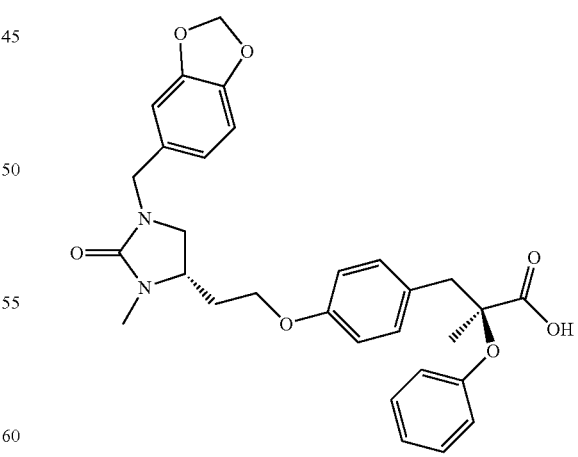

The procedures herein were utilized to prepare 3-{4-[2-(1-benzo[1,3]dioxol-5-ylmethyl-3-methyl-2-oxo-imidazolidin-4-yl)-ethoxy]-phenyl}-2-methyl-2-phenoxy-propionic acid. $^1$H NMR. HRMS (ES$^+$) m/z exact mass calc'd for $C_{30}H_{33}N_2O_7$ (M+1) 533.2288. Found m/z 533.2305.

Example 202

2-methyl-3-{4-[2-(3-methyl-2-oxo-1-quinolin-2-ylmethyl-imidazolidin-4-yl)-ethoxy]-phenyl}-2-phenoxy-propionic acid

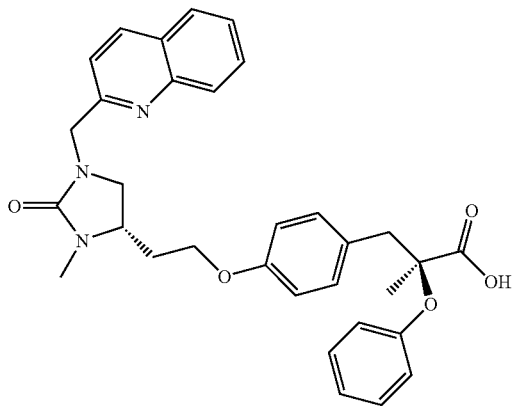

The procedures herein were utilized to prepare 2-methyl-3-{4-[2-(3-methyl-2-oxo-1-quinolin-2-ylmethyl-imidazolidin-4-yl)-ethoxy]-phenyl}-2-phenoxy-propionic acid. $^1$H NMR. HRMS (ES$^+$) m/z exact mass calc'd for $C_{32}H_{34}N_3O_5$ (M+1) 540.2498. Found m/z 540.2523.

Example 203

2-methyl-3-(4-{2-[3-methyl-2-oxo-1-(4-trifluoromethoxy-benzyl)-imidazolidin-4-yl]-ethoxy}-phenyl)-2-phenoxy-propionic acid

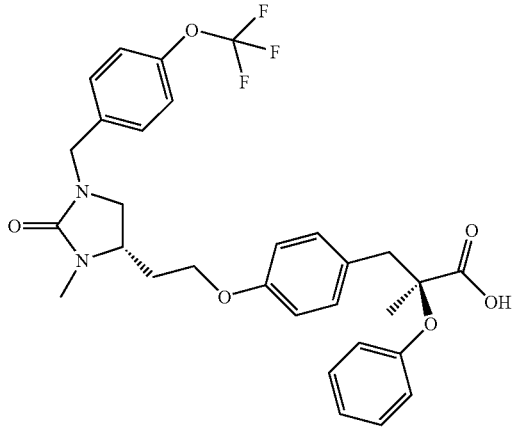

The procedures herein were utilized to prepare 2-methyl-3-(4-{2-[3-methyl-2-oxo-1-(4-trifluoromethoxy-benzyl)-imidazolidin-4-yl]-ethoxy}-phenyl)-2-phenoxy-propionic acid ethyl ester. $^1$H NMR. MS (ES$^+$) m/z calc'd for $C_{30}H_{32}N_2O_6F_3$ (M+1) 573. Found m/z 573.

Example 204

2-methyl-3-(4-{2-[3-methyl-2-oxo-1-(4-trifluoromethyl-benzyl)-imidazolidin-4-yl]-ethoxy}-phenyl)-2-p-tolyloxy-propionic acid

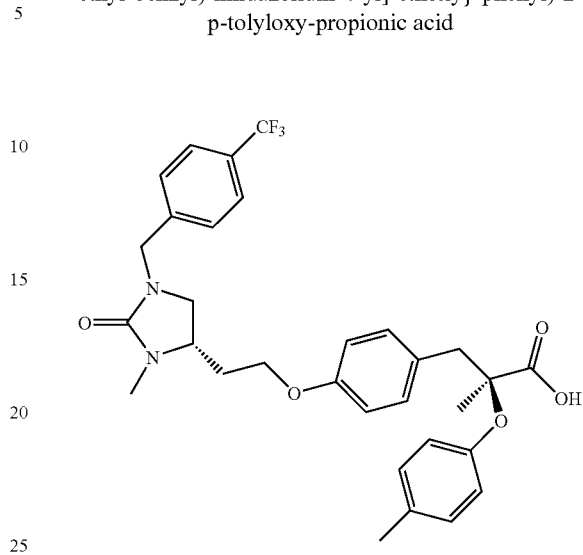

The procedures herein were utilized to prepare 2-methyl-3-(4-{2-[3-methyl-2-oxo-1-(4-trifluoromethyl-benzyl)-imidazolidin-4-yl]-ethoxy}-phenyl)-2-p-tolyloxy-propionic acid. $^1$H NMR. HRMS (ES$^+$) m/z exact mass calc'd for $C_{31}H_{34}N_2O_5F_3$ (M+1) 571.2420. Found m/z 571.2423.

Example 205

2-(benzo[1,3]dioxol-5-yloxy)-2-methyl-3-(4-{2-[3-methyl-2-oxo-(4-trifluororoethyl-benzyl)-imidazolidin-4-yl]-ethoxy}-phenyl)-propionic acid

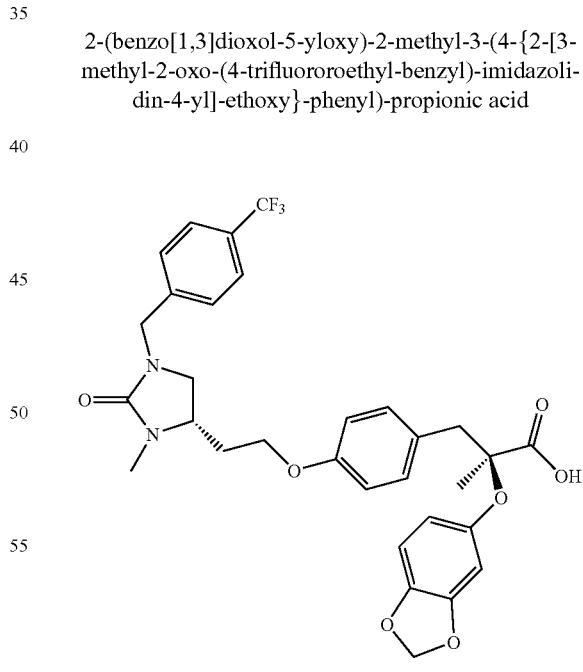

The procedures herein were utilized to prepare 2-(benzo[1,3]dioxol-5-yloxy)-2-methyl-3-(4-{2-[3-methyl-2-oxo-1-(4-trifluoromethyl-benzyl)-imidazolidin-4-yl]-ethoxy}-phenyl)-propionic acid. $^1$H NMR. HRMS (ES$^+$) m/z exact mass calc'd for $C_{31}H_{32}N_2O_7F_3$ (M+1) 601.2162. Found m/z 601.2180.

Example 206

3-(4-{2-[1-(4-hydroxy-benzyl)-3-methyl-2-oxo-imidazolidin-4-yl]-ethoxy}-phenyl)-2-methyl-2-(4-trifluoromethyl-phenoxy)-propionic acid

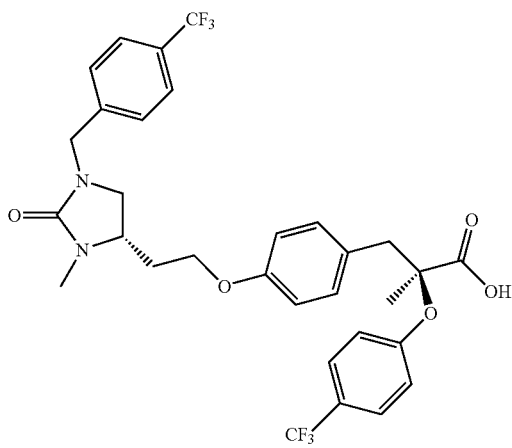

The procedures herein were utilized to prepare 3-(4-{2-[1-(4-hydroxy-benzyl)-3-methyl-2-oxo-imidazolidin-4-yl]-ethoxy}-phenyl)-2-methyl-2-(4-trifluoromethyl-phenoxy)-propionic acid. $^1$H NMR. HRMS (ES$^+$) m/z exact mass calc'd for $C_{31}H_{31}N_2O_5F_6$ (M+1) 625.2137. Found m/z 625.2144.

Example 207

3-(4-{2-[1-(3,4-dimethyl-benzyl)-3-methyl-2-oxo-imidazolidin-4-yl]-ethoxy}-phenyl)-2-methyl-2-phenoxy-propionic acid

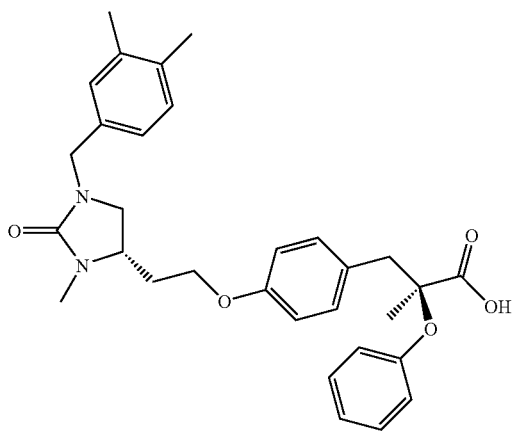

The procedures herein were utilized to prepare 3-(4-{2-[1-(3,4-dimethyl-benzyl)-3-methyl-2-oxo-imidazolidin-4-yl]-ethoxy}-phenyl)-2-methyl-2-phenoxy-propionic acid. $^1$H NMR. HRMS (ES$^+$) m/z exact mass calc'd for $C_{31}H_{37}N_2O_5$ (M+1) 517.2702. Found m/z 517.2704.

Example 208

2-(2-Butyl-4-{3-[1-(4-tert-butyl-benzyl)-3-methyl-2-oxo-imidazolidin-4-yl]-propyl}-phenoxy)-2-methyl-propionic acid

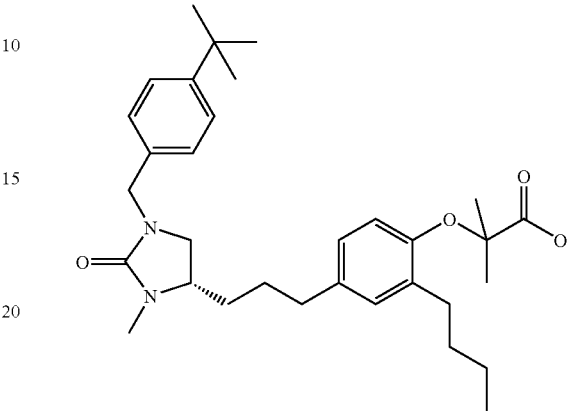

Step A 2-(2-Butyl-4-{3-[1-(4-tert-butyl-benzyl)-3-methyl-2-oxo-imidazolidin-4-yl]-propyl}-phenoxy)-2-methyl-propionic acid methyl ester

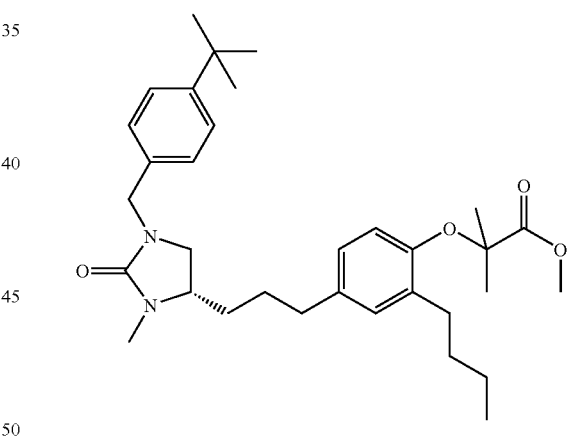

The titled compound was prepared using 2-(4-{3-[1-(4-tert-Butyl-benzyl)-3-methyl-2-oxo-imidazolidin-4-yl]-propyl}-2-iodo-phenoxy)-2-methyl-propionic acid methyl ester (0.121 g, 0.200 mmole) and n-butyl bornic acid (0.061, 0.600 mmole) to produce a colorless oil (0.046 g, 45%). Mass [EI+] 537 (M+H)$^+$.

Step B 2-(2-Butyl-4-{3-[1-(4-tert-butyl-benzyl)-3-methyl-2-oxo-imidazolidin-4-yl]-propyl}-phenoxy)-2-methyl-propionic acid The titled compound was prepared using 2-(2-Butyl-4-{3-[1-(4-tert-butyl-benzyl)-3-methyl-2-oxo-imidazolidin-4-yl]-propyl}-phenoxy)-2-methyl-propionic acid methyl ester (0.043 g, 0.080 mmole) to produce a colorless oil (0.033 g, 81%). Mass [EI+] 523 (M+H)+, [EI−] 521 (M−H)−.

Example 209

2-(4-{3-[1-(4-tert-Butyl-benzyl)-3-methyl-2-oxo-imidazolidin-4-yl]-propyl}-2-isobutyl-phenoxy)-2-methyl-propionic acid

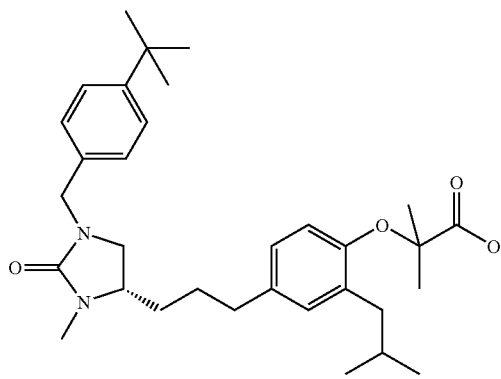

Step A 2-(4-{3-[1-(4-tert-Butyl-benzyl)-3-methyl-2-oxo-imidazolidin-4-yl]-propyl}-2-isobutyl-phenoxy)-2-methyl-propionic acid methyl ester

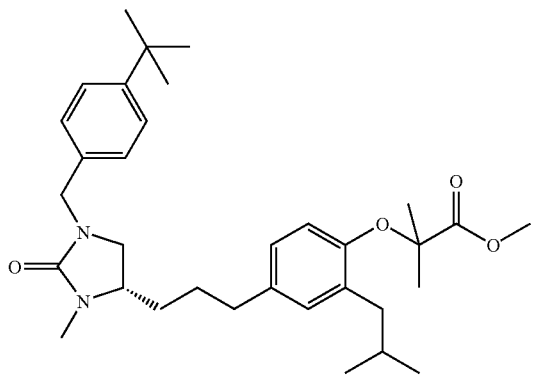

The titled compound was prepared using 2-(4-{3-[1-(4-tert-Butyl-benzyl)-3-methyl-2-oxo-imidazolidin-4-yl]-propyl}-2-iodo-phenoxy)-2-methyl-propionic acid methyl ester (0.121 g, 0.200 mmole) and isobutyl bornic acid (0.061, 0.600 mmole) to produce a colorless oil (0.089 g, 8.3%). Mass [EI+] 537 (M+H)+.

Step B 2-(4-{3-[1-(4-tert-Butyl-benzyl)-3-methyl-2-oxo-imidazolidin-4-yl]-propyl}-2-isobutyl-phenoxy)-2-methyl- propionic acid The titled compound was prepared using 2-(4-{3-[1-(4-tert-Butyl-benzyl)-3-methyl-2-oxo-imidazolidin-4-yl]-propyl}-2-isobutyl-phenoxy)-2-methyl-propionic acid methyl ester (0.088 g, 0.164 mmole) to produce colorless oil (0.0747 g, 87%). Mass [EI+] 523 (M+H)+, [EI−] 521 (M−H)−.

Example 210

2-(5-{3-[1-(4-tert-Butyl-benzyl)-3-methyl-2-oxo-imidazolidin-4-yl]-propyl}-biphenyl-2-yloxy)-2-methyl-propionic acid

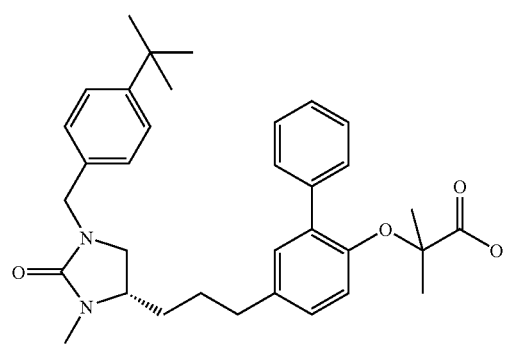

Step A 2-(5-{3-[1-(4-tert-Butyl-benzyl)-3-methyl-2-oxo-imidazolidin-4-yl]-propyl}-biphenyl-2-yloxy)-2-methyl-propionic acid methyl ester

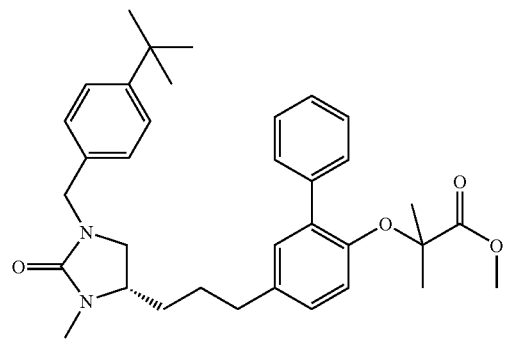

The titled compound was prepared using 2-(4-{3-[1-(4-tert-Butyl-benzyl)-3-methyl-2-oxo-imidazolidin-4-yl]-propyl}-2-iodo-phenoxy)-2-methyl-propionic acid methyl ester (0.121 g, 0.200 mmole) and phenyl bornic acid (0.073, 0.600 mmole) to produce a colorless oil (0.103 g, 93%). Mass [EI+] 557 (M+H)+.

Step B 2-(5-{3-[1-(4-tert-Butyl-benzyl)-3-methyl-2-oxo-imidazolidin-4-yl]-propyl}-biphenyl-2-yloxy)-2-methyl-propionic acid The titled compound was prepared using 2-(5-{3-[1-(4-tert-Butyl-benzyl)-3-methyl-2-oxo-imidazolidin-4-yl]-propyl}-biphenyl-2-yloxy)-2-methyl-propionic acid methyl ester (0.103 g, 0.185 mmole) to produce colorless oil (0.0967 g, 97%). Mass [EI+] 543 (M+H)⁺, [EI−] 541 (M−H)⁻.

Example 211

2-(4-{3-[1-(4-tert-Butyl-benzyl)-3-methyl-2-oxo-imidazolidin-4-yl]-propyl}-2-vinyl-phenoxy)-2-methyl-propionic acid

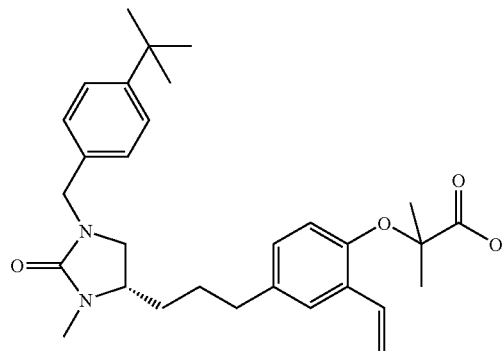

Step A 2-(4-{3-[1-(4-tert-Butyl-benzyl)-3-methyl-2-oxo-imidazolidin-4-yl]-propyl}-2-vinyl-phenoxy)-2-methyl-propionic acid methyl ester

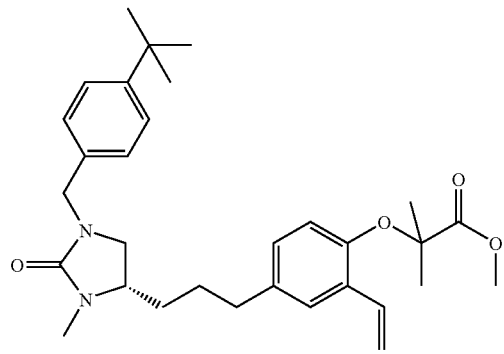

2-(4-{3-[1-(4-tert-Butyl-benzyl)-3-methyl-2-oxo-imidazolidin-4-yl]-propyl}-2-iodo-phenoxy)-2-methyl-propionic acid methyl ester (0.264 g, 0.435 mmole) and tributyl(vinyl)tin (0.207 g, 0.652 mmole) were mixed in toluene (4.0 mL). After bubbled with nitrogen for 15 minutes, tetrakis(triphenylphosphine) palladium(0) (0.050 g, 0.043 mmole) was added. The reaction was heated at 80° C. overnight. The solvent was removed on rota-vapor, and the crude product was purified by column chromatography (silica gel, gradient elution 0-30% acetone in hexane) to provide a colorless oil (0.158 g, 71%). Mass [EI+] 507 (M+H)⁺.

Step B 2-(4-{3-[1-(4-tert-Butyl-benzyl)-3-methyl-2-oxo-imidazolidin-4-yl]-propyl}-2-vinyl-phenoxy)-2-methyl-propionic acid The titled compound was prepared using 2-(4-{3-[1-(4-tert-Butyl-benzyl)-3-methyl-2-oxo-imidazolidin-4-yl]-propyl}-2-vinyl-phenoxy)-2-methyl-propionic acid methyl ester (0.048 g, 0.094 mmole) to produce an oil (0.0445 g, 95%). Mass [EI+] 493 (M+H)⁺, [EI−] 491 (M−H)⁻.

Example 212

2-(4-{3-[1-(4-tert-Butyl-benzyl)-3-methyl-2-oxo-imidazolidin-4-yl]-propyl}-2-ethyl-phenoxy)-2-methyl-propionic acid

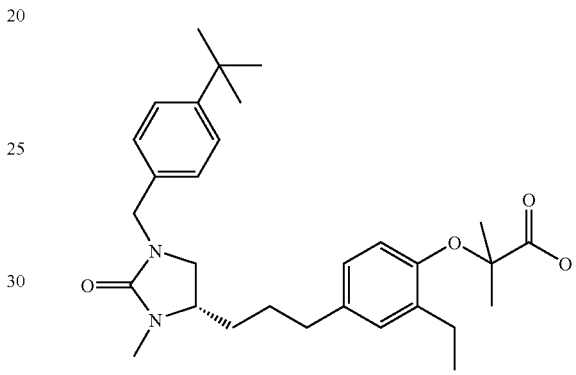

Step A 2-(4-{3-[1-(4-tert-Butyl-benzyl)-3-methyl-2-oxo-imidazolidin-4-yl]-propyl}-2-ethyl-phenoxy)-2-methyl-propionic acid methyl ester

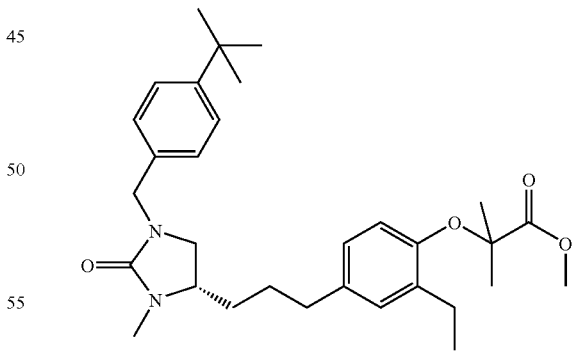

2-(4-{3-[1-(4-tert-Butyl-benzyl)-3-methyl-2-oxo-imidazolidin-4-yl]-propyl}-2-vinyl-phenoxy)-2-methyl-propionic acid methyl ester (0.110 g, 0.217 mmole) was dissolved in absolute ethanol (4 mL). After purged the solution with N₂ for 15 min, 10% Pd/C (0.040 g). The reaction was stirred under a hydrogen balloon at room temperature for 2 hours. The catalyst was removed through filtration, and solvent was removed on rota-vapor to provide a colorless oil (0.110 g, 100%). Mass [EI+] 509 (M+H)⁺.

Step B 2-(4-{3-[1-(4-tert-Butyl-benzyl)-3-methyl-2-oxo-imidazolidin-4-yl]-propyl}-2-ethyl-phenoxy)-2-methyl-propionic acid The titled compound was prepared using 2-(4-{3-[1-(4-tert-Butyl-benzyl) -3-methyl-2-oxo-imidazolidin-4-yl]-propyl}-2-ethyl-phenoxy)-2-methyl-propionic acid methyl ester (0.110 g, 0.216 mmole) to produce an oil (0.0905 g, 85%). Mass [EI+] 495 (M+H)+, [EI–] 493 (M–H)−.

Example 213

2-(2-Allyl-4-{3-[1-(4-tert-butyl-benzyl)-3-methyl-2-oxo-imidazolidin-4-yl]-propyl}-phenoxy)-2-methyl-propionic acid

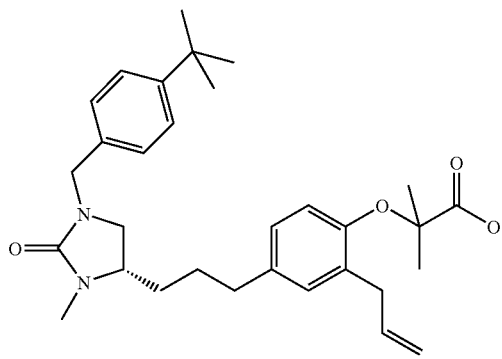

Step A 2-(2-Allyl-4-{3-[1-(4-tert-butyl-benzyl)-3-methyl-2-oxo-imidazolidin-4-yl]-propyl}-phenoxy)-2-methyl-propionic acid methyl ester

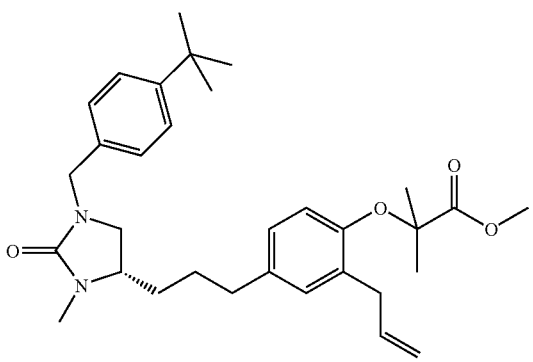

The titled compound was prepared using 2-(4-{3-[1-(4-tert-Butyl-benzyl)-3-methyl-2-oxo-imidazolidin-4-yl]-propyl}-2-iodo-phenoxy)-2-methyl-propionic acid methyl ester (0.200 g, 0.330 mmole) and allyl tributyltin (0.218, 0.659 mmole) to produce a colorless oil (0.102 g, 59%). Mass [EI+] 521 (M+H)+.

Step B 2-(2-Allyl-4-{3-[1-(4-tert-butyl-benzyl)-3-methyl-2-oxo-imidazolidin-4-yl]-propyl}-phenoxy)-2-methyl-propionic acid The titled compound was prepared using 2-(2-Allyl-4-{3-[1-(4-tert-butyl-benzyl)-3-methyl-2-oxo-imidazolidin-4-yl]-propyl}-phenoxy)-2-methyl-propionic acid methyl ester (0.040 g, 0.076 mmole) to produce a colorless oil (0.027 g, 69%). Mass [EI+] 507 (M+H)+, [EI–] 508 (M–H)−.

Example 214

2-(4-{3-[1-(4-tert-Butyl-benzyl)-3-methyl-2-oxo-imidazolidin-4-yl]-propyl}-2-propyl-phenoxy)-2-methyl-propionic acid

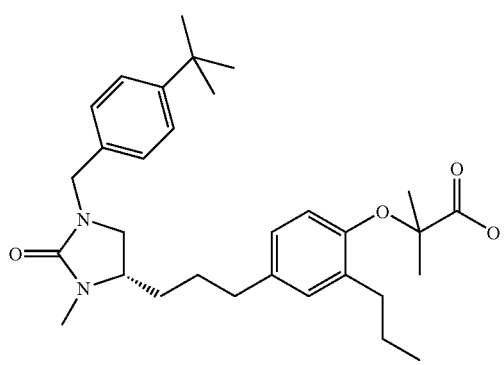

Step A 2-(4-{3-[1-(4-tert-Butyl-benzyl)-3-methyl-2-oxo-imidazolidin-4-yl]-propyl}-2-propyl-phenoxy)-2-methyl-propionic acid methyl ester

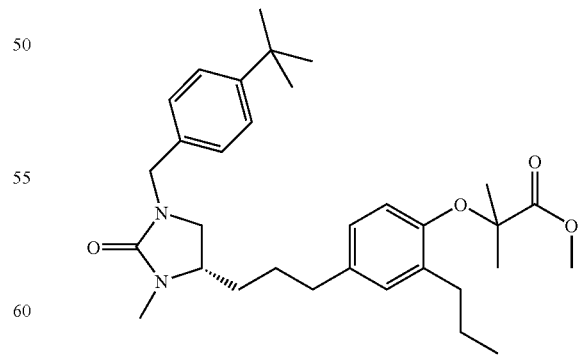

2-(2-Allyl-4-{3-[1-(4-tert-butyl-benzyl)-3-methyl-2-oxo-imidazolidin-4-yl]-propyl}-phenoxy)-2-methyl-propionic acid methyl ester (0.060 g, 0.115 mmole) was dissolved in absolute ethanol (10 mL). After purged the solution with N2 for 15 min, 10% Pd/C (0.030 g). The reaction was stirred under a hydrogen balloon at room temperature for 2 hours. The catalyst was removed through filtration, and solvent was removed on rota-vapor to provide a colorless oil (0.053 g, 88%). Mass [EI+] 523 (M+H)+.

Step B 2-(4-{3-[1-(4-tert-Butyl-benzyl)-3-methyl-2-oxo-imidazolidin-4-yl]-propyl}-2-propyl-phenoxy)-2-methyl-propionic acid The titled compound was prepared using 2-(4-{3-[1-(4-tert-Butyl-benzyl)-3-methyl-2-oxo-imidazolidin-4-yl]-propyl}-2-propyl-phenoxy)-2-methyl-propionic acid methyl ester (0.052 g, 0.100 mmole) to produce an oil (0.050 g, 100%). Mass [EI+] 509 (M+H)+, [EI−] 507 (M−H)−.

Example 215

2-Methyl-2-{2-methyl-4-[3-(3-methyl-2-oxo-imidazolidin-4-yl)-propyl]-phenoxy}-propionic acid

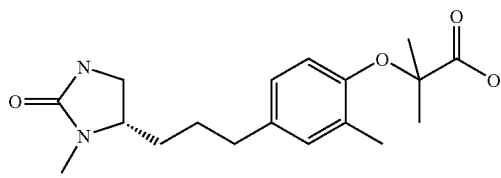

Step A 2-(4-{3-[1-(4-tert-Butyl-benzyl)-3-methyl-2-oxo-imidazolidin-4-yl]-propyl}-2-methyl-phenoxy)-2-methyl-propionic acid methyl ester

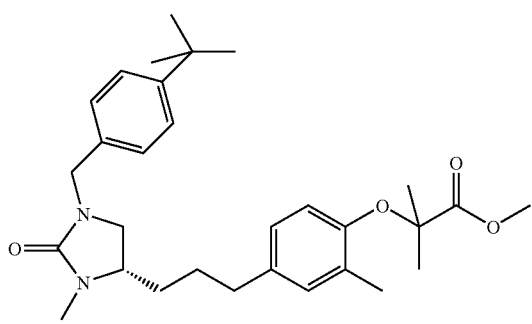

To a solution of 2-(4-{3-[1-(4-tert-Butyl-benzyl)-3-methyl-2-oxo-imidazolidin-4-yl]-propyl}-2-methyl-phenoxy)-2-methyl-propionic acid (0.610 g, 1.27 mmole) in methanol (10 mL) was added 15 drops of concentrated sulfuric acid. The mixture was stirred at room temperature overnight. After evaporated the solvent, the residue was partitioned between ethyl acetate (50 mL) and water (50 mL). The organic layer was washed by saturated sodium bicarbonate (50 mL), then brine (3×50 mL), dried over Na2SO4, filtered and concentrated in vacuo to produce an oil (0.624 g, 99%). Mass [EI+] 495 (M+H)+.

Step B

2-Methyl-2-{2-methyl-4-[3-(3-methyl-2-oxo-imidazolidin-4-yl)-propyl]-phenoxy}-propionic acid methyl ester

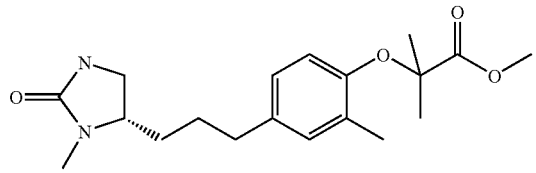

2-(4-{3-[1-(4-tert-Butyl-benzyl)-3-methyl-2-oxo-imidazolidin-4-yl]-propyl}-2-methyl-phenoxy)-2-methyl-propionic acid methyl ester (0.620 g, 1.25 mmole) was dissolved in 20% HOAc in EtOAC (50 mL). After purged the solution with N2 for 15 min, 10% Pd/C (0.600 g). The reaction was stirred under a hydrogen balloon at room temperature for overnight. The catalyst was removed through filtration, and solvent was removed on rota-vapor to provide a colorless oil (0.337 g, 77%). Mass [EI+] 349 (M+H)+.

Step C

2-Methyl-2-{2-methyl-4-[3-(3-methyl-2-oxo-imidazolidin-4-yl)-propyl]-phenoxy}-propionic acid The titled compound was prepared using 2-Methyl-2-{2-methyl-4-[3-(3-methyl-2-oxo-imidazolidin-4-yl)-propyl]-phenoxy}-propionic acid methyl ester (0.112 g, 0.322 mmole) to produce an oil (0.054 g, 50%). Mass [EI+] 335 (M+H)+, [EI−] 333 (M−H)−.

Example 216

2-{4-[3-(1-Biphenyl-4-ylmethyl-3-methyl-2-oxo-imidazolidin-4-yl)-propyl]-2-methyl-phenoxy}-2-methyl-propionic acid

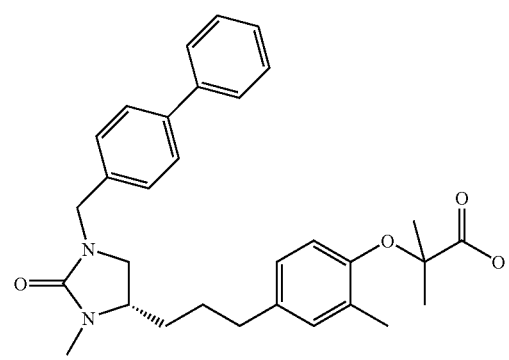

The titled compound was prepared using 2-Methyl-2-{2-methyl-4-[3-(3-methyl-2-oxo-imidazolidin-4-yl)-propyl]-phenoxy}-propionic acid methyl Ester (0.112 g, 0.322 mmole) and 4-phenyl benzyl chloride (0.078 g, 0.186 mmole) to produce an oil (0.054 g, 34%). Mass [EI+] 501 (M+H)+, [EI−] 499 (M−H)−.

Example 217

2-(4-{3-[1-(4-Bromo-benzyl)-3-methyl-2-oxo-imidazolidin-4-yl]-propyl}-2-methyl-phenoxy)-2-methyl-propionic acid

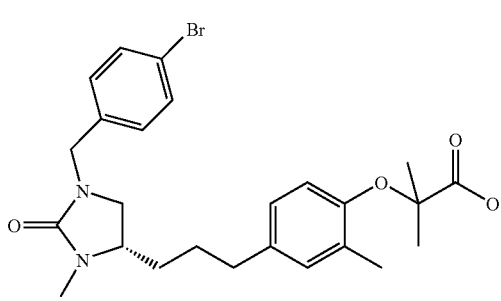

The titled compound was prepared using 2-Methyl-2-{2-methyl-4-[3-(3-methyl-2-oxo-imidazolidin-4-yl)-propyl]-phenoxy}-propionic acid methyl Ester (0.100 g, 0.287 mmole) and 4-bromo benzyl bromide (0.108 g, 0.431 mmole) to produce an oil (0.058 g, 40%). Mass [EI+] 503, 505 (M+H)+, [EI−] 501, 503 (M−H)−.

Example 218

2-(4-{3-[1-(3-Methoxy-benzyl)-3-methyl-2-oxo-imidazolidin-4-yl]-propyl}-2-methyl-phenoxy)-2-methyl-propionic acid

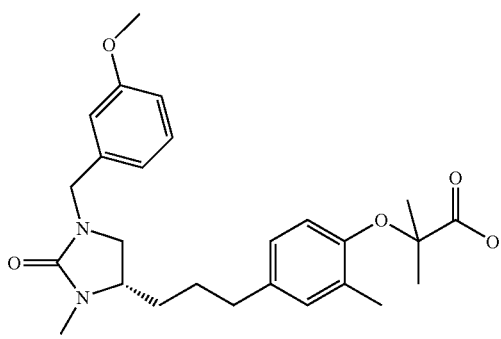

The titled compound was prepared using 2-Methyl-2-{2-methyl-4-[3-(3-methyl-2-oxo-imidazolidin-4-yl)-propyl]-phenoxy}-propionic acid methyl Ester (0.100 g, 0.287 mmole) and 3-methoxy) benzyl bromide (0.087 g, 0.431 mmole) to produce an oil (0.042 g, 32%). Mass [EI+] 455 (M+H)+, [EI−] 453 (M−H)−.

Example 219

2-Methyl-2-{2-methyl-4-[3-(3-methyl-2-oxo-1-quinolin-2-ylmethyl-imidazolidin-4-yl)-propyl]-phenoxy}-propionic acid The titled compound was prepared using 2-Methyl-2-{2-methyl-4-[3-(3-methyl-2-oxo-imidazolidin-4-yl)-propyl]-phenoxy}-propionic acid methyl Ester (0.100 g, 0.287 mmole) and 2-chloromethyl-quinoline (0.092 g, 0.431 mmole) to produce an oil (0.023 g, 17%). Mass [EI+] 476 (M+H)+, [EI−] 474 (M−H)−.

Example 220

2-Methyl-2-{2-methyl-4-[3-(3-methyl-1-naphthalen-2-ylmethyl-2-oxo-imidazolidin-4-yl)-propyl]-phenoxy}-propionic acid The titled compound was prepared using 2-Methyl-2-{2-methyl-4-[3-(3-methyl-2-oxo-imidazolidin-4-yl)-propyl]-phenoxy}-propionic acid methyl Ester (0.100 g, 0.287 mmole) and 2-Bromomethyl-naphthalene (0.095 g, 0.431 mmole) to produce an oil (0.080 g, 59%). Mass [EI+] 476 (M+H)+, [EI−] 474 (M−H)−.

Example 221

2-{4-[3-(1-Biphenyl-4-ylmethyl-3-methyl-2-oxo-imidazolidin-4-yl)-propyl]-2-butyl-phenoxy}-2-methyl-propionic acid

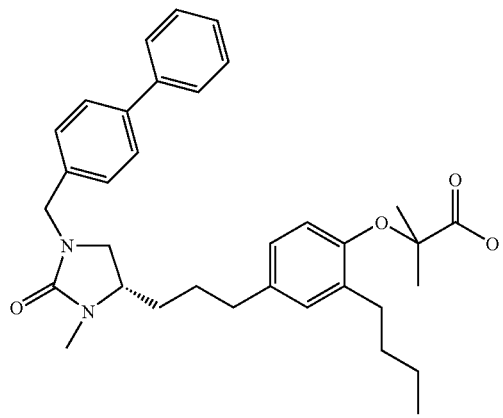

Step A

2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester

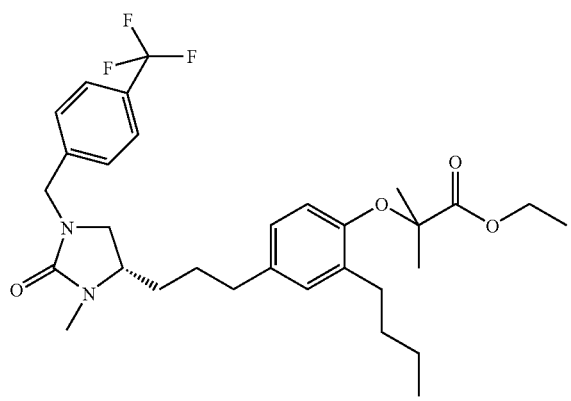

The titled compound was prepared using 4-[3-(3-Butyl-4-hydroxy-phenyl)-propyl]-3-methyl-1-(4-trifluoromethyl-benzyl)-imidazolidin-2-one (0.210 g, 0.468 mmole) to produce an oil (0.258 g, 98%). Mass [EI+] 563 (M+H)+.

Step B

2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester

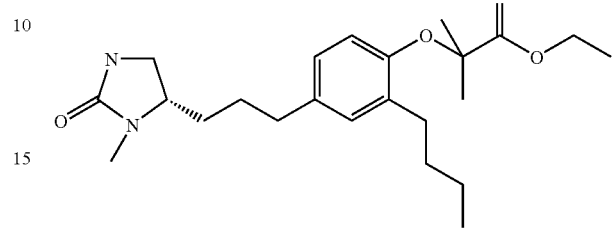

The titled compound was prepared using 2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester (0.215 g, 0.382 mmole) to produce an oil (0.049 g, 32%). Mass [EI+] 405 (M+H)+.

Step C

2-{4-[3-(1-Biphenyl-4-ylmethyl-3-methyl-2-oxo-imidazolidin-4-yl)-propyl]-2-butyl-phenoxy}-2-methyl-propionic acid The titled compound was prepared using 2-(2-Butyl-4-{3-[3-methyl-2-oxo-1-(4-trifluoromethyl-benzyl)-imidazolidin-4-yl]-propyl}-phenoxy)-2-methyl-propionic acid ethyl ester (0.049 g, 0.120 mmole) and 4-phenyl benzyl bromide (0.029 g, 0.144 mmole) to produce an oil (0.042 g, 65%). Mass [EI+] 543 (M+H)+, [EI−] 541 (M−H)−.

Certain compounds of the present invention can be prepared using the methods illustrated by the following schemes:

Cyclic Urea Synthesis-V

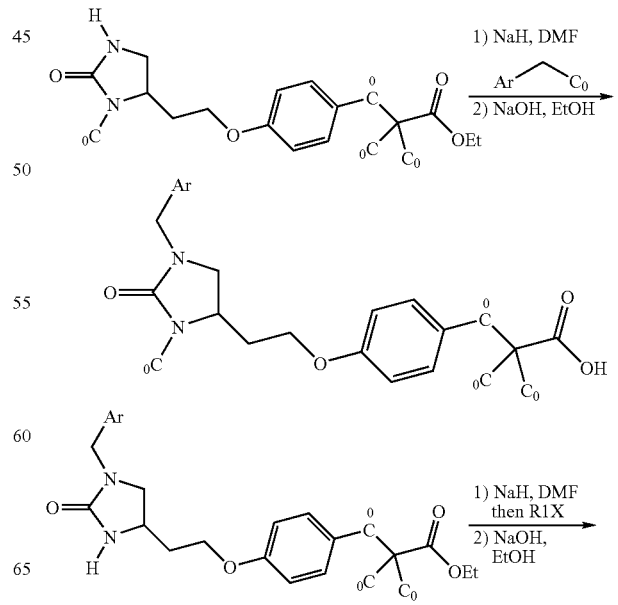

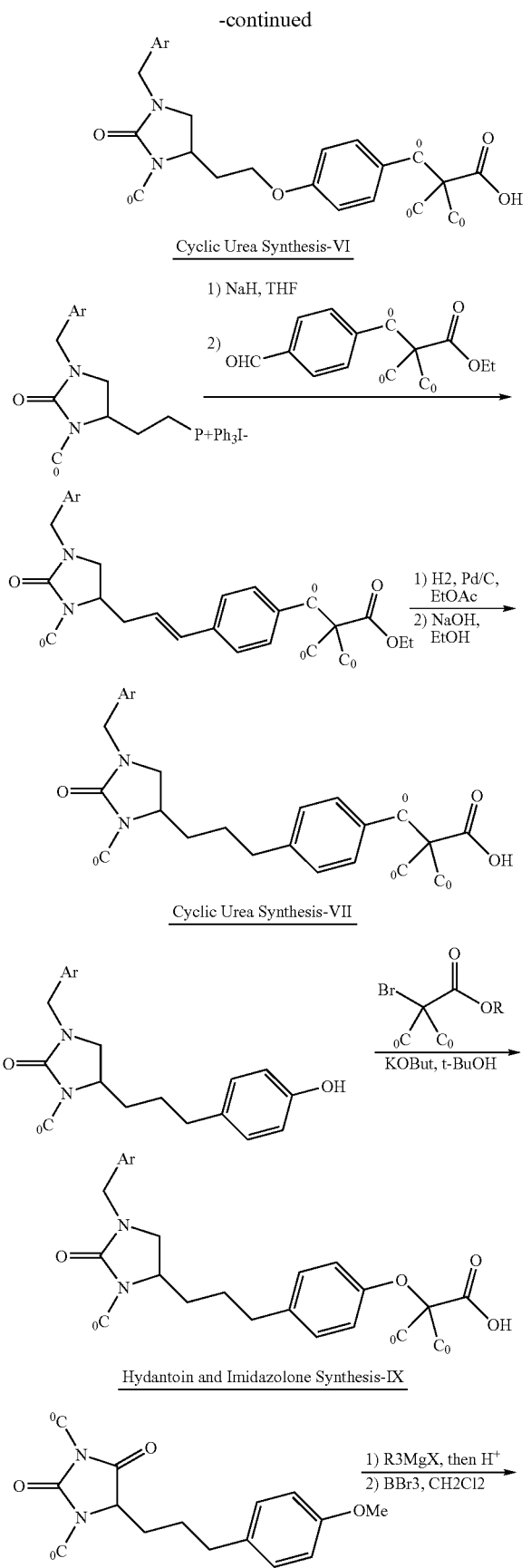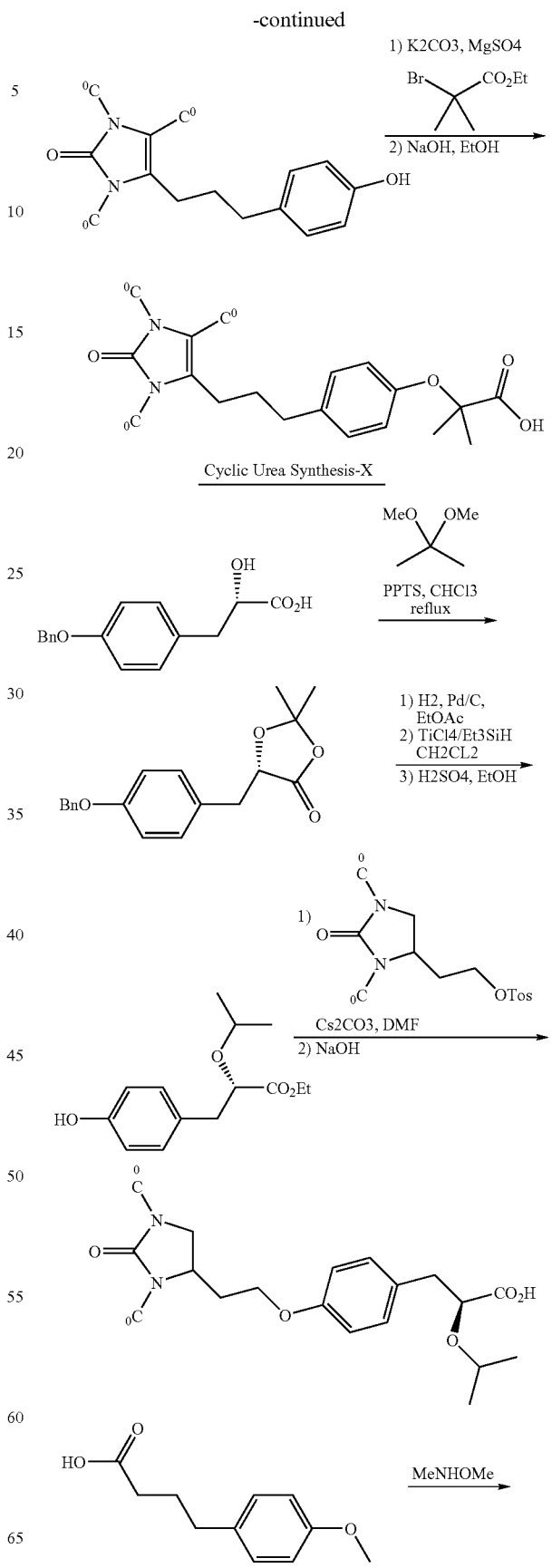

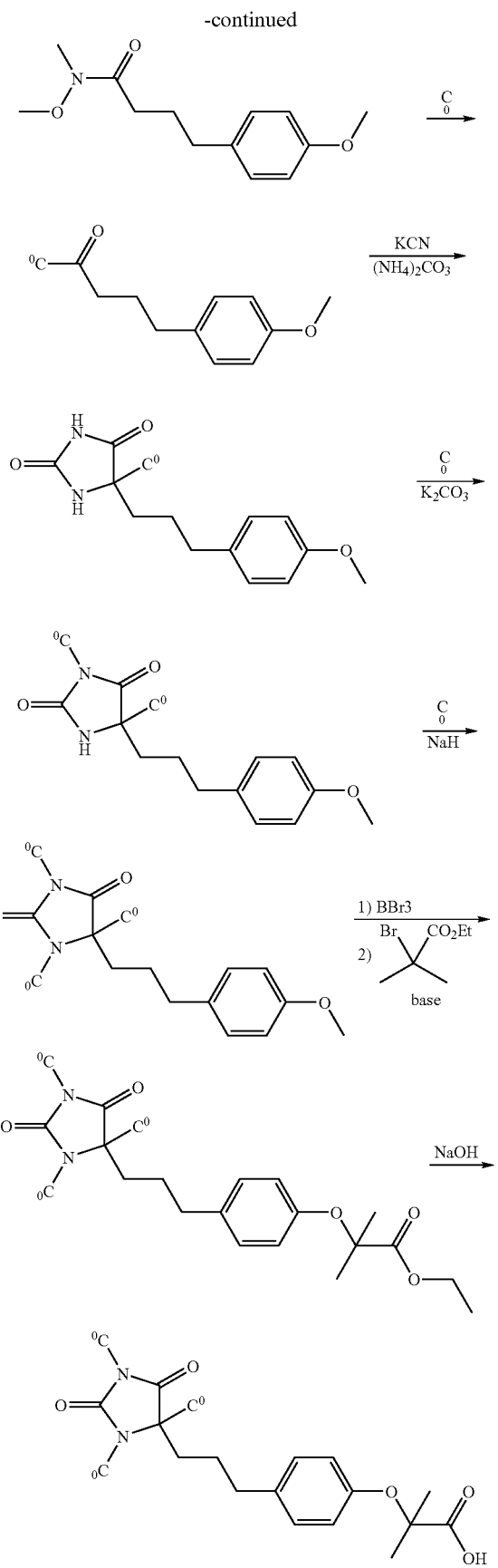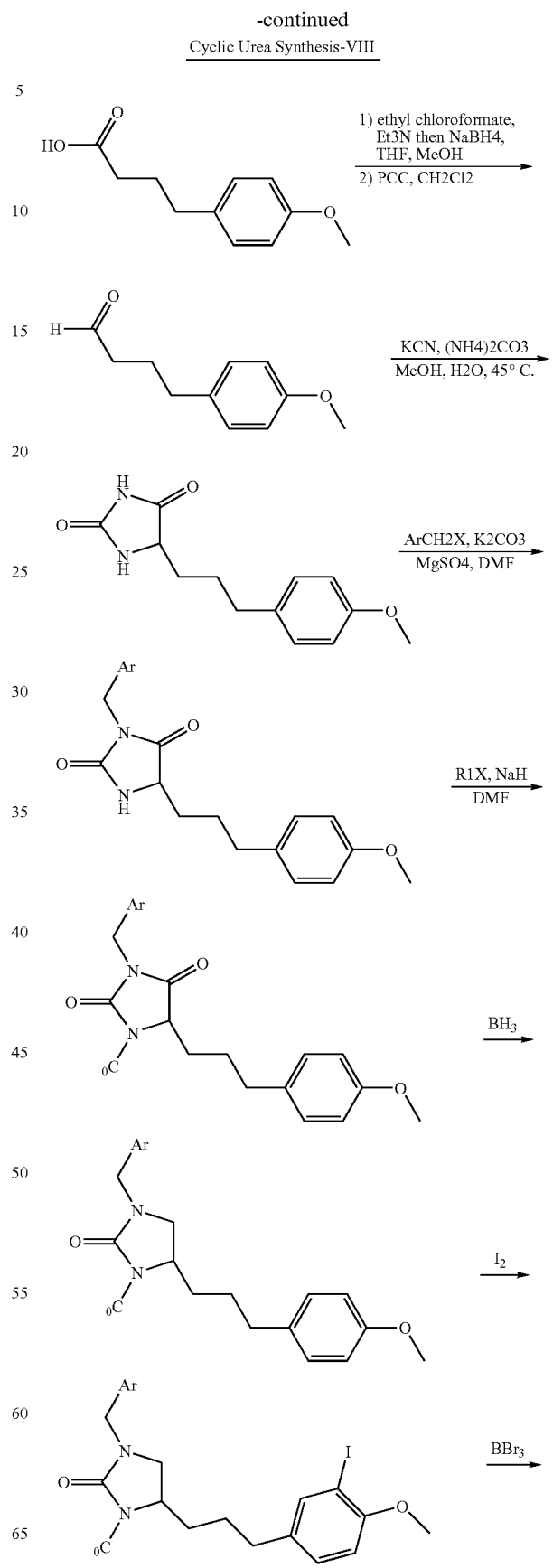

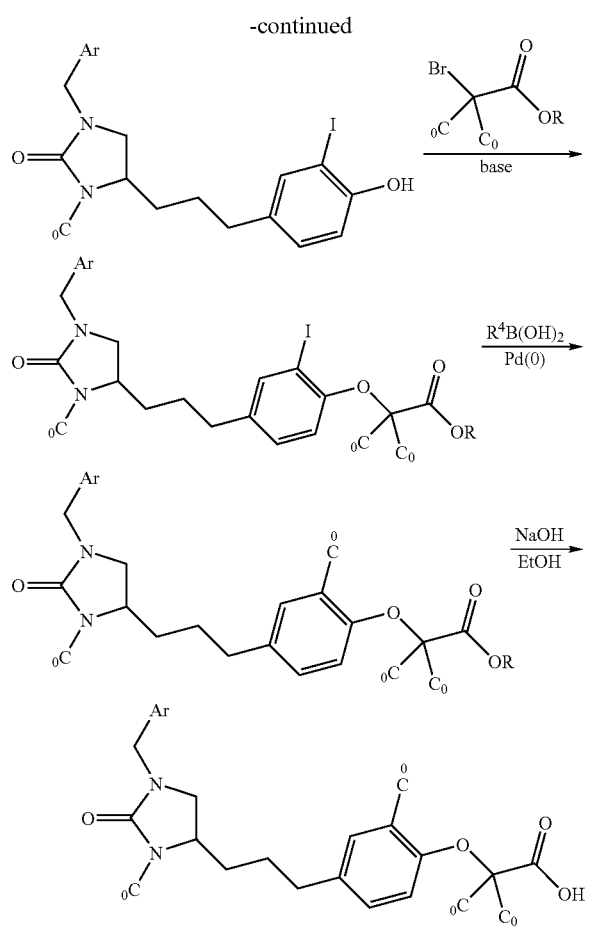

Biological Assays

Binding and Cotransfection Studies

The in vitro potency of compounds in modulating PPARγ and PPARα receptors are determined by the procedures detailed below. DNA-dependent binding (ABCD binding) is carried out using SPA technology with PPAR receptors. Tritium-labeled PPARα and PPARγ agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs and RXRα are constitutively expressed using plasmids containing the CMV promoter. For PPARα and PPARδ, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist and PPARγ agonist reference molecules. Efficacies are determined by computer fit to a concentration-response curve, or in some cases at a single high concentration of agonist (10 μM). For binding or cotransfection studies with receptors other than PPARs, similar assays are carried out using appropriate ligands, receptors, reporter constructs, etc., for that particular receptor.

These studies are carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention are compared with corresponding data for marketed compounds that act on either huPPARα or huPPARγ.

Binding and cotransfection data for representative compounds of the invention are compared with corresponding data for reference to determine the binding.

The binding and cotransfection efficacy values found, for compounds of the invention and compounds of this invention which are useful for modulating a PPAR alpha receptor, are ≦100 nM and ≧50%, respectively. When coagoanist modulators are desired, the values may be balanced against selectivity for the alpha, gamma, delta, or another desired PPAR receptor subtype.

Evaluation of Triglyceride Reduction and HDL Cholesterol Elevation in HuapoAI Transgenic Mice Studies are performed to evaluate the effect of compounds of the present invention upon HDL and triglyceride levels in human apoAI mice. For each compound tested, seven to eight week old male mice, transgenic for human apoAI (C57 BL/6-tgn(apoal)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1-½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542, 1983; Allain C. C. et al., Clin Chem 20:470-475, 1974. Commercially available standards for triglycerides and total cholesterol, respectively, commercial quality control plasma, and samples are measured in duplicate using 200 μl of reagent. An additional aliquot of sample, added to a well containing 200 μl water, provides a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min is mixed with the column effluent through a T-connection and the mixture passed through a 15 m×0.5 mm id knitted tubing reactor immersed in a 37 C water bath. The colored product produced in the presence of cholesterol is monitored in the flow stream at 505 nm and the analog voltage from the monitor is converted to a digital signal for collection and analysis. The change in voltage corresponding to change in cholesterol concentration is plotted vs. time and the area under the curve corresponding to the elution of very low density lipoprotein (VLDL), low density lipoprotein (LDL) and high density lipoprotein (HDL) is calculated using Perkin Elmer Turbochrome software.

Triglyceride serum levels in mice dosed with a compound of the invention are compared to mice receiving the vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLC serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of different compounds of the present invention is studied using the following methods.

Five-week-old male diabetic (db/db) mice [for example, C57BlKs/j-m+/+Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the 7$^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays were further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provides a blank for each specimen. Plates are incubated at room temperature for 18 minutes for glucose on a plate shaker (DPC Micormix 5) and absorbance is read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements reveal a significant reduction in respiratory quotient (RQ) in treated animals during the dark cycle [$0.864 \pm 0.013$ (Control) vs. $0.803 \pm 0.007$ (Treated); $p<0.001$]. This reduction in RQ is indicative of an increased utilization of fat during the animals' active (dark) cycle. Additionally, treated animals display significantly higher rates of energy expenditure than control animals.

Male KK/A$^y$ Mice

Male KK/A$^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-Cholesterol Total-Cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster receives once a day approx. 1 ml of the solution by gavage at doses 3 and 30 mg/kg body weight. The blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's procedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. The LDL-lowering efficacy for certain compounds of this invention can be especially desired. Compounds of this invention that decrease LDL greater than or equal to 30% (thirty percent) compared to vehicle can be especially desired.

The total-cholesterol and triglyceride lowering effects of a Compound of this invention are also studied. The data for reduction in total cholesterol and triglyceride levels after treatment with a compound of this invention for 14 days is compared to the vehicle to suggest compounds that can be particularly desired.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a ½0 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples.

Compounds of this invention may lowering fibrinogen level in vivo. Compounds that lower fibrinogen level greater than vehicle can be especially desired.

Method to Elucidate the Anti-Body Weight Gain and Anti-Appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat receives once a day approximately 1 ml of the solution by gavage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Equivalents:

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound that is represented by the following structural formula:

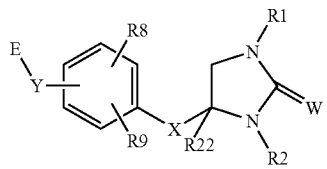

(a) R1 is optionally substituted, aryl-$C_{1-4}$-alkyl;
(b) R2 is $C_1$-$C_6$ alkyl;
(c) W is O or S;
(d) X is an optionally substituted $C_1$-$C_5$ alkylene linker wherein one carbon atom of the linker may optionally be replaced with O, NH, and S, and optionally two carbons together may form a double bond;
(e) Y is selected from the group consisting of $CH_2$, O, S, NH and a single bond; and
(f) E is selected from the group consisting of C(R3)(R4)A, A, and a substituted or unsubstituted group selected from the group consisting of $(CH_2)_n$COOR19; and wherein
  (i) n is 0, 1, 2 or 3;
  (ii) A is an functional group selected from the group consisting of carboxyl, $C_1$-$C_3$alkylnitrile, carboxamide, substituted or unsubstituted sulfonamide, substituted or unsubstituted acylsulfonamide, substituted or unsubstituted tetrazole, and substituted or unsubstituted isoxazole;
  (iii) R3 is selected from the group consisting of H, $C_1$-$C_5$ alkyl, and $C_1$-$C_5$ alkoxy, and
  (iv) R4 is selected from the group consisting of H, halo, and a substituted or unsubstituted group selected from $C_1$-$C_5$ alkyl, $C_1$-$C_5$ alkoxy, $C_3$-$C_6$ cycloalkyl, aryl $C_0$-$C_4$ alkyl, aryl$C_0$-$C_2$alkoxy and phenyl; or R3 and R4 are combined to form a $C_3$-$C_8$ cycloalkyl;
  (v) R19 is selected from the group consisting of hydrogen, optionally substituted arylmethyl and optionally substituted C1-C4alkyl;
(g) R8 is selected from the group consisting of hydrogen, $C_1$-$C_4$ alkyl, $C_2$-$C_4$ alkenyl, and halo;
(h) R9 is selected from the group consisting of hydrogen, $C_1$-$C_4$ alkyl, halo, substituted or unsubstituted aryl, substituted or unsubstituted aryl-$C_1$-$C_4$ alkyl, substituted or unsubstituted heteroaryl, $C_2$-$C_6$ alkenyl, and OR10;
(i) R10 is independently selected from the group consisting of hydrogen and $C_1$-$C_4$ alkyl;
(k) R22 is selected from the group consisting of hydrogen, and a substituted or unsubstituted group selected from the group consisting of $C_1$-$C_6$ alkyl, aryl, $C_1$-$C_4$ alkylaryl, and heteroaryl;
and salts thereof.

2. A compound as claimed by claim 1 that is represented by the following structural formula:

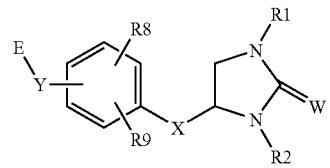

and salts thereof.

3. A compound as claimed by claim 1 wherein W is O.
4. A compound as claimed by claim 1 wherein E is A.
5. A compound as claimed by claim 1 wherein A is COOH.
6. A compound as claimed by claim 1 wherein Y is O.
7. A compound as claimed by claim 1 wherein Y is $CH_2$.
8. A compound as claimed by claim 1 wherein E is C(R3)(R4)A.
9. A compound as claimed by claim 1 wherein E is a group of the formula:

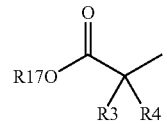

wherein R17 is H; and R3 and R4 are each H.

10. A compound as claimed by claim 1 wherein X is optionally substituted $C_2$-$C_5$ alkylene.
11. A compound as claimed by claim 1 wherein X is propylene.
12. A compound as claimed by claim 6 wherein R2 is $C_1$-$C_2$ alkyl.
13. A compound as claimed by claim 1 wherein R1 is substituted benzyl.
14. A compound as claimed by claim 13 wherein R1 is substituted benzyl wherein the benzyl substituent is one or two independently selected from the group consisting of $CF_3$, $C_1$-$C_4$ alkyl, and halo.
15. A compound as claimed by claim 1 wherein X is $C_1$-$C_3$alkyl-O—.
16. A compound as claimed by claim 8 wherein R4 is aryloxy.
17. A compound as claimed by claim 1 that is represented by the following structural formula:

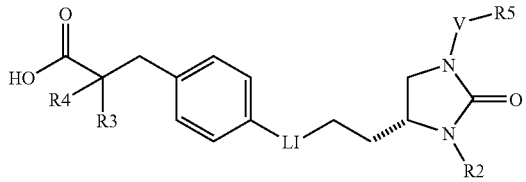

wherein
(a) LI is O or $CH_2$;
(b) V is a C1-C3 alkylene group;
(c) R5 is substituted or unsubstituted aryl; and
(d) salts thereof.

18. A compound as claimed by claim 1 represented by the following structural Formula:

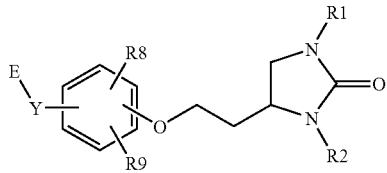

and salts thereof.

19. A compound as claimed by claim 15 represented by the following structural formula:

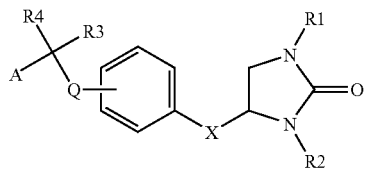

wherein Q is $CH_2$, O or S; X is $C_1$-$C_3$alkyl-O—; and salts thereof.

20. A compound as claimed by claim 1 that is represented by the following structural formula:

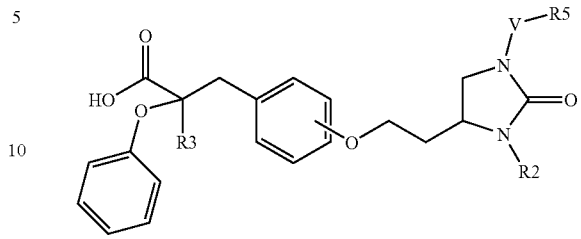

and salts thereof; wherein
(a) R3 is H or $C_1$-$C_5$ alkyl;
(b) V is C1-C3 alkylene;
(c) R5 is substituted or unsubstituted aryl.

21. A compound as claimed by claim 2 that is 2-methyl-3-(4-{3-[3-methyl-2-oxo-1-(4-trifluoromethyl-benzyl)-imidazolidin-4-yl]-propyl}-phenyl)-2-phenoxy-propionic acid or 2-Methyl-3-(4-{2-[3-methyl-2-oxo-1-(4-trifluoromethyl-benzyl)-imidazolidin-4-yl]-ethoxy}-phenyl)-2-phenoxy-propionic acid.

22. A pharmaceutical composition, comprising a pharmaceutically acceptable carrier and at least one compound as claimed by claim 1 or a pharmaceutically acceptable salt thereof.

23. A compound of claim 1 which is 2-Methyl-2-{4-[3-(1-naphthalen-2-ylmethyl-2-oxo-imidazolidin-4-yl)-propyl]-phenoxy}-propionic acid.

* * * * *